(12) United States Patent
Bacher et al.

(10) Patent No.: US 7,297,509 B2
(45) Date of Patent: Nov. 20, 2007

(54) INTERMEDIATES AND ENZYMES OF THE NON-MEVALONATE ISOPRENOID PATHWAY

(75) Inventors: Adelbert Bacher, Königsberger Str. 74, 85748 Garching (DE); Felix Rohdich, Moosburger Str. 16, 85406 Zolling (DE); Petra Adam, Kramsach (AT); Sabine Amslinger, Weiden (DE); Wolfgang Eisenreich, Freising (DE); Stefan Hecht, Bad Aibling (DE)

(73) Assignees: Adelbert Bacher, Garching (DE); Felix Rohdich, Zolling (DE)

( * ) Notice: Subject to any disclaimer, the term of this patent is extended or adjusted under 35 U.S.C. 154(b) by 73 days.

(21) Appl. No.: 10/474,536

(22) PCT Filed: Apr. 10, 2002

(86) PCT No.: PCT/EP02/04005

§ 371 (c)(1),
(2), (4) Date: Apr. 7, 2004

(87) PCT Pub. No.: WO02/083720

PCT Pub. Date: Oct. 24, 2002

(65) Prior Publication Data

US 2004/0176570 A1    Sep. 9, 2004

(30) Foreign Application Priority Data

Apr. 11, 2001 (DE) ............................. 101 18 166
Jun. 22, 2001 (DE) ............................. 101 30 236

(51) Int. Cl.
*A12Q 1/18* (2006.01)
(52) U.S. Cl. ........................... 435/32; 435/29; 530/350

(58) Field of Classification Search ............... None
See application file for complete search history.

(56) References Cited

U.S. PATENT DOCUMENTS 4,297,960 A     11/1981    Tonnessen (Continued)

FOREIGN PATENT DOCUMENTS

CA            2374608         11/2000

(Continued)

OTHER PUBLICATIONS

Campos, AN et al, FEBS Letters, vol. 488(3), Jan. 19, 2001, pp. 170-173, reference of record.*

(Continued)

*Primary Examiner*—Mark Navarro
*Assistant Examiner*—Ginny Portner
(74) *Attorney, Agent, or Firm*—Myers Bigel Sibley & Sajovec

(57) ABSTRACT

The invention provides a protein in a form that is functional for the enzymatic conversion of 2C-methyl-D-erythritol 2,4-cyclodiphosphate to 1-hydroxy-2-methyl-2-butenyl 4-diphosphate notably in its (E)-form of the non-mevalonate biosynthetic pathway to isoprenoids. The invention also provides a protein in a form that is functional for the enzymatic conversion of 1-hydroxy-2-methyl-2-butenyl 4-diphosphate, notably in its (E)-form, to isopentenyl diphosphate and/or dimethylallyl diphosphate. Further, screening methods for inhibitors of these proteins are provided. Further, 1-hydroxy-2-methyl-2-butenyl 4-diphosphate is provided and chemical and enzymatic methods of its preparation.

12 Claims, 42 Drawing Sheets

U.S. PATENT DOCUMENTS

| | | | |
|---|---|---|---|
| 4,950,797 | A | 8/1990 | Kummer et al. |
| 5,824,873 | A | 10/1998 | Grierson et al. ............ 800/205 |
| 5,885,782 | A | 3/1999 | Edwards ..................... 435/7.1 |
| 6,841,717 | B2* | 1/2005 | Boronat et al. ............. 800/278 |
| 6,872,815 | B1* | 3/2005 | Subramaniam et al. .... 536/23.7 |
| 7,122,331 | B1* | 10/2006 | Eisenreich et al. .......... 435/7.4 |
| 2003/0115634 | A1* | 6/2003 | Jomaa ....................... 800/284 |
| 2003/0170847 | A1* | 9/2003 | Bramucci et al. .......... 435/193 |
| 2003/0182687 | A1* | 9/2003 | Cheng et al. ............... 800/282 |
| 2004/0033994 | A1* | 2/2004 | Jomaa ......................... 514/90 |
| 2004/0072142 | A1* | 4/2004 | Bacher et al. .................. 435/4 |
| 2004/0161819 | A1* | 8/2004 | Aharoni et al. ............ 435/69.1 |
| 2004/0176370 | A1* | 9/2004 | Bacher et al. ............... 530/350 |
| 2004/0209365 | A1* | 10/2004 | Rouviere et al. ........... 435/456 |
| 2004/0219629 | A1* | 11/2004 | Cheng et al. ................. 435/67 |
| 2004/0219656 | A1* | 11/2004 | Poulter et al. ......... 435/252.33 |
| 2004/0226502 | A1* | 11/2004 | Bacher et al. .................. 117/2 |
| 2005/0014219 | A1* | 1/2005 | Cheng et al. ................. 435/67 |
| 2005/0019852 | A1* | 1/2005 | Cheng et al. ................. 435/67 |
| 2005/0124033 | A1* | 6/2005 | Sharpe et al. ................. 435/67 |
| 2005/0221467 | A1* | 10/2005 | Brzostowicz et al. ..... 435/252.3 |
| 2005/0223435 | A1* | 10/2005 | Boronat et al. ............. 800/298 |
| 2005/0227311 | A1* | 10/2005 | Cheng et al. ................. 435/67 |
| 2005/0289664 | A1* | 12/2005 | Moshiri et al. ............. 800/278 |
| 2006/0030546 | A1* | 2/2006 | Jomaa et al. ................ 514/109 |
| 2006/0035312 | A1* | 2/2006 | Cheng et al. ................. 435/67 |
| 2007/0004000 | A1* | 1/2007 | Miyake et al. ................ 435/67 |
| 2007/0015216 | A1* | 1/2007 | Eisenreich et al. .......... 435/7.1 |

FOREIGN PATENT DOCUMENTS

| | | |
|---|---|---|
| DE | 298 00 547 U1 | 4/1999 |
| EP | 0 154 204 A2 | 9/1985 |
| EP | 0 309 906 A1 | 4/1989 |
| EP | 0841394 | 5/1998 |
| EP | 0 985 664 A2 | 3/2000 |
| WO | WO98/42875 | 10/1998 |
| WO | WO99/11757 | 3/1999 |
| WO | WO99/52938 | 10/1999 |
| WO | WO99/58649 | 11/1999 |
| WO | WO 00/17233 | 3/2000 |
| WO | 00/36138 | 6/2000 |
| WO | WO 00/72022 | 11/2000 |
| WO | WO 01/11055 | 2/2001 |
| WO | WO 01/85950 | 11/2001 |
| WO | WO 01/94561 A2 | 12/2001 |
| WO | WO 02/12478 A2 | 2/2002 |
| WO | WO 02/092800 A2 | 11/2002 |
| WO | WO 02/102991 | 12/2002 |

OTHER PUBLICATIONS

Cunningham, FX Jr et al, Journal of Bacteriology, vol. 182(20)pp. 5841-5848, Oct. 2000, Evidence of a role for LytB in the nonmevalonate pathway of Isoprenoid biosynthesis.*

Mueller, C et al, Biochemical Society Transactions, 2000, vol. 28(6), Properties and Inhibition of the first two enzymes of the non-mevalonate pathway of isoprenoid biosynthesis.*

Campos, Narciso et al, FEBS Letters, vol. 488,pp. 170-173, 2001, Identification of gcpE as a novel gene of the 2-C-methyl-D-erythritol-4-phosphate pathway for isoprenoid biosynthesis in *Escherichia coli*.*

Gil, Ma Jose et al, The Plant Journal, vol. 44, pp. 155-166, 2005, The Arabidopsis csb3 mutant reveals a regulatory link between salicylic acid-medicated disease resistance and the methyl-erythritol 4-phosphate pathway.*

Takahashi, Shunji et al, PNAS (USA), vol. 95, pp. 9879-9884, Aug. 1998.*

Hect, Stefan et al, PNAS, Dec. 18, 2001, vol. 98(26), pp. 14837-14842, Studies on the nonmevalonate pathway to terpenes:The role of the GcpE(IspG) protein.*

Baker et al. 1992. Sequence and Characterization of the *gcpE* Gene of *Escherichia coli*. *FEMS Microbiology Letters* 94:175-180.

Campos et al. 2001. Identification of *gcpE* as a Novel Gene of the 2-C-methyl-D-erythritol 4-phosphate Pathway for Isoprenoid Biosynthesis in *Escherichia coli*. *FEBS Letters* 488:170-173.

Cunningham et al. 2000. Evidence of a Role for LytB in the Nonmevalonate Pathway of Isoprenoid Biosynthesis. *Journal of Bacteriology* 182:5841-5848.

Gustafson et al. 1993. Identification of the *Escherichia coli lytB* Gene, Which is Involved in Penicillin Tolerance and Control of the Stringent Response. *Journal of Bacteriology* 175:1203-1205.

Herz et al. 2000. Biosynthesis of Terpenoids: YgbB Protein Converts 4-diphosphocytidyl-2C-methyl-D-erythritol 2-phosphate to 2C-methyl-D-erythritol 2,4-cyclodiphosphate. *PNAS* 97:2486-2490.

Lüttgen et al. 2000. Biosynthesis of Terpenoids: YchB Protein of *Escherichia coli* Phosphorylates the 2-hydroxy Group of 4-diphosphocytidyl-2C-methyl-D-erythritol. *PNAS* 97:1062-1067.

Ostrovsky et al. 1993. Bacterial Oxidative-Stress Substance is 2-C-methyl-D-erythritol 2,4-cyclopyrophosphate. *Biochemical Journal* 295:901-902.

Potter et al. 1998. Occurrence of Homologs of the *Escherichia coli lytB* Gene in Gram-Negative Bacterial Species. *Journal of Bacteriology* 180:1959-1961.

Rodríguez-Concepción et al. 2000. Genetic Evidence of Branching in the Isoprenoid Pathway for the Production of Isopentenyl Disphosphate and Dimethylallyl Disphosphate in *Escherichia coli*. *FEBS Letters* 473:328-332.

Rohdich et al. 1999. Cytidine 5'-triphosphate-dependent Biosynthesis of Isoprenoids: YgbP Protein of *Escherichia coli* Catalyzes the Formation of 4-diphosphocytidyl-2-C-methylerythritol. *PNAS* 96:11758-11763.

Rohdich et al. 2002. Studies of the Nonmevalonate Terpene Biosynthetic Pathway: Metabolic Role of IspH (LytB) Protein. *PNAS* 99:1158-1163.

Rohmer. 1998. Isoprenoid Biosynthesis via the Mevalonate-independent Route, a Novel Target for Antibacterial Drugs? *Progress in Drug Research* 50:135-154.

International Search Report for International Application Serial No. PCT/EP01/06255, mailed Apr. 2, 2002.

Blattner et al. (1997) "The Complete Genome Sequence of *Escherichia coli* K12" *Science* 277:1453-1462.

Post et al. (1993) "Characterization of the *hemA-prs* region of the *Escherichia coli* and *Salmonella typhimurium* chromosomes: identification of two open reading frames and implications for *prs* expression" *J. Gen. Microbiol.* 139:259-266.

International Search Report for International Application Serial No. PCT/EP00/07548, mailed Dec. 12, 2000.

Abola et al. (2000) "Automation of X-ray crystallography" *Nature Structural Biology* 7:973-977.

Richard et al. (2002) "Structural and Mechanism of 2-C-Methyl-D-erythritol 2,4-Cyclodiphosphate Synthase" *The Journal of Biological Chemistry* 277:8667-8672.

Skelly et al. (1996) "Overexpression, Isolation, and Crystallization of Proteins" *Methods in Molecular Biology* 56:23-53.

Steinbacher et al. (2002) "Structure of 2C-Methyl-D-erythritol-2,4-cyclodiphosphate Synthase Involved in Mevalonate-independent Biosynthesis of Isoprenoids" *J. Mol. Biol.* 316:79-88.

Ridley, R.G. (1999) "Planting the seeds of new antimalarial drugs" *Science* 285:1502-1503.

GenBank Accession No. P36663 "2-C-methyl-D-erythritol 2,4-cyclodiphosphate synthase" Jun. 1, 1994.

International Search Report mailed on Jun. 13, 2003 for application No. PCT/EP 02/05238.

Gabrielsen et al. (2004) "Hexameric Assembly of the Bifunctional Methylerythritol 2,4-Cyclodiphosphate Synthase and Protein—Protein Associations in the Deoxy-xylulose-dependent Pathway of Isoprenoid Precurser Biosynthesis" *The Journal of Biological Chemistry*, 279:52753-52761.

Kuzuyama et al. "Fosmidomycin, a Specific Inhibitor of 1-Deoxy-D-Xylulose 5 Phosphate Reductoisomerase in the Nonmevalonate Pathway for Terpenoid Biosynthesis" *Tetrahedron Letters* 39:7913-7916 (1998).

Eisenreich et al. "The deoxyxylulose phosphate pathway of terpenoid biosynthesis in plants and microorganisms" *Chemistry and Biology* 5:R221-R233 (1998).

Tohidi et al. 1990. "Polymerization of the cyclic pyrophosphates of nucleosides and their analogs" *Journal of Molecular Evolution* 30:97-103 (Abstract).

Tagaki et al. "Studies on the nonmevalonate pathway: formation of 2-C-methyl-D-erythritol 2,4-cyclodiphosphate from 2-phospho-4-(cytidine 5'-diphospho)-2-C-methyl-D-erythritol" *Tetrahedron Letters* 41:3395-3398 (2000).

Kuzuyama et al. "Studies on the nonmevalonate pathway: conversion of 4-(cytidine 5'-diphospho)-2-C-methyl-D-erythritol to its 2-phospho derivative by 4-(cytidine 5'-diphospho)-2-C-methyl-D-erythritol kinase" *Tetrahedron Letters* 41:2925-2928 (2000).

Campos et al. (2001) "Identification of gcpE as a novel gene of the 2-C-methyl-D-erythritol 4-phosphate pathway for isoprenoid biosynthesis in *Escherichia coli*" *FEBS Letters* 488:170-173.

Altincicek et al. (2001) "GcpE Is Involved in the 2-C-Methyl-D-Erythritol 4-Phosphate Pathway of Isoprenoid Biosynthesis in *Escherichia coli*" *Journal of Bacteriology* 183:2411-2416.

Parker, J. (1992) "*E. coli* gcpE gene" *EMBL Database* accession No. X64451 1-2.

Nakamura, Y. (1997) "*Arabiodopsis thaliana* genomic DNA, chromosome 5, P1 clone" *EMBL Database* accession No. AB005246 1-26.

Lichtenthaler, H. K. (2000) "Non-mevalonate isoprenoid biosynthesis: enzymes, genes and inhibitors" *Biochemical Society Transactions* 28:785-789.

Lichtenthaler et al. (2000) "The Non-Mevalonate Isoprenoid Biosynthesis of Plants as a Test System for New Herbicides and Drugs against Pathogenic Bacteria and the Malaria Parasite" *Journal Biosciences* 55:305-313.

Wolff et al. (2002) "Isoprenoid biosynthesis via the methylerythritol phosphate pathway. (E)-4-Hydroxy-3-methylbut-2-enyl diphosphate: chemical synthesis and formation from methylerythritol cyclodiphosphate by a cell-free system from *Escherichia coli*" *Tetrahedron Letters* 43:2555-2559.

Hecht et al. (2001) "Studies on the nonmevalonate pathway to terpenes: The role of the GcpE (IspG) protein" *Proceedings of the National Academy of Sciences USA* 98:14837-14842.

International Search Report mailed on Jan. 15, 2003 for application No. PCT/EP 02/04005.

Rohdich et al., "The deoxyxylulose phosphate pathway of isoprenoid biosynthesis: Studies on the Mechanisms of the reactions catalyzed by IspG and IspH protein," PNAS, vol. 100, No. 4, Feb. 18, 2003, pp. 1586-1591.

Zepeck et al., "Biosynthesis of Isoprenoids. Purification and Properties of IspG Protein from *Escherichia coli*," J. Org. Chem. 70, Oct. 14, 2005, pp. 9168-9174.

Fellermeier. Copy of Ph.D. thesis entitled "Investigations on the Alternative Terpene Biosynthesis Pathway in Plants" Submitted to the University Library Munich, Ludwig-Maximilians-University, Munich, Germany in July, 2000 (English translation of introductory pages, reference list, index, pp 50-53, 61-63, 128-151, 164-175, 200-207, 313-361).

Altincicek et al. "*LytB*, a novel gene of the 2-*C*-methyl-D-erythritol 3-phosphate pathway of isoprenoid biosynthesis in *Escherichia coli*" *FEBS Letters* 499:37-40 (2001).

Altincicek et al. "Cutting Edge: Human γδT Cells Are Activated by Intermediates of the 2-*C*- methyl-D-erythritol 4-phosphate Pathway of Isoprenoid Biosynethsis" *J. Immunol.* 166:3655-3658 (2001).

Belmant et al. "3-Formyl-1-butyl Pyrophosphate A Novel Mycobacterial Metabolite-activating Human γδT Cells" *The Journal of Biological Chemistry* 274(45):32079-32084 (1999).

Database Geneseq [Online] Arabidopsis thaliana protein fragment, Seq. ID No. 30653, 6 pages (2000).

Database Geneseq [Online] Altincicek: "LytB (Plasmodium falcuparum)" page 1 of 2 (2001).

Davisson et al. "Synthesis of Allylic and Homoallylic Isoprenoid Pyrophosphates" *Methods in Enzymology* 110:130-144 (1984).

Davisson et al. "Phosphorylation of Isoprenoid Alcohols" *J. Org. Chem.* 51:4768-4779 (1986).

European Search Report for EP 02 72 4284; May 31, 2007.

Fellermeier et al. "Biosynthesis of cannabinoids" *Eur. J. Biochem.* 268:1596-1604 (2001).

Gao et al. "*(E)*-4-Hydroxy-3-methylbut-2-enyl Diphosphate: An Intermediate in the Formation of Terpenoids in Plant Chromoplasts" *Angew. Chem Int. Ed.* 41(14):2604-2607 (2002).

Genbank/EMBL accession BAB09833 for "GcpE protein", 2 pages (2004).

Hinz et al. "Indentification of *(E)*-4-hydroxy-3-methyl-but-2-enyl pyrophosphate as a major activator for human γδT cells in *Escherichia coli*" *FEBS Letters* 509:317-322 (2001).

Koppisch et al. "Synthesis of 2-*C*-Methyl-D-erythritol 4-Phosphate: The First Pathway-Specific Intermediate in the Methylerythritol Phosphate Route to Isoprenoids" *Organic Letters* 2 (2):215-217 (2000).

Kuzayama et al. "Cloning and Characterization of 1-Deoxy-D-Xylulose 5-Phosphate Synthase from *Streptomyces* sp. Strain CL190, Which Uses both the Mevalonate and Nonmevalonate Pathways for Isopentenyl Diphosphate Biosynthesis" *Journal of Bacteriology* 182(4):891-897 (2000).

Latzel, C. Ph.D. "Untersuchungen zu Intermediaten und Mechanismen der alternativen Terpenbiosynthese in Pflanzen" Ludwig-Maximilian-University Munich, pp. 77, 125-132, 158-167 and English translation of text portion of page 127, line 8 to page 127 and Figure Legends 57 and 76 (2002).

McAteer et al. "The *lytB* Gene of *Escherichia coli* Is Essential and Specifies a Product Needed for Isoprenoid Biosynthesis" *Journal of Bacteriology* 183(24):7403-7407 (2001).

Querol et al. "Functional analysis of the *Arabidopsis thaliana* GCPE protein involved in plastid isoprenoid biosynthesis" *FEBS Letters* 514:343-346 (2002).

Rohdich et al. "Biosynthesis of terpenoids: 4-Diphosphocytidyl-2C-methyl-D-erythritol synthase of *Arabidopsis thaliana*" *PNAS* 97(12):6451-6456 (2000).

Rohdich et al. "The deoxyxylulose phosphate pathway or isoprenoid biosynthesis; Studies on the Mechanisms of the reactions catalyzed by IspG and IspH protein" *PNAS* 100(4):1586-1591 (2003).

Ruppert et al. "A product study of the OH radical-initiated oxidation of isoprene: formation of $C_5$-undaturated diols" *Atmospheric Enviorment* 34:1529-1542 (2000).

Schwender et al. "Cloning and heterologous expression of a cDNA encoding 1-deoxy-D-xylulose-5-phosphate reductoisomerase of *Arabidopsis thaliana*" *FEBS Letters* 455:140-144 (1999).

Seemann et al. "Isoprenoid biosynthesis via the methylerythritol phosphate pathway: accumulation of 2-*C*-methyl-D-erythritol 2,4-cyclodiphosphate in a *GcpE* deficient mutant of *Escherichia coli*" *Tetrahedron Letters* 43:775-778 (2002).

Seemann et al. "Isoprenoid biosynthesis in *Escherichia coli* via the methylerythritol phosphate pathway: enzymatic conversion of methylerythritol cyclodiphosphate into a phosphorylated derivative of *(E)*-2-methylbut-2-ene-1, 4-diol" *Tetrahedron Letters* 43:1413-1415 (2002).

Ward et al. "Synthesis of *(2E)*-4-hydroxy-e-methylbut-2-enyl diphosphate, a key intermediate in the biosynthesis of isoprenoids" *J. Chem. Soc., Perkin Trans. 1* 710-712 (2002).

Zyk et al. "Reactions of Nitrosonium Ethyl Sulfate with Olefins and dienes: An Experimental and Theoretical Study" *J. Org. Chem.* 64:7121-7128 (1999).

\* cited by examiner

DNA sequence of the vector construct pBSxylBdxr

PBSXYLBDXR      PRELIMINARY;    DNA;    5628 BP.
SEQUENCE   5628 BP;   1378 A;   1374 C;   1552 G;   1324 T; 0 OTHER;

```
GTGGCACTTT TCGGGGAAAT GTGCGCGGAA CCCCTATTTG TTTATTTTTC TAAATACATT
CAAATATGTA TCCGCTCATG AGACAATAAC CCTGATAAAT GCTTCAATAA TATTGAAAAA
GGAAGAGTAT GAGTATTCAA CATTTCCGTG TCGCCCTTAT TCCCTTTTTT GCGGCATTTT
GCCTTCCTGT TTTTGCTCAC CCAGAAACGC TGGTGAAAGT AAAAGATGCT GAAGATCAGT
TGGGTGCACG AGTGGGTTAC ATCGAACTGG ATCTCAACAG CGGTAAGATC CTTGAGAGTT
TTCGCCCCGA AGAACGTTTT CCAATGATGA GCACTTTTAA AGTTCTGCTA TGTGGCGCGG
TATTATCCCG TATTGACGCC GGGCAAGAGC AACTCGGTCG CCGCATACAC TATTCTCAGA
ATGACTTGGT TGAGTACTCA CCAGTCACAG AAAAGCATCT TACGGATGGC ATGACAGTAA
GAGAATTATG CAGTGCTGCC ATAACCATGA GTGATAACAC TGCGGCCAAC TTACTTCTGA
CAACGATCGG AGGACCGAAG GAGCTAACCG CTTTTTTGCA CAACATGGGG GATCATGTAA
CTCGCCTTGA TCGTTGGGAA CCGGAGCTGA ATGAAGCCAT ACCAAACGAC GAGCGTGACA
CCACGATGCC TGTAGCAATG GCAACAACGT TGCGCAAACT ATTAACTGGC GAACTACTTA
CTCTAGCTTC CCGGCAACAA TTAATAGACT GGATGGAGGC GGATAAAGTT GCAGGACCAC
TTCTGCGCTC GGCCCTTCCG GCTGGCTGGT TTATTGCTGA TAAATCTGGA GCCGGTGAGC
GTGGGTCTCG CGGTATCATT GCAGCACTGG GGCCAGATGG TAAGCCCTCC CGTATCGTAG
TTATCTACAC GACGGGGAGT CAGGCAACTA TGGATGAACG AAATAGACAG ATCGCTGAGA
TAGGTGCCTC ACTGATTAAG CATTGGTAAC TGTCAGACCA AGTTTACTCA TATATACTTT
AGATTGATTT AAAACTTCAT TTTTAATTTA AAAGGATCTA GGTGAAGATC CTTTTTGATA
ATCTCATGAC CAAAATCCCT TAACGTGAGT TTTCGTTCCA CTGAGCGTCA GACCCCGTAG
AAAAGATCAA AGGATCTTCT TGAGATCCTT TTTTTCTGCG CGTAATCTGC TGCTTGCAAA
CAAAAAAACC ACCGCTACCA GCGGTGGTTT GTTTGCCGGA TCAAGAGCTA CCAACTCTTT
TTCCGAAGGT AACTGGCTTC AGCAGAGCGC AGATACCAAA TACTGTCCTT CTAGTGTAGC
CGTAGTTAGG CCACCACTTC AAGAACTCTG TAGCACCGCC TACATACCTC GCTCTGCTAA
TCCTGTTACC AGTGGCTGCT GCCAGTGGCG ATAAGTCGTG TCTTACCGGG TTGGACTCAA
GACGATAGTT ACCGGATAAG GCGCAGCGGT CGGGCTGAAC GGGGGGTTCG TGCACACAGC
CCAGCTTGGA GCGAACGACC TACACCGAAC TGAGATACCT ACAGCGTGAG CTATGAGAAA
GCGCCACGCT TCCCGAAGGG AGAAAGGCGG ACAGGTATCC GGTAAGCGGC AGGGTCGGAA
CAGGAGAGCG CACGAGGGAG CTTCCAGGGG GAAACGCCTG GTATCTTTAT AGTCCTGTCG
GGTTTCGCCA CCTCTGACTT GAGCGTCGAT TTTTGTGATG CTCGTCAGGG GGGCGGAGCC
TATGGAAAAA CGCCAGCAAC GCGGCCTTTT TACGGTTCCT GGCCTTTTGC TGGCCTTTTG
CTCACATGTT CTTTCCTGCG TTATCCCCTG ATTCTGTGGA TAACCGTATT ACCGCCTTTG
AGTGAGCTGA TACCGCTCGC CGCAGCCGAA CGACCGAGCG CAGCGAGTCA GTGAGCGAGG
AAGCGGAAGA GCGCCCAATA CGCAAACCGC CTCTCCCCGC GCGTTGGCCG ATTCATTAAT
GCAGCTGGCA CGACAGGTTT CCCGACTGGA AAGCGGGCAG TGAGCGCAAC GCAATTAATG
TGAGTTAGCT CACTCATTAG GCACCCCAGG CTTTACACTT TATGCTTCCG GCTCGTATGT
TGTGTGGAAT TGTGAGCGGA TAACAATTTC ACACAGGAAA CAGCTATGAC CATGATTACG
CCAAGCGCGC AATTAACCCT CACTAAAGGG AACAAAAGCT GGAGCTCCAC CGCGGTGGCG
GCCGCTCTAG AACTAGTGGA TCCCCCGGGC TGCAGGAATT CGAGGAGAAA TTAACCATGT
ATATCGGGAT AGATCTTGGC ACCTCGGGCG TAAAAGTTAT TTTGCTCAAC GAGCAGGGTG
AGGTGGTTGC TGCGCAAACG GAAAAGCTGA CCGTTCGCGC CCGCATCCA CTCTGGTCGG
AACAAGACCC GGAACAGTGG TGGCAGGCAA CTGATCGCGC AATGAAAGCT CTGGGCGATC
AGCATTCTCT GCAGGACGTT AAAGCATTGG GTATTGCCGG CCAGATGCAC GGAGCAACCT
TGCTGGATGC TCAGCAACGG GTGTTACGCC CTGCCATTTT GTGGAACGAC GGGCGCTGTG
CGCAAGAGTG CACTTTGCTG GAAGCGCGAG TTCCGCAATC GCGGGTGATT ACCGGCAACC
TGATGATGCC CGGATTTACT GCGCCTAAAT GCTATGGGT TCAGCGGCAT GAGCCGGAGA
TATTCCGTCA AATCGACAAA GTATTATTAC CGAAAGATTA CTTGCGTCTG CGTATGACGG
```

FIG. 8

```
GGGAGTTTGC CAGCGATATG TCTGACGCAG CTGGCACCAT GTGGCTGGAT GTCGCAAAGC
GTGACTGGAG TGACGTCATG CTGCAGGCTT GCGACTTATC TCGTGACCAG ATGCCCGCAT
TATACGAAGG CAGCGAAATT ACTGGTGCTT TGTTACCTGA AGTTGCGAAA GCGTGGGGTA
TGGCGACGGT GCCAGTTGTC GCAGGCGGTG GCGACAATGC AGCTGGTGCA GTTGGTGTGG
GAATGGTTGA TGCTAATCAG GCAATGTTAT CGCTGGGGAC GTCGGGGGTC TATTTTGCTG
TCAGCGAAGG GTTCTTAAGC AAGCCAGAAA GCGCCGTACA TAGCTTTTGC CATGCGCTAC
CGCAACGTTG GCATTTAATG TCTGTGATGC TGAGTGCAGC GTCGTGTCTG GATTGGGCCG
CGAAATTAAC CGGCCTGAGC AATGTCCCAG CTTTAATCGC TGCAGCTCAA CAGGCTGATG
AAAGTGCCGA GCCAGTTTGG TTTCTGCCTT ATCTTTCCGG CGAGCGTACG CCACACAATA
ATCCCCAGGC GAAGGGGGTT TTCTTTGGTT TGACTCATCA ACATGGCCCC AATGAACTGG
CGCGAGCAGT GCTGGAAGGC GTGGGTTATG CGCTGGCAGA TGGCATGGAT GTCGTGCATG
CCTGCGGTAT TAAACCGCAA AGTGTTACGT TGATTGGGGG CGGGGCGCGT AGTGAGTACT
GGCGTCAGAT GCTGGCGGAT ATCAGCGGTC AGCAGCTCGA TTACCGTACG GGGGGGGATG
TGGGGCCAGC ACTGGGCGCA GCAAGGCTGG CGCAGATCGC GGCGAATCCA GAGAAATCGC
TCATTGAATT GTTGCCGCAA CTACCGTTAG AACAGTCGCA TCTACCAGAT GCGCAGCGTT
ATGCCGCTTA TCAGCCACGA CGAGAAACGT TCCGTCGCCT CTATCAGCAA CTTCTGCCAT
TAATGGCGTA AAAGCTTGAG GAGAAATTAA CCATGAAGCA ACTCACCATT CTGGGCTCGA
CCGGCTCGAT TGGTTGCAGC ACGCTGGACG TGGTGCGCCA TAATCCCGAA CACTTCCGCG
TAGTTGCGCT GGTGGCAGGC AAAAATGTCA CTCGCATGGT AGAACAGTGC CTGGAATTCT
CTCCCCGCTA TGCCGTAATG GACGATGAAG CGAGTGCGAA ACTTCTTAAA ACGATGCTAC
AGCAACAGGG TAGCCGCACC GAAGTCTTAA GTGGGCAACA AGCCGCTTGC GATATGGCAG
CGCTTGAGGA TGTTGATCAG GTGATGGCAG CCATTGTTGG CGCTGCTGGG CTGTTACCTA
CGCTTGCTGC GATCCGCGCG GGTAAAACCA TTTTGCTGGC CAATAAAGAA TCACTGGTTA
CCTGCGGACG TCTGTTTATG GACGCCGTAA AGCAGAGCAA AGCGCAATTG TTACCGGTCG
ATAGCGAACA TAACGCCATT TTTCAGAGTT TACCGCAACC TATCCAGCAT AATCTGGGAT
ACGCTGACCT TGAGCAAAAT GGCGTGGTGT CCATTTTACT TACCGGGTCT GGTGGCCCTT
TCCGTGAGAC GCCATTGCGC GATTTGGCAA CAATGACGCC GGATCAAGCC TGCCGTCATC
CGAACTGGTC GATGGGGCGT AAAATTTCTG TCGATTCGGC TACCATGATG AACAAAGGTC
TGGAATACAT TGAAGCGCGT TGGCTGTTTA ACGCCAGCGC CAGCCAGATG GAAGTGCTGA
TTCACCCGCA GTCAGTGATT CACTCAATGG TGCGCTATCA GGACGGCAGT GTTCTGGCGC
AGCTGGGGGA ACCGGATATG CGTACGCCAA TTGCCCACAC CATGGCATGG CCGAATCGCG
TGAACTCTGG CGTGAAGCCG CTCGATTTTT GCAAACTAAG TGCGTTGACA TTTGCCGCAC
CGGATTATGA TCGTTATCCA TGCCTGAAAC TGGCGATGGA GGCGTTCGAA CAAGGCCAGG
CAGCGACGAC AGCATTGAAT GCCGCAAACG AAATCACCGT TGCTGCTTTT CTTGCGCAAC
AAATCCGCTT TACGGATATC GCTGCGTTGA ATTTATCCGT ACTGGAAAAA ATGGATATGC
GCGAACCACA ATGTGTGGAC GATGTGTTAT CTGTTGATGC GAACGCGCGT GAAGTCGCCA
GAAAAGAGGT GATGCGTCTC GCAAGCTGAG TCGACCTCGA GGGGGGGCCC GGTACCCAAT
TCGCCCTATA GTGAGTCGTA TTACGCGCGC TCACTGGCCG TCGTTTTACA ACGTCGTGAC
TGGGAAAACC CTGGCGTTAC CCAACTTAAT CGCCTTGCAG CACATCCCCC TTTCGCCAGC
TGGCGTAATA GCGAAGAGGC CCGCACCGAT CGCCCTTCCC AACAGTTGCG CAGCCTGAAT
GGCGAATGGA AATTGTAAGC GTTAATATTT TGTTAAAATT CGCGTTAAAT TTTTGTTAAA
TCAGCTCATT TTTTAACCAA TAGGCCGAAA TCGGCAAAAT CCCTTATAAA TCAAAAGAAT
AGACCGAGAT AGGGTTGAGT GTTGTTCCAG TTTGGAACAA GAGTCCACTA TTAAAGAACG
TGGACTCCAA CGTCAAAGGG CGAAAACCG TCTATCAGGG CGATGGCCCA CTACGTGAAC
CATCACCCTA ATCAAGTTTT TTGGGGTCGA GGTGCCGTAA AGCACTAAAT CGGAACCCTA
AAGGGAGCCC CCGATTTAGA GCTTGACGGG GAAAGCCGGC GAACGTGGCG AGAAAGGAAG
GGAAGAAAGC GAAAGGAGCG GCGCTAGGG CGCTGGCAAG TGTAGCGGTC ACGCTGCGCG
TAACCACCAC ACCCGCCGCG CTTAATGCGC CGCTACAGGG CGCGTCAG
```

*FIG. 8 (CONT'D.)*

DNA sequence of the vector construct pBSxylBdxrispD

```
ID   PBSXYLBDXRISPD     PRELIMINARY;   DNA;   6354 BP.
SQ   SEQUENCE   6354 BP;   1539 A;   1573 C;   1753 G;   1489 T;
     GTGGCACTTT TCGGGGAAAT GTGCGCGGAA CCCCTATTTG TTTATTTTTC TAAATACATT
     CAAATATGTA TCCGCTCATG AGACAATAAC CCTGATAAAT GCTTCAATAA TATTGAAAAA
     GGAAGAGTAT GAGTATTCAA CATTTCCGTG TCGCCCTTAT TCCCTTTTTT GCGGCATTTT
     GCCTTCCTGT TTTTGCTCAC CCAGAAACGC TGGTGAAAGT AAAAGATGCT GAAGATCAGT
     TGGGTGCACG AGTGGGTTAC ATCGAACTGG ATCTCAACAG CGGTAAGATC CTTGAGAGTT
     TTCGCCCCGA AGAACGTTTT CCAATGATGA GCACTTTTAA AGTTCTGCTA TGTGGCGCGG
     TATTATCCCG TATTGACGCC GGGCAAGAGC AACTCGGTCG CCGCATACAC TATTCTCAGA
     ATGACTTGGT TGAGTACTCA CCAGTCACAG AAAAGCATCT TACGGATGGC ATGACAGTAA
     GAGAATTATG CAGTGCTGCC ATAACCATGA GTGATAACAC TGCGGCCAAC TTACTTCTGA
     CAACGATCGG AGGACCGAAG GAGCTAACCG CTTTTTTGCA CAACATGGGG GATCATGTAA
     CTCGCCTTGA TCGTTGGGAA CCGGAGCTGA ATGAAGCCAT ACCAAACGAC GAGCGTGACA
     CCACGATGCC TGTAGCAATG GCAACAACGT TGCGCAAACT ATTAACTGGC GAACTACTTA
     CTCTAGCTTC CCGGCAACAA TTAATAGACT GGATGGAGGC GGATAAAGTT GCAGGACCAC
     TTCTGCGCTC GGCCCTTCCG GCTGGCTGGT TTATTGCTGA TAAATCTGGA GCCGGTGAGC
     GTGGGTCTCG CGGTATCATT GCAGCACTGG GGCCAGATGG TAAGCCCTCC CGTATCGTAG
     TTATCTACAC GACGGGGAGT CAGGCAACTA TGGATGAACG AAATAGACAG ATCGCTGAGA
     TAGGTGCCTC ACTGATTAAG CATTGGTAAC TGTCAGACCA AGTTTACTCA TATATACTTT
     AGATTGATTT AAAACTTCAT TTTTAATTTA AAAGGATCTA GGTGAAGATC CTTTTTGATA
     ATCTCATGAC CAAAATCCCT TAACGTGAGT TTTCGTTCCA CTGAGCGTCA GACCCCGTAG
     AAAAGATCAA AGGATCTTCT TGAGATCCTT TTTTTCTGCG CGTAATCTGC TGCTTGCAAA
     CAAAAAAACC ACCGCTACCA GCGGTGGTTT GTTTGCCGGA TCAAGAGCTA CCAACTCTTT
     TTCCGAAGGT AACTGGCTTC AGCAGAGCGC AGATACCAAA TACTGTCCTT CTAGTGTAGC
     CGTAGTTAGG CCACCACTTC AAGAACTCTG TAGCACCGCC TACATACCTC GCTCTGCTAA
     TCCTGTTACC AGTGGCTGCT GCCAGTGGCG ATAAGTCGTG TCTTACCGGG TTGGACTCAA
     GACGATAGTT ACCGGATAAG GCGCAGCGGT CGGGCTGAAC GGGGGGTTCG TGCACACAGC
     CCAGCTTGGA GCGAACGACC TACACCGAAC TGAGATACCT ACAGCGTGAG CTATGAGAAA
     GCGCCACGCT TCCCGAAGGG AGAAAGGCGG ACAGGTATCC GGTAAGCGGC AGGGTCGGAA
     CAGGAGAGCG CACGAGGGAG CTTCCAGGGG GAAACGCCTG GTATCTTTAT AGTCCTGTCG
     GGTTTCGCCA CCTCTGACTT GAGCGTCGAT TTTTGTGATG CTCGTCAGGG GGGCGGAGCC
     TATGGAAAAA CGCCAGCAAC GCGGCCTTTT TACGGTTCCT GGCCTTTTGC TGGCCTTTTG
     CTCACATGTT CTTTCCTGCG TTATCCCCTG ATTCTGTGGA TAACCGTATT ACCGCCTTTG
     AGTGAGCTGA TACCGCTCGC CGCAGCCGAA CGACCGAGCG CAGCGAGTCA GTGAGCGAGG
     AAGCGGAAGA GCGCCCAATA CGCAAACCGC CTCTCCCCGC GCGTTGGCCG ATTCATTAAT
     GCAGCTGGCA CGACAGGTTT CCCGACTGGA AAGCGGGCAG TGAGCGCAAC GCAATTAATG
     TGAGTTAGCT CACTCATTAG GCACCCCAGG CTTTACACTT TATGCTTCCG GCTCGTATGT
     TGTGTGGAAT TGTGAGCGGA TAACAATTTC ACACAGGAAA CAGCTATGAC CATGATTACG
     CCAAGCGCGC AATTAACCCT CACTAAAGGG AACAAAAGCT GGAGCTCCAC CGCGGTGGCG
     GCCGCTCTAG AACTAGTGGA TCCCCCGGGC TGCAGGAATT CGAGGAGAAA TTAACCATGT
     ATATCGGGAT AGATCTTGGC ACCTCGGGCG TAAAAGTTAT TTTGCTCAAC GAGCAGGGTG
     AGGTGGTTGC TGCGCAAACG GAAAAGCTGA CCGTTTCGCG CCCGCATCCA CTCTGGTCGG
     AACAAGACCC GGAACAGTGG TGGCAGGCAA CTGATCGCGC AATGAAAGCT CTGGGCGATC
     AGCATTCTCT GCAGGACGTT AAAGCATTGG GTATTGCCGG CCAGATGCAC GGAGCAACCT
     TGCTGGATGC TCAGCAACGG GTGTTACGCC CTGCCATTTT GTGGAACGAC GGGCGCTGTG
     CGCAAGAGTG CACTTTGCTG GAAGCGCGAG TTCCGCAATC GCGGGTGATT ACCGGCAACC
     TGATGATGCC CGGATTTACT GCGCCTAAAT TGCTATGGGT TCAGCGGCAT GAGCCGGAGA
     TATTCCGTCA AATCGACAAA GTATTATTAC CGAAAGATTA CTTGCGTCTG CGTATGACGG
```

FIG. 9

```
GGGAGTTTGC CAGCGATATG TCTGACGCAG CTGGCACCAT GTGGCTGGAT GTCGCAAAGC
GTGACTGGAG TGACGTCATG CTGCAGGCTT GCGACTTATC TCGTGACCAG ATGCCCGCAT
TATACGAAGG CAGCGAAATT ACTGGTGCTT TGTTACCTGA AGTTGCGAAA GCGTGGGGTA
TGGCGACGGT GCCAGTTGTC GCAGGCGGTG GCGACAATGC AGCTGGTGCA GTTGGTGTGG
GAATGGTTGA TGCTAATCAG GCAATGTTAT CGCTGGGGAC GTCGGGGGTC TATTTTGCTG
TCAGCGAAGG GTTCTTAAGC AAGCCAGAAA GCGCCGTACA TAGCTTTTGC CATGCGCTAC
CGCAACGTTG GCATTTAATG TCTGTGATGC TGAGTGCAGC GTCGTGTCTG GATTGGGCCG
CGAAATTAAC CGGCCTGAGC AATGTCCCAG CTTTAATCGC TGCAGCTCAA CAGGCTGATG
AAAGTGCCGA GCCAGTTTGG TTTCTGCCTT ATCTTTCCGG CGAGCGTACG CCACACAATA
ATCCCCAGGC GAAGGGGGTT TTCTTTGGTT TGACTCATCA ACATGGCCCC AATGAACTGG
CGCGAGCAGT GCTGGAAGGC GTGGGTTATG CGCTGGCAGA TGGCATGGAT GTCGTGCATG
CCTGCGGTAT TAAACCGCAA AGTGTTACGT TGATTGGGGG CGGGGCGCGT AGTGAGTACT
GGCGTCAGAT GCTGGCGGAT ATCAGCGGTC AGCAGCTCGA TTACCGTACG GGGGGGGATG
TGGGGCCAGC ACTGGGCGCA GCAAGGCTGG CGCAGATCGC GGCGAATCCA GAGAAATCGC
TCATTGAATT GTTGCCGCAA CTACCGTTAG AACAGTCGCA TCTACCAGAT GCGCAGCGTT
ATGCCGCTTA TCAGCCACGA CGAGAAACGT TCCGTCGCCT CTATCAGCAA CTTCTGCCAT
TAATGGCGTA AAAGCTTGAG GAGAAATTAA CCATGAAGCA ACTCACCATT CTGGGCTCGA
CCGGCTCGAT TGGTTGCAGC ACGCTGGACG TGGTGCGCCA TAATCCCGAA CACTTCCGCG
TAGTTGCGCT GGTGGCAGGC AAAAATGTCA CTCGCATGGT AGAACAGTGC CTGGAATTCT
CTCCCCGCTA TGCCGTAATG GACGATGAAG CGAGTGCGAA ACTTCTTAAA ACGATGCTAC
AGCAACAGGG TAGCCGCACC GAAGTCTTAA GTGGGCAACA AGCCGCTTGC GATATGGCAG
CGCTTGAGGA TGTTGATCAG GTGATGGCAG CCATTGTTGG CGCTGCTGGG CTGTTACCTA
CGCTTGCTGC GATCCGCGCG GGTAAAACCA TTTTGCTGGC CAATAAAGAA TCACTGGTTA
CCTGCGGACG TCTGTTTATG GACGCCGTAA AGCAGAGCAA AGCGCAATTG TTACCGGTCG
ATAGCGAACA TAACGCCATT TTTCAGAGTT TACCGCAACC TATCCAGCAT AATCTGGGAT
ACGCTGACCT TGAGCAAAAT GGCGTGGTGT CCATTTTACT TACCGGGTCT GGTGGCCCTT
TCCGTGAGAC GCCATTGCGC GATTTGGCAA CAATGACGCC GGATCAAGCC TGCCGTCATC
CGAACTGGTC GATGGGGCGT AAAATTTCTG TCGATTCGGC TACCATGATG AACAAAGGTC
TGGAATACAT TGAAGCGCGT TGGCTGTTTA ACGCCAGCGC CAGCCAGATG GAAGTGCTGA
TTCACCCGCA GTCAGTGATT CACTCAATGG TGCGCTATCA GGACGGCAGT GTTCTGGCGC
AGCTGGGGGA ACCGGATATG CGTACGCCAA TTGCCCACAC CATGGCATGG CCGAATCGCG
TGAACTCTGG CGTGAAGCCG CTCGATTTTT GCAAACTAAG TGCGTTGACA TTTGCCGCAC
CGGATTATGA TCGTTATCCA TGCCTGAAAC TGGCGATGGA GGCGTTCGAA CAAGGCCAGG
CAGCGACGAC AGCATTGAAT GCCGCAAACG AAATCACCGT TGCTGCTTTT CTTGCGCAAC
AAATCCGCTT TACGGATATC GCTGCGTTGA ATTTATCCGT ACTGGAAAAA ATGGATATGC
GCGAACCACA ATGTGTGGAC GATGTGTTAT CTGTTGATGC GAACGCGCGT GAAGTCGCCA
GAAAAGAGGT GATGCGTCTC GCAAGCTGAG TCGACGAGGA GAAATTAACC ATGGCAACCA
CTCATTTGGA TGTTTGCGCC GTGGTTCCGG CGGCCGGATT TGGCCGTCGA ATGCAAACGG
AATGTCCTAA GCAATATCTC TCAATCGGTA ATCAAACCAT TCTTGAACAC TCGGTGCATG
CGCTGCTGGC GCATCCCCGG GTGAAACGTG TCGTCATTGC CATAAGTCCT GGCGATAGCC
GTTTTGCACA ACTTCCTCTG GCGAATCATC CGCAAATCAC CGTTGTAGAT GGCGGTGATG
AGCGTGCCGA TTCCGTGCTG GCAGGTCTGA AAGCCGCTGG CGACGCGCAG TGGGTATTGG
TGCATGACGC CGCTCGTCCT TGTTTGCATC AGGATGACCT CGCGCGATTG TTGGCGTTGA
GCGAAACCAG CCGCACGGGG GGGATCCTCG CCGCACCAGT GCGCGATACT ATGAAACGTG
CCGAACCGGG CAAAAATGCC ATTGCTCATA CCGTTGATCG CAACGGCTTA TGGCACGCGC
TGACGCCGCA ATTTTTCCCT CGTGAGCTGT TACATGACTG TCTGACGCGC GCTCTAAATG
AAGGCGCGAC TATTACCGAC GAAGCCTCGG CGCTGGAATA TTGCGGATTC CATCCTCAGT
TGGTCGAAGG CCGTGCGGAT AACATTAAAG TCACGCGCCC GGAAGATTTG GCACTGGCCG
AGTTTTACCT CACCCGAACC ATCCATCAGG AGAATACATA ACTCGAGGGG GGGCCCGGTA
CCCAATTCGC CCTATAGTGA GTCGTATTAC GCGCGCTCAC TGGCCGTCGT TTTACAACGT
CGTGACTGGG AAAACCCTGG CGTTACCCAA CTTAATCGCC TTGCAGCACA TCCCCCTTTC
GCCAGCTGGC GTAATAGCGA AGAGGCCCGC ACCGATCGCC CTTCCCAACA GTTGCGCAGC
```

*FIG. 9 (CONT'D.)*

```
CTGAATGGCG AATGGAAATT GTAAGCGTTA ATATTTTGTT AAAATTCGCG TTAAATTTTT
GTTAAATCAG CTCATTTTTT AACCAATAGG CCGAAATCGG CAAAATCCCT TATAAATCAA
AAGAATAGAC CGAGATAGGG TTGAGTGTTG TTCCAGTTTG AACAAGAGT CCACTATTAA
AGAACGTGGA CTCCAACGTC AAAGGGCGAA AAACCGTCTA TCAGGGCGAT GGCCCACTAC
GTGAACCATC ACCCTAATCA AGTTTTTTGG GGTCGAGGTG CCGTAAAGCA CTAAATCGGA
ACCCTAAAGG GAGCCCCCGA TTTAGAGCTT GACGGGGAAA GCCGGCGAAC GTGGCGAGAA
AGGAAGGGAA GAAAGCGAAA GGAGCGGGCG CTAGGGCGCT GGCAAGTGTA GCGGTCACGC
TGCGCGTAAC CACCACACCC GCCGCGCTTA ATGCCCGCT ACAGGGCGCG TCAG
```

FIG. 9 (CONT'D.)

DNA sequence of the vector construct pBScyclo

```
ID    PBSCYCLO        PRELIMINARY;   DNA;    7691 BP.
SQ    SEQUENCE       7691 BP;   1844 A;   1888 C;   2148 G;   1811 T;
      GTGGCACTTT  TCGGGGAAAT  GTGCGCGGAA  CCCCTATTTG  TTTATTTTTC  TAAATACATT
      CAAATATGTA  TCCGCTCATG  AGACAATAAC  CCTGATAAAT  GCTTCAATAA  TATTGAAAAA
      GGAAGAGTAT  GAGTATTCAA  CATTTCCGTG  TCGCCCTTAT  TCCCTTTTTT  GCGGCATTTT
      GCCTTCCTGT  TTTTGCTCAC  CCAGAAACGC  TGGTGAAAGT  AAAAGATGCT  GAAGATCAGT
      TGGGTGCACG  AGTGGGTTAC  ATCGAACTGG  ATCTCAACAG  CGGTAAGATC  CTTGAGAGTT
      TTCGCCCCGA  AGAACGTTTT  CCAATGATGA  GCACTTTTAA  AGTTCTGCTA  TGTGGCGCGG
      TATTATCCCG  TATTGACGCC  GGGCAAGAGC  AACTCGGTCG  CCGCATACAC  TATTCTCAGA
      ATGACTTGGT  TGAGTACTCA  CCAGTCACAG  AAAAGCATCT  TACGGATGGC  ATGACAGTAA
      GAGAATTATG  CAGTGCTGCC  ATAACCATGA  GTGATAACAC  TGCGGCCAAC  TTACTTCTGA
      CAACGATCGG  AGGACCGAAG  GAGCTAACCG  CTTTTTTGCA  CAACATGGGG  GATCATGTAA
      CTCGCCTTGA  TCGTTGGGAA  CCGGAGCTGA  ATGAAGCCAT  ACCAAACGAC  GAGCGTGACA
      CCACGATGCC  TGTAGCAATG  GCAACAACGT  TGCGCAAACT  ATTAACTGGC  GAACTACTTA
      CTCTAGCTTC  CCGGCAACAA  TTAATAGACT  GGATGGAGGC  GGATAAAGTT  GCAGGACCAC
      TTCTGCGCTC  GGCCCTTCCG  GCTGGCTGGT  TTATTGCTGA  TAAATCTGGA  GCCGGTGAGC
      GTGGGTCTCG  CGGTATCATT  GCAGCACTGG  GGCCAGATGG  TAAGCCCTCC  CGTATCGTAG
      TTATCTACAC  GACGGGGAGT  CAGGCAACTA  TGGATGAACG  AAATAGACAG  ATCGCTGAGA
      TAGGTGCCTC  ACTGATTAAG  CATTGGTAAC  TGTCAGACCA  AGTTTACTCA  TATATACTTT
      AGATTGATTT  AAAACTTCAT  TTTTAATTTA  AAAGGATCTA  GGTGAAGATC  CTTTTTGATA
      ATCTCATGAC  CAAAATCCCT  TAACGTGAGT  TTTCGTTCCA  CTGAGCGTCA  GACCCCGTAG
      AAAAGATCAA  AGGATCTTCT  TGAGATCCTT  TTTTTCTGCG  CGTAATCTGC  TGCTTGCAAA
      CAAAAAAACC  ACCGCTACCA  GCGGTGGTTT  GTTTGCCGGA  TCAAGAGCTA  CCAACTCTTT
      TTCCGAAGGT  AACTGGCTTC  AGCAGAGCGC  AGATACCAAA  TACTGTCCTT  CTAGTGTAGC
      CGTAGTTAGG  CCACCACTTC  AAGAACTCTG  TAGCACCGCC  TACATACCTC  GCTCTGCTAA
      TCCTGTTACC  AGTGGCTGCT  GCCAGTGGCG  ATAAGTCGTG  TCTTACCGGG  TTGGACTCAA
      GACGATAGTT  ACCGGATAAG  GCGCAGCGGT  CGGGCTGAAC  GGGGGGTTCG  TGCACACAGC
      CCAGCTTGGA  GCGAACGACC  TACACCGAAC  TGAGATACCT  ACAGCGTGAG  CTATGAGAAA
      GCGCCACGCT  TCCCGAAGGG  AGAAAGGCGG  ACAGGTATCC  GGTAAGCGGC  AGGGTCGGAA
      CAGGAGAGCG  CACGAGGGAG  CTTCCAGGGG  GAAACGCCTG  GTATCTTTAT  AGTCCTGTCG
      GGTTTCGCCA  CCTCTGACTT  GAGCGTCGAT  TTTTGTGATG  CTCGTCAGGG  GGGCGGAGCC
      TATGGAAAAA  CGCCAGCAAC  GCGGCCTTTT  TACGGTTCCT  GGCCTTTTGC  TGGCCTTTTG
      CTCACATGTT  CTTTCCTGCG  TTATCCCCTG  ATTCTGTGGA  TAACCGTATT  ACCGCCTTTG
      AGTGAGCTGA  TACCGCTCGC  CGCAGCCGAA  CGACCGAGCG  CAGCGAGTCA  GTGAGCGAGG
      AAGCGGAAGA  GCGCCCAATA  CGCAAACCGC  CTCTCCCCGC  GCGTTGGCCG  ATTCATTAAT
      GCAGCTGGCA  CGACAGGTTT  CCCGACTGGA  AAGCGGGCAG  TGAGCGCAAC  GCAATTAATG
      TGAGTTAGCT  CACTCATTAG  GCACCCCAGG  CTTTACACTT  TATGCTTCCG  GCTCGTATGT
      TGTGTGGAAT  TGTGAGCGGA  TAACAATTTC ACACAGGAAA  CAGCTATGAC  CATGATTACG
      CCAAGCGCGC  AATTAACCCT  CACTAAAGGG  AACAAAAGCT  GGAGCTCCAC  CGCGGTGGCG
      GCCGCTCTAG  AACTAGTGGA  TCCCCCGGGC  TGCAGGAATT  CGAGGAGAAA  TTAACCATGT
      ATATCGGGAT  AGATCTTGGC  ACCTCGGGCG  TAAAAGTTAT  TTTGCTCAAC  GAGCAGGGTG
      AGGTGGTTGC  TGCGCAAACG  GAAAAGCTGA  CCGTTTCGCG  CCCGCATCCA  CTCTGGTCGG
      AACAAGACCC  GGAACAGTGG  TGGCAGGCAA  CTGATCGCGC  AATGAAAGCT  CTGGGCGATC
      AGCATTCTCT  GCAGGACGTT  AAAGCATTGG  GTATTGCCGG  CCAGATGCAC  GGAGCAACCT
      TGCTGGATGC  TCAGCAACGG  GTGTTACGCC  CTGCCATTTT  GTGGAACGAC  GGGCGCTGTG
      CGCAAGAGTG  CACTTTGCTG  GAAGCGCGAG  TTCCGCAATC  GCGGGTGATT  ACCGGCAACC
      TGATGATGCC  CGGATTTACT  GCGCCTAAAT  TGCTATGGGT  TCAGCGGCAT  GAGCCGGAGA
      TATTCCGTCA  AATCGACAAA  GTATTATTAC  CGAAAGATTA  CTTGCGTCTG  CGTATGACGG
      GGGAGTTTGC  CAGCGATATG  TCTGACGCAG  CTGGCACCAT  GTGGCTGGAT  GTCGCAAAGC
```

*FIG. 10*

```
GTGACTGGAG TGACGTCATG CTGCAGGCTT GCGACTTATC TCGTGACCAG ATGCCCGCAT
TATACGAAGG CAGCGAAATT ACTGGTGCTT TGTTACCTGA AGTTGCGAAA GCGTGGGGTA
TGGCGACGGT GCCAGTTGTC GCAGGCGGTG GCGACAATGC AGCTGGTGCA GTTGGTGTGG
GAATGGTTGA TGCTAATCAG GCAATGTTAT CGCTGGGGAC GTCGGGGGTC TATTTTGCTG
TCAGCGAAGG GTTCTTAAGC AAGCCAGAAA GCGCCGTACA TAGCTTTTGC CATGCGCTAC
CGCAACGTTG GCATTTAATG TCTGTGATGC TGAGTGCAGC GTCGTGTCTG GATTGGGCCG
CGAAATTAAC CGGCCTGAGC AATGTCCCAG CTTTAATCGC TGCAGCTCAA CAGGCTGATG
AAAGTGCCGA GCCAGTTTGG TTTCTGCCTT ATCTTTCCGG CGAGCGTACG CCACACAATA
ATCCCCAGGC GAAGGGGGTT TTCTTTGGTT TGACTCATCA ACATGGCCCC AATGAACTGG
CGCGAGCAGT GCTGGAAGGC GTGGGTTATG CGCTGGCAGA TGGCATGGAT GTCGTGCATG
CCTGCGGTAT TAAACCGCAA AGTGTTACGT TGATTGGGGG CGGGGCGCGT AGTGAGTACT
GGCGTCAGAT GCTGGCGGAT ATCAGCGGTC AGCAGCTCGA TTACCGTACG GGGGGGGATG
TGGGCCAGC ACTGGGCGCA GCAAGGCTGG CGCAGATCGC GGCGAATCCA GAGAAATCGC
TCATTGAATT GTTGCCGCAA CTACCGTTAG AACAGTCGCA TCTACCAGAT GCGCAGCGTT
ATGCCGCTTA TCAGCCACGA CGAGAAACGT TCCGTCGCCT CTATCAGCAA CTTCTGCCAT
TAATGGCGTA AAAGCTTGAG GAGAAATTAA CCATGAAGCA ACTCACCATT CTGGGCTCGA
CCGGCTCGAT TGGTTGCAGC ACGCTGGACG TGGTGCGCCA TAATCCCGAA CACTTCCGCG
TAGTTGCGCT GGTGGCAGGC AAAAATGTCA CTCGCATGGT AGAACAGTGC CTGGAATTCT
CTCCCCGCTA TGCCGTAATG GACGATGAAG CGAGTGCGAA ACTTCTTAAA ACGATGCTAC
AGCAACAGGG TAGCCGCACC GAAGTCTTAA GTGGGCAACA AGCCGCTTGC GATATGGCAG
CGCTTGAGGA TGTTGATCAG GTGATGGCAG CCATTGTTGG CGCTGCTGGG CTGTTACCTA
CGCTTGCTGC GATCCGCGCG GGTAAAACCA TTTTGCTGGC CAATAAAGAA TCACTGGTTA
CCTGCGGACG TCTGTTTATG GACGCCGTAA AGCAGAGCAA AGCGCAATTG TTACCGGTCG
ATAGCGAACA TAACGCCATT TTTCAGAGTT TACCGCAACC TATCCAGCAT AATCTGGGAT
ACGCTGACCT TGAGCAAAAT GGCGTGGTGT CCATTTTACT TACCGGGTCT GGTGGCCCTT
TCCGTGAGAC GCCATTGCGC GATTTGGCAA CAATGACGCC GGATCAAGCC TGCCGTCATC
CGAACTGGTC GATGGGGCGT AAAATTTCTG TCGATTCGGC TACCATGATG AACAAAGGTC
TGGAATACAT TGAAGCGCGT TGGCTGTTTA ACGCCAGCGC CAGCCAGATG GAAGTGCTGA
TTCACCCGCA GTCAGTGATT CACTCAATGG TGCGCTATCA GGACGGCAGT GTTCTGGCGC
AGCTGGGGGA ACCGGATATG CGTACGCCAA TTGCCCACAC CATGGCATGG CCGAATCGCG
TGAACTCTGG CGTGAAGCCG CTCGATTTTT GCAAACTAAG TGCGTTGACA TTTGCCGCAC
CGGATTATGA TCGTTATCCA TGCCTGAAAC TGGCGATGGA GGCGTTCGAA CAAGGCCAGG
CAGCGACGAC AGCATTGAAT GCCGCAAACG AAATCACCGT TGCTGCTTTT CTTGCGCAAC
AAATCCGCTT TACGGATATC GCTGCGTTGA ATTTATCCGT ACTGGAAAAA ATGGATATGC
GCGAACCACA ATGTGTGGAC GATGTGTTAT CTGTTGATGC GAACGCGCGT GAAGTCGCCA
GAAAAGAGGT GATGCGTCTC GCAAGCTGAG TCGACGAGGA GAAATTAACC ATGGCAACCA
CTCATTTGGA TGTTTGCGCC GTGGTTCCGG CGGCCGGATT TGGCCGTCGA ATGCAAACGG
AATGTCCTAA GCAATATCTC TCAATCGGTA ATCAAACCAT TCTTGAACAC TCGGTGCATG
CGCTGCTGGC GCATCCCCGG GTGAAACGTG TCGTCATTGC CATAAGTCCT GGCGATAGCC
GTTTTGCACA ACTTCCTCTG GCGAATCATC CGCAAATCAC CGTTGTAGAT GGCGGTGATG
AGCGTGCCGA TTCCGTGCTG GCAGGTCTGA AAGCCGCTGG CGACGCGCAG TGGGTATTGG
TGCATGACGC CGCTCGTCCT TGTTTGCATC AGGATGACCT CGCGCGATTG TTGGCGTTGA
GCGAAACCAG CCGCACGGGG GGATCCTCG CCGCACCAGT GCGCGATACT ATGAAACGTG
CCGAACCGGG CAAAAATGCC ATTGCTCATA CCGTTGATCG CAACGGCTTA TGGCACGCGC
TGACGCCGCA ATTTTTCCCT CGTGAGCTGT TACATGACTG TCTGACGCGC GCTCTAAATG
AAGGCGCGAC TATTACCGAC GAAGCCTCGG CGCTGGAATA TTGCGGATTC CATCCTCAGT
TGGTCGAAGG CCGTGCGGAT AACATTAAAG TCACGCGCCC GGAAGATTTG GCACTGGCCG
AGTTTTACCT CACCCGAACC ATCCATCAGG AGAATACATA ATGCGAATTG ACACGGTTT
TGACGTACAT GCCTTTGGCG GTGAAGGCCC AATTATCATT GGTGGCGTAC GCATTCCTTA
CGAAAAAGGA TTGCTGGCGC ATTCTGATGG CGACGTGGCG CTCCATGCGT TGACCGATGC
ATTGCTTGGC GCGGCGGCGC TGGGGGATAT CGGCAAGCTG TTCCCGGATA CCGATCCGGC
ATTTAAAGGT GCCGATAGCC GCGAGCTGCT ACGCGAAGCC TGGCGTCGTA TTCAGGCGAA
```

FIG. 10 (CONT'D.)

```
GGGTTATACC CTTGGCAACG TCGATGTCAC TATCATCGCT CAGGCACCGA AGATGTTGCC
GCACATTCCA CAAATGCGCG TGTTTATTGC CGAAGATCTC GGCTGCCATA TGGATGATGT
TAACGTGAAA GCCACTACTA CGGAAAAACT GGGATTTACC GGACGTGGGG AAGGGATTGC
CTGTGAAGCG GTGGCGCTAC TCATTAAGGC AACAAAATGA CTCGAGGAGG AGAAATTAAC
CATGCGGACA CAGTGGCCCT CTCCGGCAAA ACTTAATCTG TTTTTATACA TTACCGGTCA
GCGTGCGGAT GGTTACCACA CGCTGCAAAC GCTGTTTCAG TTTCTTGATT ACGGCGACAC
CATCAGCATT GAGCTTCGTG ACGATGGGGA TATTCGTCTG TTAACGCCCG TTGAAGGCGT
GGAACATGAA GATAACCTGA TCGTTCGCGC AGCGCGATTG TTGATGAAAA CTGCGGCAGA
CAGCGGGCGT CTTCCGACGG GAAGCGGTGC GAATATCAGC ATTGACAAGC GTTTGCCGAT
GGGCGGCGGT CTCGGCGGTG GTTCATCCAA TGCCGCGACG GTCCTGGTGG CATTAAATCA
TCTCTGGCAA TGCGGGCTAA GCATGGATGA GCTGGCGGAA ATGGGGCTGA CGCTGGGCGC
AGATGTTCCT GTCTTTGTTC GGGGGCATGC CGCGTTTGCC GAAGGCGTTG GTGAAATACT
AACGCCGGTG GATCCGCCAG AGAAGTGGTA TCTGGTGGCG CACCCTGGTG TAAGTATTCC
GACTCCGGTG ATTTTTAAAG ATCCTGAACT CCCGCGCAAT ACGCCAAAAA GGTCAATAGA
AACGTTGCTA AATGTGAAT TCAGCAATGA TTGCGAGGTT ATCGCAAGAA AACGTTTTCG
CGAGGTTGAT GCGGTGCTTT CCTGGCTGTT AGAATACGCC CCGTCGCGCC TGACTGGGAC
AGGGGCCTGT GTCTTTGCTG AATTTGATAC AGAGTCTGAA GCCCGCCAGG TGCTAGAGCA
AGCCCCGGAA TGGCTCAATG GCTTTGTGGC GAAAGGCGCT AATCTTTCCC CATTGCACAG
AGCCATGCTT TAAGGTACCC AATTCGCCCT ATAGTGAGTC GTATTACGCG CGCTCACTGG
CCGTCGTTTT ACAACGTCGT GACTGGGAAA ACCCTGGCGT TACCCAACTT AATCGCCTTG
CAGCACATCC CCCTTTCGCC AGCTGGCGTA ATAGCGAAGA GGCCCGCACC GATCGCCCTT
CCCAACAGTT GCGCAGCCTG AATGGCGAAT GGAAATTGTA AGCGTTAATA TTTTGTTAAA
ATTCGCGTTA AATTTTTGTT AAATCAGCTC ATTTTTTAAC CAATAGGCCG AAATCGGCAA
AATCCCTTAT AAATCAAAAG AATAGACCGA GATAGGGTTG AGTGTTGTTC CAGTTTGGAA
CAAGAGTCCA CTATTAAAGA ACGTGGACTC CAACGTCAAA GGGCGAAAAA CCGTCTATCA
GGGCGATGGC CCACTACGTG AACCATCACC CTAATCAAGT TTTTTGGGGT CGAGGTGCCG
TAAAGCACTA AATCGGAACC CTAAAGGGAG CCCCCGATTT AGAGCTTGAC GGGGAAAGCC
GGCGAACGTG GCGAGAAAGG AAGGGAAGAA AGCGAAAGGA GCGGGCGCTA GGGCGCTGGC
AAGTGTAGCG GTCACGCTGC GCGTAACCAC CACACCCGCC GCGCTTAATG CGCCGCTACA
GGGCGCGTCA G
```

FIG. 10 (CONT'D.)

DNA sequence of the vector construct pACYCgcpE

| ID | PACYCGCPE | PRELIMINARY; | DNA; | 5109 BP. | | |
|---|---|---|---|---|---|---|
| SQ | SEQUENCE | 5109 BP; | 1194 A; | 1365 C; | 1324 G; | 1226 T; 0 OTHER; |

```
GAATTCCGGA TGAGCATTCA TCAGGCGGGC AAGAATGTGA ATAAAGGCCG GATAAAACTT
GTGCTTATTT TTCTTTACGG TCTTTAAAAA GGCCGTAATA TCCAGCTGAA CGGTCTGGTT
ATAGGTACAT TGAGCAACTG ACTGAAATGC CTCAAAATGT TCTTTACGAT GCCATTGGGA
TATATCAACG GTGGTATATC CAGTGATTTT TTTCTCCATT TTAGCTTCCT TAGCTCCTGA
AAATCTCGAT AACTCAAAAA ATACGCCCGG TAGTGATCTT ATTTCATTAT GGTGAAAGTT
GGAACCTCTT ACGTGCCGAT CAACGTCTCA TTTTCGCCAA AAGTTGGCCC AGGGCTTCCC
GGTATCAACA GGGACACCAG GATTTATTTA TTCTGCGAAG TGATCTTCCG TCACAGGTAT
TTATTCGGCG CAAAGTGCGT CGGGTGATGC TGCCAACTTA CTGATTTAGT GTATGATGGT
GTTTTTGAGG TGCTCCAGTG GCTTCTGTTT CTATCAGCTG TCCCTCCTGT TCAGCTACTG
ACGGGGTGGT GCGTAACGGC AAAAGCACCG CCGGACATCA GCGCTAGCGG AGTGTATACT
GGCTTACTAT GTTGGCACTG ATGAGGGTGT CAGTGAAGTG CTTCATGTGG CAGGAGAAAA
AAGGCTGCAC CGGTGCGTCA GCAGAATATG TGATACAGGA TATATTCCGC TTCCTCGCTC
ACTGACTCGC TACGCTCGGT CGTTCGACTG CGGCGAGCGG AAATGGCTTA CGAACGGGGC
GGAGATTTCC TGGAAGATGC CAGGAAGATA CTTAACAGGG AAGTGAGAGG GCCGCGGCAA
AGCCGTTTTT CCATAGGCTC CGCCCCCCTG ACAAGCATCA CGAAATCTGA CGCTCAAATC
AGTGGTGGCG AAACCCGACA GGACTATAAA GATACCAGGC GTTTCCCCCT GGCGGCTCCC
TCGTGCGCTC TCCTGTTCCT GCCTTTCGGT TTACCGGTGT CATTCCGCTG TTATGGCCGC
GTTTGTCTCA TTCCACGCCT GACACTCAGT TCCGGGTAGG CAGTTCGCTC CAAGCTGGAC
TGTATGCACG AACCCCCCGT TCAGTCCGAC CGCTGCGCCT TATCCGGTAA CTATCGTCTT
GAGTCCAACC CGGAAAGACA TGCAAAAGCA CCACTGGCAG CAGCCACTGG TAATTGATTT
AGAGGAGTTA GTCTTGAAGT CATGCGCCGG TTAAGGCTAA ACTGAAAGGA CAAGTTTTGG
TGACTGCGCT CCTCCAAGCC AGTTACCTCG GTTCAAAGAG TTGGTAGCTC AGAGAACCTT
CGAAAAACCG CCCTGCAAGG CGGTTTTTTC GTTTTCAGAG CAAGAGATTA CGCGCAGACC
AAAACGATCT CAAGAAGATC ATCTTATTAA TCAGATAAAA TATTTCTAGA TTTCAGTGCA
ATTTATCTCT TCAAATGTAG CACCTGAAGT CAGCCCCATA CGATATAAGT TGTAATTCTC
ATGTTTGACA GCTTATCATC GATAAGCTTT AATGCGGTAG TTTATCACAG TTAAATTGCT
AACGCAGTCA GGCACCGTGT ATGAAATCTA ACAATGCGCT CATCGTCATC CTCGGCACCG
TCACCCTGGA TGCTGTAGGC ATAGGCTTGG TTATGCCGGT ACTGCCGGGC CTCTTGCGGG
ATATCGTCCA TTCCGACAGC ATCGCCAGTC ACTATGGCGT GCTGCTAGCG CTATATGCGT
TGATGCAATT TCTATGCGCA CCCGTTCTCG GAGCACTGTC CGACCGCTTT GGCCGCCGCC
CAGTCCTGCT CGCTTCGCTA CTTGGAGCCA CTATCGACTA CGCGATCATG GCGACCACAC
CCGTCCTGTG GATCCGAGGA GAAATTAACC ATGCATAACC AGGCTCCAAT TCAACGTAGA
AAATCAACAC GTATTTACGT TGGGAATGTG CCGATTGGCG ATGGTGCTCC CATCGCCGTA
CAGTCCATGA CCAATACGCG TACGACAGAC GTCGAAGCAA CGGTCAATCA AATCAAGGCG
CTGGAACGCG TTGGCGCTGA TATCGTCCGT GTATCCGTAC CGACGATGGA CGCGGCAGAA
GCGTTCAAAC TCATCAAACA GCAGGTTAAC GTGCCGCTGG TGCTGACAT CCACTTCGAC
TATCGCATTG CGCTGAAAGT AGCGGAATAC GGCGTCGATT GTCTGCGTAT TAACCCTGGC
AATATCGGTA ATGAAGAGCG TATTCGCATG GTGGTTGACT GTGCGCGCGA TAAAAACATT
CCGATCCGTA TTGGCGTTAA CGCCGGATCG CTGGAAAAAG ATCTGCAAGA AAAGTATGGC
GAACCGACGC CGCAGGCGTT GCTGGAATCT GCCATGCGTC ATGTTGATCA TCTCGATCGC
CTGAACTTCG ATCAGTTCAA AGTCAGCGTG AAAGCGTCTG ACGTCTTCCT CGCTGTTGAG
TCTTATCGTT TGCTGGCAAA ACAGATCGAT CAGCCGTTGC ATCTGGGGAT CACCGAAGCC
GGTGGTGCGC GCAGCGGGGC AGTAAATCC GCCATTGGTT TAGGTCTGCT GCTGTCTGAA
GGCATCGGCG ACACGCTGCG CGTATCGCTG GCGGCCGATC CGGTCGAAGA GATCAAAGTC
GGTTTCGATA TTTTGAAATC GCTGCGTATC CGTTCGCGAG GGATCAACTT CATCGCCTGC
CCGACCTGTT CGCGTCAGGA ATTTGATGTT ATCGGTACGG TTAACGCGCT GGAGCAACGC
```

FIG. 11

CTGGAAGATA TCATCACTCC GATGGACGTT TCGATTATCG GCTGCGTGGT GAATGGCCCA
GGTGAGGCGC TGGTTTCTAC ACTCGGCGTC ACCGGCGGCA ACAAGAAAAG CGGCCTCTAT
GAAGATGGCG TGCGCAAAGA CCGTCTGGAC AACAACGATA TGATCGACCA GCTGGAAGCA
CGCATTCGTG CGAAAGCCAG TCAGCTGGAC GAAGCGCGTC GAATTGACGT TCAGCAGGTT
GAAAAATAAG TCGACCGATG CCCTTGAGAG CCTTCAACCC AGTCAGCTCC TTCCGGTGGG
CGCGGGGCAT GACTATCGTC GCCGCACTTA TGACTGTCTT CTTTATCATG CAACTCGTAG
GACAGGTGCC GGCAGCGCTC TGGGTCATTT TCGGCGAGGA CCGCTTTCGC TGGAGCGCGA
CGATGATCGG CCTGTCGCTT GCGGTATTCG GAATCTTGCA CGCCCTCGCT CAAGCCTTCG
TCACTGGTCC CGCCACCAAA CGTTTCGGCG AGAAGCAGGC CATTATCGCC GGCATGGCGG
CCGACGCGCT GGGCTACGTC TTGCTGGCGT TCGCGACGCG AGGCTGGATG GCCTTCCCCA
TTATGATTCT TCTCGCTTCC GGCGGCATCG GGATGCCCGC GTTGCAGGCC ATGCTGTCCA
GGCAGGTAGA TGACGACCAT CAGGGACAGC TTCAAGGATC GCTCGCGGCT CTTACCAGCC
TAACTTCGAT CACTGGACCG CTGATCGTCA CGGCGATTTA TGCCGCCTCG GCGAGCACAT
GGAACGGGTT GGCATGGATT GTAGGCGCCG CCCTATACCT TGTCTGCCTC CCCGCGTTGC
GTCGCGGTGC ATGGAGCCGG GCCACCTCGA CCTGAATGGA AGCCGGCGGC ACCTCGCTAA
CGGATTCACC ACTCCAAGAA TTGGAGCCAA TCAATTCTTG CGGAGAACTG TGAATGCGCA
AACCAACCCT TGGCAGAACA TATCCATCGC GTCCGCCATC TCCAGCAGCC GCACGCGGCG
CATCTCGGGC AGCGTTGGGT CCTGGCCACG GGTGCGCATG ATCGTGCTCC TGTCGTTGAG
GACCCGGCTA GGCTGGCGGG GTTGCCTTAC TGGTTAGCAG AATGAATCAC CGATACGCGA
GCGAACGTGA AGCGACTGCT GCTGCAAAAC GTCTGCGACC TGAGCAACAA CATGAATGGT
CTTCGGTTTC CGTGTTTCGT AAAGTCTGGA AACGCGGAAG TCCCCTACGT GCTGCTGAAG
TTGCCCGCAA CAGAGAGTGG AACCAACCGG TGATACCACG ATACTATGAC TGAGAGTCAA
CGCCATGAGC GGCCTCATTT CTTATTCTGA GTTACAACAG TCCGCACCGC TGTCCGGTAG
CTCCTTCCGG TGGGCGCGGG GCATGACTAT CGTCGCCGCA CTTATGACTG TCTTCTTTAT
CATGCAACTC GTAGGACAGG TGCCGGCAGC GCCCAACAGT CCCCCGGCCA CGGGGCCTGC
CACCATACCC ACGCCGAAAC AAGCGCCCTG CACCATTATG TTCCGGATCT GCATCGCAGG
ATGCTGCTGG CTACCCTGTG GAACACCTAC ATCTGTATTA ACGAAGCGCT AACCGTTTTT
ATCAGGCTCT GGGAGGCAGA ATAAATGATC ATATCGTCAA TTATTACCTC CACGGGGAGA
GCCTGAGCAA ACTGGCCTCA GGCATTTGAG AAGCACACGG TCACACTGCT TCCGGTAGTC
AATAAACCGG TAAACCAGCA ATAGACATAA GCGGCTATTT AACGACCCTG CCCTGAACCG
ACGACCGGGT CGAATTTGCT TTCGAATTTC TGCCATTCAT CCGCTTATTA TCACTTATTC
AGGCGTAGCA CCAGGCGTTT AAGGGCACCA ATAACTGCCT TAAAAAAATT ACGCCCCGCC
CTGCCACTCA TCGCAGTACT GTTGTAATTC ATTAAGCATT CTGCCGACAT GGAAGCCATC
ACAGACGGCA TGATGAACCT GAATCGCCAG CGGCATCAGC ACCTTGTCGC CTTGCGTATA
ATATTTGCCC ATGGTGAAAA CGGGGGCGAA GAAGTTGTCC ATATTGGCCA CGTTTAAATC
AAAACTGGTG AAACTCACCC AGGGATTGGC TGAGACGAAA AACATATTCT CAATAAACCC
TTTAGGGAAA TAGGCCAGGT TTTCACCGTA ACACGCCACA TCTTGCGAAT ATATGTGTAG
AAACTGCCGG AAATCGTCGT GGTATTCACT CCAGAGCGAT GAAAACGTTT CAGTTTGCTC
ATGGAAAACG GTGTAACAAG GGTGAACACT ATCCCATATC ACCAGCTCAC CGTCTTTCAT
TGCCATACG

*FIG. 11 (CONT'D.)*

DNA sequence of the plasmid pBScaro14

```
ID   PBSCARO14     PRELIMINARY;   DNA;   7494 BP.

SQ   SEQUENCE   7494 BP;   1722 A;   1935 C;   2026 G;   1811 T;
     GTGGCACTTT TCGGGGAAAT GTGCGCGGAA CCCCTATTTG TTTATTTTTC TAAATACATT
     CAAATATGTA TCCGCTCATG AGACAATAAC CCTGATAAAT GCTTCAATAA TATTGAAAAA
     GGAAGAGTAT GAGTATTCAA CATTTCCGTG TCGCCCTTAT TCCCTTTTTT GCGGCATTTT
     GCCTTCCTGT TTTTGCTCAC CCAGAAACGC TGGTGAAAGT AAAAGATGCT GAAGATCAGT
     TGGGTGCACG AGTGGGTTAC ATCGAACTGG ATCTCAACAG CGGTAAGATC CTTGAGAGTT
     TTCGCCCCGA AGAACGTTTT CCAATGATGA GCACTTTTAA AGTTCTGCTA TGTGGCGCGG
     TATTATCCCG TATTGACGCC GGGCAAGAGC AACTCGGTCG CCGCATACAC TATTCTCAGA
     ATGACTTGGT TGAGTACTCA CCAGTCACAG AAAAGCATCT TACGGATGGC ATGACAGTAA
     GAGAATTATG CAGTGCTGCC ATAACCATGA GTGATAACAC TGCGGCCAAC TTACTTCTGA
     CAACGATCGG AGGACCGAAG GAGCTAACCG CTTTTTTGCA CAACATGGGG GATCATGTAA
     CTCGCCTTGA TCGTTGGGAA CCGGAGCTGA ATGAAGCCAT ACCAAACGAC GAGCGTGACA
     CCACGATGCC TGTAGCAATG GCAACAACGT TGCGCAAACT ATTAACTGGC GAACTACTTA
     CTCTAGCTTC CCGGCAACAA TTAATAGACT GGATGGAGGC GGATAAAGTT GCAGGACCAC
     TTCTGCGCTC GGCCCTTCCG GCTGGCTGGT TTATTGCTGA TAAATCTGGA GCCGGTGAGC
     GTGGGTCTCG CGGTATCATT GCAGCACTGG GGCCAGATGG TAAGCCCTCC CGTATCGTAG
     TTATCTACAC GACGGGGAGT CAGGCAACTA TGGATGAACG AAATAGACAG ATCGCTGAGA
     TAGGTGCCTC ACTGATTAAG CATTGGTAAC TGTCAGACCA AGTTTACTCA TATATACTTT
     AGATTGATTT AAAACTTCAT TTTTAATTTA AAAGGATCTA GGTGAAGATC CTTTTTGATA
     ATCTCATGAC CAAAATCCCT TAACGTGAGT TTTCGTTCCA CTGAGCGTCA GACCCCGTAG
     AAAAGATCAA AGGATCTTCT TGAGATCCTT TTTTTCTGCG CGTAATCTGC TGCTTGCAAA
     CAAAAAAACC ACCGCTACCA GCGGTGGTTT GTTTGCCGGA TCAAGAGCTA CCAACTCTTT
     TTCCGAAGGT AACTGGCTTC AGCAGAGCGC AGATACCAAA TACTGTCCTT CTAGTGTAGC
     CGTAGTTAGG CCACCACTTC AAGAACTCTG TAGCACCGCC TACATACCTC GCTCTGCTAA
     TCCTGTTACC AGTGGCTGCT GCCAGTGGCG ATAAGTCGTG TCTTACCGGG TTGGACTCAA
     GACGATAGTT ACCGGATAAG GCGCAGCGGT CGGGCTGAAC GGGGGGTTCG TGCACACAGC
     CCAGCTTGGA GCGAACGACC TACACCGAAC TGAGATACCT ACAGCGTGAG CTATGAGAAA
     GCGCCACGCT TCCCGAAGGG AGAAAGGCGG ACAGGTATCC GGTAAGCGGC AGGGTCGGAA
     CAGGAGAGCG CACGAGGGAG CTTCCAGGGG GAAACGCCTG GTATCTTTAT AGTCCTGTCG
     GGTTTCGCCA CCTCTGACTT GAGCGTCGAT TTTTGTGATG CTCGTCAGGG GGGCGGAGCC
     TATGGAAAAA CGCCAGCAAC GCGGCCTTTT TACGGTTCCT GGCCTTTTGC TGGCCTTTTG
     CTCACATGTT CTTTCCTGCG TTATCCCCTG ATTCTGTGGA TAACCGTATT ACCGCCTTTG
     AGTGAGCTGA TACCGCTCGC CGCAGCCGAA CGACCGAGCG CAGCGAGTCA GTGAGCGAGG
     AAGCGGAAGA GCGCCCAATA CGCAAACCGC CTCTCCCCGC GCGTTGGCCG ATTCATTAAT
     GCAGCTGGCA CGACAGGTTT CCCGACTGGA AAGCGGGCAG TGAGCGCAAC GCAATTAATG
     TGAGTTAGCT CACTCATTAG GCACCCCAGG CTTTACACTT TATGCTTCCG GCTCGTATGT
     TGTGTGGAAT TGTGAGCGGA TAACAATTTC ACACAGGAAA CAGCTATGAC CATGATTACG
     CCAAGCGCGC AATTAACCCT CACTAAAGGG AACAAAAGCT GGAGCTCCAC CGCGGTGGCG
     GCCGCTCTAG AACTAGTGGA TCCCCCGGGC TGCAGGAATT GCCGTAAATG TATCCGTTTA
     TAAGGACAGC CCGAATGACG GTCTGCGCAA AAAAACACGT TCATCTCACT CGCGATGCTG
     CGGAGCAGTT ACTGGCTGAT ATTGATCGAC GCCTTGATCA GTTATTGCCC GTGGAGGGAG
     AACGGGATGT TGTGGGTGCC GCGATGCGTG AAGGTGCGCT GGCACCGGGA AAACGTATTC
     GCCCCATGTT GCTGTTGCTG ACCGCCCGCG ATCGGGTTTG CGCTGTCAGC CATGACGGAT
     TACTGGATTT GGCCTGTGCG GTGGAAATGG TCCACGCGGC TTCGCTGATC CTTGACGATA
     TGCCCTGCAT GGACGATGCG AAGCTGCGGC GCGGACGCCC TACCATTCAT TCTCATTACG
     GAGAGCATGT GGCAATACTG GCGGCGGTTG CCTTGCTGAG TAAAGCCTTT GGCGTAATTG
     CCGATGCAGA TGGCCTCACG CCGCTGGCAA AAATCGGGC GGTTTCTGAA CTGTCAAACG
```

FIG. 12

CCATCGGCAT GCAAGGATTG GTTCAGGGTC AGTTCAAGGA TCTGTCTGAA GGGGATAAGC
CGCGCAGCGC TGAAGCTATT TTGATGACGA ATCACTTTAA AACCAGCACG CTGTTTTGTG
CCTCCATGCA GATGGCCTCG ATTGTTGCGA ATGCCTCCAG CGAAGCGCGT GATTGCCTGC
ATCGTTTTTC ACTTGATCTT GGTCAGGCAT TTCAACTGCT GGACGATTTG ACCGATGGCA
TGACCGACAC CGGTAAGGAT AGCAATCAGG ACGCCGGTAA ATCGACGCTG GTCAATCTGT
TAGGCCCGAG GGCGGTTGAA GAACGTCTGA GACAACATCT TCAGCTTGCC AGTGAGCATC
TCTCTGCGGC CTGCCAACAC GGGCACGCCA CTCAACATTT TATTCAGGCC TGGTTTGACA
AAAAACTCGC TGCCGTCAGT TAAGCTTATG TGCACCGGTC AGCCTGTCTT AAGTGGGAGC
GGCTATGCAA CCGCATTATG ATCTGATTCT CGTGGGGCT GGACTCGCGA ATGGCCTTAT
CGCCCTGCGT CTTCAGCAGC AGCAACCTGA TATGCGTATT TTGCTTATCG ACGCCGCACC
CCAGGCGGGC GGGAATCATA CGTGGTCATT TCACCACGAT GATTTGACTG AGAGCCAACA
TCGTTGGATA GCTCCGCTGG TGGTTCATCA CTGGCCCGAC TATCAGGTAC GCTTTCCCAC
ACGCCGTCGT AAGCTGAACA GCGGCTACTT TTGTATTACT TCTCAGCGTT TCGCTGAGGT
TTTACAGCGA CAGTTTGGCC CGCACTTGTG GATGGATACC GCGGTCGCAG AGGTTAATGC
GGAATCTGTT CGGTTGAAAA AGGGTCAGGT TATCGGTGCC CGCGCGGTGA TTGACGGGCG
GGGTTATGCG GCAAATTCAG CACTGAGCGT GGGCTTCCAG GCGTTTATTG GCCAGGAATG
GCGATTGAGC CACCCGCATG GTTTATCGTC TCCCATTATC ATGGATGCCA CGGTCGATCA
GCAAAATGGT TATCGCTTCG TGTACAGCCT GCCGCTCTCG CCGACCAGAT TGTTAATTGA
AGACACGCAC TATATTGATA ATGCGACATT AGATCCTGAA TGCGCGCGGC AAAATATTTG
CGACTATGCC GCGCAACAGG GTTGGCAGCT TCAGACACTG CTGCGAGAAG AACAGGGCGC
CTTACCCATT ACTCTGTCGG GCAATGCCGA CGCATTCTGG CAGCAGCGCC CCCTGGCCTG
TAGTGGATTA CGTGCCGGTC TGTTCCATCC TACCACCGGC TATTCACTGC CGCTGGCGGT
TGCCGTGGCC GACCGCCTGA GTGCACTTGA TGTCTTTACG TCGGCCTCAA TTCACCATGC
CATTACGCAT TTTGCCCGCG AGCGCTGGCA GCAGCAGGGC TTTTTCCGCA TGCTGAATCG
CATGCTGTTT TTAGCCGGAC CCGCCGATTC ACGCTGGCGG GTTATGCAGC GTTTTTATGG
TTTACCTGAA GATTTAATTG CCCGTTTTTA TGCGGGAAAA CTCACGCTGA CCGATCGGCT
ACGTATTCTG AGCGGCAAGC CGCCTGTTCC GGTATTAGCA GCATTGCAAG CCATTATGAC
GACTCATCGT TAAAGAGCGA CTACATGAAA CCAACTACGG TAATTGGTGC AGGCTTCGGT
GGCCTGGCAC TGGCAATTCG TCTACAAGCT GCGGGGATCC CCGTCTTACT GCTTGAACAA
CGTGATAAAC CCGGCGGTCG GGCTTATGTC TACGAGGATC AGGGGTTTAC CTTTGATGCA
GGCCCGACGG TTATCACCGA TCCCAGTGCC ATTGAAGAAC TGTTTGCACT GGCAGGAAAA
CAGTTAAAAG AGTATGTCGA ACTGCTGCCG GTTACGCCGT TTTACCGCCT GTGTTGGGAG
TCAGGGAAGG TCTTTAATTA CGATAACGAT CAAACCCGGC TCGAAGCGCA GATTCAGCAG
TTTAATCCCC GCGATGTCGA AGGTTATCGT CAGTTTCTGG ACTATTCACG CGCGGTGTTT
AAAGAAGGCT ATCTAAAGCT CGGTACTGTC CCTTTTTTAT CGTTCAGAGA CATGCTTCGC
GCCGCACCTC AACTGGCGAA ACTGCAGGCA TGGAGAAGCG TTTACAGTAA GGTTGCCAGT
TACATCGAAG ATGAACATCT GCGCCAGGCG TTTTCTTTCC ACTCGCTGTT GGTGGGCGGC
AATCCCTTCG CCACCTCATC CATTTATACG TTGATACACG CGCTGGAGCG TGAGTGGGGC
GTCTGGTTTC CGCGTGGCGG CACCGGCGCA TTAGTTCAGG GGATGATAAA GCTGTTTCAG
GATCTGGGTG GCGAAGTCGT GTTAAACGCC AGAGTCAGCC ATATGGAAAC GACAGGAAAC
AAGATTGAAG CCGTGCATTT AGAGGACGGT CGCAGGTTCC TGACGCAAGC CGTCGCGTCA
AATGCAGATG TGGTTCATAC CTATCGCGAC CTGTTAAGCC AGCACCCTGC CGCGGTTAAG
CAGTCCAACA AACTGCAGAC TAAGCGCATG AGTAACTCTC TGTTTGTGCT CTATTTTGGT
TTGAATCACC ATCATGATCA GCTCGCGCAT CACACGGTTT GTTTCGGCCC GCGTTACCGC
GAGCTGATTG ACGAAATTTT TAATCATGAT GGCCTCGCAG AGGACTTCTC ACTTTATCTG
CACGCGCCCT GTGTCACGGA TTCGTCACTG GCGCCTGAAG GTTGCGGCAG TTACTATGTG
TTGGCGCCGG TGCCGCATTT AGGCACCGCG AACCTCGACT GGACGGTTGA GGGGCCAAAA
CTACGCGACC GTATTTTTGC GTACCTTGAG CAGCATTACA TGCCTGGCTT ACGGAGTCAG
CTGGTCACGC ACCGGATGTT TACGCCGTTT GATTTCGCG ACCAGCTTAA TGCCTATCAT
GGCTCAGCCT TTTCTGTGGA GCCCGTTCTT ACCCAGAGCG CCTGGTTTCG GCCGCATAAC
CGCGATAAAA CCATTACTAA TCTCTACCTG GTCGGCGCAG GCACGCATCC CGGCGCAGGC
ATTCCTGGCG TCATCGGCTC GGCAAAAGCG ACAGCAGGTT TGATGCTGGA GGATCTGATT

FIG. 12 (CONT'D.)

```
TGAATAATCC GTCGTTACTC AATCATGCGG TCGAAACGAT GGCAGTTGGC TCGAAAAGTT
TTGCGACAGC CTCAAAGTTA TTTGATGCAA AAACCCGGCG CAGCGTACTG ATGCTCTACG
CCTGGTGCCG CCATTGTGAC GATGTTATTG ACGATCAGAC GCTGGGCTTT CAGGCCCGGC
AGCCTGCCTT ACAAACGCCC GAACAACGTC TGATGCAACT TGAGATGAAA ACGCGCCAGG
CCTATGCAGG ATCGCAGATG CACGAACCGG CGTTTGCGGC TTTTCAGGAA GTGGCTATGG
CTCATGATAT CGCCCCGGCT TACGCGTTTG ATCATCTGGA AGGCTTCGCC ATGGATGTAC
GCGAAGCGCA ATACAGCCAA CTGGATGATA CGCTGCGCTA TTGCTATCAC GTTGCAGGCG
TTGTCGGCTT GATGATGGCG CAAATCATGG GCGTGCGGGA TAACGCCACG CTGGACCGCG
CCTGTGACCT TGGGCTGGCA TTTCAGTTGA CCAATATTGC TCGCGATATT GTGGACGATG
CGCATGCGGG CCGCTGTTAT CTGCCGGCAA GCTGGCTGGA GCATGAAGGT CTGAACAAAG
AGAATTATGC GGCACCTGAA AACCGTCAGG CGCTGAGCCG TATCGCCCGT CGTTTGGTGC
AGGAAGCAGA ACCTTACTAT TTGTCTGCCA CAGCCGGCCT GGCAGGGTTG CCCCTGCGTT
CCGCCTGGGC AATCGCTACG GCGAAGCAGG TTTACCGGAA AATAGGTGTC AAAGTTGAAC
AGGCCGGTCA GCAAGCCTGG GATCAGCGGC AGTCAACGAC CACGCCCGAA AAATTAACGC
TGCTGCTGGC CGCCTCTGGT CAGGCCCTTA CTTCCCGGAT GCGGGCTCAT CCTCCCCGCC
CTGCGCATCT CTGGCAGCGC CCGCTCTAGC GCCATGTCGA CCTCGAGGGG GGGCCCGGTA
CCCAATTCGC CCTATAGTGA GTCGTATTAC GCGCGCTCAC TGGCCGTCGT TTTACAACGT
CGTGACTGGG AAAACCCTGG CGTTACCCAA CTTAATCGCC TTGCAGCACA TCCCCCTTTC
GCCAGCTGGC GTAATAGCGA AGAGGCCCGC ACCGATCGCC CTTCCCAACA GTTGCGCAGC
CTGAATGGCG AATGGAAATT GTAAGCGTTA ATATTTTGTT AAAATTCGCG TTAAATTTTT
GTTAAATCAG CTCATTTTTT AACCAATAGG CCGAAATCGG CAAAATCCCT TATAAATCAA
AAGAATAGAC CGAGATAGGG TTGAGTGTTG TTCCAGTTTG AACAAGAGT CCACTATTAA
AGAACGTGGA CTCCAACGTC AAAGGGCGAA AAACCGTCTA TCAGGGCGAT GGCCCACTAC
GTGAACCATC ACCCTAATCA AGTTTTTTGG GGTCGAGGTG CCGTAAAGCA CTAAATCGGA
ACCCTAAAGG GAGCCCCCGA TTTAGAGCTT GACGGGGAAA GCCGGCGAAC GTGGCGAGAA
AGGAAGGGAA GAAAGCGAAA GGAGCGGGCG CTAGGGCGCT GGCAAGTGTA GCGGTCACGC
TGCGCGTAAC CACCACACCC GCCGCGCTTA ATGCGCCGCT ACAGGGCGCG TCAG
```

FIG. 12 (CONT'D.)

DNA sequence of the vector construct pACYCcaro14

```
ID    PACYCCARO14     PRELIMINARY;    DNA;    8547 BP.
SQ    SEQUENCE    8547 BP;    1884 A;    2296 C;    2279 G;    2088 T;    0 OTHER;
      GAATTCCGGA  TGAGCATTCA  TCAGGCGGGC  AAGAATGTGA  ATAAAGGCCG  GATAAAACTT
      GTGCTTATTT  TTCTTTACGG  TCTTTAAAAA  GGCCGTAATA  TCCAGCTGAA  CGGTCTGGTT
      ATAGGTACAT  TGAGCAACTG  ACTGAAATGC  CTCAAAATGT  TCTTTACGAT  GCCATTGGGA
      TATATCAACG  GTGGTATATC  CAGTGATTTT  TTTCTCCATT  TTAGCTTCCT  TAGCTCCTGA
      AAATCTCGAT  AACTCAAAAA  ATACGCCCGG  TAGTGATCTT  ATTTCATTAT  GGTGAAAGTT
      GGAACCTCTT  ACGTGCCGAT  CAACGTCTCA  TTTTCGCCAA  AAGTTGGCCC  AGGGCTTCCC
      GGTATCAACA  GGGACACCAG  GATTTATTTA  TTCTGCGAAG  TGATCTTCCG  TCACAGGTAT
      TTATTCGGCG  CAAAGTGCGT  CGGGTGATGC  TGCCAACTTA  CTGATTTAGT  GTATGATGGT
      GTTTTTGAGG  TGCTCCAGTG  GCTTCTGTTT  CTATCAGCTG  TCCCTCCTGT  TCAGCTACTG
      ACGGGGTGGT  GCGTAACGGC  AAAAGCACCG  CCGGACATCA  GCGCTAGCGG  AGTGTATACT
      GGCTTACTAT  GTTGGCACTG  ATGAGGGTGT  CAGTGAAGTG  CTTCATGTGG  CAGGAGAAAA
      AAGGCTGCAC  CGGTGCGTCA  GCAGAATATG  TGATACAGGA  TATATTCCGC  TTCCTCGCTC
      ACTGACTCGC  TACGCTCGGT  CGTTCGACTG  CGGCGAGCGG  AAATGGCTTA  CGAACGGGGC
      GGAGATTTCC  TGGAAGATGC  CAGGAAGATA  CTTAACAGGG  AAGTGAGAGG  GCCGCGGCAA
      AGCCGTTTTT  CCATAGGCTC  CGCCCCCCTG  ACAAGCATCA  CGAAATCTGA  CGCTCAAATC
      AGTGGTGGCG  AAACCCGACA  GGACTATAAA  GATACCAGGC  GTTTCCCCCT  GGCGGCTCCC
      TCGTGCGCTC  TCCTGTTCCT  GCCTTTCGGT  TTACCGGTGT  CATTCCGCTG  TTATGGCCGC
      GTTTGTCTCA  TTCCACGCCT  GACACTCAGT  TCCGGGTAGG  CAGTTCGCTC  CAAGCTGGAC
      TGTATGCACG  AACCCCCCGT  TCAGTCCGAC  CGCTGCGCCT  TATCCGGTAA  CTATCGTCTT
      GAGTCCAACC  CGGAAAGACA  TGCAAAAGCA  CCACTGGCAG  CAGCCACTGG  TAATTGATTT
      AGAGGAGTTA  GTCTTGAAGT  CATGCGCCGG  TTAAGGCTAA  ACTGAAAGGA  CAAGTTTTGG
      TGACTGCGCT  CCTCCAAGCC  AGTTACCTCG  GTTCAAAGAG  TTGGTAGCTC  AGAGAACCTT
      CGAAAAACCG  CCCTGCAAGG  CGGTTTTTTC  GTTTTCAGAG  CAAGAGATTA  CGCGCAGACC
      AAAACGATCT  CAAGAAGATC  ATCTTATTAA  TCAGATAAAA  TATTTCTAGA  TTTCAGTGCA
      ATTTATCTCT  TCAAATGTAG  CACCTGAAGT  CAGCCCCATA  CGATATAAGT  TGTAATTCTC
      ATGTTTGACA  GCTTATCATC  GATAAGCTTT  AATGCGGTAG  TTTATCACAG  TTAAATTGCT
      AACGCAGTCA  GGCACCGTGT  ATGAAATCTA  ACAATGCGCT  CATCGTCATC  CTCGGCACCG
      TCACCCTGGA  TGCTGTAGGC  ATAGGCTTGG  TTATGCCGGT  ACTGCCGGGC  CTCTTGCGGG
      ATATCGTCCA  TTCCGACAGC  ATCGCCAGTC  ACTATGGCGT  GCTGCTAGCG  CTATATGCGT
      TGATGCAATT  TCTATGCGCA  CCCGTTCTCG  GAGCACTGTC  CGACCGCTTT  GGCCGCCGCC
      CAGTCCTGCT  CGCTTCGCTA  CTTGGAGCCA  CTATCGACTA  CGCGATCATG  GCGACCACAC
      CCGTCCTGTG  GATCCCCCGG  GCTGCAGGAA  TTGCCGTAAA  TGTATCCGTT  TATAAGGACA
      GCCCGAATGA  CGGTCTGCGC  AAAAAAACAC  GTTCATCTCA  CTCGCGATGC  TGCGGAGCAG
      TTACTGGCTG  ATATTGATCG  ACGCCTTGAT  CAGTTATTGC  CCGTGGAGGG  AGAACGGGAT
      GTTGTGGGTG  CCGCGATGCG  TGAAGGTGCG  CTGGCACCGG  AAAACGTAT   TCGCCCCATG
      TTGCTGTTGC  TGACCGCCCG  CGATCTGGGT  TGCGCTGTCA  GCCATGACGG  ATTACTGGAT
      TTGGCCTGTG  CGGTGGAAAT  GGTCCACGCG  GCTTCGCTGA  TCCTTGACGA  TATGCCCTGC
      ATGGACGATG  CGAAGCTGCG  GCGCGGACGC  CTACCATTC   ATTCTCATTA  CGGAGAGCAT
      GTGGCAATAC  TGGCGGCGGT  TGCCTTGCTG  AGTAAAGCCT  TTGGCGTAAT  TGCCGATGCA
      GATGGCCTCA  CGCCGCTGGC  AAAAAATCGG  GCGGTTTCTG  AACTGTCAAA  CGCCATCGGC
      ATGCAAGGAT  TGGTTCAGGG  TCAGTTCAAG  GATCTGTCTG  AAGGGGATAA  GCCGCGCAGC
      GCTGAAGCTA  TTTTGATGAC  GAATCACTTT  AAAACCAGCA  CGCTGTTTTG  TGCCTCCATG
      CAGATGGCCT  CGATTGTTGC  GAATGCCTCC  AGCGAAGCGC  GTGATTGCCT  GCATCGTTTT
      TCACTTGATC  TTGGTCAGGC  ATTTCAACTG  CTGGACGATT  TGACCGATGG  CATGACCGAC
      ACCGGTAAGG  ATAGCAATCA  GGACGCCGGT  AAATCGACGC  TGGTCAATCT  GTTAGGCCCG
      AGGGCGGTTG  AAGAACGTCT  GAGACAACAT  CTTCAGCTTG  CCAGTGAGCA  TCTCTCTGCG
```

FIG. 13

```
GCCTGCCAAC ACGGGCACGC CACTCAACAT TTTATTCAGG CCTGGTTTGA CAAAAAACTC
GCTGCCGTCA GTTAAGCTTA TGTGCACCGG TCAGCCTGTC TTAAGTGGGA GCGGCTATGC
AACCGCATTA TGATCTGATT CTCGTGGGGG CTGGACTCGC GAATGGCCTT ATCGCCCTGC
GTCTTCAGCA GCAGCAACCT GATATGCGTA TTTTGCTTAT CGACGCCGCA CCCCAGGCGG
GCGGGAATCA TACGTGGTCA TTTCACCACG ATGATTTGAC TGAGAGCCAA CATCGTTGGA
TAGCTCCGCT GGTGGTTCAT CACTGGCCCG ACTATCAGGT ACGCTTTCCC ACACGCCGTC
GTAAGCTGAA CAGCGGCTAC TTTTGTATTA CTTCTCAGCG TTTCGCTGAG GTTTTACAGC
GACAGTTTGG CCCGCACTTG TGGATGGATA CCGCGGTCGC AGAGGTTAAT GCGGAATCTG
TTCGGTTGAA AAAGGGTCAG GTTATCGGTG CCCGCGCGGT GATTGACGGG CGGGGTTATG
CGGCAAATTC AGCACTGAGC GTGGGCTTCC AGGCGTTTAT TGGCCAGGAA TGGCGATTGA
GCCACCCGCA TGGTTTATCG TCTCCCATTA TCATGGATGC CACGGTCGAT CAGCAAAATG
GTTATCGCTT CGTGTACAGC CTGCCGCTCT CGCCGACCAG ATTGTTAATT GAAGACACGC
ACTATATTGA TAATGCGACA TTAGATCCTG AATGCGCGCG GCAAAATATT TGCGACTATG
CCGCGCAACA GGGTTGGCAG CTTCAGACAC TGCTGCGAGA AGAACAGGGC GCCTTACCCA
TTACTCTGTC GGGCAATGCC GACGCATTCT GGCAGCAGCG CCCCCTGGCC TGTAGTGGAT
TACGTGCCGG TCTGTTCCAT CCTACCACCG GCTATTCACT GCCGCTGGCG GTTGCCGTGG
CCGACCGCCT GAGTGCACTT GATGTCTTTA CGTCGGCCTC AATTCACCAT GCCATTACGC
ATTTTGCCCG CGAGCGCTGG CAGCAGCAGG GCTTTTTCCG CATGCTGAAT CGCATGCTGT
TTTTAGCCGG ACCGCCGAT TCACGCTGGC GGGTTATGCA GCGTTTTTAT GGTTTACCTG
AAGATTTAAT TGCCCGTTTT TATGCGGGAA AACTCACGCT GACCGATCGG CTACGTATTC
TGAGCGGCAA GCCGCCTGTT CCGGTATTAG CAGCATTGCA AGCCATTATG ACGACTCATC
GTTAAAGAGC GACTACATGA AACCAACTAC GGTAATTGGT GCAGGCTTCG GTGGCCTGGC
ACTGGCAATT CGTCTACAAG CTGCGGGGAT CCCCGTCTTA CTGCTTGAAC AACGTGATAA
ACCCGGCGGT CGGGCTTATG TCTACGAGGA TCAGGGGTTT ACCTTTGATG CAGGCCCGAC
GGTTATCACC GATCCCAGTG CCATTGAAGA ACTGTTTGCA CTGGCAGGAA AACAGTTAAA
AGAGTATGTC GAACTGCTGC CGGTTACGCC GTTTTACCGC CTGTGTTGGG AGTCAGGGAA
GGTCTTTAAT TACGATAACG ATCAAACCCG GCTCGAAGCG CAGATTCAGC AGTTTAATCC
CCGCGATGTC GAAGGTTATC GTCAGTTTCT GGACTATTCA CGCGCGGTGT TTAAAGAAGG
CTATCTAAAG CTCGGTACTG TCCCTTTTTT ATCGTTCAGA GACATGCTTC GCGCCGCACC
TCAACTGGCG AAACTGCAGG CATGGAGAAG CGTTTACAGT AAGGTTGCCA GTTACATCGA
AGATGAACAT CTGCGCCAGG CGTTTTCTTT CCACTCGCTG TTGGTGGGCG GCAATCCCTT
CGCCACCTCA TCCATTTATA CGTTGATACA CGCGCTGGAG CGTGAGTGGG GCGTCTGGTT
TCCGCGTGGC GGCACCGGCG CATTAGTTCA GGGGATGATA AAGCTGTTTC AGGATCTGGG
TGGCGAAGTC GTGTTAAACG CCAGAGTCAG CCATATGGAA ACGACAGGAA ACAAGATTGA
AGCCGTGCAT TTAGAGGACG GTCGCAGGTT CCTGACGCAA GCCGTCGCGT CAAATGCAGA
TGTGGTTCAT ACCTATCGCG ACCTGTTAAG CCAGCACCCT GCCGCGGTTA AGCAGTCCAA
CAAACTGCAG ACTAAGCGCA TGAGTAACTC TCTGTTTGTG CTCTATTTTG GTTTGAATCA
CCATCATGAT CAGCTCGCGC ATCACACGGT TTGTTTCGGC CCGCGTTACC GCGAGCTGAT
TGACGAAATT TTTAATCATG ATGGCCTCGC AGAGGACTTC TCACTTTATC TGCACGCGCC
CTGTGTCACG GATTCGTCAC TGGCGCCTGA AGGTTGCGGC AGTTACTATG TGTTGGCGCC
GGTGCCGCAT TTAGGCACCG CGAACCTCGA CTGGACGGTT GAGGGGCCAA AACTACGCGA
CCGTATTTTT GCGTACCTTG AGCAGCATTA CATGCCTGGC TTACGGAGTC AGCTGGTCAC
GCACCGGATG TTTACGCCGT TTGATTTTCG CGACCAGCTT AATGCCTATC ATGGCTCAGC
CTTTTCTGTG GAGCCCGTTC TTACCCAGAG CGCCTGGTTT CGGCCGCATA ACCGCGATAA
AACCATTACT AATCTCTACC TGGTCGGCGC AGGCACGCAT CCCGGCGCAG GCATTCCTGG
CGTCATCGGC TCGGCAAAAG CGACAGCAGG TTTGATGCTG GAGGATCTGA TTTGAATAAT
CCGTCGTTAC TCAATCATGC GGTCGAAACG ATGGCAGTTG GCTCGAAAAG TTTTGCGACA
GCCTCAAAGT TATTTGATGC AAAAACCCGG CGCAGCGTAC TGATGCTCTA CGCCTGGTGC
CGCCATTGTG ACGATGTTAT TGACGATCAG ACGCTGGGCT TCAGGCCCG CAGCCTGCC
TTACAAACGC CCGAACAACG TCTGATGCAA CTTGAGATGA AAACGCGCCA GGCCTATGCA
GGATCGCAGA TGCACGAACC GGCGTTTGCG GCTTTTCAGG AAGTGGCTAT GGCTCATGAT
ATCGCCCCGG CTTACGCGTT TGATCATCTG GAAGGCTTCG CCATGGATGT ACGCGAAGCG
```

FIG. 13 (CONT'D.)

```
CAATACAGCC AACTGGATGA TACGCTGCGC TATTGCTATC ACGTTGCAGG CGTTGTCGGC
TTGATGATGG CGCAAATCAT GGGCGTGCGG GATAACGCCA CGCTGGACCG CGCCTGTGAC
CTTGGGCTGG CATTTCAGTT GACCAATATT GCTCGCGATA TTGTGGACGA TGCGCATGCG
GGCCGCTGTT ATCTGCCGGC AAGCTGGCTG GAGCATGAAG GTCTGAACAA AGAGAATTAT
GCGGCACCTG AAAACCGTCA GGCGCTGAGC CGTATCGCCC GTCGTTTGGT GCAGGAAGCA
GAACCTTACT ATTTGTCTGC CACAGCCGGC CTGGCAGGGT TGCCCCTGCG TTCCGCCTGG
GCAATCGCTA CGGCGAAGCA GGTTTACCGG AAAATAGGTG TCAAAGTTGA ACAGGCCGGT
CAGCAAGCCT GGGATCAGCG GCAGTCAACG ACCACGCCCG AAAAATTAAC GCTGCTGCTG
GCCGCCTCTG GTCAGGCCCT TACTTCCCGG ATGCGGGCTC ATCCTCCCCG CCCTGCGCAT
CTCTGGCAGC GCCCGCTCTA GCGCCATGTC GACCGATGCC CTTGAGAGCC TTCAACCCAG
TCAGCTCCTT CCGGTGGGCG CGGGGCATGA CTATCGTCGC CGCACTTATG ACTGTCTTCT
TTATCATGCA ACTCGTAGGA CAGGTGCCGG CAGCGCTCTG GGTCATTTTC GGCGAGGACC
GCTTTCGCTG GAGCGCGACG ATGATCGGCC TGTCGCTTGC GGTATTCGGA ATCTTGCACG
CCCTCGCTCA AGCCTTCGTC ACTGGTCCCG CCACCAAACG TTTCGGCGAG AAGCAGGCCA
TTATCGCCGG CATGGCGGCC GACGCGCTGG GCTACGTCTT GCTGGCGTTC GCGACGCGAG
GCTGGATGGC CTTCCCCATT ATGATTCTTC TCGCTTCCGG CGGCATCGGG ATGCCCGCGT
TGCAGGCCAT GCTGTCCAGG CAGGTAGATG ACGACCATCA GGGACAGCTT CAAGGATCGC
TCGCGGCTCT TACCAGCCTA ACTTCGATCA CTGGACCGCT GATCGTCACG GCGATTTATG
CCGCCTCGGC GAGCACATGG AACGGGTTGG CATGGATTGT AGGCGCCGCC CTATACCTTG
TCTGCCTCCC CGCGTTGCGT CGCGGTGCAT GGAGCCGGGC CACCTCGACC TGAATGGAAG
CCGGCGGCAC CTCGCTAACG GATTCACCAC TCCAAGAATT GGAGCCAATC AATTCTTGCG
GAGAACTGTG AATGCGCAAA CCAACCCTTG GCAGAACATA TCCATCGCGT CCGCCATCTC
CAGCAGCCGC ACGCGGCGCA TCTCGGGCAG CGTTGGGTCC TGGCCACGGG TGCGCATGAT
CGTGCTCCTG TCGTTGAGGA CCCGGCTAGG CTGGCGGGGT TGCCTTACTG GTTAGCAGAA
TGAATCACCG ATACGCGAGC GAACGTGAAG CGACTGCTGC TGCAAAACGT CTGCGACCTG
AGCAACAACA TGAATGGTCT TCGGTTTCCG TGTTTCGTAA AGTCTGGAAA CGCGGAAGTC
CCCTACGTGC TGCTGAAGTT GCCCGCAACA GAGAGTGGAA CCAACCGGTG ATACCACGAT
ACTATGACTG AGAGTCAACG CCATGAGCGG CCTCATTTCT TATTCTGAGT TACAACAGTC
CGCACCGCTG TCCGGTAGCT CCTTCCGGTG GGCGCGGGGC ATGACTATCG TCGCCGCACT
TATGACTGTC TTCTTTATCA TGCAACTCGT AGGACAGGTG CCGGCAGCGC CAACAGTCC
CCCGGCCACG GGGCCTGCCA CCATACCCAC GCCGAAACAA GCGCCCTGCA CCATTATGTT
CCGGATCTGC ATCGCAGGAT GCTGCTGGCT ACCCTGTGGA ACACCTACAT CTGTATTAAC
GAAGCGCTAA CCGTTTTTAT CAGGCTCTGG GAGGCAGAAT AAATGATCAT ATCGTCAATT
ATTACCTCCA CGGGGAGAGC CTGAGCAAAC TGGCCTCAGG CATTTGAGAA GCACACGGTC
ACACTGCTTC CGGTAGTCAA TAAACCGGTA AACCAGCAAT AGACATAAGC GGCTATTTAA
CGACCCTGCC CTGAACCGAC GACCGGGTCG AATTTGCTTT CGAATTTCTG CCATTCATCC
GCTTATTATC ACTTATTCAG GCGTAGCACC AGGCGTTTAA GGGCACCAAT AACTGCCTTA
AAAAAATTAC GCCCCGCCCT GCCACTCATC GCAGTACTGT TGTAATTCAT TAAGCATTCT
GCCGACATGG AAGCCATCAC AGACGGCATG ATGAACCTGA ATCGCCAGCG GCATCAGCAC
CTTGTCGCCT TGCGTATAAT ATTTGCCCAT GGTGAAAACG GGGCGAAGA AGTTGTCCAT
ATTGGCCACG TTTAAATCAA AACTGGTGAA ACTCACCCAG GGATTGGCTG AGACGAAAAA
CATATTCTCA ATAAACCCTT TAGGGAAATA GGCCAGGTTT TCACCGTAAC ACGCCACATC
TTGCGAATAT ATGTGTAGAA ACTGCCGGAA ATCGTCGTGG TATTCACTCC AGAGCGATGA
AAACGTTTCA GTTTGCTCAT GGAAAACGGT GTAACAAGGG TGAACACTAT CCCATATCAC
CAGCTCACCG TCTTTCATTG CCATACG
```

FIG. 13 (CONT'D.)

**DNA and corresponding amino acid sequence of the *ispG* (formely *gcpE*) gene of *Escherichia coli***

```
         10         20         30         40         50         60
          |          |          |          |          |          |
ATGCATAACCAGGCTCCAATTCAACGTAGAAAATCAACACGTATTTACGTTGGGAATGTG
 M  H  N  Q  A  P  I  Q  R  R  K  S  T  R  I  Y  V  G  N  V 70         80         90        100        110        120
          |          |          |          |          |          |
CCGATTGGCGATGGTGCTCCCATCGCCGTACAGTCCATGACCAATACGCGTACGACAGAC
 P  I  G  D  G  A  P  I  A  V  Q  S  M  T  N  T  R  T  T  D 130        140        150        160        170        180
          |          |          |          |          |          |
GTCGAAGCAACGGTCAATCAAATCAAGGCGCTGGAACGCGTTGGCGCTGATATCGTCCGT
 V  E  A  T  V  N  Q  I  K  A  L  E  R  V  G  A  D  I  V  R 190        200        210        220        230        240
          |          |          |          |          |          |
GTATCCGTACCGACGATGGACGCGGCAGAAGCGTTCAAACTCATCAAACAGCAGGTTAAC
 V  S  V  P  T  M  D  A  A  E  A  F  K  L  I  K  Q  Q  V  N 250        260        270        280        290        300
          |          |          |          |          |          |
GTGCCGCTGGTGGCTGACATCCACTTCGACTATCGCATTGCGCTGAAAGTAGCGGAATAC
 V  P  L  V  A  D  I  H  F  D  Y  R  I  A  L  K  V  A  E  Y 310        320        330        340        350        360
          |          |          |          |          |          |
GGCGTCGATTGTCTGCGTATTAACCCTGGCAATATCGGTAATGAAGAGCGTATTCGCATG
 G  V  D  C  L  R  I  N  P  G  N  I  G  N  E  E  R  I  R  M 370        380        390        400        410        420
          |          |          |          |          |          |
GTGGTTGACTGTGCGCGCGATAAAAACATTCCGATCCGTATTGGCGTTAACGCCGGATCG
 V  V  D  C  A  R  D  K  N  I  P  I  R  I  G  V  N  A  G  S 430        440        450        460        470        480
          |          |          |          |          |          |
CTGGAAAAAGATCTGCAAGAAAAGTATGGCGAACCGACGCCGCAGGCGTTGCTGGAATCT
 L  E  K  D  L  Q  E  K  Y  G  E  P  T  P  Q  A  L  L  E  S 490        500        510        520        530        540
          |          |          |          |          |          |
GCCATGCGTCATGTTGATCATCTCGATCGCCTGAACTTCGATCAGTTCAAAGTCAGCGTG
 A  M  R  H  V  D  H  L  D  R  L  N  F  D  Q  F  K  V  S  V 550        560        570        580        590        600
          |          |          |          |          |          |
```

*FIG. 14*

```
AAAGCGTCTGACGTCTTCCTCGCTGTTGAGTCTTATCGTTTGCTGGCAAAACAGATCGAT
 K  A  S  D  V  F  L  A  V  E  S  Y  R  L  L  A  K  Q  I  D 610       620       630       640       650       660
          |         |         |         |         |         |
CAGCCGTTGCATCTGGGGATCACCGAAGCCGGTGGTGCGCGCAGCGGGGCAGTAAAATCC
 Q  P  L  H  L  G  I  T  E  A  G  G  A  R  S  G  A  V  K  S 670       680       690       700       710       720
          |         |         |         |         |         |
GCCATTGGTTTAGGTCTGCTGCTGTCTGAAGGCATCGGCGACACGCTGCGCGTATCGCTG
 A  I  G  L  G  L  L  L  S  E  G  I  G  D  T  L  R  V  S  L 730       740       750       760       770       780
          |         |         |         |         |         |
GCGGCCGATCCGGTCGAAGAGATCAAAGTCGGTTTCGATATTTTGAAATCGCTGCGTATC
 A  A  D  P  V  E  E  I  K  V  G  F  D  I  L  K  S  L  R  I 790       800       810       820       830       840
          |         |         |         |         |         |
CGTTCGCGAGGGATCAACTTCATCGCCTGCCCGACCTGTTCGCGTCAGGAATTTGATGTT
 R  S  R  G  I  N  F  I  A  C  P  T  C  S  R  Q  E  F  D  V 850       860       870       880       890       900
          |         |         |         |         |         |
ATCGGTACGGTTAACGCGCTGGAGCAACGCCTGGAAGATATCATCACTCCGATGGACGTT
 I  G  T  V  N  A  L  E  Q  R  L  E  D  I  I  T  P  M  D  V 910       920       930       940       950       960
          |         |         |         |         |         |
TCGATTATCGGCTGCGTGGTGAATGGCCCAGGTGAGGCGCTGGTTTCTACACTCGGCGTC
 S  I  I  G  C  V  V  N  G  P  G  E  A  L  V  S  T  L  G  V 970       980       990      1000      1010      1020
          |         |         |         |         |         |
ACCGGCGGCAACAAGAAAAGCGGCCTCTATGAAGATGGCGTGCGCAAAGACCGTCTGGAC
 T  G  G  N  K  K  S  G  L  Y  E  D  G  V  R  K  D  R  L  D 1030      1040      1050      1060      1070      1080
          |         |         |         |         |         |
AACAACGATATGATCGACCAGCTGGAAGCACGCATTCGTGCGAAAGCCAGTCAGCTGGAC
 N  N  D  M  I  D  Q  L  E  A  R  I  R  A  K  A  S  Q  L  D 1090      1100      1110
          |         |         |
GAAGCGCGTCGAATTGACGTTCAGCAGGTTGAAAAATAA
 E  A  R  R  I  D  V  Q  Q  V  E  K  -
```

FIG. 14 (CONT'D.)

DNA sequence of the vector construct pBScyclogcpE

| ID | PBSCYCLOG | PRELIMINARY; | DNA; | 8823 BP. | | |
|---|---|---|---|---|---|---|
| SQ | SEQUENCE | 8823 BP; | 2123 A; | 2169 C; | 2468 G; | 2063 T; 0 OTHER; |

```
GTGGCACTTT TCGGGGAAAT GTGCGCGGAA CCCCTATTTG TTTATTTTTC TAAATACATT
CAAATATGTA TCCGCTCATG AGACAATAAC CCTGATAAAT GCTTCAATAA TATTGAAAAA
GGAAGAGTAT GAGTATTCAA CATTTCCGTG TCGCCCTTAT TCCCTTTTTT GCGGCATTTT
GCCTTCCTGT TTTTGCTCAC CCAGAAACGC TGGTGAAAGT AAAAGATGCT GAAGATCAGT
TGGGTGCACG AGTGGGTTAC ATCGAACTGG ATCTCAACAG CGGTAAGATC CTTGAGAGTT
TTCGCCCCGA AGAACGTTTT CCAATGATGA GCACTTTTAA AGTTCTGCTA TGTGGCGCGG
TATTATCCCG TATTGACGCC GGGCAAGAGC AACTCGGTCG CCGCATACAC TATTCTCAGA
ATGACTTGGT TGAGTACTCA CCAGTCACAG AAAAGCATCT TACGGATGGC ATGACAGTAA
GAGAATTATG CAGTGCTGCC ATAACCATGA GTGATAACAC TGCGGCCAAC TTACTTCTGA
CAACGATCGG AGGACCGAAG GAGCTAACCG CTTTTTTGCA CAACATGGGG GATCATGTAA
CTCGCCTTGA TCGTTGGGAA CCGGAGCTGA ATGAAGCCAT ACCAAACGAC GAGCGTGACA
CCACGATGCC TGTAGCAATG GCAACAACGT TGCGCAAACT ATTAACTGGC GAACTACTTA
CTCTAGCTTC CCGGCAACAA TTAATAGACT GGATGGAGGC GGATAAAGTT GCAGGACCAC
TTCTGCGCTC GGCCCTTCCG GCTGGCTGGT TTATTGCTGA TAAATCTGGA GCCGGTGAGC
GTGGGTCTCG CGGTATCATT GCAGCACTGG GGCCAGATGG TAAGCCCTCC CGTATCGTAG
TTATCTACAC GACGGGGAGT CAGGCAACTA TGGATGAACG AAATAGACAG ATCGCTGAGA
TAGGTGCCTC ACTGATTAAG CATTGGTAAC TGTCAGACCA AGTTTACTCA TATATACTTT
AGATTGATTT AAAACTTCAT TTTTAATTTA AAAGGATCTA GGTGAAGATC CTTTTTGATA
ATCTCATGAC CAAAATCCCT TAACGTGAGT TTTCGTTCCA CTGAGCGTCA GACCCCGTAG
AAAAGATCAA AGGATCTTCT TGAGATCCTT TTTTTCTGCG CGTAATCTGC TGCTTGCAAA
CAAAAAAACC ACCGCTACCA GCGGTGGTTT GTTTGCCGGA TCAAGAGCTA CCAACTCTTT
TTCCGAAGGT AACTGGCTTC AGCAGAGCGC AGATACCAAA TACTGTCCTT CTAGTGTAGC
CGTAGTTAGG CCACCACTTC AAGAACTCTG TAGCACCGCC TACATACCTC GCTCTGCTAA
TCCTGTTACC AGTGGCTGCT GCCAGTGGCG ATAAGTCGTG TCTTACCGGG TTGGACTCAA
GACGATAGTT ACCGGATAAG GCGCAGCGGT CGGGCTGAAC GGGGGGTTCG TGCACACAGC
CCAGCTTGGA GCGAACGACC TACACCGAAC TGAGATACCT ACAGCGTGAG CTATGAGAAA
GCGCCACGCT TCCCGAAGGG AGAAAGGCGG ACAGGTATCC GGTAAGCGGC AGGGTCGGAA
CAGGAGAGCG CACGAGGGAG CTTCCAGGGG GAAACGCCTG GTATCTTTAT AGTCCTGTCG
GGTTTCGCCA CCTCTGACTT GAGCGTCGAT TTTTGTGATG CTCGTCAGGG GGGCGGAGCC
TATGAAAAA CGCCAGCAAC GCGGCCTTTT TACGGTTCCT GGCCTTTTGC TGGCCTTTTG
CTCACATGTT CTTTCCTGCG TTATCCCCTG ATTCTGTGGA TAACCGTATT ACCGCCTTTG
AGTGAGCTGA TACCGCTCGC CGCAGCCGAA CGACCGAGCG CAGCGAGTCA GTGAGCGAGG
AAGCGGAAGA GCGCCCAATA CGCAAACCGC CTCTCCCCGC GCGTTGGCCG ATTCATTAAT
GCAGCTGGCA CGACAGGTTT CCCGACTGGA AAGCGGGCAG TGAGCGCAAC GCAATTAATG
TGAGTTAGCT CACTCATTAG GCACCCCAGG CTTTACACTT TATGCTTCCG GCTCGTATGT
TGTGTGGAAT TGTGAGCGGA TAACAATTTC ACACAGGAAA CAGCTATGAC CATGATTACG
CCAAGCGCGC AATTAACCCT CACTAAAGGG AACAAAAGCT GGAGCTCCAC CGCGGGAGGA
GAAATTAACC ATGCATAACC AGGCTCCAAT TCAACGTAGA AAATCAACAC GTATTTACGT
TGGGAATGTG CCGATTGGCG ATGGTGCTCC CATCGCCGTA CAGTCCATGA CCAATACGCG
TACGACAGAC GTCGAAGCAA CGGTCAATCA AATCAAGGCG CTGGAACGCG TTGGCGCTGA
TATCGTCCGT GTATCCGTAC CGACGATGGA CGCGGCAGAA GCGTTCAAAC TCATCAAACA
GCAGGTTAAC GTGCCGCTGG TGGCTGACAT CCACTTCGAC TATCGCATTG CGCTGAAAGT
AGCGGAATAC GGCGTCGATT GTCTGCGTAT TAACCCTGGC AATATCGGTA ATGAAGAGCG
TATTCGCATG GTGGTTGACT GTGCGCGCGA TAAAAACATT CCGATCCGTA TTGGCGTTAA
CGCCGGATCG CTGGAAAAAG ATCTGCAAGA AAAGTATGGC GAACCGACGC CGCAGGCGTT
GCTGGAATCT GCCATGCGTC ATGTTGATCA TCTCGATCGC CTGAACTTCG ATCAGTTCAA
```

FIG. 15

```
AGTCAGCGTG AAAGCGTCTG ACGTCTTCCT CGCTGTTGAG TCTTATCGTT TGCTGGCAAA
ACAGATCGAT CAGCCGTTGC ATCTGGGGAT CACCGAAGCC GGTGGTGCGC GCAGCGGGGC
AGTAAAATCC GCCATTGGTT TAGGTCTGCT GCTGTCTGAA GGCATCGGCG ACACGCTGCG
CGTATCGCTG GCGGCCGATC CGGTCGAAGA GATCAAAGTC GGTTTCGATA TTTTGAAATC
GCTGCGTATC CGTTCGCGAG GGATCAACTT CATCGCCTGC CCGACCTGTT CGCGTCAGGA
ATTTGATGTT ATCGGTACGG TTAACGCGCT GGAGCAACGC CTGGAAGATA TCATCACTCC
GATGGACGTT TCGATTATCG GCTGCGTGGT GAATGGCCCA GGTGAGGCGC TGGTTTCTAC
ACTCGGCGTC ACCGGCGGCA ACAAGAAAAG CGGCCTCTAT GAAGATGGCG TGCGCAAAGA
CCGTCTGGAC AACAACGATA TGATCGACCA GCTGGAAGCA CGCATTGTG CGAAAGCCAG
TCAGCTGGAC GAAGCGCGTC GAATTGACGT TCAGCAGGTT GAAAAATAAG CGGCCGCTCT
AGAACTAGTG GATCCCCCGG GCTGCAGGAA TTCGAGGAGA AATTAACCAT GTATATCGGG
ATAGATCTTG GCACCTCGGG CGTAAAAGTT ATTTGCTCA ACGAGCAGGG TGAGGTGGTT
GCTGCGCAAA CGGAAAAGCT GACCGTTTCG CGCCCGCATC CACTCTGGTC GGAACAAGAC
CCGGAACAGT GGTGGCAGGC AACTGATCGC GCAATGAAAG CTCTGGGCGA TCAGCATTCT
CTGCAGGACG TTAAAGCATT GGGTATTGCC GGCCAGATGC ACGGAGCAAC CTTGCTGGAT
GCTCAGCAAC GGGTGTTACG CCCTGCCATT TTGTGGAACG ACGGGCGCTG TGCGCAAGAG
TGCACTTTGC TGGAAGCGCG AGTTCCGCAA TCGCGGGTGA TTACCGGCAA CCTGATGATG
CCCGGATTTA CTGCGCCTAA ATTGCTATGG GTTCAGCGGC ATGAGCCGGA GATATTCCGT
CAAATCGACA AAGTATTATT ACCGAAAGAT TACTTGCGTC TGCGTATGAC GGGGGAGTTT
GCCAGCGATA TGTCTGACGC AGCTGGCACC ATGTGGCTGG ATGTCGCAAA GCGTGACTGG
AGTGACGTCA TGCTGCAGGC TTGCGACTTA TCTCGTGACC AGATGCCCGC ATTATACGAA
GGCAGCGAAA TTACTGGTGC TTTGTTACCT GAAGTTGCGA AAGCGTGGGG TATGGCGACG
GTGCCAGTTG TCGCAGGCGG TGGCGACAAT GCAGCTGGTG CAGTTGGTGT GGGAATGGTT
GATGCTAATC AGGCAATGTT ATCGCTGGGG ACGTCGGGGG TCTATTTTGC TGTCAGCGAA
GGGTTCTTAA GCAAGCCAGA AAGCGCCGTA CATAGCTTTT GCCATGCGCT ACCGCAACGT
TGGCATTTAA TGTCTGTGAT GCTGAGTGCA GCGTCGTGTC TGGATTGGGC CGCGAAATTA
ACCGGCCTGA GCAATGTCCC AGCTTTAATC GCTGCAGCTC AACAGGCTGA TGAAAGTGCC
GAGCCAGTTT GGTTTCTGCC TTATCTTTCC GGCGAGCGTA CGCCACACAA TAATCCCCAG
GCGAAGGGGG TTTTCTTTGG TTTGACTCAT CAACATGGCC CCAATGAACT GGCGCGAGCA
GTGCTGGAAG GCGTGGGTTA TGCGCTGGCA GATGGCATGG ATGTCGTGCA TGCCTGCGGT
ATTAAACCGC AAAGTGTTAC GTTGATTGGG GGCGGGGCGC GTAGTGAGTA CTGGCGTCAG
ATGCTGGCGG ATATCAGCGG TCAGCAGCTC GATTACCGTA CGGGGGGGGA TGTGGGGCCA
GCACTGGGCG CAGCAAGGCT GGCGCAGATC GCGGCGAATC CAGAGAAATC GCTCATTGAA
TTGTTGCCGC AACTACCGTT AGAACAGTCG CATCTACCAG ATGCGCAGCG TTATGCCGCT
TATCAGCCAC GACGAGAAAC GTTCCGTCGC CTCTATCAGC AACTTCTGCC ATTAATGGCG
TAAAAGCTTG AGGAGAAATT AACCATGAAG CAACTCACCA TTCTGGGCTC GACCGGCTCG
ATTGGTTGCA GCACGCTGGA CGTGGTGCGC CATAATCCCG AACACTTCCG CGTAGTTGCG
CTGGTGGCAG GCAAAAATGT CACTCGCATG GTAGAACAGT GCCTGGAATT CTCTCCCCGC
TATGCCGTAA TGGACGATGA AGCGAGTGCG AAACTTCTTA AAACGATGCT ACAGCAACAG
GGTAGCCGCA CCGAAGTCTT AAGTGGGCAA CAAGCCGCTT GCGATATGGC AGCGCTTGAG
GATGTTGATC AGGTGATGGC AGCCATTGTT GGCGCTGCTG GGCTGTTACC TACGCTTGCT
GCGATCCGCG CGGGTAAAAC CATTTTGCTG GCCAATAAAG AATCACTGGT TACCTGCGGA
CGTCTGTTTA TGGACGCCGT AAAGCAGAGC AAAGCGCAAT GTTACCGGT CGATAGCGAA
CATAACGCCA TTTTTCAGAG TTTACCGCAA CCTATCCAGC ATAATCTGGG ATACGCTGAC
CTTGAGCAAA ATGGCGTGGT GTCCATTTTA CTTACCGGGT CTGGTGGCCC TTTCCGTGAG
ACGCCATTGC GCGATTTGGC AACAATGACG CCGGATCAAG CCTGCCGTCA TCCGAACTGG
TCGATGGGGC GTAAATTTC TGTCGATTCG GCTACCATGA TGAACAAAGG TCTGGAATAC
ATTGAAGCGC GTTGGCTGTT TAACGCCAGC GCCAGCCAGA TGGAAGTGCT GATTCACCCG
CAGTCAGTGA TTCACTCAAT GGTGCGCTAT CAGGACGGCA GTGTTCTGGC GCAGCTGGGG
GAACCGGATA TGCGTACGCC AATTGCCCAC ACCATGGCAT GGCCGAATCG CGTGAACTCT
GGCGTGAAGC CGCTCGATTT TTGCAAACTA AGTGCGTTGA CATTTGCCGC ACCGGATTAT
GATCGTTATC CATGCCTGAA ACTGGCGATG GAGGCGTTCG AACAAGGCCA GGCAGCGACG
```

*FIG. 15 (CONT'D.)*

```
ACAGCATTGA ATGCCGCAAA CGAAATCACC GTTGCTGCTT TTCTTGCGCA ACAAATCCGC
TTTACGGATA TCGCTGCGTT GAATTTATCC GTACTGGAAA AAATGGATAT GCGCGAACCA
CAATGTGTGG ACGATGTGTT ATCTGTTGAT GCGAACGCGC GTGAAGTCGC CAGAAAAGAG
GTGATGCGTC TCGCAAGCTG AGTCGACGAG GAGAAATTAA CCATGGCAAC CACTCATTTG
GATGTTTGCG CCGTGGTTCC GGCGGCCGGA TTTGGCCGTC GAATGCAAAC GGAATGTCCT
AAGCAATATC TCTCAATCGG TAATCAAACC ATTCTTGAAC ACTCGGTGCA TGCGCTGCTG
GCGCATCCCC GGGTGAAACG TGTCGTCATT GCCATAAGTC CTGGCGATAG CCGTTTTGCA
CAACTTCCTC TGGCGAATCA TCCGCAAATC ACCGTTGTAG ATGGCGGTGA TGAGCGTGCC
GATTCCGTGC TGGCAGGTCT GAAAGCCGCT GGCGACGCGC AGTGGGTATT GGTGCATGAC
GCCGCTCGTC CTTGTTTGCA TCAGGATGAC CTCGCGCGAT TGTTGGCGTT GAGCGAAACC
AGCCGCACGG GGGGGATCCT CGCCGCACCA GTGCGCGATA CTATGAAACG TGCCGAACCG
GGCAAAAATG CCATTGCTCA TACCGTTGAT CGCAACGGCT TATGGCACGC GCTGACGCCG
CAATTTTTCC CTCGTGAGCT GTTACATGAC TGTCTGACGC GCGCTCTAAA TGAAGGCGCG
ACTATTACCG ACGAAGCCTC GGCGCTGGAA TATTGCGGAT CCATCCTCA GTTGGTCGAA
GGCCGTGCGG ATAACATTAA AGTCACGCGC CCGGAAGATT TGGCACTGGC CGAGTTTTAC
CTCACCCGAA CCATCCATCA GGAGAATACA TAATGCGAAT TGGACACGGT TTTGACGTAC
ATGCCTTTGG CGGTGAAGGC CCAATTATCA TTGGTGGCGT ACGCATTCCT TACGAAAAAG
GATTGCTGGC GCATTCTGAT GGCGACGTGG CGCTCCATGC GTTGACCGAT GCATTGCTTG
GCGCGGCGGC GCTGGGGGAT ATCGGCAAGC TGTTCCCGGA TACCGATCCG GCATTTAAAG
GTGCCGATAG CCGCGAGCTG CTACGCGAAG CCTGGCGTCG TATTCAGGCG AAGGGTTATA
CCCTTGGCAA CGTCGATGTC ACTATCATCG CTCAGGCACC GAAGATGTTG CCGCACATTC
CACAAATGCG CGTGTTTATT GCCGAAGATC TCGGCTGCCA TATGGATGAT GTTAACGTGA
AAGCCACTAC TACGGAAAAA CTGGGATTTA CCGGACGTGG GGAAGGGATT GCCTGTGAAG
CGGTGGCGCT ACTCATTAAG GCAACAAAAT GACTCGAGGA GGAGAAATTA CCATGCGGA
CACAGTGGCC CTCTCCGGCA AAACTTAATC TGTTTTTATA CATTACCGGT CAGCGTGCGG
ATGGTTACCA CACGCTGCAA ACGCTGTTTC AGTTTCTTGA TTACGGCGAC ACCATCAGCA
TTGAGCTTCG TGACGATGGG GATATTCGTC TGTTAACGCC CGTTGAAGGC GTGGAACATG
AAGATAACCT GATCGTTCGC GCAGCGCGAT TGTTGATGAA AACTGCGGCA GACAGCGGGC
GTCTTCCGAC GGGAAGCGGT GCGAATATCA GCATTGACAA GCGTTTGCCG ATGGGCGGCG
GTCTCGGCGG TGGTTCATCC AATGCCGCGA CGGTCCTGGT GGCATTAAAT CATCTCTGGC
AATGCGGGCT AAGCATGGAT GAGCTGGCGG AAATGGGGCT GACGCTGGGC GCAGATGTTC
CTGTCTTTGT TCGGGGGCAT GCCGCGTTTG CCGAAGGCGT TGGTGAAATA CTAACGCCGG
TGGATCCGCC AGAGAAGTGG TATCTGGTGG CGCACCCTGG TGTAAGTATT CCGACTCCGG
TGATTTTTAA AGATCCTGAA CTCCCGCGCA ATACGCCAAA AAGGTCAATA GAAACGTTGC
TAAAATGTGA ATTCAGCAAT GATTGCGAGG TTATCGCAAG AAAACGTTTT CGCGAGGTTG
ATGCGGTGCT TTCCTGGCTG TTAGAATACG CCCCGTCGCG CCTGACTGGG ACAGGGGCCT
GTGTCTTTGC TGAATTTGAT ACAGAGTCTG AAGCCCGCCA GGTGCTAGAG CAAGCCCCGG
AATGGCTCAA TGGCTTTGTG GCGAAAGGCG CTAATCTTTC CCCATTGCAC AGAGCCATGC
TTTAAGGTAC CCAATTCGCC CTATAGTGAG TCGTATTACG CGCGCTCACT GGCCGTCGTT
TTACAACGTC GTGACTGGGA AAACCCTGGC GTTACCCAAC TTAATCGCCT TGCAGCACAT
CCCCCTTTCG CCAGCTGGCG TAATAGCGAA GAGGCCCGCA CCGATCGCCC TTCCCAACAG
TTGCGCAGCC TGAATGGCGA ATGGAAATTG TAAGCGTTAA TATTTTGTTA AAATTCGCGT
TAAATTTTTG TTAAATCAGC TCATTTTTTA ACCAATAGGC CGAAATCGGC AAAATCCCTT
ATAAATCAAA AGAATAGACC GAGATAGGGT TGAGTGTTGT TCCAGTTTGG AACAAGAGTC
CACTATTAAA GAACGTGGAC TCCAACGTCA AAGGGCGAAA AACCGTCTAT CAGGGCGATG
GCCCACTACG TGAACCATCA CCCTAATCAA GTTTTTTGGG GTCGAGGTGC CGTAAAGCAC
TAAATCGGAA CCCTAAAGGG AGCCCCCGAT TTAGAGCTTG ACGGGGAAAG CCGGCGAACG
TGGCGAGAAA GGAAGGGAAG AAAGCGAAAG GAGCGGGCGC TAGGGCGCTG GCAAGTGTAG
CGGTCACGCT GCGCGTAACC ACCACACCCG CCGCGCTTAA TGCCGCTA CAGGGCGCGT
CAG
```

*FIG. 15 (CONT'D.)*

DNA sequence of the vectorconstruct pACYClytBgcpE

| ID | PACYCGCLY | PRELIMINARY; | DNA; | 5793 BP. | | |
|---|---|---|---|---|---|---|
| SQ | SEQUENCE | 5793 BP; | 1375 A; | 1506 C; | 1543 G; | 1369 T; 0 OTHER; |

```
GAATTCCGGA TGAGCATTCA TCAGGCGGGC AAGAATGTGA ATAAAGGCCG GATAAAACTT
GTGCTTATTT TTCTTTACGG TCTTTAAAAA GGCCGTAATA TCCAGCTGAA CGGTCTGGTT
ATAGGTACAT TGAGCAACTG ACTGAAATGC CTCAAAATGT TCTTTACGAT GCCATTGGGA
TATATCAACG GTGGTATATC CAGTGATTTT TTTCTCCATT TTAGCTTCCT TAGCTCCTGA
AAATCTCGAT AACTCAAAAA ATACGCCCGG TAGTGATCTT ATTTCATTAT GGTGAAAGTT
GGAACCTCTT ACGTGCCGAT CAACGTCTCA TTTTCGCCAA AAGTTGGCCC AGGGCTTCCC
GGTATCAACA GGGACACCAG GATTTATTTA TTCTGCGAAG TGATCTTCCG TCACAGGTAT
TTATTCGGCG CAAAGTGCGT CGGGTGATGC TGCCAACTTA CTGATTTAGT GTATGATGGT
GTTTTTGAGG TGCTCCAGTG GCTTCTGTTT CTATCAGCTG TCCCTCCTGT TCAGCTACTG
ACGGGGTGGT GCGTAACGGC AAAAGCACCG CCGGACATCA GCGCTAGCGG AGTGTATACT
GGCTTACTAT GTTGGCACTG ATGAGGGTGT CAGTGAAGTG CTTCATGTGG CAGGAGAAAA
AAGGCTGCAC CGGTGCGTCA GCAGAATATG TGATACAGGA TATATTCCGC TTCCTCGCTC
ACTGACTCGC TACGCTCGGT CGTTCGACTG CGGCGAGCGG AAATGGCTTA CGAACGGGGC
GGAGATTTCC TGGAAGATGC CAGGAAGATA CTTAACAGGG AAGTGAGAGG GCCGCGGCAA
AGCCGTTTTT CCATAGGCTC CGCCCCCCTG ACAAGCATCA CGAAATCTGA CGCTCAAATC
AGTGGTGGCG AAACCCGACA GGACTATAAA GATACCAGGC GTTTCCCCCT GGCGGCTCCC
TCGTGCGCTC TCCTGTTCCT GCCTTTCGGT TTACCGGTGT CATTCCGCTG TTATGGCCGC
GTTTGTCTCA TTCCACGCCT GACACTCAGT TCCGGGTAGG CAGTTCGCTC CAAGCTGGAC
TGTATGCACG AACCCCCCGT TCAGTCCGAC CGCTGCGCCT TATCCGGTAA CTATCGTCTT
GAGTCCAACC CGGAAAGACA TGCAAAGCA CCACTGGCAG CAGCCACTGG TAATTGATTT
AGAGGAGTTA GTCTTGAAGT CATGCGCCGG TTAAGGCTAA ACTGAAAGGA CAAGTTTTGG
TGACTGCGCT CCTCCAAGCC AGTTACCTCG GTTCAAAGAG TTGGTAGCTC AGAGAACCTT
CGAAAAACCG CCCTGCAAGG CGGTTTTTTC GTTTTCAGAG CAAGAGATTA CGCGCAGACC
AAAACGATCT CAAGAAGATC ATCTTATTAA TCAGATAAAA TATTTCTAGA TTTCAGTGCA
ATTTATCTCT TCAAATGTAG CACCTGAAGT CAGCCCCATA CGATATAAGT TGTAATTCTC
ATGTTTGACA GCTTATCATC GATAAGCTTT AATGCGGTAG TTTATCACAG TTAAATTGCT
AACGCAGTCA GGCACCGTGT ATGAAATCTA ACAATGCGCT CATCGTCATC CTCGGCACCG
TCACCCTGGA TGCTGTAGGC ATAGGCTTGG TTATGCCGGT ACTGCCGGGC CTCTTGCGGG
ATATCGTCCA TTCCGACAGC ATCGCCAGTC ACTATGGCGT GCTGCTAGCG CTATATGCGT
TGATGCAATT TCTATGCGCA CCCGTTCTCG GAGCACTGTC CGACCGCTTT GGCCGCCGCC
CAGTCCTGCT CGCTTCGCTA CTTGGAGCCA CTATCGACTA CGCGATCATG GCGACCACAC
CGTCCTGTG GATCCGAGGA GAAATTAACC ATGCATAACC AGGCTCCAAT TCAACGTAGA
AAATCAACAC GTATTTACGT TGGGAATGTG CCGATTGGCG ATGGTGCTCC CATCGCCGTA
CAGTCCATGA CCAATACGCG TACGACAGAC GTCGAAGCAA CGGTCAATCA AATCAAGGCG
CTGGAACGCG TTGGCGCTGA TATCGTCCGT GTATCCGTAC CGACGATGGA CGCGGCAGAA
GCGTTCAAAC TCATCAAACA GCAGGTTAAC GTGCCGCTGG TGGCTGACAT CCACTTCGAC
TATCGCATTG CGCTGAAAGT AGCGGAATAC GGCGTCGATT GTCTGCGTAT TAACCCTGGC
AATATCGGTA ATGAAGAGCG TATTCGCATG GTGGTTGACT GTGCGCGCGA TAAAAACATT
CCGATCCGTA TTGGCGTTAA CGCCGGATCG CTGGAAAAAG ATCTGCAAGA AAAGTATGGC
GAACCGACGC CGCAGGCGTT GCTGGAATCT GCCATGCGTC ATGTTGATCA TCTCGATCGC
CTGAACTTCG ATCAGTTCAA AGTCAGCGTG AAAGCGTCTG ACGTCTTCCT CGCTGTTGAG
TCTTATCGTT TGCTGGCAAA ACAGATCGAT CAGCCGTTGC ATCTGGGGAT CACCGAAGCC
GGTGGTGCGC GCAGCGGGGC AGTAAAATCC GCCATTGGTT TAGGTCTGCT GCTGTCTGAA
GGCATCGGCG ACACGCTGCG CGTATCGCTG GCGGCCGATC CGGTCGAAGA GATCAAAGTC
GGTTTCGATA TTTTGAAATC GCTGCGTATC CGTTCGCGAG GGATCAACTT CATCGCCTGC
CCGACCTGTT CGCGTCAGGA ATTTGATGTT ATCGGTACGG TTAACGCGCT GGAGCAACGC
```

*FIG. 16*

```
CTGGAAGATA TCATCACTCC GATGGACGTT TCGATTATCG GCTGCGTGGT GAATGGCCCA
GGTGAGGCGC TGGTTTCTAC ACTCGGCGTC ACCGGCGGCA ACAAGAAAAG CGGCCTCTAT
GAAGATGGCG TGCGCAAAGA CCGTCTGGAC AACAACGATA TGATCGACCA GCTGGAAGCA
CGCATTCGTG CGAAAGCCAG TCAGCTGGAC GAAGCGCGTC GAATTGACGT TCAGCAGGTT
GAAAAATAAG TCGACGAGGA GAAATTAACC ATGCAGATCC TGTTGGCCAA CCCGCGTGGT
TTTTGTGCCG GGGTAGACCG CGCTATCAGC ATTGTTGAAA ACGCGCTGGC CATTTACGGC
GCACCGATAT ATGTCCGTCA CGAAGTGGTA CATAACCGCT ATGTGGTCGA TAGCTTGCGT
GAGCGTGGGG CTATCTTTAT TGAGCAGATT AGCGAAGTAC CGGACGGCGC GATCCTGATT
TTCTCCGCAC ACGGTGTTTC TCAGGCGGTA CGTAACGAAG CAAAAAGTCG CGATTTGACG
GTGTTTGATG CCACCTGTCC GCTGGTGACC AAAGTGCATA TGGAAGTCGC CCGCGCCAGT
CGCCGTGGCG AAGAATCTAT TCTCATCGGT CACGCCGGGC ACCCGGAAGT GGAAGGGACA
ATGGGCCAGT ACAGTAACCC GGAAGGGGA ATGTATCTGG TCAATCGCC GGACGATGTG
TGGAAACTGA CGGTCAAAAA CGAAGAGAAG CTCTCCTTTA TGACCCAGAC CACGCTGTCG
GTGGATGACA CGTCTGATGT GATCGACGCG CTGCGTAAAC GCTTCCCGAA AATTGTCGGT
CCGCGCAAAG ATGACATCTG CTACGCCACG ACTAACCGTC AGGAAGCGGT ACGCGCCCTG
GCAGAACAGG CGGAAGTTGT GTTGGTGGTC GGTTCGAAAA ACTCCTCCAA CTCCAACCGT
CTGGCGGAGC TGGCCCAGCG TATGGGCAAA CGCGCGTTTT TGATTGACGA TGCGAAAGAC
ATCCAGGAAG AGTGGGTGAA AGAGGTTAAA TGCGTCGGCG TGACTGCGGG CGCATCGGCT
CCGGATATTC TGGTGCAGAA TGTGGTGGCA CGTTTGCAGC AGCTGGGCGG TGGTGAAGCC
ATTCCGCTGG AAGGCCGTGA AGAAACATT GTTTTCGAAG TGCCGAAAGA GCTGCGTGTC
GATATTCGTG AAGTCGATTA ACGGCCGACG CGCTGGGCTA CGTCTTGCTG GCGTTCGCGA
CGCGAGGCTG GATGGCCTTC CCCATTATGA TTCTTCTCGC TTCCGGCGGC ATCGGGATGC
CCGCGTTGCA GGCCATGCTG TCCAGGCAGG TAGATGACGA CCATCAGGGA CAGCTTCAAG
GATCGCTCGC GGCTCTTACC AGCCTAACTT CGATCACTGG ACCGCTGATC GTCACGGCGA
TTTATGCCGC CTCGGCGAGC ACATGGAACG GGTTGGCATG GATTGTAGGC GCCGCCCTAT
ACCTTGTCTG CCTCCCCGCG TTGCGTCGCG GTGCATGGAG CCGGGCCACC TCGACCTGAA
TGGAAGCCGG CGGCACCTCG CTAACGGATT CACCACTCCA AGAATTGGAG CCAATCAATT
CTTGCGGAGA ACTGTGAATG CGCAAACCAA CCCTTGGCAG AACATATCCA TCGCGTCCGC
CATCTCCAGC AGCCGCACGC GGCGCATCTC GGGCAGCGTT GGGTCCTGGC CACGGGTGCG
CATGATCGTG CTCCTGTCGT TGAGGACCCG GCTAGGCTGG CGGGGTTGCC TTACTGGTTA
GCAGAATGAA TCACCGATAC GCGAGCGAAC GTGAAGCGAC TGCTGCTGCA AAACGTCTGC
GACCTGAGCA ACAACATGAA TGGTCTTCGG TTTCCGTGTT TCGTAAAGTC TGGAAACGCG
GAAGTCCCCT ACGTGCTGCT GAAGTTGCCC GCAACAGAGA GTGGAACCAA CCGGTGATAC
CACGATACTA TGACTGAGAG TCAACGCCAT GAGCGGCCTC ATTTCTTATT CTGAGTTACA
ACAGTCCGCA CCGCTGTCCG GTAGCTCCTT CCGGTGGGCG CGGGGCATGA CTATCGTCGC
CGCACTTATG ACTGTCTTCT TTATCATGCA ACTCGTAGGA CAGGTGCCGG CAGCGCCCAA
CAGTCCCCCG GCCACGGGGC CTGCCACCAT ACCCACGCCG AAACAAGCGC CCTGCACCAT
TATGTTCCGG ATCTGCATCG CAGGATGCTG CTGGCTACCC TGTGGAACAC CTACATCTGT
ATTAACGAAG CGCTAACCGT TTTTATCAGG CTCTGGGAGG CAGAATAAAT GATCATATCG
TCAATTATTA CCTCCACGGG GAGAGCCTGA GCAAACTGGC CTCAGGCATT TGAGAAGCAC
ACGGTCACAC TGCTTCCGGT AGTCAATAAA CCGGTAAACC AGCAATAGAC ATAAGCGGCT
ATTTAACGAC CCTGCCCTGA ACCGACGACC GGGTCGAATT TGCTTTCGAA TTTCTGCCAT
TCATCCGCTT ATTATCACTT ATTCAGGCGT AGCACCAGGC GTTTAAGGGC ACCAATAACT
GCCTTAAAAA AATTACGCCC CGCCCTGCCA CTCATCGCAG TACTGTTGTA ATTCATTAAG
CATTCTGCCG ACATGGAAGC CATCACAGAC GGCATGATGA ACCTGAATCG CCAGCGGCAT
CAGCACCTTG TCGCCTTGCG TATAATATTT GCCCATGGTG AAAACGGGGG CGAAGAAGTT
GTCCATATTG GCCACGTTTA AATCAAAACT GGTGAAACTC ACCCAGGGAT TGGCTGAGAC
GAAAAACATA TTCTCAATAA ACCCTTTAGG GAAATAGGCC AGGTTTTCAC CGTAACACGC
CACATCTTGC GAATATATGT GTAGAAACTG CCGGAAATCG TCGTGGTATT CACTCCAGAG
CGATGAAAAC GTTTCAGTTT GCTCATGGAA AACGGTGTAA CAAGGGTGAA CACTATCCCA
TATCACCAGC TCACCGTCTT TCATTGCCAT ACG
```

*FIG. 16 (CONT'D.)*

A and corresponding amino acid sequence of the *ispH* (formerly *lytB*) gene from
*Escherichia coli*

```
          10        20        30        40        50        60        70
          |         |         |         |         |         |         |
ATGCAGATCCTGTTGGCCAACCCGCGTGGTTTTTGTGCCGGGGTAGACCGCGCTATCAGCATTGTTGAAAAC
 M  Q  I  L  L  A  N  P  R  G  F  C  A  G  V  D  R  A  I  S  I  V  E  N 80        90       100       110       120       130       140
      |         |         |         |         |         |         |
GCGCTGGCCATTTACGGCGCACCGATATATGTCCGTCACGAAGTGGTACATAACCGCTATGTGGTCGATAGC
 A  L  A  I  Y  G  A  P  I  Y  V  R  H  E  V  V  H  N  R  Y  V  V  D  S 150       160       170       180       190       200       210
      |         |         |         |         |         |         |
TTGCGTGAGCGTGGGGCTATCTTTATTGAGCAGATTAGCGAAGTACCGGACGGCGCGATCCTGATTTTCTCC
 L  R  E  R  G  A  I  F  I  E  Q  I  S  E  V  P  D  G  A  I  L  I  F  S 220       230       240       250       260       270       280
      |         |         |         |         |         |         |
GCACACGGTGTTTCTCAGGCGGTACGTAACGAAGCAAAAAGTCGCGATTTGACGGTGTTTGATGCCACCTGT
 A  H  G  V  S  Q  A  V  R  N  E  A  K  S  R  D  L  T  V  F  D  A  T  C 290       300       310       320       330       340       350       360
  |         |         |         |         |         |         |         |
CCGCTGGTGACCAAAGTGCATATGGAAGTCGCCCGCGCCAGTCGCCGTGGCGAAGAATCTATTCTCATCGGT
 P  L  V  T  K  V  H  M  E  V  A  R  A  S  R  R  G  E  E  S  I  L  I  G 370       380       390       400       410       420       430
      |         |         |         |         |         |         |
CACGCCGGGCACCCGGAAGTGGAAGGGACAATGGGCCAGTACAGTAACCCGGAAGGGGGAATGTATCTGGTC
 H  A  G  H  P  E  V  E  G  T  M  G  Q  Y  S  N  P  E  G  G  M  Y  L  V 440       450       460       470       480       490       500
          |         |         |         |         |         |         |
GAATCGCCGGACGATGTGTGGAAACTGACGGTCAAAAACGAAGAGAAGCTCTCCTTTATGACCCAGACCACG
 E  S  P  D  D  V  W  K  L  T  V  K  N  E  E  K  L  S  F  M  T  Q  T  T 510       520       530       540       550       560       570
          |         |         |         |         |         |         |
CTGTCGGTGGATGACACGTCTGATGTGATCGACGCGCTGCGTAAACGCTTCCCGAAAATTGTCGGTCCGCGC
 L  S  V  D  D  T  S  D  V  I  D  A  L  R  K  R  F  P  K  I  V  G  P  R 580       590       600       610       620       630       640
      |         |         |         |         |         |         |
AAAGATGACATCTGCTACGCCACGACTAACCGTCAGGAAGCGGTACGCGCCCTGGCAGAACAGGCGGAAGTT
 K  D  D  I  C  Y  A  T  T  N  R  Q  E  A  V  R  A  L  A  E  Q  A  E  V 650       660       670       680       690       700       710       720
  |         |         |         |         |         |         |         |
GTGTTGGTGGTCGGTTCGAAAAACTCCTCCAACTCCAACCGTCTGGCGGAGCTGGCCCAGCGTATGGGCAAA
 V  L  V  V  G  S  K  N  S  S  N  S  N  R  L  A  E  L  A  Q  R  M  G  K 730       740       750       760       770       780       790
      |         |         |         |         |         |         |
```

*FIG. 17*

```
CGCGCGTTTTTGATTGACGATGCGAAAGACATCCAGGAAGAGTGGGTGAAAGAGGTTAAATGCGTCGGCGTG
  R  A  F  L  I  D  D  A  K  D  I  Q  E  E  W  V  K  E  V  K  C  V  G  V 800       810       820       830       840       850       860
        |         |         |         |         |         |         |
ACTGCGGGCGCATCGGCTCCGGATATTCTGGTGCAGAATGTGGTGGCACGTTTGCAGCAGCTGGGCGGTGGT
  T  A  G  A  S  A  P  D  I  L  V  Q  N  V  V  A  R  L  Q  Q  L  G  G  G 870       880       890       900       910       920       930
    |         |         |         |         |         |         |
GAAGCCATTCCGCTGGAAGGCCGTGAAGAAAACATTGTTTTCGAAGTGCCGAAAGAGCTGCGTGTCGATATT
  E  A  I  P  L  E  G  R  E  E  N  I  V  F  E  V  P  K  E  L  R  V  D  I 940       950
   |         |
CGTGAAGTCGATTAA
  R  E  V  D  -
```

*FIG. 17 (CONT'D.)*

DNA Sequence of the plasmid construct pBScyclogcpElytB2

| ID | PBSXICH2 | | PRELIMINARY; | DNA; | 9795 BP. | |
|---|---|---|---|---|---|---|
| SQ | SEQUENCE | 9795 BP; | 2351 A; | 2401 C; | 2770 G; | 2273 T; 0 OTHER; |

```
GTGGCACTTT TCGGGGAAAT GTGCGCGGAA CCCCTATTTG TTTATTTTTC TAAATACATT
CAAATATGTA TCCGCTCATG AGACAATAAC CCTGATAAAT GCTTCAATAA TATTGAAAAA
GGAAGAGTAT GAGTATTCAA CATTTCCGTG TCGCCCTTAT TCCCTTTTTT GCGGCATTTT
GCCTTCCTGT TTTTGCTCAC CCAGAAACGC TGGTGAAAGT AAAAGATGCT GAAGATCAGT
TGGGTGCACG AGTGGGTTAC ATCGAACTGG ATCTCAACAG CGGTAAGATC CTTGAGAGTT
TTCGCCCCGA AGAACGTTTT CCAATGATGA GCACTTTTAA AGTTCTGCTA TGTGGCGCGG
TATTATCCCG TATTGACGCC GGGCAAGAGC AACTCGGTCG CCGCATACAC TATTCTCAGA
ATGACTTGGT TGAGTACTCA CCAGTCACAG AAAAGCATCT TACGGATGGC ATGACAGTAA
GAGAATTATG CAGTGCTGCC ATAACCATGA GTGATAACAC TGCGGCCAAC TTACTTCTGA
CAACGATCGG AGGACCGAAG GAGCTAACCG CTTTTTTGCA ACATGGGG GATCATGTAA
CTCGCCTTGA TCGTTGGGAA CCGGAGCTGA ATGAAGCCAT ACCAAACGAC GAGCGTGACA
CCACGATGCC TGTAGCAATG GCAACAACGT TGCGCAAACT ATTAACTGGC GAACTACTTA
CTCTAGCTTC CCGGCAACAA TTAATAGACT GGATGGAGGC GGATAAAGTT GCAGGACCAC
TTCTGCGCTC GGCCCTTCCG GCTGGCTGGT TTATTGCTGA TAAATCTGGA GCCGGTGAGC
GTGGGTCTCG CGGTATCATT GCAGCACTGG GGCCAGATGG TAAGCCCTCC CGTATCGTAG
TTATCTACAC GACGGGGAGT CAGGCAACTA TGGATGAACG AAATAGACAG ATCGCTGAGA
TAGGTGCCTC ACTGATTAAG CATTGGTAAC TGTCAGACCA AGTTTACTCA TATATACTTT
AGATTGATTT AAAACTTCAT TTTTAATTTA AAAGGATCTA GGTGAAGATC CTTTTTGATA
ATCTCATGAC CAAAATCCCT TAACGTGAGT TTTCGTTCCA CTGAGCGTCA GACCCCGTAG
AAAAGATCAA AGGATCTTCT TGAGATCCTT TTTTTCTGCG CGTAATCTGC TGCTTGCAAA
CAAAAAAACC ACCGCTACCA GCGGTGGTTT GTTTGCCGGA TCAAGAGCTA CCAACTCTTT
TTCCGAAGGT AACTGGCTTC AGCAGAGCGC AGATACCAAA TACTGTCCTT CTAGTGTAGC
CGTAGTTAGG CCACCACTTC AAGAACTCTG TAGCACCGCC TACATACCTC GCTCTGCTAA
TCCTGTTACC AGTGGCTGCT GCCAGTGGCG ATAAGTCGTG TCTTACCGGG TTGGACTCAA
GACGATAGTT ACCGGATAAG GCGCAGCGGT CGGGCTGAAC GGGGGGTTCG TGCACACAGC
CCAGCTTGGA GCGAACGACC TACACCGAAC TGAGATACCT ACAGCGTGAG CTATGAGAAA
GCGCCACGCT TCCCGAAGGG AGAAAGGCGG ACAGGTATCC GGTAAGCGGC AGGGTCGGAA
CAGGAGAGCG CACGAGGGAG CTTCCAGGGG GAAACGCCTG GTATCTTTAT AGTCCTGTCG
GGTTTCGCCA CCTCTGACTT GAGCGTCGAT TTTTGTGATG CTCGTCAGGG GGGCGGAGCC
TATGGAAAAA CGCCAGCAAC GCGGCCTTTT TACGGTTCCT GGCCTTTTGC TGGCCTTTTG
CTCACATGTT CTTTCCTGCG TTATCCCCTG ATTCTGTGGA TAACCGTATT ACCGCCTTTG
AGTGAGCTGA TACCGCTCGC CGCAGCCGAA CGACCGAGCG CAGCGAGTCA GTGAGCGAGG
AAGCGGAAGA GCGCCCAATA CGCAAACCGC CTCTCCCCGC GCGTTGGCCG ATTCATTAAT
GCAGCTGGCA CGACAGGTTT CCCGACTGGA AAGCGGGCAG TGAGCGCAAC GCAATTAATG
TGAGTTAGCT CACTCATTAG GCACCCCAGG CTTTACACTT TATGCTTCCG GCTCGTATGT
TGTGTGGAAT TGTGAGCGGA TAACAATTTC ACACAGGAAA CAGCTATGAC CATGATTACG
CCAAGCGCGC AATTAACCCT CACTAAAGGG AACAAAAGCT GGAGCTCCAC CGCGGGAGGA
GAAATTAACC ATGCATAACC AGGCTCCAAT TCAACGTAGA AAATCAACAC GTATTTACGT
TGGGAATGTG CCGATTGGCG ATGGTGCTCC CATCGCCGTA CAGTCCATGA CCAATACGCG
TACGACAGAC GTCGAAGCAA CGGTCAATCA AATCAAGGCG CTGGAACGCG TTGGCGCTGA
TATCGTCCGT GTATCCGTAC CGACGATGGA CGCGGCAGAA GCGTTCAAAC TCATCAAACA
GCAGGTTAAC GTGCCGCTGG TGGCTGACAT CCACTTCGAC TATCGCATTG CGCTGAAAGT
AGCGGAATAC GGCGTCGATT GTCTGCGTAT TAACCCTGGC AATATCGGTA ATGAAGAGCG
TATTCGCATG GTGGTTGACT GTGCGCGCGA TAAAAACATT CCGATCCGTA TTGGCGTTAA
CGCCGGATCG CTGGAAAAAG ATCTGCAAGA AAAGTATGGC GAACCGACGC CGCAGGCGTT
GCTGGAATCT GCCATGCGTC ATGTTGATCA TCTCGATCGC CTGAACTTCG ATCAGTTCAA
```

FIG. 18

```
AGTCAGCGTG AAAGCGTCTG ACGTCTTCCT CGCTGTTGAG TCTTATCGTT TGCTGGCAAA
ACAGATCGAT CAGCCGTTGC ATCTGGGGAT CACCGAAGCC GGTGGTGCGC GCAGCGGGGC
AGTAAAATCC GCCATTGGTT TAGGTCTGCT GCTGTCTGAA GGCATCGGCG ACACGCTGCG
CGTATCGCTG GCGGCCGATC CGGTCGAAGA GATCAAAGTC GGTTTCGATA TTTTGAAATC
GCTGCGTATC CGTTCGCGAG GGATCAACTT CATCGCCTGC CCGACCTGTT CGCGTCAGGA
ATTTGATGTT ATCGGTACGG TTAACGCGCT GGAGCAACGC CTGGAAGATA TCATCACTCC
GATGGACGTT TCGATTATCG GCTGCGTGGT GAATGGCCCA GGTGAGGCGC TGGTTTCTAC
ACTCGGCGTC ACCGGCGGCA ACAAGAAAAG CGGCCTCTAT GAAGATGGCG TGCGCAAAGA
CCGTCTGGAC AACAACGATA TGATCGACCA GCTGGAAGCA CGCATTCGTG CGAAAGCCAG
TCAGCTGGAC GAAGCGCGTC GAATTGACGT TCAGCAGGTT GAAAAATAAG TCGACGAGGA
GAAATTAACC ATGCAGATCC TGTTGGCCAA CCCGCGTGGT TTTTGTGCCG GGGTAGACCG
CGCTATCAGC ATTGTTGAAA ACGCGCTGGC CATTTACGGC GCACCGATAT ATGTCCGTCA
CGAAGTGGTA CATAACCGCT ATGTGGTCGA TAGCTTGCGT GAGCGTGGGG CTATCTTTAT
TGAGCAGATT AGCGAAGTAC CGGACGGCGC GATCCTGATT TTCTCCGCAC ACGGTGTTTC
TCAGGCGGTA CGTAACGAAG CAAAAGTCG CGATTTGACG GTGTTTGATG CCACCTGTCC
GCTGGTGACC AAAGTGCATA TGGAAGTCGC CCGCGCCAGT CGCCGTGGCG AAGAATCTAT
TCTCATCGGT CACGCCGGGC ACCCGGAAGT GGAAGGGACA ATGGGCCAGT ACAGTAACCC
GGAAGGGGGA ATGTATCTGG TCGAATCGCC GGACGATGTG TGGAAACTGA CGGTCAAAAA
CGAAGAGAAG CTCTCCTTTA TGACCCAGAC CACGCTGTCG GTGGATGACA CGTCTGATGT
GATCGACGCG CTGCGTAAAC GCTTCCCGAA AATTGTCGGT CCGCGCAAAG ATGACATCTG
CTACGCCACG ACTAACCGTC AGGAAGCGGT ACGCGCCCTG GCAGAACAGG CGGAAGTTGT
GTTGGTGGTC GGTTCGAAAA ACTCCTCCAA CTCCAACCGT CTGGCGGAGC TGGCCCAGCG
TATGGGCAAA CGCGCGTTTT TGATTGACGA TGCGAAAGAC ATCCAGGAAG AGTGGGTGAA
AGAGGTTAAA TGCGTCGGCG TGACTGCGGG CGCATCGGCT CCGGATATTC TGGTGCAGAA
TGTGGTGGCA CGTTTGCAGC AGCTGGGCGG TGGTGAAGCC ATTCCGCTGG AAGGCCGTGA
AGAAAACATT GTTTTCGAAG TGCCGAAAGA GCTGCGTGTC GATATTCGTG AAGTCGATTA
AGCGGCCGCT CTAGAACTAG TGGATCCCCC GGGCTGCAGG AATTCGAGGA GAAATTAACC
ATGTATATCG GGATAGATCT TGGCACCTCG GGCGTAAAAG TTATTTTGCT CAACGAGCAG
GGTGAGGTGG TTGCTGCGCA AACGGAAAAG CTGACCGTTT CGCGCCCGCA TCCACTCTGG
TCGGAACAAG ACCCGGAACA GTGGTGGCAG GCAACTGATC GCGCAATGAA AGCTCTGGGC
GATCAGCATT CTCTGCAGGA CGTTAAAGCA TTGGGTATTG CCGGCCAGAT GCACGGAGCA
ACCTTGCTGG ATGCTCAGCA ACGGGTGTTA CGCCCTGCCA TTTTGTGGAA CGACGGGCGC
TGTGCGCAAG AGTGCACTTT GCTGGAAGCG CGAGTTCCGC AATCGCGGGT GATTACCGGC
AACCTGATGA TGCCCGGATT TACTGCGCCT AAATTGCTAT GGGTTCAGCG GCATGAGCCG
GAGATATTCC GTCAAATCGA CAAAGTATTA TTACCGAAAG ATTACTTGCG TCTGCGTATG
ACGGGGGAGT TTGCCAGCGA TATGTCTGAC GCAGCTGGCA CCATGTGGCT GGATGTCGCA
AAGCGTGACT GGAGTGACGT CATGCTGCAG GCTTGCGACT TATCTCGTGA CCAGATGCCC
GCATTATACG AAGGCAGCGA AATTACTGGT GCTTTGTTAC CTGAAGTTGC GAAAGCGTGG
GGTATGGCGA CGGTGCCAGT TGTCGCAGGC GGTGGCGACA ATGCAGCTGG TGCAGTTGGT
GTGGGAATGG TTGATGCTAA TCAGGCAATG TTATCGCTGG GGACGTCGGG GGTCTATTTT
GCTGTCAGCG AAGGGTTCTT AAGCAAGCCA GAAAGCGCCG TACATAGCTT TTGCCATGCG
CTACCGCAAC GTTGGCATTT AATGTCTGTG ATGCTGAGTG CAGCGTCGTG TCTGGATTGG
GCCGCGAAAT TAACCGGCCT GAGCAATGTC CCAGCTTTAA TCGCTGCAGC TCAACAGGCT
GATGAAAGTG CCGAGCCAGT TTGGTTTCTG CCTTATCTTT CCGGCGAGCG TACGCCACAC
AATAATCCCC AGGCGAAGGG GGTTTTCTTT GGTTTGACTC ATCAACATGG CCCCAATGAA
CTGGCGCGAG CAGTGCTGGA AGGCGTGGGT TATGCGCTGG CAGATGGCAT GGATGTCGTG
CATGCCTGCG GTATTAAACC GCAAAGTGTT ACGTTGATTG GGGGCGGGGC GCGTAGTGAG
TACTGGCGTC AGATGCTGGC GGATATCAGC GGTCAGCAGC TCGATTACCG TACGGGGGGG
GATGTGGGGC CAGCACTGGG CGCAGCAAGG CTGGCGCAGA TCGCGGCGAA TCCAGAGAAA
TCGCTCATTG AATTGTTGCC GCAACTACCG TTAGAACAGT CGCATCTACC AGATGCGCAG
CGTTATGCCG CTTATCAGCC ACGACGAGAA ACGTTCCGTC GCCTCTATCA GCAACTTCTG
CCATTAATGG CGTAAAAGCT TGAGGAGAAA TTAACCATGA AGCAACTCAC CATTCTGGGC
```

FIG. 18 (CONT'D.)

```
TCGACCGGCT CGATTGGTTG CAGCACGCTG GACGTGGTGC GCCATAATCC CGAACACTTC
CGCGTAGTTG CGCTGGTGGC AGGCAAAAAT GTCACTCGCA TGGTAGAACA GTGCCTGGAA
TTCTCTCCCC GCTATGCCGT AATGGACGAT GAAGCGAGTG CGAAACTTCT TAAAACGATG
CTACAGCAAC AGGGTAGCCG CACCGAAGTC TTAAGTGGGC AACAAGCCGC TTGCGATATG
GCAGCGCTTG AGGATGTTGA TCAGGTGATG GCAGCCATTG TTGGCGCTGC TGGGCTGTTA
CCTACGCTTG CTGCGATCCG CGCGGGTAAA ACCATTTTGC TGGCCAATAA AGAATCACTG
GTTACCTGCG GACGTCTGTT TATGGACGCC GTAAAGCAGA GCAAAGCGCA ATTGTTACCG
GTCGATAGCG AACATAACGC CATTTTTCAG AGTTTACCGC AACCTATCCA GCATAATCTG
GGATACGCTG ACCTTGAGCA AAATGGCGTG GTGTCCATTT TACTTACCGG GTCTGGTGGC
CCTTTCCGTG AGACGCCATT GCGCGATTTG GCAACAATGA CGCCGGATCA AGCCTGCCGT
CATCCGAACT GGTCGATGGG GCGTAAAATT TCTGTCGATT CGGCTACCAT GATGAACAAA
GGTCTGGAAT ACATTGAAGC GCGTTGGCTG TTTAACGCCA GCGCCAGCCA GATGGAAGTG
CTGATTCACC CGCAGTCAGT GATTCACTCA ATGGTGCGCT ATCAGGACGG CAGTGTTCTG
GCGCAGCTGG GGGAACCGGA TATGCGTACG CCAATTGCCC ACACCATGGC ATGGCCGAAT
CGCGTGAACT CTGGCGTGAA GCCGCTCGAT TTTTGCAAAC TAAGTGCGTT GACATTTGCC
GCACCGGATT ATGATCGTTA TCCATGCCTG AAACTGGCGA TGGAGGCGTT CGAACAAGGC
CAGGCAGCGA CGACAGCATT GAATGCCGCA AACGAAATCA CCGTTGCTGC TTTTCTTGCG
CAACAAATCC GCTTTACGGA TATCGCTGCG TTGAATTTAT CCGTACTGGA AAAAATGGAT
ATGCGCGAAC CACAATGTGT GGACGATGTG TTATCTGTTG ATGCGAACGC GCGTGAAGTC
GCCAGAAAAG AGGTGATGCG TCTCGCAAGC TGAGTCGACG AGGAGAAATT AACCATGGCA
ACCACTCATT TGGATGTTTG CGCCGTGGTT CCGGCGGCCG GATTTGGCCG TCGAATGCAA
ACGGAATGTC CTAAGCAATA TCTCTCAATC GGTAATCAAA CCATTCTTGA ACACTCGGTG
CATGCGCTGC TGGCGCATCC CCGGGTGAAA CGTGTCGTCA TTGCCATAAG TCCTGGCGAT
AGCCGTTTTG CACAACTTCC TCTGGCGAAT CATCCGCAAA TCACCGTTGT AGATGGCGGT
GATGAGCGTG CCGATTCCGT GCTGGCAGGT CTGAAAGCCG CTGGCGACGC GCAGTGGGTA
TTGGTGCATG ACGCCGCTCG TCCTTGTTTG CATCAGGATG ACCTCGCGCG ATTGTTGGCG
TTGAGCGAAA CCAGCCGCAC GGGGGGGATC CTCGCCGCAC CAGTGCGCGA TACTATGAAA
CGTGCCGAAC CGGGCAAAAA TGCCATTGCT CATACCGTTG ATCGCAACGG CTTATGGCAC
GCGCTGACGC CGCAATTTTT CCCTCGTGAG CTGTTACATG ACTGTCTGAC GCGCGCTCTA
AATGAAGGCG CGACTATTAC CGACGAAGCC TCGGCGCTGG AATATTGCGG ATTCCATCCT
CAGTTGGTCG AAGGCCGTGC GGATAACATT AAAGTCACGC GCCCGGAAGA TTTGGCACTG
GCCGAGTTTT ACCTCACCCG AACCATCCAT CAGGAGAATA CATAATGCGA ATTGGACACG
GTTTTGACGT ACATGCCTTT GGCGGTGAAG GCCCAATTAT CATTGGTGGC GTACGCATTC
CTTACGAAAA AGGATTGCTG GCGCATTCTG ATGGCGACGT GGCGCTCCAT GCGTTGACCG
ATGCATTGCT TGGCGCGGCG GCGCTGGGGG ATATCGGCAA GCTGTTCCCG GATACCGATC
CGGCATTTAA AGGTGCCGAT AGCCGCGAGC TGCTACGCGA AGCCTGGCGT CGTATTCAGG
CGAAGGGTTA TACCCTTGGC AACGTCGATG TCACTATCAT CGCTCAGGCA CCGAAGATGT
TGCCGCACAT TCCACAAATG CGCGTGTTTA TTGCCGAAGA TCTCGGCTGC CATATGGATG
ATGTTAACGT GAAAGCCACT ACTACGGAAA AACTGGGATT TACCGGACGT GGGGAAGGGA
TTGCCTGTGA AGCGGTGGCG CTACTCATTA AGGCAACAAA ATGACTCGAG GAGGAGAAAT
TAACCATGCG GACACAGTGG CCCTCTCCGG CAAAACTTAA TCTGTTTTTA TACATTACCG
GTCAGCGTGC GGATGGTTAC CACACGCTGC AAACGCTGTT TCAGTTTCTT GATTACGGCG
ACACCATCAG CATTGAGCTT CGTGACGATG GGATATTCG TCTGTTAACG CCCGTTGAAG
GCGTGGAACA TGAAGATAAC CTGATCGTTC GCGCAGCGCG ATTGTTGATG AAAACTGCGG
CAGACAGCGG GCGTCTTCCG ACGGGAAGCG GTGCGAATAT CAGCATTGAC AAGCGTTTGC
CGATGGGCGG CGGTCTCGGC GGTGGTTCAT CCAATGCCGC GACGGTCCTG GTGGCATTAA
ATCATCTCTG GCAATGCGGG CTAAGCATGG ATGAGCTGGC GGAAATGGGG CTGACGCTGG
GCGCAGATGT TCCTGTCTTT GTTCGGGGGC ATGCCGCGTT TGCCGAAGGC GTTGGTGAAA
TACTAACGCC GGTGGATCCG CCAGAGAAGT GGTATCTGGT GGCGCACCCT GGTGTAAGTA
TTCCGACTCC GGTGATTTTT AAAGATCCTG AACTCCCGCG CAATACGCCA AAAAGGTCAA
TAGAAACGTT GCTAAAATGT GAATTCAGCA ATGATTGCGA GGTTATCGCA AGAAACGTT
TTCGCGAGGT TGATGCGGTG CTTTCCTGGC TGTTAGAATA CGCCCCGTCG CGCCTGACTG
```

*FIG. 18 (CONT'D.)*

```
GGACAGGGGC CTGTGTCTTT GCTGAATTTG ATACAGAGTC TGAAGCCCGC CAGGTGCTAG
AGCAAGCCCC GGAATGGCTC AATGGCTTTG TGGCGAAAGG CGCTAATCTT TCCCCATTGC
ACAGAGCCAT GCTTTAAGGT ACCCAATTCG CCCTATAGTG AGTCGTATTA CGCGCGCTCA
CTGGCCGTCG TTTTACAACG TCGTGACTGG GAAAACCCTG GCGTTACCCA ACTTAATCGC
CTTGCAGCAC ATCCCCCTTT CGCCAGCTGG CGTAATAGCG AAGAGGCCCG CACCGATCGC
CCTTCCCAAC AGTTGCGCAG CCTGAATGGC GAATGGAAAT TGTAAGCGTT AATATTTTGT
TAAAATTCGC GTTAAATTTT TGTTAAATCA GCTCATTTTT TAACCAATAG GCCGAAATCG
GCAAAATCCC TTATAAATCA AAAGAATAGA CCGAGATAGG GTTGAGTGTT GTTCCAGTTT
GGAACAAGAG TCCACTATTA AAGAACGTGG ACTCCAACGT CAAAGGGCGA AAAACCGTCT
ATCAGGGCGA TGGCCCACTA CGTGAACCAT CACCCTAATC AAGTTTTTTG GGGTCGAGGT
GCCGTAAAGC ACTAAATCGG AACCCTAAAG GGAGCCCCG ATTTAGAGCT TGACGGGGAA
AGCCGGCGAA CGTGGCGAGA AAGGAAGGGA AGAAAGCGAA AGGAGCGGGC GCTAGGGCGC
TGGCAAGTGT AGCGGTCACG CTGCGCGTAA CCACCACACC CGCCGCGCTT AATGCCCGC
TACAGGGCGC GTCAG
```

FIG. 18 (CONT'D.)

DNA and corresponding amino acid sequence of the *ispG* gene (fragment) from *Arabidopsis thaliana*

```
         10        20        30        40        50        60        70
          |         |         |         |         |         |         |
>AAGACGGTGAGAAGGAAGACTCGTACTGTTATGGTTGGAAATGTCGCCCTTGGAAGCGAACATCCGATAAGG
  K  T  V  R  R  K  T  R  T  V  M  V  G  N  V  A  L  G  S  E  H  P  I  R 80        90       100       110       120       130       140
          |         |         |         |         |         |         |
ATTCAAACGATGACTACTTCGGATACAAAAGATATTACTGGAACTGTTGATGAGGTTATGAGAATAGCGGAT
 I  Q  T  M  T  T  S  D  T  K  D  I  T  G  T  V  D  E  V  M  R  I  A  D 150       160       170       180       190       200       210
          |         |         |         |         |         |
AAAGGAGCTGATATTGTAAGGATAACTGTTCAAGGGAAGAAAGAGGCGGATGCGTGCTTTGAAATAAAAGAT
  K  G  A  D  I  V  R  I  T  V  Q  G  K  K  E  A  D  A  C  F  E  I  K  D 220       230       240       250       260       270       280
          |         |         |         |         |         |         |
AAACTCGTTCAGCTTAATTACAATACACCGCTGGTTGCAGGTATTCATTTTGCCCCTACTGTAGCCTTACGA
  K  L  V  Q  L  N  Y  N  T  P  L  V  A  G  I  H  F  A  P  T  V  A  L  R 290       300       310       320       330       340       350       360
  |         |         |         |         |         |         |         |
GTCGCTGAATGCTTTGACAAGATCCGTGTCAACCCCGGAAATTTTGCGGACAGGCGGGCCCAGTTTGAGACG
 V  A  E  C  F  D  K  I  R  V  N  P  G  N  F  A  D  R  R  A  Q  F  E  T 370       380       390       400       410       420       430
          |         |         |         |         |         |         |
ATAGATTATACAGAAGATGAATATCAGAAAGAACTCCAGCATATCGAGCAGGTCTTCACTCCTTTGGTTGAG
 I  D  Y  T  E  D  E  Y  Q  K  E  L  Q  H  I  E  Q  V  F  T  P  L  V  E 440       450       460       470       480       490       500
          |         |         |         |         |         |         |
AAATGCAAAAAGTACGGGAGAGCAATGCGTATTGGGACAAATCATGGAAGTCTTTCTGACCGTATCATGAGC
  K  C  K  K  Y  G  R  A  M  R  I  G  T  N  H  G  S  L  S  D  R  I  M  S 510       520       530       540       550       560       570
          |         |         |         |         |         |         |
TATTACGGGGATTCTCCCCGAGGAATGGTTGAATCTGCGTTTGAGTTTGCAAGAATATGTCGGAAATTAGAC
  Y  Y  G  D  S  P  R  G  M  V  E  S  A  F  E  F  A  R  I  C  R  K  L  D 580       590       600       610       620       630       640
          |         |         |         |         |         |
TATCACAACTTTGTTTTCTCAATGAAAGCGAGCAACCCAGTGATCATGGTCCAGGCGTACCGTTTACTTGTG

Y  H  N  F  V  F  S  M  K  A  S  N  P  V  I  M  V  Q  A  Y  R  L  L  V 650       660       670       680       690       700       710       720
  |         |         |         |         |         |         |         |
GCTGAGATGTATGTTCATGGATGGGATTATCCTTTGCATTTGGGAGTTACTGAGGCAGGAGAAGGCGAAGAT
  A  E  M  Y  V  H  G  W  D  Y  P  L  H  L  G  V  T  E  A  G  E  G  E  D 730       740       750       760       770       780       790
```

*FIG. 19*

```
          |         |         |         |         |         |         |
       GGACGGATGAAATCTGCGATTGGAATTGGGACGCTTCTTCAGGACGGGCTCGGTGACACAACAAGAGTTTCA
        G  R  M  K  S  A  I  G  I  G  T  L  L  Q  D  G  L  G  D  T  T  R  V  S 800       810       820       830       840       850       860
              |         |         |         |         |         |         |
       CTGACGGAGCCACCAGAAGAGGAGATAGATCCCTGCAGGCGATTGGCTAACCTCGGGACAAAAGCTGCCAAA
        L  T  E  P  P  E  E  E  I  D  P  C  R  R  L  A  N  L  G  T  K  A  A  K 870       880       890       900       910       920       930
              |         |         |         |         |         |         |
       CTTCAACAAGGCGCTGCACCGTTTGAAGAAAAGCATAGGCATTACTTTGATTTTCAGCGTCGGACGGGTGAT
        L  Q  Q  G  A  A  P  F  E  E  K  H  R  H  Y  F  D  F  Q  R  R  T  G  D 940       950       960       970       980       990      1000
              |         |         |         |         |         |         |
       CTACCTGTACAAAAGAGGGAGAAGAGGTTGATTACAGAAATGTCCTTCACCGTGATGGTTCTGTTCTGATG
        L  P  V  Q  K  E  G  E  E  V  D  Y  R  N  V  L  H  R  D  G  S  V  L  M 1010      1020      1030      1040      1050      1060      1070      1080
      |         |         |         |         |         |         |         |
       TCGATTTCTCTGGATCAACTAAAGGCACCTGAACTCCTCTACAGATCACTCGCCACAAAGCTTGTCGTGGGT
        S  I  S  L  D  Q  L  K  A  P  E  L  L  Y  R  S  L  A  T  K  L  V  V  G 1090      1100      1110      1120      1130      1140      1150
              |         |         |         |         |         |         |
       ATGCCATTCAAGGATCTGGCAACTGTTGATTCAATCTTATTAAGAGAGCTACCGCCTGTAGATGATCAAGTG
        M  P  F  K  D  L  A  T  V  D  S  I  L  L  R  E  L  P  P  V  D  D  Q  V 1160      1170      1180      1190      1200      1210      1220
              |         |         |         |         |         |         |
       GCTCGTTTGGCTCTCAAACGGTTGATTGATGTCAGTATGGGAGTTATAGCACCTTTATCAGAGCAACTAACA
        A  R  L  A  L  K  R  L  I  D  V  S  M  G  V  I  A  P  L  S  E  Q  L  T 1230      1240      1250      1260      1270      1280      1290
              |         |         |         |         |         |         |
       AAGCCATTGCCCAATGCCATGGTTCTTGTCAACCTCAAGGAACTATCTGGTGGCGCTTACAAGCTTCTCCCT
        K  P  L  P  N  A  M  V  L  V  N  L  K  E  L  S  G  G  A  Y  K  L  L  P 1300      1310      1320      1330      1340      1350      1360
              |         |         |         |         |         |         |
       GAAGGTACACGCTTGGTTGTCTCTCTACGAGGCGATGAGCCTTACGAGGAGCTTGAAATACTCAAAAACATT
        E  G  T  R  L  V  V  S  L  R  G  D  E  P  Y  E  E  L  E  I  L  K  N  I 1370      1380      1390      1400      1410      1420      1430      1440
      |         |         |         |         |         |         |         |
       GATGCTACTATGATTCTCCATGATGTACCTTTCACTGAAGACAAAGTTAGCAGAGTACATGCAGCTCGGAGG
        D  A  T  M  I  L  H  D  V  P  F  T  E  D  K  V  S  R  V  H  A  A  R  R 1450      1460      1470      1480      1490      1500      1510
              |         |         |         |         |         |         |
       CTATTCGAGTTCTTATCCGAGAATTCAGTTAACTTTCCTGTTATTCATCGCATAAACTTCCCAACCGGAATC
        L  F  E  F  L  S  E  N  S  V  N  F  P  V  I  H  R  I  N  F  P  T  G  I 1520      1530      1540      1550      1560      1570      1580
              |         |         |         |         |         |         |
       CACAGAGACGAATTGGTGATTCATGCAGGGACATATGCTGGAGGCCTTCTTGTGGATGGACTAGGTGATGGC
```

*FIG. 19 (CONT'D.)*

```
              H  R  D  E  L  V  I  H  A  G  T  Y  A  G  G  L  L  V  D  G  L  G  D  G
         1590        1600        1610        1620        1630        1640        1650
           |           |           |           |           |           |           |
        GTAATGCTCGAAGCACCTGACCAAGATTTTGATTTTCTTAGGAATACTTCCTTCAACTTATTACAAGGATGC
         V  M  L  E  A  P  D  Q  D  F  D  F  L  R  N  T  S  F  N  L  L  Q  G  C 1660        1670        1680        1690        1700        1710        1720
           |           |           |           |           |           |           |
        AGAATGCGTAACACTAAGACGGAATATGTATCGTGCCCGTCTTGTGGAAGAACGCTTTTCGACTTGCAAGAA
         R  M  R  N  T  K  T  E  Y  V  S  C  P  S  C  G  R  T  L  F  D  L  Q  E 1730        1740        1750        1760        1770        1780        1790        1800
      |           |           |           |           |           |           |           |
    ATCAGCGCCGAGATCCGAGAAAAGACTTCCCATTTACCTGGCGTTTCGATCGCAATCATGGGATGCATTGTG
     I  S  A  E  I  R  E  K  T  S  H  L  P  G  V  S  I  A  I  M  G  C  I  V 1810        1820        1830        1840        1850        1860        1870
           |           |           |           |           |           |           |
        AATGGACCAGGAGAAATGGCAGATGCTGATTTCGGATATGTAGGTGGTTCTCCCGGAAAAATCGACCTTTAT
         N  G  P  G  E  M  A  D  A  D  F  G  Y  V  G  G  S  P  G  K  I  D  L  Y 1880        1890        1900        1910        1920        1930        1940
           |           |           |           |           |           |           |
        GTCGGAAAGACGGTGGTGAAGCGTGGGATAGCTATGACGGAGGCAACAGATGCTCTGATCGGTCTGATCAAA
         V  G  K  T  V  V  K  R  G  I  A  M  T  E  A  T  D  A  L  I  G  L  I  K 1950        1960        1970        1980
           |           |           |           |
        GAACATGGTCGTTGGGTCGACCCGCCCGTGGCTGATGAGTAG
         E  H  G  R  W  V  D  P  P  V  A  D  E  -
```

*FIG. 19 (CONT'D.)*

DNA and corresponding amino acid sequence of the *ispG* (forrmly *gcpE*) gene of
*Arabidopsis thaliana*

```
ATGGCGACTGGAGTATTGCCAGCTCCGGTTTCTGGGATCAAGATACCGGATTCGAAAGTC    60
 M  A  T  G  V  L  P  A  P  V  S  G  I  K  I  P  D  S  K  V    20

GGGTTTGGTAAAAGCATGAATCTTGTGAGAATTTGTGATGTTAGGAGTCTAAGATCTGCT   120
 G  F  G  K  S  M  N  L  V  R  I  C  D  V  R  S  L  R  S  A    40

AGGAGAAGAGTTTCGGTTATCCGGAATTCAAACCAAGGCTCTGATTTAGCTGAGCTTCAA   180
 R  R  R  V  S  V  I  R  N  S  N  Q  G  S  D  L  A  E  L  Q    60

CCTGCATCCGAAGGAAGCCCTCTCTTAGTGCCAAGACAGAAATATTGTGAATCATTGCAT   240
 P  A  S  E  G  S  P  L  L  V  P  R  Q  K  Y  C  E  S  L  H    80

AAGACGGTGAGAAGGAAGACTCGTACTGTTATGGTTGGAAATGTCGCCCTTGGAAGCGAA   300
 K  T  V  R  R  K  T  R  T  V  M  V  G  N  V  A  L  G  S  E   100

CATCCGATAAGGATTCAAACGATGACTACTTCGGATACAAAAGATATTACTGGAACTGTT   360
 H  P  I  R  I  Q  T  M  T  T  S  D  T  K  D  I  T  G  T  V   120

GATGAGGTTATGAGAATAGCGGATAAAGGAGCTGATATTGTAAGGATAACTGTTCAAGGG   420
 D  E  V  M  R  I  A  D  K  G  A  D  I  V  R  I  T  V  Q  G   140

AAGAAAGAGGCGGATGCGTGCTTTGAAATAAAAGATAAACTCGTTCAGCTTAATTACAAT   480
 K  K  E  A  D  A  C  F  E  I  K  D  K  L  V  Q  L  N  Y  N   160

ACACCGCTGGTTGCAGGTATTCATTTTGCCCCTACTGTAGCCTTACGAGTCGCTGAATGC   540
 T  P  L  V  A  G  I  H  F  A  P  T  V  A  L  R  V  A  E  C   180

TTTGACAAGATCCGTGTCAACCCCGGAAATTTTGCGGACAGGCGGGCCCAGTTTGAGACG   600
 F  D  K  I  R  V  N  P  G  N  F  A  D  R  R  A  Q  F  E  T   200

ATAGATTATACAGAAGATGAATATCAGAAAGAACTCCAGCATATCGAGCAGGTCTTCACT   660
 I  D  Y  T  E  D  E  Y  Q  K  E  L  Q  H  I  E  Q  V  F  T   220

CCTTTGGTTGAGAAATGCAAAAAGTACGGGAGAGCAATGCGTATTGGGACAAATCATGGA   720
 P  L  V  E  K  C  K  K  Y  G  R  A  M  R  I  G  T  N  H  G   240

AGTCTTTCTGACCGTATCATGAGCTATTACGGGGATTCTCCCCGAGGAATGGTTGAATCT   780
 S  L  S  D  R  I  M  S  Y  Y  G  D  S  P  R  G  M  V  E  S   260

GCGTTTGAGTTTGCAAGAATATGTCGGAAATTAGACTATCACAACTTTGTTTTCTCAATG   840
 A  F  E  F  A  R  I  C  R  K  L  D  Y  H  N  F  V  F  S  M   280

AAAGCGAGCAACCCAGTGATCATGGTCCAGGCGTACCGTTTACTTGTGGCTGAGATGTAT   900
 K  A  S  N  P  V  I  M  V  Q  A  Y  R  L  L  V  A  E  M  Y   300

GTTCATGGATGGGATTATCCTTTGCATTTGGGAGTTACTGAGGCAGGAGAAGGCGAAGAT   960
 V  H  G  W  D  Y  P  L  H  L  G  V  T  E  A  G  E  G  E  D   320
```

FIG. 20

```
GGACGGATGAAATCTGCGATTGGAATTGGGACGCTTCTTCAGGACGGGCTCGGTGACACA 1020
 G  R  M  K  S  A  I  G  I  G  T  L  L  Q  D  G  L  G  D  T

ACAAGAGTTTCACTGACGGAGCCACCAGAAGAGGAGATAGATCCCTGCAGGCGATTGGCT 1080
 T  R  V  S  L  T  E  P  P  E  E  E  I  D  P  C  R  R  L  A    360

AACCTCGGGACAAAAGCTGCCAAACTTCAACAAGGCGCTGCACCGTTTGAAGAAAAGCAT 1140
 N  L  G  T  K  A  A  K  L  Q  Q  G  A  A  P  F  E  E  K  H    380

AGGCATTACTTTGATTTTCAGCGTCGGACGGGTGATCTACCTGTACAAAAAGAGGGAGAA 1200
 R  H  Y  F  D  F  Q  R  R  T  G  D  L  P  V  Q  K  E  G  E    400

GAGGTTGATTACAGAAATGTCCTTCACCGTGATGGTTCTGTTCTGATGTCGATTTCTCTG 1260
 E  V  D  Y  R  N  V  L  H  R  D  G  S  V  L  M  S  I  S  L    420

GATCAACTAAAGGCACCTGAACTCCTCTACAGATCACTCGCCACAAAGCTTGTCGTGGGT 1320
 D  Q  L  K  A  P  E  L  L  Y  R  S  L  A  T  K  L  V  V  G    440

ATGCCATTCAAGGATCTGGCAACTGTTGATTCAATCTTATTAAGAGAGCTACCGCCTGTA 1380
 M  P  F  K  D  L  A  T  V  D  S  I  L  L  R  E  L  P  P  V    460

GATGATCAAGTGGCTCGTTTGGCTCTCAAACGGTTGATTGATGTCAGTATGGGAGTTATA 1440
 D  D  Q  V  A  R  L  A  L  K  R  L  I  D  V  S  M  G  V  I    480

GCACCTTTATCAGAGCAACTAACAAAGCCATTGCCCAATGCCATGGTTCTTGTCAACCTC 1500
 A  P  L  S  E  Q  L  T  K  P  L  P  N  A  M  V  L  V  N  L    500

AAGGAACTATCTGGTGGCGCTTACAAGCTTCTCCCTGAAGGTACACGCTTGGTTGTCTCT 1560
 K  E  L  S  G  G  A  Y  K  L  L  P  E  G  T  R  L  V  V  S    520

CTACGAGGCGATGAGCCTTACGAGGAGCTTGAAATACTCAAAAACATTGATGCTACTATG 1620
 L  R  G  D  E  P  Y  E  E  L  E  I  L  K  N  I  D  A  T  M    540

ATTCTCCATGATGTACCTTTCACTGAAGACAAAGTTAGCAGAGTACATGCAGCTCGGAGG 1680
 I  L  H  D  V  P  F  T  E  D  K  V  S  R  V  H  A  A  R  R    560

CTATTCGAGTTCTTATCCGAGAATTCAGTTAACTTTCCTGTTATTCATCGCATAAACTTC 1740
 L  F  E  F  L  S  E  N  S  V  N  F  P  V  I  H  R  I  N  F    580

CCAACCGGAATCCACAGAGACGAATTGGTGATTCATGCAGGGACATATGCTGGAGGCCTT 1800
 P  T  G  I  H  R  D  E  L  V  I  H  A  G  T  Y  A  G  G  L    600

CTTGTGGATGGACTAGGTGATGGCGTAATGCTCGAAGCACCTGACCAAGATTTTGATTTT 1860
 L  V  D  G  L  G  D  G  V  M  L  E  A  P  D  Q  D  F  D  F    620

CTTAGGAATACTTCCTTCAACTTATTACAAGGATGCAGAATGCGTAACACTAAGACGGAA 1920
 L  R  N  T  S  F  N  L  L  Q  G  C  R  M  R  N  T  K  T  E    640

TATGTATCGTGCCCGTCTTGTGGAAGAACGCTTTTCGACTTGCAAGAAATCAGCGCCGAG 1980
 Y  V  S  C  P  S  C  G  R  T  L  F  D  L  Q  E  I  S  A  E    660
```

*FIG. 20 (CONT'D.)*

```
ATCCGAGAAAAGACTTCCCATTTACCTGGCGTTTCGATCGCAATCATGGGATGCATTGTG 2040
 I  R  E  K  T  S  H  L  P  G  V  S  I  A  I  M  G  C  I  V   680

AATGGACCAGGAGAAATGGCAGATGCTGATTTCGGATATGTAGGTGGTTCTCCCGGAAAA 2100
 N  G  P  G  E  M  A  D  A  D  F  G  Y  V  G  G  S  P  G  K   700

ATCGACCTTTATGTCGGAAAGACGGTGGTGAAGCGTGGGATAGCTATGACGGAGGCAACA 2160
 I  D  L  Y  V  G  K  T  V  V  K  R  G  I  A  M  T  E  A  T   720

GATGCTCTGATCGGTCTGATCAAAGAACATGGTCGTTGGGTCGACCCGCCCGTGGCTGAT 2220
 D  A  L  I  G  L  I  K  E  H  G  R  W  V  D  P  P  V  A  D   740

GAGTAG 2226
 E  -   741
```

*FIG. 20 (CONT'D.)* cDNA sequence of 1-hydroxy-2-methyl-2-(E)-butenyl 4-diphosphate reductase (IspH)
from *Arabidopsis thaliana*

```
ATGGCTGTTGCGCTCCAATTCAGCCGATTATGCGTTCGACCGGATACTTTCGTGCGGGAGAATCATCTCTCT    72
 M  A  V  A  L  Q  F  S  R  L  C  V  R  P  D  T  F  V  R  E  N  H  L  S     24

GGATCCGGATCTCTCCGCCGCCGGAAAGCTTTATCAGTCCGGTGCTCGTCTGGCGATGAGAACGCTCCTTCG   144
 G  S  G  S  L  R  R  R  K  A  L  S  V  R  C  S  S  G  D  E  N  A  P  S    48

CCATCGGTGGTGATGGACTCCGATTTCGACGCCAAGGTGTTCCGTAAGAACTTGACGAGAAGCGATAATTAC   216
 P  S  V  V  M  D  S  D  F  D  A  K  V  F  R  K  N  L  T  R  S  D  N  Y    72

AATCGTAAAGGGTTCGGTCATAAGGAGGAGACACTCAAGCTCATGAATCGAGAGTACACCAGTGATATATTG   288
 N  R  K  G  F  G  H  K  E  E  T  L  K  L  M  N  R  E  Y  T  S  D  I  L    96

GAGACACTGAAAACAAATGGGTATACTTATTCTTGGGGAGATGTTACTGTGAAACTCGCTAAAGCATATGGT   360
 E  T  L  K  T  N  G  Y  T  Y  S  W  G  D  V  T  V  K  L  A  K  A  Y  G   120

TTTTGCTGGGGTGTTGAGCGTGCTGTTCAGATTGCATATGAAGCACGAAAGCAGTTTCCAGAGGAGAGGCTT   432
 F  C  W  G  V  E  R  A  V  Q  I  A  Y  E  A  R  K  Q  F  P  E  E  R  L   144

TGGATTACTAACGAAATCATTCATAACCCGACCGTCAATAAGAGGTTGGAAGATATGGATGTTAAAATTATT   504
 W  I  T  N  E  I  I  H  N  P  T  V  N  K  R  L  E  D  M  D  V  K  I  I   168

CCGGTTGAGGATTCAAAGAAACAGTTTGATGTAGTAGAGAAAGATGATGTGGTTATCCTTCCTGCGTTTGGA   576
 P  V  E  D  S  K  K  Q  F  D  V  V  E  K  D  D  V  V  I  L  P  A  F  G   192

GCTGGTGTTGACGAGATGTATGTTCTTAATGATAAAAAGGTGCAAATTGTTGACACGACTTGTCCTTGGGTG   648
 A  G  V  D  E  M  Y  V  L  N  D  K  K  V  Q  I  V  D  T  T  C  P  W  V   216

ACAAAGGTCTGGAACACGGTTGAGAAGCACAAGAAGGGGGAATACACATCAGTAATCCATGGTAAATATAAT   720
 T  K  V  W  N  T  V  E  K  H  K  R  G  E  Y  T  S  V  I  H  G  K  Y  N   240

CATGAAGAGACGATTGCAACTGCGTCTTTTGCAGGAAAGTACATCATTGTAAAGAACATGAAAGAGGCAAAT   792
 H  E  E  T  I  A  T  A  S  F  A  G  K  Y  I  I  V  K  N  M  K  E  A  N   264

TACGTTTGTGATTACATTCTCGGTGGCCAATACGATGGATCTAGCTCCACAAAAGAGGAGTTCATGGAGAAA   864
 Y  V  C  D  Y  I  L  G  G  Q  Y  D  G  S  S  S  T  K  E  E  F  M  E  K   288

TTCAAATACGCAATTTCGAAGGGTTTCGATCCCGACAATGACCTTGTCAAAGTTGGTATTGCAAACCAAACA   936
 F  K  Y  A  I  S  K  G  F  D  P  D  N  D  L  V  K  V  G  I  A  N  Q  T   312

ACGATGCTAAAGGGAGAAACAGAGGAGATAGGAAGATTACTCGAGACAACAATGATGCGCAAGTATGGAGTG  1008
 T  M  L  K  G  E  T  E  E  I  G  R  L  L  E  T  T  M  M  R  K  Y  G  V   336

GAAAATGTAAGCGGACATTTCATCAGCTTCAACACAATATGCGACGCTACTCAAGAGCGACAAGACGCAATC  1080
 E  N  V  S  G  H  F  I  S  F  N  T  I  C  D  A  T  Q  E  R  Q  D  A  I   360

TATGAGCTAGTGGAAGAGAAGATTGACCTCATGCTAGTGGTTGGCGGATGGAATTCAAGTAACACCTCTCAC  1152
 Y  E  L  V  E  E  K  I  D  L  M  L  V  V  G  G  W  N  S  S  N  T  S  H   384
```

*FIG. 21*

```
CTTCAGGAAATCTCAGAGGCACGGGGAATCCCATCTTACTGGATCGATAGTGAGAAACGGATAGGACCTGGG  1224
  L  Q  E  I  S  E  A  R  G  I  P  S  Y  W  I  D  S  E  K  R  I  G  P  G   408

AATAAAATAGCCTATAAGCTCCACTATGGAGAACTGGTCGAGAAGGAAAACTTTCTCCCAAAGGGACCAATA  1296
  N  K  I  A  Y  K  L  H  Y  G  E  L  V  E  K  E  N  F  L  P  K  G  P  I   432

ACAATCGGTGTGACATCAGGTGCATCAACCCCGGATAAGGTCGTGGAAGATGCTTTGGTGAAGGTGTTCGAC  1368
  T  I  G  V  T  S  G  A  S  T  P  D  K  V  V  E  D  A  L  V  K  V  F  D   456

ATTAAACGTGAAGAGTTATTGCAGCTGGCTTGA                                          1398
  I  K  R  E  E  L  L  Q  L  A  -                                           466
```

*FIG. 21 (CONT'D.)*

SEQUENCE LISTING

```
<160> NUMBER OF SEQ ID NOS: 58

<210> SEQ ID NO 1
<211> LENGTH: 50
<212> TYPE: DNA
<213> ORGANISM: Artificial Sequence
<220> FEATURE:
<223> OTHER INFORMATION: xylB 5' PCR primer

<400> SEQUENCE: 1
ccgtcggaat tcgaggagaa attaaccatg tatatcggga tagatcttgg          50

<210> SEQ ID NO 2
<211> LENGTH: 37
<212> TYPE: DNA
<213> ORGANISM: Artificial Sequence
<220> FEATURE:
<223> OTHER INFORMATION: xyl B 3' PCR primer

<400> SEQUENCE: 2
gcagtgaagc ttttacgcca ttaatggcag aagttgc                       37

<210> SEQ ID NO 3
<211> LENGTH: 49
<212> TYPE: DNA
<213> ORGANISM: Artificial Sequence
<220> FEATURE:
<223> OTHER INFORMATION: dxr PCR primer 1

<400> SEQUENCE: 3
ctagccaagc ttgaggagaa attaaccatg aagcaactca ccattctgg           49

<210> SEQ ID NO 4
<211> LENGTH: 28
<212> TYPE: DNA
<213> ORGANISM: Artificial Sequence
<220> FEATURE:
<223> OTHER INFORMATION: dxr PCR primer 2

<400> SEQUENCE: 4
ggagatgtcg actcagcttg cgagacgc                                 28

<210> SEQ ID NO 5
<211> LENGTH: 49
<212> TYPE: DNA
<213> ORGANISM: Artificial Sequence
<220> FEATURE:
<223> OTHER INFORMATION: ispD PCR primer 1

<400> SEQUENCE: 5
ccgggagtcg acgaggagaa attaaccatg gcaaccactc atttggatg           49

<210> SEQ ID NO 6
<211> LENGTH: 32
<212> TYPE: DNA
<213> ORGANISM: Artificial Sequence
<220> FEATURE:
<223> OTHER INFORMATION: ispD PCR primer 2
```

```
<400> SEQUENCE: 6
gtccaactcg agttatgtat tctccttgat gg                              32

<210> SEQ ID NO 7
<211> LENGTH: 49
<212> TYPE: DNA
<213> ORGANISM: Artificial Sequence
<220> FEATURE:
<223> OTHER INFORMATION: ispD/ispF PCR primer 1

<400> SEQUENCE: 7
ccgggagtcg acgaggagaa attaaccatg gcaaccactc atttggatg            49

<210> SEQ ID NO 8
<211> LENGTH: 33
<212> TYPE: DNA
<213> ORGANISM: Artificial Sequence
<220> FEATURE:
<223> OTHER INFORMATION: ispD/ispF PCR primer 2

<400> SEQUENCE: 8
tatcaactcg agtcattttg ttgccttaat gag                             33

<210> SEQ ID NO 9
<211> LENGTH: 45
<212> TYPE: DNA
<213> ORGANISM: Artificial Sequence
<220> FEATURE:
<223> OTHER INFORMATION: ispE PCR primer 1

<400> SEQUENCE: 9
gcgaacctcg aggaggagaa attaaccatg cggacacagt ggccc                45

<210> SEQ ID NO 10
<211> LENGTH: 31
<212> TYPE: DNA
<213> ORGANISM: Artificial Sequence
<220> FEATURE:
<223> OTHER INFORMATION: ispE PCR primer 2

<400> SEQUENCE: 10
cctgacggta ccttaaagca tggctctgtg c                               31

<210> SEQ ID NO 11
<211> LENGTH: 49
<212> TYPE: DNA
<213> ORGANISM: Artificial Sequence
<220> FEATURE:
<223> OTHER INFORMATION: gcpE PCR primer 1

<400> SEQUENCE: 11
cgtaccggat ccgaggagaa attaaccatg cataaccagg ctccaattc            49

<210> SEQ ID NO 12
<211> LENGTH: 36
<212> TYPE: DNA
<213> ORGANISM: Artificial Sequence
<220> FEATURE:
<223> OTHER INFORMATION: gcpE PCR primer 2

<400> SEQUENCE: 12
cccatcgtcg acttattttt caacctgctg aacgtc                          36

<210> SEQ ID NO 13
<211> LENGTH: 23
```

<212> TYPE: DNA
<213> ORGANISM: Artificial Sequence
<220> FEATURE:
<223> OTHER INFORMATION: crtY/crtI/crtB PCR primer 1

<400> SEQUENCE: 13
cattgagaag cttatgtgca ccg                                              23

<210> SEQ ID NO 14
<211> LENGTH: 20
<212> TYPE: DNA
<213> ORGANISM: Artificial Sequence
<220> FEATURE:
<223> OTHER INFORMATION: crtY/crtI/crtB PCR primer 2

<400> SEQUENCE: 14
ctccggggtc gacatggcgc                                                  20

<210> SEQ ID NO 15
<211> LENGTH: 20
<212> TYPE: DNA
<213> ORGANISM: Artificial Sequence
<220> FEATURE:
<223> OTHER INFORMATION: crtE PCR primer 1

<400> SEQUENCE: 15
ccgcatcttt ccaattgccg                                                  20

<210> SEQ ID NO 16
<211> LENGTH: 23
<212> TYPE: DNA
<213> ORGANISM: Artificial Sequence
<220> FEATURE:
<223> OTHER INFORMATION: crtE PCR primer 2

<400> SEQUENCE: 16
atgcagcaag cttaactgac ggc                                              23

<210> SEQ ID NO 17
<211> LENGTH: 52
<212> TYPE: DNA
<213> ORGANISM: Artificial Sequence
<220> FEATURE:
<223> OTHER INFORMATION: ispG PCR primer 1

<400> SEQUENCE: 17
gcgggagacc gcgggaggag aaattaacca tgcataacca ggctccaatt cg              52

<210> SEQ ID NO 18
<211> LENGTH: 39
<212> TYPE: DNA
<213> ORGANISM: Artificial Sequence
<220> FEATURE:
<223> OTHER INFORMATION: ispG PCR primer 2

<400> SEQUENCE: 18
cgcttcccag cggccgctta tttttcaacc tgctgaacg                             39

<210> SEQ ID NO 19
<211> LENGTH: 45
<212> TYPE: DNA
<213> ORGANISM: Artificial Sequence
<220> FEATURE:
<223> OTHER INFORMATION: lytB PCR primer 1

<400> SEQUENCE: 19

```
aaatcggagc tcgaggagaa attaaccatg cagatcctgt tggcc            45
```

<210> SEQ ID NO 20
<211> LENGTH: 34
<212> TYPE: DNA
<213> ORGANISM: Artificial Sequence
<220> FEATURE:
<223> OTHER INFORMATION: lytB PCR primer 2

<400> SEQUENCE: 20

```
gctgctccgc ggttaatcga cttcacgaat atcg                        34
```

<210> SEQ ID NO 21
<211> LENGTH: 48
<212> TYPE: DNA
<213> ORGANISM: Artificial Sequence
<220> FEATURE:
<223> OTHER INFORMATION: ispH PCR primer 1

<400> SEQUENCE: 21

```
gcttgcgtcg acgaggagaa attaaccatg cagatcctgt tggccacc         48
```

<210> SEQ ID NO 22
<211> LENGTH: 34
<212> TYPE: DNA
<213> ORGANISM: Artificial Sequence
<220> FEATURE:
<223> OTHER INFORMATION: ispH PCR primer 2

<400> SEQUENCE: 22

```
gctgctcggc cgttaatcga cttcacgaat atcg                        34
```

<210> SEQ ID NO 23
<211> LENGTH: 49
<212> TYPE: DNA
<213> ORGANISM: Artificial Sequence
<220> FEATURE:
<223> OTHER INFORMATION: ispG (gcpE) primer 1

<400> SEQUENCE: 23

```
cgtaccggat ccgaggagaa attaaccatg cataaccagg ctccaattc        49
```

<210> SEQ ID NO 24
<211> LENGTH: 36
<212> TYPE: DNA
<213> ORGANISM: Artificial Sequence
<220> FEATURE:
<223> OTHER INFORMATION: ispG (gcpE) primer 2

<400> SEQUENCE: 24

```
cccatcgtcg acttattttt caacctgctg aacgtc                      36
```

<210> SEQ ID NO 25
<211> LENGTH: 55
<212> TYPE: DNA
<213> ORGANISM: Artificial Sequence
<220> FEATURE:
<223> OTHER INFORMATION: ispG/ispH primer 1

<400> SEQUENCE: 25

```
gcgggagacc gcgggaggag aaattaacca tgcataacca ggctccaatt caacg  55
```

<210> SEQ ID NO 26
<211> LENGTH: 36
<212> TYPE: DNA
<213> ORGANISM: Artificial Sequence

```
<220> FEATURE:
<223> OTHER INFORMATION: ispG/ispH primer 2

<400> SEQUENCE: 26
aggctggcgg ccgcttaatc gacttcacga atatcg                              36

<210> SEQ ID NO 27
<211> LENGTH: 20
<212> TYPE: DNA
<213> ORGANISM: Artificial Sequence
<220> FEATURE:
<223> OTHER INFORMATION: ispG primer 1

<400> SEQUENCE: 27
cctgcatccg aaggaagccc                                                20

<210> SEQ ID NO 28
<211> LENGTH: 20
<212> TYPE: DNA
<213> ORGANISM: Artificial Sequence
<220> FEATURE:
<223> OTHER INFORMATION: ispG primer 2

<400> SEQUENCE: 28
cagttttcaa agaatggccc                                                20

<210> SEQ ID NO 29
<211> LENGTH: 28
<212> TYPE: DNA
<213> ORGANISM: Artificial Sequence
<220> FEATURE:
<223> OTHER INFORMATION: PCR primer 1 (example 31)

<400> SEQUENCE: 29
tgaatcagga tccaagacgg tgagaagg                                       28

<210> SEQ ID NO 30
<211> LENGTH: 30
<212> TYPE: DNA
<213> ORGANISM: Artificial Sequence
<220> FEATURE:
<223> OTHER INFORMATION: PCR primer 2 (example 31)

<400> SEQUENCE: 30
tccgtttggt accctactca tcagccacgg                                     30

<210> SEQ ID NO 31
<211> LENGTH: 52
<212> TYPE: DNA
<213> ORGANISM: Artificial Sequence
<220> FEATURE:
<223> OTHER INFORMATION: dxs primer 1 (example 34)

<400> SEQUENCE: 31
ggcgactcgc gagaggagaa attaaccatg gatcttttat caatacagga cc            52

<210> SEQ ID NO 32
<211> LENGTH: 35
<212> TYPE: DNA
<213> ORGANISM: Artificial Sequence
<220> FEATURE:
<223> OTHER INFORMATION: dxs primer 2 (example 34)

<400> SEQUENCE: 32
ggcacccggc cgtcatgatc caattccttt gtgtg                               35
```

<210> SEQ ID NO 33
<211> LENGTH: 48
<212> TYPE: DNA
<213> ORGANISM: Artificial Sequence
<220> FEATURE:
<223> OTHER INFORMATION: ispH primer 1 (example 35)

<400> SEQUENCE: 33
gcttgcgtcg acgaggagaa attaaccatg cagatcctgt tggccacc                    48

<210> SEQ ID NO 34
<211> LENGTH: 34
<212> TYPE: DNA
<213> ORGANISM: Artificial Sequence
<220> FEATURE:
<223> OTHER INFORMATION: ispH primer 2 (example 35)

<400> SEQUENCE: 34
gctgctctcg agttaatcga cttcacgaat atcg                                    34

<210> SEQ ID NO 35
<211> LENGTH: 49
<212> TYPE: DNA
<213> ORGANISM: Artificial Sequence
<220> FEATURE:
<223> OTHER INFORMATION: ispG primer 1 (example 35)

<400> SEQUENCE: 35
ggtcgagtcg acgaggagaa attaaccatg cataaccagg ctccaattc                    49

<210> SEQ ID NO 36
<211> LENGTH: 36
<212> TYPE: DNA
<213> ORGANISM: Artificial Sequence
<220> FEATURE:
<223> OTHER INFORMATION: ispG primer 2 (example 35)

<400> SEQUENCE: 36
cccatcctcg agttattttt caacctgctg aacgtc                                  36

<210> SEQ ID NO 37
<211> LENGTH: 34
<212> TYPE: DNA
<213> ORGANISM: Artificial Sequence
<220> FEATURE:
<223> OTHER INFORMATION: ispG primer 1 (example 38)

<400> SEQUENCE: 37
gaaccggaat tcatgcataa ccaggctcca attc                                    34

<210> SEQ ID NO 38
<211> LENGTH: 19
<212> TYPE: DNA
<213> ORGANISM: Artificial Sequence
<220> FEATURE:
<223> OTHER INFORMATION: ispG primer 2 (example 38)

<400> SEQUENCE: 38
cgaggcggat cccatcacg                                                     19

<210> SEQ ID NO 39
<211> LENGTH: 33
<212> TYPE: DNA
<213> ORGANISM: Artificial Sequence
<220> FEATURE:
<223> OTHER INFORMATION: ispH primer 1 (example 39)

<400> SEQUENCE: 39

| tggaggggat ccatgcagat cctgttggcc acc | 33 |

<210> SEQ ID NO 40
<211> LENGTH: 21
<212> TYPE: DNA
<213> ORGANISM: Artificial Sequence
<220> FEATURE:
<223> OTHER INFORMATION: ispH primer 2 (example 39)

<400> SEQUENCE: 40

| gcatttctgc agaacttagg c | 21 |

<210> SEQ ID NO 41
<211> LENGTH: 5628
<212> TYPE: DNA
<213> ORGANISM: Artificial Sequence
<220> FEATURE:
<223> OTHER INFORMATION: pBSxylBdxr

<400> SEQUENCE: 41

| gtggcacttt tcggggaaat gtgcgcggaa cccctatttg tttattttc taaatacatt | 60 |
| caaatatgta tccgctcatg agacaataac cctgataaat gcttcaataa tattgaaaaa | 120 |
| ggaagagtat gagtattcaa catttccgtg tcgcccttat cccttttttt gcggcatttt | 180 |
| gccttcctgt ttttgctcac ccagaaacgc tggtgaaagt aaaagatgct gaagatcagt | 240 |
| tgggtgcacg agtgggttac atcgaactgg atctcaacag cggtaagatc cttgagagtt | 300 |
| ttcgccccga agaacgtttt ccaatgatga gcactttaa agttctgcta tgtggcgcgg | 360 |
| tattatcccg tattgacgcc gggcaagagc aactcggtcg ccgcatacac tattctcaga | 420 |
| atgacttggt tgagtactca ccagtcacag aaaagcatct tacggatggc atgacagtaa | 480 |
| gagaattatg cagtgctgcc ataaccatga gtgataacac tgcggccaac ttacttctga | 540 |
| caacgatcgg aggaccgaag gagctaaccg cttttttgca acatggggg atcatgtaa | 600 |
| ctcgccttga tcgttgggaa ccggagctga atgaagccat accaaacgac gagcgtgaca | 660 |
| ccacgatgcc tgtagcaatg gcaacaacgt tgcgcaaact attaactggc gaactactta | 720 |
| ctctagcttc ccggcaacaa ttaatagact ggatggaggc ggataaagtt gcaggaccac | 780 |
| ttctgcgctc ggcccttccg gctggctggt ttattgctga taaatctgga gccggtgagc | 840 |
| gtgggtctcg cggtatcatt gcagcactgg ggccagatgg taagccctcc cgtatcgtag | 900 |
| ttatctacac gacggggagt caggcaacta tggatgaacg aaatagacag atcgctgaga | 960 |
| taggtgcctc actgattaag cattggtaac tgtcagacca agtttactca tatatacttt | 1020 |
| agattgattt aaaacttcat ttttaattta aaaggatcta ggtgaagatc ctttttgata | 1080 |
| atctcatgac caaaatccct taacgtgagt tttcgttcca ctgagcgtca gaccccgtag | 1140 |
| aaaagatcaa aggatcttct tgagatcctt ttttctgcg cgtaatctgc tgcttgcaaa | 1200 |
| caaaaaaacc accgctacca gcggtggttt gtttgccgga tcaagagcta ccaactcttt | 1260 |
| ttccgaaggt aactggcttc agcagagcgc agataccaaa tactgtcctt ctagtgtagc | 1320 |
| cgtagttagg ccaccacttc aagaactctg tagcaccgcc tacatacctc gctctgctaa | 1380 |
| tcctgttacc agtggctgct gccagtggcg ataagtcgtg tcttaccggg ttggactcaa | 1440 |
| gacgatagtt accggataag gcgcagcggt cgggctgaac ggggggttcg tgcacacagc | 1500 |
| ccagcttgga gcgaacgacc tacaccgaac tgagatacct acagcgtgag ctatgagaaa | 1560 |

-continued

```
gcgccacgct tcccgaaggg agaaaggcgg acaggtatcc ggtaagcggc agggtcggaa      1620
caggagagcg cacgagggag cttccagggg gaaacgcctg gtatctttat agtcctgtcg      1680
ggtttcgcca cctctgactt gagcgtcgat ttttgtgatg ctcgtcaggg gggcggagcc      1740
tatggaaaaa cgccagcaac gcggccttt  tacggttcct ggccttttgc tggcttttg       1800 ctcacatgtt ctttcctgcg ttatcccctg attctgtgga taaccgtatt accgcctttg      1860
agtgagctga taccgctcgc cgcagccgaa cgaccgagcg cagcgagtca gtgagcgagg      1920
aagcggaaga gcgcccaata cgcaaaccgc ctctccccgc gcgttggccg attcattaat      1980
gcagctggca cgacaggttt cccgactgga aagcgggcag tgagcgcaac gcaattaatg      2040
tgagttagct cactcattag gcaccccagg ctttacactt tatgcttccg gctcgtatgt      2100
tgtgtggaat tgtgagcgga taacaatttc acacaggaaa cagctatgac catgattacg      2160
ccaagcgcgc aattaaccct cactaaaggg aacaaaagct ggagctccac cgcggtggcg      2220
gccgctctag aactagtgga tcccccgggc tgcaggaatt cgaggagaaa ttaaccatgt      2280
atatcgggat agatcttggc acctcgggcg taaaagttat tttgctcaac gagcagggtg      2340
aggtggtttg tgcgcaaacg gaaaagctga ccgtttcgcg cccgcatcca ctctggtcgg      2400
aacaagaccc ggaacagtgg tggcaggcaa ctgatcgcgc aatgaaagct ctgggcgatc      2460
agcattctct gcaggacgtt aaagcattgg gtattgccgg ccagatgcac ggagcaacct      2520
tgctggatgc tcagcaacgg gtgttacgcc ctgccatttt gtggaacgac gggcgctgtg      2580
cgcaagagtg cactttgctg gaagcgcgag ttccgcaatc gcgggtgatt accggcaacc      2640
tgatgatgcc cggatttact gcgcctaaat tgctatgggt tcagcggcat gagccggaga      2700
tattccgtca aatcgacaaa gtattattac cgaaagatta cttgcgtctg cgtatgacgg      2760
gggagtttgc cagcgatatg tctgacgcag ctggcaccat gtggctggat gtcgcaaagc      2820
gtgactggag tgacgtcatg ctgcaggctt gcgacttatc tcgtgaccag atgcccgcat      2880
tatacgaagg cagcgaaatt actggtgctt tgttacctga agttgcgaaa gcgtggggta      2940
tggcgacggt gccagttgtc gcaggcggtg gcgacaatgc agctggtgca gttggtgtgg      3000
gaatggttga tgctaatcag gcaatgttat cgctggggac gtcgggggtc tattttgctg      3060
tcagcgaagg gttcttaagc aagccagaaa gcgccgtaca tagcttttgc catgcgctac      3120
cgcaacgttg gcatttaatg tctgtgatgc tgagtgcagc gtcgtgtctg gattgggccg      3180
cgaaattaac cggcctgagc aatgtcccag ctttaatcgc tgcagctcaa caggctgatg      3240
aaagtgccga gccagtttgg tttctgcctt atctttccgg cgagcgtacg ccacacaata      3300
atccccaggc gaagggggtt ttctttggtt tgactcatca acatggcccc aatgaactgg      3360
cgcgagcagt gctggaaggc gtgggttatg cgctggcaga tggcatggat gtcgtgcatg      3420
cctgcggtat taaaccgcaa agtgttacgt tgattggggg cggggcgcgt agtgagtact      3480
ggcgtcagat gctggcggat atcagcgtc  agcagctcga ttaccgtacg ggggggggatg      3540 tggggccagc actgggcgca gcaaggctgg cgcagatcgc ggcgaatcca gagaaatcgc      3600
tcattgaatt gttccgcaa  ctaccgttag aacagtcgca tctaccagat gcgcagcgtt      3660
atgccgctta tcagccacga cgagaaacgt tccgtcgcct ctatcagcaa cttctgccat      3720
taatggcgta aaagcttgag gagaaattaa ccatgaagca actcaccatt ctgggctcga      3780
ccggctcgat tggttgcagc acgctggacg tggtgcgcca taatcccgaa cacttccgcg      3840
tagttgcgct ggtggcaggc aaaaatgtca ctcgcatggt agaacagtgc ctggaattct      3900
ctccccgcta tgccgtaatg gacgatgaag cgagtgcgaa acttcttaaa acgatgctac      3960
```

-continued

```
agcaacaggg tagccgcacc gaagtcttaa gtgggcaaca agccgcttgc gatatggcag      4020
cgcttgagga tgttgatcag gtgatggcag ccattgttgg cgctgctggg ctgttaccta      4080
cgcttgctgc gatccgcgcg ggtaaaacca ttttgctggc caataaagaa tcactggtta      4140
cctgcggacg tctgtttatg gacgccgtaa agcagagcaa agcgcaattg ttaccggtcg      4200
atagcgaaca taacgccatt tttcagagtt taccgcaacc tatccagcat aatctgggat      4260
acgctgacct tgagcaaaat ggcgtggtgt ccattttact taccgggtct ggtggccctt      4320
tccgtgagac gccattgcgc gatttggcaa caatgacgcc ggatcaagcc tgccgtcatc      4380
cgaactggtc gatggggcgt aaaatttctg tcgattcggc taccatgatg aacaaaggtc      4440
tggaatacat tgaagcgcgt tggctgttta acgccagcgc cagccagatg gaagtgctga      4500
ttcacccgca gtcagtgatt cactcaatgg tgcgctatca ggacggcagt gttctggcgc      4560
agctggggga accggatatg cgtacgccaa ttgcccacac catggcatgg ccgaatcgcg      4620
tgaactctgg cgtgaagccg ctcgattttt gcaaactaag tgcgttgaca tttgccgcac      4680
cggattatga tcgttatcca tgcctgaaac tggcgatgga ggcgttcgaa caaggccagg      4740
cagcgacgac agcattgaat gccgcaaacg aaatcaccgt tgctgctttt cttgcgcaac      4800
aaatccgctt tacggatatc gctgcgttga atttatccgt actggaaaaa atggatatgc      4860
gcgaaccaca atgtgtggac gatgtgttat ctgttgatgc gaacgcgcgt gaagtcgcca      4920
gaaaagaggt gatgcgtctc gcaagctgag tcgacctcga ggggggccc ggtacccaat      4980 tcgccctata gtgagtcgta ttacgcgcgc tcactggccg tcgttttaca acgtcgtgac      5040
tgggaaaacc ctggcgttac ccaacttaat cgccttgcag cacatccccc tttcgccagc      5100
tggcgtaata gcgaagaggc ccgcaccgat cgcccttccc aacagttgcg cagcctgaat      5160
ggcgaatgga aattgtaagc gttaatattt tgttaaaatt cgcgttaaat ttttgttaaa      5220
tcagctcatt ttttaaccaa taggccgaaa tcggcaaaat cccttataaa tcaaaagaat      5280
agaccgagat agggttgagt gttgttccag tttggaacaa gagtccacta ttaaagaacg      5340
tggactccaa cgtcaaaggg cgaaaaaccg tctatcaggg cgatggccca ctacgtgaac      5400
catcacccta atcaagtttt tggggtcga ggtgccgtaa agcactaaat cggaaccta      5460 aagggagccc ccgatttaga gcttgacggg gaaagccggc gaacgtggcg agaaaggaag      5520
ggaagaaagc gaaaggagcg ggcgctaggg cgctggcaag tgtagcggtc acgctgcgcg      5580
taaccaccac acccgccgcg cttaatgcgc cgctacaggg cgcgtcag                   5628
```

<210> SEQ ID NO 42
<211> LENGTH: 6354
<212> TYPE: DNA
<213> ORGANISM: Artificial Sequence
<220> FEATURE:
<223> OTHER INFORMATION: pBSxylBdxrispD

<400> SEQUENCE: 42

```
gtggcacttt tcggggaaat gtgcgcggaa cccctatttg tttatttttc taaatacatt       60
caaatatgta tccgctcatg agacaataac cctgataaat gcttcaataa tattgaaaaa      120
ggaagagtat gagtattcaa catttccgtg tcgcccttat tccctttttt gcggcatttt      180
gccttcctgt ttttgctcac ccagaaacgc tggtgaaagt aaaagatgct gaagatcagt      240
tgggtgcacg agtgggttac atcgaactgg atctcaacag cggtaagatc cttgagagtt      300
ttcgccccga agaacgtttt ccaatgatga gcacttttaa agttctgcta tgtggcgcgg      360
```

```
tattatcccg tattgacgcc gggcaagagc aactcggtcg ccgcatacac tattctcaga    420
atgacttggt tgagtactca ccagtcacag aaaagcatct tacggatggc atgacagtaa    480
gagaattatg cagtgctgcc ataaccatga gtgataacac tgcggccaac ttacttctga    540
caacgatcgg aggaccgaag gagctaaccg cttttttgca caacatgggg gatcatgtaa    600
ctcgccttga tcgttgggaa ccggagctga atgaagccat accaaacgac gagcgtgaca    660
ccacgatgcc tgtagcaatg gcaacaacgt tgcgcaaact attaactggc gaactactta    720
ctctagcttc ccggcaacaa ttaatagact ggatggaggc ggataaagtt gcaggaccac    780
ttctgcgctc ggcccttccg gctggctggt ttattgctga taaatctgga gccggtgagc    840
gtgggtctcg cggtatcatt gcagcactgg ggccagatgg taagccctcc cgtatcgtag    900
ttatctacac gacggggagt caggcaacta tggatgaacg aaatagacag atcgctgaga    960
taggtgcctc actgattaag cattggtaac tgtcagacca agtttactca tatatacttt   1020
agattgattt aaaacttcat tttaatttta aaaggatcta ggtgaagatc ctttttgata   1080
atctcatgac caaaatccct taacgtgagt tttcgttcca ctgagcgtca gaccccgtag   1140
aaaagatcaa aggatcttct tgagatcctt ttttctgcg cgtaatctgc tgcttgcaaa    1200
caaaaaaacc accgctacca gcggtggttt gtttgccgga tcaagagcta ccaactcttt   1260
ttccgaaggt aactggcttc agcagagcgc agataccaaa tactgtcctt ctagtgtagc   1320
cgtagttagg ccaccacttc aagaactctg tagcaccgcc tacatacctc gctctgctaa   1380
tcctgttacc agtggctgct gccagtggcg ataagtcgtg tcttaccggg ttggactcaa   1440
gacgatagtt accggataag gcgcagcggt cgggctgaac ggggggttcg tgcacacagc   1500
ccagcttgga gcgaacgacc tacaccgaac tgagatacct acagcgtgag ctatgagaaa   1560
gcgccacgct tcccgaaggg agaaaggcgg acaggtatcc ggtaagcggc agggtcggaa   1620
caggagagcg cacgagggag cttccagggg gaaacgcctg gtatctttat agtcctgtcg   1680
ggtttcgcca cctctgactt gagcgtcgat ttttgtgatg ctcgtcaggg ggcggagcc    1740 tatgaaaaaa cgccagcaac gcggcctttt tacggttcct ggccttttgc tggccttttg   1800
ctcacatgtt ctttcctgcg ttatcccctg attctgtgga taaccgtatt accgcctttg   1860
agtgagctga taccgctcgc cgcagccgaa cgaccgagcg cagcgagtca gtgagcgagg   1920
aagcggaaga gcgcccaata cgcaaaccgc ctctccccgc gcgttggccg attcattaat   1980
gcagctggca cgacaggttt cccgactgga aagcgggcag tgagcgcaac gcaattaatg   2040
tgagttagct cactcattag gcaccccagg ctttacactt tatgcttccg gctcgtatgt   2100
tgtgtggaat tgtgagcgga taacaatttc acacaggaaa cagctatgac catgattacg   2160
ccaagcgcgc aattaaccct cactaaaggg aacaaaagct ggagctccac cgcggtggcg   2220
gccgctctag aactagtgga tcccccgggc tgcaggaatt cgaggagaaa ttaaccatgt   2280
atatcgggat agatcttggc acctcgggcg taaaagttat tttgctcaac gagcagggtg   2340
aggtggttgc tgcgcaaacg gaaaagctga ccgtttcgcg cccgcatcca ctctggtcgg   2400
aacaagaccc ggaacagtgg tggcaggcaa ctgatcgcgc aatgaaagct ctgggcgatc   2460
agcattctct gcaggacgtt aaagcattgg gtattgccgg ccagatgcac ggagcaacct   2520
tgctggatgc tcagcaacgg gtgttacgcc ctgccatttt gtggaacgac gggcgctgtg   2580
cgcaagagtg cactttgctg gaagcgcgag ttccgcaatc gcgggtgatt accggcaacc   2640
tgatgatgcc cggatttact gcgcctaaat tgctatgggt tcagcggcat gagccggaga   2700
tattccgtca aatcgacaaa gtattattac cgaaagatta cttgcgtctg cgtatgacgg   2760
```

```
gggagtttgc cagcgatatg tctgacgcag ctggcaccat gtggctggat gtcgcaaagc      2820
gtgactggag tgacgtcatg ctgcaggctt gcgacttatc tcgtgaccag atgcccgcat      2880
tatacgaagg cagcgaaatt actggtgctt tgttacctga agttgcgaaa gcgtggggta      2940
tggcgacggt gccagttgtc gcaggcggtg gcgacaatgc agctggtgca gttggtgtgg      3000
gaatggttga tgctaatcag gcaatgttat cgctggggac gtcggggggtc tattttgctg     3060 tcagcgaagg gttcttaagc aagccagaaa gcgccgtaca tagcttttgc catgcgctac      3120
cgcaacgttg gcatttaatg tctgtgatgc tgagtgcagc gtcgtgtctg gattgggccg      3180
cgaaattaac cggcctgagc aatgtcccag ctttaatcgc tgcagctcaa caggctgatg      3240
aaagtgccga gccagtttgg tttctgcctt atctttccgg cgagcgtacg ccacacaata      3300
atccccaggc gaagggggtt ttctttggtt tgactcatca acatggcccc aatgaactgg      3360
cgcgagcagt gctggaaggc gtgggttatg cgctggcaga tggcatggat gtcgtgcatg      3420
cctgcggtat taaaccgcaa agtgttacgt tgattggggg cggggcgcgt agtgagtact      3480
ggcgtcagat gctggcggat atcagcggtc agcagctcga ttaccgtacg ggggggggatg     3540 tggggccagc actgggcgca gcaaggctgg cgcagatcgc ggcgaatcca gagaaatcgc      3600
tcattgaatt gttgccgcaa ctaccgttag aacagtcgca tctaccagat gcgcagcgtt      3660
atgccgctta tcagccacga cgagaaacgt tccgtcgcct ctatcagcaa cttctgccat      3720
taatggcgta aaagcttgag gagaaattaa ccatgaagca actcaccatt ctgggctcga      3780
ccggctcgat tggttgcagc acgctggacg tggtgcgcca taatcccgaa cacttccgcg      3840
tagttgcgct ggtggcaggc aaaaatgtca ctcgcatggt agaacagtgc ctggaattct      3900
ctccccgcta tgccgtaatg gacgatgaag cgagtgcgaa acttcttaaa acgatgctac      3960
agcaacaggg tagccgcacc gaagtcttaa gtgggcaaca agccgcttgc gatatggcag      4020
cgcttgagga tgttgatcag gtgatggcag ccattgttgg cgctgctggg ctgttaccta      4080
cgcttgctgc gatccgcgcg ggtaaaacca ttttgctggc caataaagaa tcactggtta      4140
cctgcggacg tctgtttatg gacgccgtaa agcagagcaa agcgcaattg ttaccggtcg      4200
atagcgaaca taacgccatt tttcagagtt taccgcaacc tatccagcat aatctgggat      4260
acgctgacct tgagcaaaat ggcgtggtgt ccatttttact taccgggtct ggtggcccctt     4320 tccgtgagac gccattgcgc gatttggcaa caatgacgcc ggatcaagcc tgccgtcatc      4380
cgaactggtc gatgggggcgt aaaatttctg tcgattcggc taccatgatg aacaaaggtc     4440
tggaatacat tgaagcgcgt tggctgtttta acgccagcgc cagccagatg gaagtgctga     4500
ttcacccgca gtcagtgatt cactcaatgg tgcgctatca ggacggcagt gttctggcgc      4560
agctggggga accggatatg cgtacgccaa ttgcccacac catggcatgg ccgaatcgcg      4620
tgaactctgg cgtgaagccg ctcgatttttt gcaaactaag tgcgttgaca tttgccgcac     4680
cggattatga tcgttatcca tgcctgaaac tggcgatgga ggcgttcgaa caaggccagg      4740
cagcgacgac agcattgaat gccgcaaacg aaatcaccgt tgctgctttt cttgcgcaac      4800
aaatccgctt tacggatatc gctgcgttga atttatccgt actggaaaaa atggatatgc      4860
gcgaaccaca atgtgtggac gatgtgttat ctgttgatgc gaacgcgcgt gaagtcgcca      4920
gaaaagaggt gatgcgtctc gcaagctgag tcgacgagga gaaattaacc atggcaacca      4980
ctcatttgga tgtttgcgcc gtggttccgg cggccggatt tggccgtcga atgcaaacgg      5040
aatgtcctaa gcaatatctc tcaatcggta atcaaaccat tcttgaacac tcggtgcatg      5100
```

```
cgctgctggc gcatcccegg gtgaaacgtg tcgtcattge cataagtcct ggcgatagce    5160 gttttgcaca acttcctctg gcgaatcatc cgcaaatcac cgttgtagat ggcggtgatg    5220
agcgtgccga ttccgtgctg gcaggtctga aagccgctgg cgacgcgcag tgggtattgg    5280
tgcatgacgc cgctcgtcct tgtttgcatc aggatgacct cgcgcgattg ttggcgttga    5340
gcgaaaccag ccgcacgggg gggatcctcg ccgcaccagt gcgcgatact atgaaacgtg    5400
ccgaaccggg caaaaatgcc attgctcata ccgttgatcg caacggctta tggcacgcgc    5460
tgacgccgca atttttccct cgtgagctgt tacatgactg tctgacgcgc gctctaaatg    5520
aaggcgcgac tattaccgac gaagcctcgg cgctggaata ttgcggattc catcctcagt    5580
tggtcgaagg ccgtgcggat aacattaaag tcacgcgccc ggaagatttg cactggccg     5640 agttttacct cacccgaacc atccatcagg agaatacata actcgagggg gggcccggta    5700
cccaattcgc cctatagtga gtcgtattac gcgcgctcac tggccgtcgt tttacaacgt    5760
cgtgactggg aaaaccctgg cgttacccaa cttaatcgcc ttgcagcaca tccccctttc    5820
gccagctggc gtaatagcga agaggcccgc accgatcgcc cttcccaaca gttgcgcagc    5880
ctgaatggcg aatggaaatt gtaagcgtta atattttgtt aaaattcgcg ttaaattttt    5940
gttaaatcag ctcatttttt aaccaatagg ccgaaatcgg caaaatccct tataaatcaa    6000
aagaatagac cgagataggg ttgagtgttg ttccagtttg gaacaagagt ccactattaa    6060
agaacgtgga ctccaacgtc aaagggcgaa aaaccgtcta tcagggcgat ggcccactac    6120
gtgaaccatc accctaatca agttttttgg ggtcgaggtg ccgtaaagca ctaaatcgga    6180 acccctaaagg gagcccccga tttagagctt gacggggaaa gccggcgaac gtggcgagaa    6240
aggaagggaa gaaagcgaaa ggagcgggcg ctagggcgct ggcaagtgta gcggtcacgc    6300
tgcgcgtaac caccacaccc gccgcgctta atgcgccgct acagggcgcg tcag         6354
```

<210> SEQ ID NO 43
<211> LENGTH: 7691
<212> TYPE: DNA
<213> ORGANISM: Artificial Sequence
<220> FEATURE:
<223> OTHER INFORMATION: pBScyclo

<400> SEQUENCE: 43

```
gtggcacttt tcggggaaat gtgcgcggaa cccctatttg tttatttttc taaatacatt     60
caaatatgta tccgctcatg agacaataac cctgataaat gcttcaataa tattgaaaaa    120
ggaagagtat gagtattcaa catttccgtg tcgcccttat tcccttttt gcggcatttt    180 gccttcctgt ttttgctcac ccagaaacgc tggtgaaagt aaaagatgct gaagatcagt    240
tgggtgcacg agtgggttac atcgaactgg atctcaacag cggtaagatc cttgagagtt    300
ttcgccccga agaacgtttt ccaatgatga gcacttttaa agttctgcta tgtggcgcgg    360
tattatcccg tattgacgcc gggcaagagc aactcggtcg ccgcatacac tattctcaga    420
atgacttggt tgagtactca ccagtcacag aaaagcatct tacggatggc atgacagtaa    480
gagaattatg cagtgctgcc ataaccatga gtgataacac tgcggccaac ttacttctga    540
caacgatcgg aggaccgaag gagctaaccg cttttttgca acatggggga tcatgtaa     600 ctcgccttga tcgttgggaa ccggagctga atgaagccat accaaacgac gagcgtgaca    660
ccacgatgcc tgtagcaatg gcaacaacgt tgcgcaaact attaactggc gaactactta    720
ctctagcttc ccggcaacaa ttaatagact ggatggaggc ggataaagtt gcaggaccac    780
ttctgcgctc ggcccttccg gctggctggt ttattgctga taaatctgga gccggtgagc    840
```

```
gtgggtctcg cggtatcatt gcagcactgg ggccagatgg taagccctcc cgtatcgtag    900
ttatctacac gacggggagt caggcaacta tggatgaacg aaatagacag atcgctgaga    960
taggtgcctc actgattaag cattggtaac tgtcagacca agtttactca tatatacttt   1020
agattgattt aaaacttcat ttttaattta aaaggatcta ggtgaagatc cttttttgata  1080
atctcatgac caaatccct taacgtgagt tttcgttcca ctgagcgtca gaccccgtag    1140
aaagatcaa aggatcttct tgagatcctt ttttctgcg cgtaatctgc tgcttgcaaa    1200
caaaaaaacc accgctacca gcggtggttt gtttgccgga tcaagagcta ccaactcttt   1260
ttccgaaggt aactggcttc agcagagcgc agataccaaa tactgtcctt ctagtgtagc   1320
cgtagttagg ccaccacttc aagaactctg tagcaccgcc tacataccct gctctgctaa   1380
tcctgttacc agtggctgct gccagtggcg ataagtcgtg tcttaccggg ttggactcaa   1440
gacgatagtt accggataag cgcagcggt cgggctgaac ggggggttcg tgcacacagc   1500
ccagcttgga gcgaacgacc tacaccgaac tgagatacct acagcgtgag ctatgagaaa   1560
gcgccacgct tcccgaaggg agaaaggcgg acaggtatcc ggtaagcggc agggtcggaa   1620
caggagagcg cacgagggag cttccagggg gaaacgcctg gtatctttat agtcctgtcg   1680
ggtttcgcca cctctgactt gagcgtcgat ttttgtgatg ctcgtcaggg gggcggagcc   1740
tatgaaaaa cgccagcaac gcggcctttt tacggttcct ggccttttgc tggccttttg    1800
ctcacatgtt ctttcctgcg ttatcccctg attctgtgga taaccgtatt accgcctttg   1860
agtgagctga taccgctcgc cgcagccgaa cgaccgagcg cagcgagtca gtgagcgagg   1920
aagcggaaga gcgcccaata cgcaaaccgc ctctccccgc gcgttggccg attcattaat   1980
gcagctggca cgacaggttt cccgactgga aagcgggcag tgagcgcaac gcaattaatg   2040
tgagttagct cactcattag gcaccccagg ctttacactt tatgcttccg gctcgtatgt   2100
tgtgtggaat tgtgagcgga taacaatttc acacaggaaa cagctatgac catgattacg   2160
ccaagcgcgc aattaaccct cactaaaggg aacaaaagct ggagctccac cgcggtggcg   2220
gccgctctag aactagtgga tcccccgggc tgcaggaatt cgaggagaaa ttaaccatgt   2280
atatcgggat agatcttggc acctcgggcg taaaagttat tttgctcaac gagcagggtg   2340
aggtggttgc tgcgcaaacg gaaaagctga ccgtttcgcg cccgcatcca ctctggtcgg   2400
aacaagaccc ggaacagtgg tggcaggcaa ctgatcgcgc aatgaaagct ctgggcgatc   2460
agcattctct gcaggacgtt aaagcattgg gtattgccgg ccagatgcac ggagcaacct   2520
tgctggatgc tcagcaacgg gtgttacgcc ctgccatttt gtggaacgac gggcgctgtg   2580
cgcaagagtg cactttgctg gaagcgcgag ttccgcaatc gcgggtgatt accggcaacc   2640
tgatgatgcc cggatttact gcgcctaaat gctatgggt tcagcggcat gagccggaga    2700
tattccgtca aatcgacaaa gtattattac gaaagatta cttgcgtctg cgtatgacgg    2760
gggagtttgc cagcgatatg tctgacgcag ctggcaccat gtggctggat gtcgcaaagc   2820
gtgactggag tgacgtcatg ctgcaggctt gcgacttatc tcgtgaccag atgcccgcat   2880
tatacgaagg cagcgaaatt actggtgctt tgttacctga agttgcgaaa gcgtgggta   2940
tggcgacggt gccagttgtc gcaggcggtg gcgacaatgc agctggtgca gttggtgtgg   3000
gaatggttga tgctaatcag gcaatgttat cgctgggac gtcgggggtc tattttgctg   3060
tcagcgaagg gttcttaagc aagccagaaa gcgccgtaca tagcttttgc catgcgctac   3120
cgcaacgttg gcatttaatg tctgtgatgc tgagtgcagc gtcgtgtctg gattgggccg   3180
```

```
cgaaattaac cggcctgagc aatgtcccag ctttaatcgc tgcagctcaa caggctgatg   3240
aaagtgccga gccagtttgg tttctgcctt atctttccgg cgagcgtacg ccacacaata   3300
atccccaggc gaaggggtt ttctttggtt tgactcatca acatggcccc aatgaactgg    3360
cgcgagcagt gctggaaggc gtgggttatg cgctggcaga tggcatggat gtcgtgcatg   3420
cctgcggtat taaaccgcaa agtgttacgt tgattggggg cggggcgcgt agtgagtact   3480
ggcgtcagat gctggcggat atcagcggtc agcagctcga ttaccgtacg ggggggggatg  3540 tggggccagc actgggcgca gcaaggctgg cgcagatcgc ggcgaatcca gagaaatcgc   3600
tcattgaatt gttgccgcaa ctaccgttag aacagtcgca tctaccagat gcgcagcgtt   3660
atgccgctta tcagccacga cgagaaacgt tccgtcgcct ctatcagcaa cttctgccat   3720
taatggcgta aaagcttgag gagaaattaa ccatgaagca actcaccatt ctgggctcga   3780
ccggctcgat tggttgcagc acgctggacg tggtgcgcca taatcccgaa cacttccgcg   3840
tagttgcgct ggtggcaggc aaaaatgtca ctcgcatggt agaacagtgc ctggaattct   3900
ctccccgcta tgccgtaatg gacgatgaag cgagtgcgaa acttcttaaa acgatgctac   3960
agcaacaggg tagccgcacc gaagtcttaa gtgggcaaca agccgcttgc gatatggcag   4020
cgcttgagga tgttgatcag gtgatggcag ccattgttgg cgctgctggg ctgttaccta   4080
cgcttgctgc gatccgcgcg ggtaaaacca ttttgctggc caataaagaa tcactggtta   4140
cctgcggacg tctgtttatg gacgccgtaa agcagagcaa agcgcaattg ttaccggtcg   4200
atagcgaaca taacgccatt tttcagagtt taccgcaacc tatccagcat aatctgggat   4260
acgctgacct tgagcaaaat ggcgtggtgt ccatttttact taccgggtct ggtggcccttt  4320 tccgtgagac gccattgcgc gatttggcaa caatgacgcc ggatcaagcc tgccgtcatc   4380
cgaactggtc gatgggggcgt aaaatttctg tcgattcggc taccatgatg aacaaaggtc   4440
tggaatacat tgaagcgcgt tggctgtttta acgccagcgc cagccagatg gaagtgctga   4500
ttcacccgca gtcagtgatt cactcaatgg tgcgctatca ggacggcagt gttctggcgc   4560
agctggggga accggatatg cgtacgccaa ttgcccacac catggcatgg ccgaatcgcg   4620
tgaactctgg cgtgaagccg ctcgattttt gcaaactaag tgcgttgaca tttgccgcac   4680
cggattatga tcgttatcca tgcctgaaac tggcgatgga ggcgttcgaa caaggccagg   4740
cagcgacgac agcattgaat gccgcaaacg aaatcaccgt tgctgctttt cttgcgcaac   4800
aaatccgctt tacggatatc gctgcgttga atttatccgt actggaaaaa atggatatgc   4860
gcgaaccaca atgtgtggac gatgtgttat ctgttgatgc gaacgcgcgt gaagtcgcca   4920
gaaaagaggt gatgcgtctc gcaagctgag tcgacgagga gaaattaacc atggcaacca   4980
ctcatttgga tgtttgcgcc gtggttccgg cggccggatt tggccgtcga atgcaaacgg   5040
aatgtcctaa gcaatatctc tcaatcggta atcaaaccat tcttgaacac tcggtgcatg   5100
cgctgctggc gcatccccgg gtgaaacgtg tcgtcattgc cataagtcct ggcgatagcc   5160
gttttgcaca acttcctctg gcgaatcatc gcaaatcac cgttgtagat ggcggtgatg    5220
agcgtgccga ttccgtgctg gcaggtctga aagccgctgg cgacgcgcag tgggtattgg   5280
tgcatgacgc cgctcgtcct tgtttgcatc aggatgacct cgcgcgattg ttggcgttga   5340
gcgaaaccag ccgcacgggg gggatcctcg ccgcaccagt gcgcgatact atgaaacgtg   5400
ccgaaccggg caaaaatgcc attgctcata ccgttgatcg caacggctta tggcacgcgc   5460
tgacgccgca ttttttccct cgtgagctgt tacatgactg tctgacgcgc gctctaaatg   5520
aaggcgcgac tattaccgac gaagcctcgg cgctggaata ttgcggattc catcctcagt   5580
```

-continued

```
tggtcgaagg ccgtgcggat aacattaaag tcacgcgccc ggaagatttg gcactggccg      5640
agttttacct cacccgaacc atccatcagg agaatacata atgcgaattg gacacggttt      5700
tgacgtacat gcctttggcg gtgaaggccc aattatcatt ggtggcgtac gcattcctta      5760
cgaaaaagga ttgctggcgc attctgatgg cgacgtggcg ctccatgcgt tgaccgatgc      5820
attgcttggc gcggcggcgc tgggggatat cggcaagctg ttcccggata ccgatccggc      5880
atttaaaggt gccgatagcc gcgagctgct acgcgaagcc tggcgtcgta ttcaggcgaa      5940
gggttatacc cttggcaacg tcgatgtcac tatcatcgct caggcaccga agatgttgcc      6000
gcacattcca caaatgcgcg tgtttattgc cgaagatctc ggctgccata tggatgatgt      6060
taacgtgaaa gccactacta cggaaaaact gggatttacc ggacgtgggg aagggattgc      6120
ctgtgaagcg gtggcgctac tcattaaggc aacaaaatga ctcgaggagg agaaattaac      6180
catgcggaca cagtggccct ctccggcaaa acttaatctg ttttttataca ttaccggtca      6240 gcgtgcggat ggttaccaca cgctgcaaac gctgtttcag tttcttgatt acggcgacac      6300
catcagcatt gagcttcgtg acgatgggga tattcgtctg ttaacgcccg ttgaaggcgt      6360
ggaacatgaa gataacctga tcgttcgcgc agcgcgattg ttgatgaaaa ctgcggcaga      6420
cagcgggcgt cttccgacgg gaagcggtgc gaatatcagc attgacaagc gtttgccgat      6480
gggcggcggt ctcggcggtg gttcatccaa tgccgcgacg gtcctggtgg cattaaatca      6540
tctctggcaa tgcgggctaa gcatggatga gctggcggaa atggggctga cgctgggcgc      6600
agatgttcct gtctttgttc gggggcatgc cgcgtttgcc gaaggcgttg gtgaaatact      6660
aacgccggtg gatccgccag agaagtggta tctggtggcg caccctggtg taagtattcc      6720
gactccggta atttttaaag atcctgaact cccgcgcaat acgccaaaaa ggtcaataga      6780
aacgttgcta aaatgtgaat tcagcaatga ttgcgaggtt atcgcaagaa acgttttcg      6840 cgaggttgat gcggtgcttt cctggctgtt agaatacgcc ccgtcgcgcc tgactgggac      6900
aggggcctgt gtctttgctg aatttgatac agagtctgaa gcccgccagg tgctagagca      6960
agccccggaa tggctcaatg gctttgtggc gaaaggcgct aatctttccc cattgcacag      7020
agccatgctt taaggtaccc aattcgccct atagtgagtc gtattacgcg cgctcactgg      7080
ccgtcgtttt acaacgtcgt gactgggaaa accctggcgt tacccaactt aatcgccttg      7140
cagcacatcc ccctttcgcc agctggcgta atagcgaaga ggcccgcacc gatcgccctt      7200
cccaacagtt gcgcagcctg aatggcgaat ggaaattgta agcgttaata ttttgttaaa      7260
attcgcgtta aattttgtt aaatcagctc attttttaac caataggccg aaatcggcaa      7320
aatcccttat aaatcaaaag aatagaccga gatagggttg agtgttgttc cagtttggaa      7380
caagagtcca ctattaaaga acgtggactc caacgtcaaa gggcgaaaaa ccgtctatca      7440
gggcgatggc ccactacgtg aaccatcacc ctaatcaagt tttttggggt cgaggtgccg      7500
taaagcacta atcggaacc ctaaagggag cccccgattt agagcttgac ggggaaagcc      7560
ggcgaacgtg cgagaaagg aagggaagaa agcgaaagga gcgggcgcta gggcgctggc      7620
aagtgtagcg gtcacgctgc gcgtaaccac cacacccgcc gcgcttaatg cgccgctaca      7680
gggcgcgtca g                                                         7691
```

<210> SEQ ID NO 44
<211> LENGTH: 5109
<212> TYPE: DNA
<213> ORGANISM: Artificial Sequence
<220> FEATURE:

<223> OTHER INFORMATION: pACYCgcpE

<400> SEQUENCE: 44

```
gaattccgga tgagcattca tcaggcgggc aagaatgtga ataaaggccg gataaaactt     60
gtgcttattt ttctttacgg tctttaaaaa ggccgtaata tccagctgaa cggtctggtt    120
ataggtacat tgagcaactg actgaaatgc ctcaaaatgt tctttacgat gccattggga    180
tatatcaacg gtggtatatc cagtgatttt tttctccatt ttagcttcct tagctcctga    240
aaatctcgat aactcaaaaa atacgcccgg tagtgatctt atttcattat ggtgaaagtt    300
ggaacctctt acgtgccgat caacgtctca ttttcgccaa aagttggccc agggcttccc    360
ggtatcaaca gggacaccag gatttattta ttctgcgaag tgatcttccg tcacaggtat    420
ttattcggcg caaagtgcgt cgggtgatgc tgccaactta ctgatttagt gtatgatggt    480
gtttttgagg tgctccagtg gcttctgttt ctatcagctg tccctcctgt tcagctactg    540
acggggtggt gcgtaacggc aaaagcaccg ccggacatca gcgctagcgg agtgtatact    600
ggcttactat gttggcactg atgagggtgt cagtgaagtg cttcatgtgg caggagaaaa    660
aaggctgcac cggtgcgtca gcagaatatg tgatacagga tatattccgc ttcctcgctc    720
actgactcgc tacgctcggt cgttcgactg cggcgagcgg aaatggctta cgaacggggc    780
ggagatttcc tggaagatgc caggaagata cttaacaggg aagtgagagg gccgcggcaa    840
agccgttttt ccataggctc cgcccccctg acaagcatca cgaaatctga cgctcaaatc    900
agtggtggcg aaacccgaca ggactataaa gataccaggc gtttcccct ggcggctccc    960
tcgtgcgctc tcctgttcct gcctttcggt ttaccggtgt cattccgctg ttatggccgc   1020
gtttgtctca ttccacgcct gacactcagt tccgggtagg cagttcgctc caagctggac   1080
tgtatgcacg aaccccccgt tcagtccgac cgctgcgcct tatccggtaa ctatcgtctt   1140
gagtccaacc cggaaagaca tgcaaaagca ccactggcag cagccactgg taattgattt   1200
agaggagtta gtcttgaagt catgcgccgg ttaaggctaa actgaaagga caagttttgg   1260
tgactgcgct cctccaagcc agttacctcg gttcaaagag ttggtagctc agagaacctt   1320
cgaaaaaccg ccctgcaagg cggttttttc gttttcagag caagagatta cgcgcagacc   1380
aaaacgatct caagaagatc atcttattaa tcagataaaa tatttctaga tttcagtgca   1440
atttatctct tcaaatgtag cacctgaagt cagccccata cgatataagt tgtaattctc   1500
atgtttgaca gcttatcatc gataagcttt aatgcggtag tttatcacag ttaaattgct   1560
aacgcagtca ggcaccgtgt atgaaatcta acaatgcgct catcgtcatc ctcggcaccg   1620
tcaccctgga tgctgtaggc ataggcttgg ttatgccggt actgccgggc ctcttgcggg   1680
atatcgtcca ttccgacagc atcgccagtc actatgcgct gctgctagcg ctatatgcgt   1740
tgatgcaatt tctatgcgca cccgttctcg gagcactgtc cgaccgcttt ggccgccgcc   1800
cagtcctgct cgcttcgcta cttggagcca ctatcgacta cgcgatcatg gcgaccacac   1860
ccgtcctgtg gatccgagga gaaattaacc atgcataacc aggctccaat tcaacgtaga   1920
aaatcaacac gtatttacgt tgggaatgtg ccgattggcg atggtgctcc catcgccgta   1980
cagtccatga ccaatacgcg tacgacagac gtcgaagcaa cggtcaatca aatcaaggcg   2040
ctggaacgcg ttggcgctga tatcgtccgt gtatccgtac cgacgatgga cgcggcagaa   2100
gcgttcaaac tcatcaaaca gcaggttaac gtgccgctgg tgctgacat ccacttcgac   2160
tatcgcattg cgctgaaagt agcggaatac ggcgtcgatt gtctgcgtat taaccctggc   2220
aatatcggta atgaagagcg tattcgcatg gtggttgact gtgcgcgcga taaaaacatt   2280
```

```
ccgatccgta ttggcgttaa cgccggatcg ctggaaaaag atctgcaaga aaagtatggc    2340
gaaccgacgc cgcaggcgtt gctggaatct gccatgcgtc atgttgatca tctcgatcgc    2400
ctgaacttcg atcagttcaa agtcagcgtg aaagcgtctg acgtcttcct cgctgttgag    2460
tcttatcgtt tgctggcaaa acagatcgat cagccgttgc atctggggat caccgaagcc    2520
ggtggtgcgc gcagcggggc agtaaaatcc gccattggtt taggtctgct gctgtctgaa    2580
ggcatcggcg acacgctgcg cgtatcgctg gcggccgatc cggtcgaaga gatcaaagtc    2640
ggtttcgata ttttgaaatc gctgcgtatc cgttcgcgag ggatcaactt catcgcctgc    2700
ccgacctgtt cgcgtcagga atttgatgtt atcggtacgg ttaacgcgct ggagcaacgc    2760
ctggaagata tcatcactcc gatggacgtt tcgattatcg gctgcgtggt gaatggccca    2820
ggtgaggcgc tggtttctac actcggcgtc accggcggca acaagaaaag cggcctctat    2880
gaagatggcg tgcgcaaaga ccgtctggac aacaacgata tgatcgacca gctggaagca    2940
cgcattcgtg cgaaagccag tcagctggac gaagcgcgtc gaattgacgt tcagcaggtt    3000
gaaaaataag tcgaccgatg cccttgagag ccttcaaccc agtcagctcc ttccggtggg    3060
cgcggggcat gactatcgtc gccgcactta tgactgtctt ctttatcatg caactcgtag    3120
gacaggtgcc ggcagcgctc tgggtcattt tcggcgagga ccgctttcgc tggagcgcga    3180
cgatgatcgg cctgtcgctt gcggtattcg gaatcttgca cgccctcgct caagccttcg    3240
tcactggtcc cgccaccaaa cgtttcggcg agaagcaggc cattatcgcc ggcatggcgg    3300
ccgacgcgct gggctacgtc ttgctggcgt tcgcgacgcg aggctggatg gccttcccca    3360
ttatgattct tctcgcttcc ggcggcatcg ggatgcccgc gttgcaggcc atgctgtcca    3420
ggcaggtaga tgacgaccat cagggacagc ttcaaggatc gctcgcggct cttaccagcc    3480
taacttcgat cactggaccg ctgatcgtca cggcgattta tgccgcctcg gcgagcacat    3540
ggaacgggtt ggcatggatt gtaggcgccg ccctataccT tgtctgcctc cccgcgttgc    3600
gtcgcggtgc atggagccgg gccacctcga cctgaatgga agccggcggc acctcgctaa    3660
cggattcacc actccaagaa ttggagccaa tcaattcttg cggagaactg tgaatgcgca    3720
aaccaaccct tggcagaaca tatccatcgc gtccgccatc tccagcagcc gcacgcggcg    3780
catctcgggc agcgttgggt cctggccacg ggtgcgcatg atcgtgctcc tgtcgttgag    3840
gacccggcta ggctggcggg gttgccttac tggttagcag aatgaatcac cgatacgcga    3900
gcgaacgtga agcgactgct gctgcaaaac gtctgcgacc tgagcaacaa catgaatggt    3960
cttcggtttc cgtgtttcgt aaagtctgga aacgcggaag tcccctacgt gctgctgaag    4020
ttgcccgcaa cagagagtgg aaccaaccgg tgataccacg atactatgac tgagagtcaa    4080
cgccatgagc ggcctcattt cttattctga gttacaacag tccgcaccgc tgtccggtag    4140
ctccttccgg tgggcgcggg gcatgactat cgtcgccgca cttatgactg tcttcttttat   4200 catgcaactc gtaggacagg tgccggcagc gcccaacagt cccccggcca cggggcctgc    4260
caccataccc acgccgaaac aagcgccctg caccattatg ttccggatct gcatcgcagg    4320
atgctgctgg ctaccctgtg aacacctac atctgtatta acgaagcgct aaccgttttt     4380
atcaggctct gggaggcaga ataaatgatc atatcgtcaa ttattacctc cacggggaga    4440
gcctgagcaa actggcctca ggcatttgag aagcacacgg tcacactgct tccggtagtc    4500
aataaaccgg taaccagca atagacataa gcggctattt aacgaccctg ccctgaaccg     4560
acgaccgggt cgaatttgct ttcgaatttc tgccattcat ccgcttatta tcacttattc    4620
```

-continued

```
aggcgtagca ccaggcgttt aagggcacca ataactgcct taaaaaaatt acgccccgcc    4680
ctgccactca tcgcagtact gttgtaattc attaagcatt ctgccgacat ggaagccatc    4740
acagacggca tgatgaacct gaatcgccag cggcatcagc accttgtcgc cttgcgtata    4800
atatttgccc atggtgaaaa cgggggcgaa gaagttgtcc atattggcca cgtttaaatc    4860
aaaactggtg aaactcaccc agggattggc tgagacgaaa aacatattct caataaaccc    4920
tttagggaaa taggccaggt tttcaccgta acacgccaca tcttgcgaat atatgtgtag    4980
aaactgccgg aaatcgtcgt ggtattcact ccagagcgat gaaaacgttt cagtttgctc    5040
atggaaaacg gtgtaacaag ggtgaacact atcccatatc accagctcac cgtctttcat    5100
tgccatacg                                                            5109
```

<210> SEQ ID NO 45
<211> LENGTH: 7494
<212> TYPE: DNA
<213> ORGANISM: Artificial Sequence
<220> FEATURE:
<223> OTHER INFORMATION: pBScaro14

<400> SEQUENCE: 45

```
gtggcacttt cgggaaat gtgcgcggaa cccctatttg tttattttc taaatacatt      60 caaatatgta tccgctcatg agacaataac cctgataaat gcttcaataa tattgaaaaa    120
ggaagagtat gagtattcaa catttccgtg tcgcccttat tcccttttt gcggcatttt     180 gccttcctgt ttttgctcac ccagaaacgc tggtgaaagt aaaagatgct gaagatcagt    240
tgggtgcacg agtgggttac atcgaactgg atctcaacag cggtaagatc cttgagagtt    300
ttcgccccga gaacgtttt ccaatgatga gcacttttaa agttctgcta tgtggcgcgg     360
tattatcccg tattgacgcc gggcaagagc aactcggtcg ccgcatacac tattctcaga    420
atgacttggt tgagtactca ccagtcacag aaaagcatct tacggatggc atgacagtaa    480
gagaattatg cagtgctgcc ataaccatga gtgataacac tgcggccaac ttacttctga    540
caacgatcgg aggaccgaag gagctaaccg ctttttttgca caacatgggg gatcatgtaa    600
ctcgccttga tcgttgggaa ccggagctga atgaagccat accaaacgac gagcgtgaca    660
ccacgatgcc tgtagcaatg gcaacaacgt tgcgcaaact attaactggc gaactactta    720
ctctagcttc ccggcaacaa ttaatagact ggatggaggc ggataaagtt gcaggaccac    780
ttctgcgctc ggcccttccg gctggctggt ttattgctga taaatctgga gccggtgagc    840
gtgggtctcg cggtatcatt gcagcactgg ggccagatgg taagccctcc cgtatcgtag    900
ttatctacac gacggggagt caggcaacta tggatgaacg aaatagacag atcgctgaga    960
taggtgcctc actgattaag cattggtaac tgtcagacca agtttactca tatatacttt    1020
agattgattt aaaacttcat ttttaattta aaaggatcta ggtgaagatc ctttttgata    1080
atctcatgac caaaatccct taacgtgagt tttcgttcca ctgagcgtca gaccccgtag    1140
aaaagatcaa aggatcttct tgagatcctt ttttctgcg cgtaatctgc tgcttgcaaa     1200
caaaaaaacc accgctacca gcggtggttt gtttgccgga tcaagagcta ccaactcttt    1260
ttccgaaggt aactggcttc agcagagcgc agataccaaa tactgtcctt ctagtgtagc    1320
cgtagttagg ccaccacttc aagaactctg tagcaccgcc tacatacctc gctctgctaa    1380
tcctgttacc agtggctgct gccagtggcg ataagtcgtg tcttaccggg ttggactcaa    1440
gacgatagtt accggataag gcgcagcggt cgggctgaac ggggggttcg tgcacacagc    1500
ccagcttgga gcgaacgacc tacaccgaac tgagatacct acagcgtgag ctatgagaaa    1560
```

-continued

```
gcgccacgct tcccgaaggg agaaaggcgg acaggtatcc ggtaagcggc agggtcggaa    1620
caggagagcg cacgagggag cttccagggg gaaacgcctg gtatctttat agtcctgtcg    1680
ggtttcgcca cctctgactt gagcgtcgat ttttgtgatg ctcgtcaggg gggcggagcc    1740
tatggaaaaa cgccagcaac gcggcctttt tacggttcct ggccttttgc tggccttttg    1800
ctcacatgtt ctttcctgcg ttatcccctg attctgtgga taaccgtatt accgcctttg    1860
agtgagctga taccgctcgc cgcagccgaa cgaccgagcg cagcgagtca gtgagcgagg    1920
aagcggaaga gcgcccaata cgcaaaccgc ctctccccgc gcgttggccg attcattaat    1980
gcagctggca cgacaggttt cccgactgga aagcgggcag tgagcgcaac gcaattaatg    2040
tgagttagct cactcattag gcaccccagg ctttacactt tatgcttccg gctcgtatgt    2100
tgtgtggaat tgtgagcgga taacaatttc acacaggaaa cagctatgac catgattacg    2160
ccaagcgcgc aattaaccct cactaaaggg aacaaaagct ggagctccac cgcggtggcg    2220
gccgctctag aactagtgga tcccccgggc tgcaggaatt gccgtaaatg tatccgttta    2280
taaggacagc ccgaatgacg gtctgcgcaa aaaaacacgt tcatctcact cgcgatgctg    2340
cggagcagtt actggctgat attgatcgac gccttgatca gttattgccc gtggagggag    2400
aacgggatgt tgtgggtgcc gcgatgcgtg aaggtgcgct ggcaccggga aaacgtattc    2460
gccccatgtt gctgttgctg accgcccgcg atctgggttg cgctgtcagc catgacggat    2520
tactggattt ggcctgtgcg gtggaaatgg tccacgcggc ttcgctgatc cttgacgata    2580
tgccctgcat ggacgatgcg aagctgcggc gcggacgccc taccattcat tctcattacg    2640
gagagcatgt ggcaatactg gcggcggttg ccttgctgag taaagccttt ggcgtaattg    2700
ccgatgcaga tggcctcacg ccgctggcaa aaaatcgggc ggtttctgaa ctgtcaaacg    2760
ccatcggcat gcaaggattg gttcagggtc agttcaagga tctgtctgaa ggggataagc    2820
cgcgcagcgc tgaagctatt ttgatgacga atcactttaa aaccagcacg ctgttttgtg    2880
cctccatgca gatggcctcg attgttgcga atgcctccag cgaagcgcgt gattgcctgc    2940
atcgtttttc acttgatctt ggtcaggcat ttcaactgct ggacgatttg accgatggca    3000
tgaccgacac cggtaaggat agcaatcagg acgccggtaa atcgacgctg gtcaatctgt    3060
taggcccgag ggcggttgaa gaacgtctga gacaacatct tcagcttgcc agtgagcatc    3120
tctctgcggc ctgccaacac gggcacgcca ctcaacattt tattcaggcc tggtttgaca    3180
aaaaactcgc tgccgtcagt taagcttatg tgcaccggtc agcctgtctt aagtgggagc    3240
ggctatgcaa ccgcattatg atctgattct cgtggggggct ggactcgcga atggccttat    3300
cgccctgcgt cttcagcagc agcaacctga tatgcgtatt ttgcttatcg acgccgcacc    3360
ccaggcgggc gggaatcata cgtggtcatt tcaccacgat gatttgactg agagccaaca    3420
tcgttggata gctccgctgg tggttcatca ctggcccgac tatcaggtac gctttcccac    3480
acgccgtcgt aagctgaaca gcggctactt ttgtattact tctcagcgtt cgctgaggt     3540
tttacagcga cagtttggcc cgcacttgtg gatggatacc gcggtcgcag aggttaatgc    3600
ggaatctgtt cggttgaaaa agggtcaggt tatcggtgcc cgcgcggtga ttgacgggcg    3660
gggttatgcg gcaaattcag cactgagcgt gggcttccag gcgtttattg gccaggaatg    3720
gcgattgagc caccgcatg gtttatcgtc tcccattatc atggatgcca cggtcgatca    3780
gcaaaatggt tatcgcttcg tgtacagcct gccgctctcg ccgaccagat tgttaattga    3840
agacacgcac tatattgata atgcgacatt agatcctgaa tgcgcgcggc aaaatatttg    3900
```

```
cgactatgcc gcgcaacagg gttggcagct tcagacactg ctgcgagaag aacagggcgc  3960
cttacccatt actctgtcgg gcaatgccga cgcattctgg cagcagcgcc ccctggcctg  4020
tagtggatta cgtgccggtc tgttccatcc taccaccggc tattcactgc cgctggcggt  4080
tgccgtggcc gaccgcctga gtgcacttga tgtctttacg tcggcctcaa ttcaccatgc  4140
cattacgcat tttgcccgcg agcgctggca gcagcagggc ttttccgca tgctgaatcg  4200
catgctgttt ttagccggac ccgccgattc acgctggcgg gttatgcagc gtttttatgg  4260
tttacctgaa gatttaattg cccgttttta tgcgggaaaa ctcacgctga ccgatcggct  4320
acgtattctg agcggcaagc cgcctgttcc ggtattagca gcattgcaag ccattatgac  4380
gactcatcgt taaagagcga ctacatgaaa ccaactacgg taattggtgc aggcttcggt  4440
ggcctggcac tggcaattcg tctacaagct gcggggatcc ccgtcttact gcttgaacaa  4500
cgtgataaac ccggcggtcg ggcttatgtc tacgaggatc aggggtttac ctttgatgca  4560
ggcccgacgg ttatcaccga tcccagtgcc attgaagaac tgtttgcact ggcaggaaaa  4620
cagttaaaag agtatgtcga actgctgccg gttacgccgt tttaccgcct gtgttgggag  4680
tcagggaagg tctttaatta cgataacgat caaacccggc tcgaagcgca gattcagcag  4740
tttaatcccc gcgatgtcga aggttatcgt cagtttctgg actattcacg cgcggtgttt  4800
aaagaaggct atctaaagct cggtactgtc cctttttat cgttcagaga catgcttcgc  4860
gccgcacctc aactggcgaa actgcaggca tggagaagcg tttacagtaa ggttgccagt  4920
tacatcgaag atgaacatct cgccaggcg ttttctttcc actcgctgtt ggtgggcggc  4980
aatcccttcg ccacctcatc catttatacg ttgatacacg cgctggagcg tgagtggggc  5040
gtctggtttc gcgtggcgg caccggcgca ttagttcagg ggatgataaa gctgttcag  5100
gatctgggtg gcgaagtcgt gttaaacgcc agagtcagcc atatggaaac gacaggaaac  5160
aagattgaag ccgtgcattt agaggacggt cgcaggttcc tgacgcaagc cgtcgcgtca  5220
aatgcagatg tggttcatac ctatcgcgac ctgttaagcc agcaccctgc cgcggttaag  5280
cagtccaaca aactgcagac taagcgcatg agtaactctc tgtttgtgct ctattttggt  5340
ttgaatcacc atcatgatca gctcgcgcat cacacggttt gtttcggccc gcgttaccgc  5400
gagctgattg acgaaatttt taatcatgat ggcctcgcag aggacttctc actttatctg  5460
cacgcgccct gtgtcacgga ttcgtcactg gcgcctgaag gttgcggcag ttactatgtg  5520
ttggcgccgg tgccgcattt aggcaccgcg aacctgact ggacggttga ggggccaaaa  5580
ctacgcgacc gtattttgc gtaccttgag cagcattaca tgcctggctt acggagtcag  5640
ctggtcacgc accggatgtt tacgccgttt gattttcgcg accagcttaa tgcctatcat  5700
ggctcagcct tttctgtgga gcccgttctt acccagagcg cctggtttcg gccgcataac  5760
cgcgataaaa ccattactaa tctctacctg gtcggcgcag gcacgcatcc cggcgcaggc  5820
attcctggcg tcatcggctc ggcaaaagcg acagcaggtt tgatgctgga ggatctgatt  5880
tgaataatcc gtcgttactc aatcatgcgg tcgaaacgat ggcagttggc tcgaaaagtt  5940
ttgcgacagc ctcaaagtta tttgatgcaa aaacccggcg cagcgtactg atgctctacg  6000
cctggtgccg ccattgtgac gatgttattg acgatcagac gctgggcttt caggcccggc  6060
agcctgcctt acaaacgccc gaacaacgtc tgatgcaact tgagatgaaa acgcgccagg  6120
cctatgcagg atcgcagatg cacgaaccgg cgtttgcggc ttttcaggaa gtggctatgg  6180
ctcatgatat cgcccggct tacgcgtttg atcatctgga aggcttcgcc atggatgtac  6240
gcgaagcgca atacagccaa ctggatgata cgctgcgcta ttgctatcac gttgcaggcg  6300
```

```
ttgtcggctt gatgatggcg caaatcatgg gcgtgcggga taacgccacg ctggaccgcg    6360
cctgtgacct tgggctggca tttcagttga ccaatattgc tcgcgatatt gtggacgatg    6420
cgcatgcggg ccgctgttat ctgccggcaa gctggctgga gcatgaaggt ctgaacaaag    6480
agaattatgc ggcacctgaa accgtcagg cgctgagccg tatcgcccgt cgtttggtgc     6540
aggaagcaga accttactat ttgtctgcca cagccggcct ggcagggttg cccctgcgtt    6600
ccgcctgggc aatcgctacg gcgaagcagg tttaccggaa aataggtgtc aaagttgaac    6660
aggccggtca gcaagcctgg gatcagcggc agtcaacgac cacgcccgaa aaattaacgc    6720
tgctgctggc cgcctctggt caggccctta cttcccggat gcgggctcat cctccccgcc    6780
ctgcgcatct ctggcagcgc ccgctctagc gccatgtcga cctcgagggg gggcccggta    6840
cccaattcgc cctatagtga gtcgtattac gcgcgctcac tggccgtcgt tttacaacgt    6900
cgtgactggg aaaaccctgg cgttacccaa cttaatcgcc ttgcagcaca tccccctttc    6960
gccagctggc gtaatagcga agaggcccgc accgatcgcc cttcccaaca gttgcgcagc    7020
ctgaatggcg aatggaaatt gtaagcgtta atattttgtt aaaattcgcg ttaaattttt    7080
gttaaatcag ctcattttt aaccaatagg ccgaaatcgg caaaatccct tataaatcaa    7140
aagaatagac cgagataggg ttgagtgttg ttccagtttg gaacaagagt ccactattaa    7200
agaacgtgga ctccaacgtc aaagggcgaa aaaccgtcta tcagggcgat ggcccactac    7260
gtgaaccatc accctaatca agttttttgg ggtcgaggtg ccgtaaagca ctaaatcgga    7320
accctaaagg gagcccccga tttagagctt gacggggaaa gccggcgaac gtggcgagaa    7380
aggaagggaa gaaagcgaaa ggagcgggcg ctagggcgct ggcaagtgta gcggtcacgc    7440
tgcgcgtaac caccacaccc gccgcgctta atgcgccgct acagggcgcg tcag          7494

<210> SEQ ID NO 46
<211> LENGTH: 8547
<212> TYPE: DNA
<213> ORGANISM: Artificial Sequence
<220> FEATURE:
<223> OTHER INFORMATION: pACYCcaro14

<400> SEQUENCE: 46
gaattccgga tgagcattca tcaggcgggc aagaatgtga ataaaggccg gataaaactt       60
gtgcttattt ttctttacgg tctttaaaaa ggccgtaata tccagctgaa cggtctggtt     120
ataggtacat tgagcaactg actgaaatgc ctcaaaatgt tctttacgat gccattggga     180
tatatcaacg gtggtatatc cagtgatttt tttctccatt ttagcttcct tagctcctga    240
aaatctcgat aactcaaaaa atacgcccgg tagtgatctt atttcattat ggtgaaagtt    300
ggaacctctt acgtgccgat caacgtctca ttttcgccaa agttggccc agggcttccc     360 ggtatcaaca gggacaccag gatttattta ttctgcgaag tgatcttccg tcacaggtat    420
ttattcggcg caaagtgcgt cgggtgatgc tgccaactta ctgatttagt gtatgatggt    480 gttttttgagg tgctccagtg gcttctgttt ctatcagctg tccctcctgt tcagctactg    540
acggggtggt gcgtaacggc aaaagcaccg ccggacatca gcgctagcgg agtgtatact    600
ggcttactat gttggcactg atgagggtgt cagtgaagtg cttcatgtgg caggagaaaa    660
aaggctgcac cggtgcgtca gcagaatatg tgatacagga tatattccgc ttcctcgctc    720
actgactcgc tacgctcggt cgttcgactg cggcgagcgg aaatggctta cgaacggggc    780
ggagatttcc tggaagatgc caggaagata cttaacaggg aagtgagagg gccgcggcaa    840
```

-continued

```
agccgttttt ccataggctc cgccccctg acaagcatca cgaaatctga cgctcaaatc      900
agtggtggcg aaacccgaca ggactataaa gataccaggc gtttccccct ggcggctccc      960
tcgtgcgctc tcctgttcct gcctttcggt ttaccggtgt cattccgctg ttatggccgc     1020
gtttgtctca ttccacgcct gacactcagt tccgggtagg cagttcgctc caagctggac     1080
tgtatgcacg aaccccccgt tcagtccgac cgctgcgcct tatccggtaa ctatcgtctt     1140
gagtccaacc cggaaagaca tgcaaaagca ccactggcag cagccactgg taattgattt     1200
agaggagtta gtcttgaagt catgcgccgg ttaaggctaa actgaaagga caagttttgg     1260
tgactgcgct cctccaagcc agttacctcg gttcaaagag ttggtagctc agagaaacctt     1320
cgaaaaccg ccctgcaagg cggttttttc gttttcagag caagagatta cgcgcagacc     1380
aaacgatct caagaagatc atcttattaa tcagataaaa tatttctaga tttcagtgca     1440
atttatctct tcaaatgtag cacctgaagt cagccccata cgatataagt tgtaattctc     1500
atgtttgaca gcttatcatc gataagcttt aatgcggtag tttatcacag ttaaattgct     1560
aacgcagtca ggcaccgtgt atgaaatcta acaatgcgct catcgtcatc ctcggcaccg     1620
tcaccctgga tgctgtaggc ataggcttgg ttatgccggt actgccgggc ctcttgcggg     1680
atatcgtcca ttccgacagc atcgccagtc actatggcgt gctgctagcg ctatatgcgt     1740
tgatgcaatt tctatgcgca cccgttctcg gagcactgtc cgaccgcttt ggccgccgcc     1800
cagtcctgct cgcttcgcta cttggagcca ctatcgacta cgcgatcatg gcgaccacac     1860
ccgtcctgtg gatcccccgg gctgcaggaa ttgccgtaaa tgtatccgtt tataaggaca     1920
gcccgaatga cggtctgcgc aaaaaaacac gttcatctca ctcgcgatgc tgcggagcag     1980
ttactggctg atattgatcg acgccttgat cagttattgc ccgtggaggg agaacgggat     2040
gttgtgggtg ccgcgatgcg tgaaggtgcg ctggcaccgg gaaaacgtat tcgccccatg     2100
ttgctgttgc tgaccgcccg cgatctgggt tgcgctgtca gccatgacgg attactggat     2160
ttggcctgtg cggtggaaat ggtccacgcg gcttcgctga tccttgacga tatgccctgc     2220
atggacgatg cgaagctgcg gcgcggacgc cctaccattc attctcatta cggagagcat     2280
gtggcaatac tggcggcggt tgccttgctg agtaaagcct ttggcgtaat tgccgatgca     2340
gatggcctca cgccgctggc aaaaaatcgg gcggtttctg aactgtcaaa cgccatcggc     2400
atgcaaggat tggttcaggg tcagttcaag gatctgtctg aagggataa gccgcgcagc     2460
gctgaagcta ttttgatgac gaatcacttt aaaaccagca cgctgttttg tgcctccatg     2520
cagatggcct cgattgttgc gaatgcctcc agcgaagcgc gtgattgcct gcatcgtttt     2580
tcacttgatc ttggtcaggc atttcaactg ctggacgatt tgaccgatgg catgaccgac     2640
accggtaagg atagcaatca ggacgccggt aaatcgacgc tggtcaatct gttaggcccg     2700
agggcggttg aagaacgtct gagacaacat cttcagcttg ccagtgagca tctctctgcg     2760
gcctgccaac acgggcacgc cactcaacat tttattcagg cctggtttga caaaaaactc     2820
gctgccgtca gttaagctta tgtgcaccgg tcagcctgtc ttaagtggga gcggctatgc     2880
aaccgcatta tgatctgatt ctcgtggggg ctggactcgc gaatggcctt atcgccctgc     2940
gtcttcagca gcagcaacct gatatgcgta ttttgcttat cgacgccgca ccccaggcgg     3000
gcgggaatca tacgtggtca tttcaccacg atgatttgac tgagagccaa catcgttgga     3060
tagctccgct ggtggttcat cactggcccg actatcaggt acgctttccc acacgccgtc     3120
gtaagctgaa cagcggctac ttttgtatta cttctcagcg tttcgctgag gttttacagc     3180
gacagtttgg cccgcacttg tggatggata ccgcggtcgc agaggttaat gcggaatctg     3240
```

-continued

```
ttcggttgaa aaagggtcag gttatcggtg cccgcgcggt gattgacggg cggggttatg    3300
cggcaaattc agcactgagc gtgggcttcc aggcgtttat tggccaggaa tggcgattga    3360
gccacccgca tggtttatcg tctcccatta tcatggatgc cacggtcgat cagcaaaatg    3420
gttatcgctt cgtgtacagc ctgccgctct cgccgaccag attgttaatt gaagacacgc    3480
actatattga taatgcgaca ttagatcctg aatgcgcgcg gcaaaatatt tgcgactatg    3540
ccgcgcaaca gggttggcag cttcagacac tgctgcgaga agaacagggc gccttaccca    3600
ttactctgtc gggcaatgcc gacgcattct ggcagcagcg ccccctggcc tgtagtggat    3660
tacgtgccgg tctgttccat cctaccaccg gctattcact gccgctggcg gttgccgtgg    3720
ccgaccgcct gagtgcactt gatgtcttta cgtcggcctc aattcaccat gccattacgc    3780
attttgcccg cgagcgctgg cagcagcagg gcttttttccg catgctgaat cgcatgctgt    3840
ttttagccgg acccgccgat tcacgctggc gggttatgca gcgttttttat ggtttacctg    3900
aagatttaat tgcccgtttt tatgcgggaa aactcacgct gaccgatcgg ctacgtattc    3960
tgagcggcaa gccgcctgtt ccggtattag cagcattgca agccattatg acgactcatc    4020
gttaaagagc gactacatga aaccaactac ggtaattggt gcaggcttcg gtggcctggc    4080
actggcaatt cgtctacaag ctgcggggat ccccgtctta ctgcttgaac aacgtgataa    4140
acccggcggt cgggcttatg tctacgagga tcagggtttt acctttgatg caggcccgac    4200
ggttatcacc gatcccagtg ccattgaaga actgtttgca ctggcaggaa aacagttaaa    4260
agagtatgtc gaactgctgc cggttacgcc gttttaccgc ctgtgttggg agtcagggaa    4320
ggtctttaat tacgataacg atcaaacccg gctcgaagcg cagattcagc agtttaatcc    4380
ccgcgatgtc gaaggttatc gtcagtttct ggactattca cgcgcggtgt ttaaagaagg    4440
ctatctaaag ctcggtactg tccctttttt atcgttcaga gacatgcttc gcgccgcacc    4500
tcaactggcg aaactgcagg catggagaag cgtttacagt aaggttgcca gttacatcga    4560
agatgaacat ctgcgccagg cgttttcttt ccactcgctg ttggtgggcg gcaatccctt    4620
cgccacctca tccatttata cgttgataca cgcgctggag cgtgagtggg gcgtctggtt    4680
tccgcgtggc ggcaccggcg cattagttca ggggatgata aagctgtttc aggatctggg    4740
tggcgaagtc gtgttaaacg ccagagtcag ccatatggaa acgacaggaa acaagattga    4800
agccgtgcat ttagaggacg gtcgcaggtt cctgacgcaa gccgtcgcgt caaatgcaga    4860
tgtggttcat acctatcgcg acctgttaag ccagcaccct gccgcggtta agcagtccaa    4920
caaactgcag actaagcgca tgagtaactc tctgtttgtg ctctatttg gtttgaatca    4980
ccatcatgat cagctcgcgc atcacacggt ttgtttcggc ccgcgttacc gcagagctgat    5040
tgacgaaatt tttaatcatg atggcctcgc agaggacttc tcactttatc tgcacgcgcc    5100
ctgtgtcacg gattcgtcac tggcgcctga aggttcggc agttactatg tgttggcgcc    5160
ggtgccgcat ttaggcaccg cgaacctcga ctggacggtt gaggggccaa aactacgcga    5220
ccgtatttttt gcgtaccttg agcagcatta catgcctggc ttacggagtc agctggtcac    5280
gcaccggatg tttacgccgt tgatttttcg cgaccagctt aatgcctatc atggctcagc    5340
cttttctgtg gagcccgttc ttacccgag cgcctggttt cggccgcata accgcgataa    5400
aaccattact aatctctacc tggtcggcgc aggcacgcat cccggcgcag gcattcctgg    5460
cgtcatcggc tcggcaaaag cgacagcagg tttgatgctg gaggatctga tttgaataat    5520
ccgtcgttac tcaatcatgc ggtcgaaacg atggcagttg gctcgaaaag ttttgcgaca    5580
```

-continued

```
gcctcaaagt tatttgatgc aaaaacccgg cgcagcgtac tgatgctcta cgcctggtgc    5640
cgccattgtg acgatgttat tgacgatcag acgctgggct ttcaggcccg gcagcctgcc    5700
ttacaaacgc ccgaacaacg tctgatgcaa cttgagatga aaacgcgcca ggcctatgca    5760
ggatcgcaga tgcacgaacc ggcgtttgcg gcttttcagg aagtggctat ggctcatgat    5820
atcgccccgg cttacgcgtt tgatcatctg gaaggcttcg ccatggatgt acgcgaagcg    5880
caatacagcc aactggatga tacgctgcgc tattgctatc acgttgcagg cgttgtcggc    5940
ttgatgatgg cgcaaatcat gggcgtgcgg gataacgcca cgctggaccg cgcctgtgac    6000
cttgggctgg catttcagtt gaccaatatt gctcgcgata ttgtgacgca tgcgcatgcg    6060
ggccgctgtt atctgccggc aagctggctg gagcatgaag gtctgaacaa agagaattat    6120
gcggcacctg aaaaccgtca ggcgctgagc cgtatcgccc gtcgtttggt gcaggaagca    6180
gaaccttact atttgtctgc cacagccggc ctggcagggt tgccctgcg ttccgcctgg     6240
gcaatcgcta cggcgaagca ggtttaccgg aaaataggtg tcaaagttga acaggccggt    6300
cagcaagcct gggatcagcg gcagtcaacg accacgcccg aaaaattaac gctgctgctg    6360
gccgcctctg tcaggcccct tacttcccgg atgcgggctc atcctccccg ccctgcgcat    6420
ctctggcagc gcccgctcta gcgccatgtc gaccgatgcc cttgagagcc ttcaacccag    6480
tcagctcctt ccggtgggcg cggggcatga ctatcgtcgc cgcacttatg actgtcttct    6540
ttatcatgca actcgtagga caggtgccgg cagcgctctg ggtcattttc ggcgaggacc    6600
gctttcgctg gagcgcgacg atgatcggcc tgtcgcttgc ggtattcgga atcttgcacg    6660
ccctcgctca agccttcgtc actggtcccg ccaccaaacg tttcggcgag aagcaggcca    6720
ttatcgccgg catggcggcc gacgcgctgg gctacgtctt gctggcgttc gcgacgcgag    6780
gctggatggc cttccccatt atgattcttc tcgcttccgg cggcatcggg atgcccgcgt    6840
tgcaggccat gctgtccagg caggtagatg acgaccatca gggacagctt caaggatcgc    6900
tcgcggctct taccagccta acttcgatca ctggaccgct gatcgtcacg gcgatttatg    6960
ccgcctcggc gagcacatgg aacgggttgg catggattgt aggcgccgcc ctataccttg    7020
tctgcctccc cgcgttgcgt cgcggtgcat ggagccgggc cacctcgacc tgaatggaag    7080
ccggcggcac ctcgctaacg gattcaccac tccaagaatt ggagccaatc aattcttgcg    7140
gagaactgtg aatgcgcaaa ccaacccttg gcagaacata tccatcgcgt ccgccatctc    7200
cagcagccgc acgcggcgca tctcgggcag cgttgggtcc tggccacggg tgcgcatgat    7260
cgtgctcctg tcgttgagga cccggctagg ctggcggggt tgccttactg gttagcagaa    7320
tgaatcaccg atacgcgagc gaacgtgaag cgactgctgc tgcaaaacgt ctgcgacctg    7380
agcaacaaca tgaatggtct tcggtttccg tgtttcgtaa agtctggaaa cgcggaagtc    7440
ccctacgtgc tgctgaagtt gcccgcaaca gagagtggaa ccaaccggtg ataccacgat    7500
actatgactg agagtcaacg ccatgagcgg cctcatttct tattctgagt tacaacagtc    7560
cgcaccgctg tccggtagct ccttccggtg ggcgcggggc atgactatcg tcgccgcact    7620
tatgactgtc ttctttatca tgcaactcgt aggacaggtg ccggcagcgc ccaacagtcc    7680
cccggccacg gggcctgcca ccatacccac gccgaaacaa gcgccctgca ccattatgtt    7740
ccggatctgc atcgcaggat gctgctggct accctgtgga acacctacat ctgtattaac    7800
gaagcgctaa ccgttttat caggctctgg gaggcagaat aaatgatcat atcgtcaatt     7860
attacctcca cggggagagc ctgagcaaac tggcctcagg catttgagaa gcacacggtc    7920
acactgcttc cggtagtcaa taaaccggta aaccagcaat agacataagc ggctatttaa    7980
```

-continued

| | |
|---|---|
| cgaccctgcc ctgaaccgac gaccgggtcg aatttgcttt cgaatttctg ccattcatcc | 8040 |
| gcttattatc acttattcag gcgtagcacc aggcgtttaa gggcaccaat aactgcctta | 8100 |
| aaaaaattac gccccgccct gccactcatc gcagtactgt tgtaattcat taagcattct | 8160 |
| gccgacatgg aagccatcac agacggcatg atgaacctga atcgccagcg gcatcagcac | 8220 |
| cttgtcgcct tgcgtataat atttgcccat ggtgaaaacg ggggcgaaga agttgtccat | 8280 |
| attggccacg tttaaatcaa aactggtgaa actcacccag ggattggctg agacgaaaaa | 8340 |
| catattctca ataaacccTT tagggaaata ggccaggttt tcaccgtaac acgccacatc | 8400 |
| ttgcgaatat atgtgtagaa actgccggaa atcgtcgtgg tattcactcc agagcgatga | 8460 |
| aaacgtttca gtttgctcat ggaaaacggt gtaacaaggg tgaacactat cccatatcac | 8520 |
| cagctcaccg tctttcattg ccatacg | 8547 |

<210> SEQ ID NO 47
<211> LENGTH: 1119
<212> TYPE: DNA
<213> ORGANISM: Escherichia coli
<220> FEATURE:
<221> NAME/KEY: CDS
<222> LOCATION: (1)..(1116)

<400> SEQUENCE: 47

| | |
|---|---|
| atg cat aac cag gct cca att caa cgt aga aaa tca aca cgt att tac<br>Met His Asn Gln Ala Pro Ile Gln Arg Arg Lys Ser Thr Arg Ile Tyr<br>1               5                   10                  15 | 48 |
| gtt ggg aat gtg ccg att ggc gat ggt gct ccc atc gcc gta cag tcc<br>Val Gly Asn Val Pro Ile Gly Asp Gly Ala Pro Ile Ala Val Gln Ser<br>            20                  25                  30 | 96 |
| atg acc aat acg cgt acg aca gac gtc gaa gca acg gtc aat caa atc<br>Met Thr Asn Thr Arg Thr Thr Asp Val Glu Ala Thr Val Asn Gln Ile<br>        35                  40                  45 | 144 |
| aag gcg ctg gaa cgc gtt ggc gct gat atc gtc cgt gta tcc gta ccg<br>Lys Ala Leu Glu Arg Val Gly Ala Asp Ile Val Arg Val Ser Val Pro<br>    50                  55                  60 | 192 |
| acg atg gac gcg gca gaa gcg ttc aaa ctc atc aaa cag cag gtt aac<br>Thr Met Asp Ala Ala Glu Ala Phe Lys Leu Ile Lys Gln Gln Val Asn<br>65                  70                  75                  80 | 240 |
| gtg ccg ctg gtg gct gac atc cac ttc gac tat cgc att gcg ctg aaa<br>Val Pro Leu Val Ala Asp Ile His Phe Asp Tyr Arg Ile Ala Leu Lys<br>                85                  90                  95 | 288 |
| gta gcg gaa tac ggc gtc gat tgt ctg cgt att aac cct ggc aat atc<br>Val Ala Glu Tyr Gly Val Asp Cys Leu Arg Ile Asn Pro Gly Asn Ile<br>            100                 105                 110 | 336 |
| ggt aat gaa gag cgt att cgc atg gtg gtt gac tgt gcg cgc gat aaa<br>Gly Asn Glu Glu Arg Ile Arg Met Val Val Asp Cys Ala Arg Asp Lys<br>        115                 120                 125 | 384 |
| aac att ccg atc cgt att ggc gtt aac gcc gga tcg ctg gaa aaa gat<br>Asn Ile Pro Ile Arg Ile Gly Val Asn Ala Gly Ser Leu Glu Lys Asp<br>    130                 135                 140 | 432 |
| ctg caa gaa aag tat ggc gaa ccg acg ccg cag gcg ttg ctg gaa tct<br>Leu Gln Glu Lys Tyr Gly Glu Pro Thr Pro Gln Ala Leu Leu Glu Ser<br>145                 150                 155                 160 | 480 |
| gcc atg cgt cat gtt gat cat ctc gat cgc ctg aac ttc gat cag ttc<br>Ala Met Arg His Val Asp His Leu Asp Arg Leu Asn Phe Asp Gln Phe<br>                165                 170                 175 | 528 |
| aaa gtc agc gtg aaa gcg tct gac gtc ttc ctc gct gtt gag tct tat<br>Lys Val Ser Val Lys Ala Ser Asp Val Phe Leu Ala Val Glu Ser Tyr<br>            180                 185                 190 | 576 |

```
cgt ttg ctg gca aaa cag atc gat cag ccg ttg cat ctg ggg atc acc      624
Arg Leu Leu Ala Lys Gln Ile Asp Gln Pro Leu His Leu Gly Ile Thr
        195                 200                 205 gaa gcc ggt ggt gcg cgc agc ggg gca gta aaa tcc gcc att ggt tta      672
Glu Ala Gly Gly Ala Arg Ser Gly Ala Val Lys Ser Ala Ile Gly Leu
    210                 215                 220 ggt ctg ctg ctg tct gaa ggc atc ggc gac acg ctg cgc gta tcg ctg      720
Gly Leu Leu Leu Ser Glu Gly Ile Gly Asp Thr Leu Arg Val Ser Leu
225                 230                 235                 240 gcg gcc gat ccg gtc gaa gag atc aaa gtc ggt ttc gat att ttg aaa      768
Ala Ala Asp Pro Val Glu Glu Ile Lys Val Gly Phe Asp Ile Leu Lys
                245                 250                 255 tcg ctg cgt atc cgt tcg cga ggg atc aac ttc atc gcc tgc ccg acc      816
Ser Leu Arg Ile Arg Ser Arg Gly Ile Asn Phe Ile Ala Cys Pro Thr
            260                 265                 270 tgt tcg cgt cag gaa ttt gat gtt atc ggt acg gtt aac gcg ctg gag      864
Cys Ser Arg Gln Glu Phe Asp Val Ile Gly Thr Val Asn Ala Leu Glu
        275                 280                 285 caa cgc ctg gaa gat atc atc act ccg atg gac gtt tcg att atc ggc      912
Gln Arg Leu Glu Asp Ile Ile Thr Pro Met Asp Val Ser Ile Ile Gly
    290                 295                 300 tgc gtg gtg aat ggc cca ggt gag gcg ctg gtt tct aca ctc ggc gtc      960
Cys Val Val Asn Gly Pro Gly Glu Ala Leu Val Ser Thr Leu Gly Val
305                 310                 315                 320 acc ggc ggc aac aag aaa agc ggc ctc tat gaa gat ggc gtg cgc aaa     1008
Thr Gly Gly Asn Lys Lys Ser Gly Leu Tyr Glu Asp Gly Val Arg Lys
                325                 330                 335 gac cgt ctg gac aac aac gat atg atc gac cag ctg gaa gca cgc att     1056
Asp Arg Leu Asp Asn Asn Asp Met Ile Asp Gln Leu Glu Ala Arg Ile
            340                 345                 350 cgt gcg aaa gcc agt cag ctg gac gaa gcg cgt cga att gac gtt cag     1104
Arg Ala Lys Ala Ser Gln Leu Asp Glu Ala Arg Arg Ile Asp Val Gln
        355                 360                 365 cag gtt gaa aaa taa                                                  1119
Gln Val Glu Lys
    370
```

<210> SEQ ID NO 48
<211> LENGTH: 372
<212> TYPE: PRT
<213> ORGANISM: Escherichia coli

<400> SEQUENCE: 48

```
Met His Asn Gln Ala Pro Ile Gln Arg Arg Lys Ser Thr Arg Ile Tyr
1               5                   10                  15

Val Gly Asn Val Pro Ile Gly Asp Gly Ala Pro Ile Ala Val Gln Ser
                20                  25                  30

Met Thr Asn Thr Arg Thr Thr Asp Val Glu Ala Thr Val Asn Gln Ile
            35                  40                  45

Lys Ala Leu Glu Arg Val Gly Ala Asp Ile Val Arg Val Ser Val Pro
        50                  55                  60

Thr Met Asp Ala Ala Glu Ala Phe Lys Leu Ile Lys Gln Gln Val Asn
65                  70                  75                  80

Val Pro Leu Val Ala Asp Ile His Phe Asp Tyr Arg Ile Ala Leu Lys
                85                  90                  95

Val Ala Glu Tyr Gly Val Asp Cys Leu Arg Ile Asn Pro Gly Asn Ile
                100                 105                 110

Gly Asn Glu Glu Arg Ile Arg Met Val Val Asp Cys Ala Arg Asp Lys
```

```
                     115                 120                 125
Asn Ile Pro Ile Arg Ile Gly Val Asn Ala Gly Ser Leu Glu Lys Asp
    130                 135                 140

Leu Gln Glu Lys Tyr Gly Glu Pro Thr Pro Gln Ala Leu Leu Glu Ser
145                 150                 155                 160

Ala Met Arg His Val Asp His Leu Asp Arg Leu Asn Phe Asp Gln Phe
                165                 170                 175

Lys Val Ser Val Lys Ala Ser Asp Val Phe Leu Ala Val Glu Ser Tyr
            180                 185                 190

Arg Leu Leu Ala Lys Gln Ile Asp Gln Pro Leu His Leu Gly Ile Thr
        195                 200                 205

Glu Ala Gly Gly Ala Arg Ser Gly Ala Val Lys Ser Ala Ile Gly Leu
    210                 215                 220

Gly Leu Leu Leu Ser Glu Gly Ile Gly Asp Thr Leu Arg Val Ser Leu
225                 230                 235                 240

Ala Ala Asp Pro Val Glu Glu Ile Lys Val Gly Phe Asp Ile Leu Lys
                245                 250                 255

Ser Leu Arg Ile Arg Ser Arg Gly Ile Asn Phe Ile Ala Cys Pro Thr
            260                 265                 270

Cys Ser Arg Gln Glu Phe Asp Val Ile Gly Thr Val Asn Ala Leu Glu
        275                 280                 285

Gln Arg Leu Glu Asp Ile Ile Thr Pro Met Asp Val Ser Ile Ile Gly
    290                 295                 300

Cys Val Val Asn Gly Pro Gly Glu Ala Leu Val Ser Thr Leu Gly Val
305                 310                 315                 320

Thr Gly Gly Asn Lys Lys Ser Gly Leu Tyr Glu Asp Gly Val Arg Lys
                325                 330                 335

Asp Arg Leu Asp Asn Asn Asp Met Ile Asp Gln Leu Glu Ala Arg Ile
            340                 345                 350

Arg Ala Lys Ala Ser Gln Leu Asp Glu Ala Arg Arg Ile Asp Val Gln
        355                 360                 365

Gln Val Glu Lys
    370

<210> SEQ ID NO 49
<211> LENGTH: 8823
<212> TYPE: DNA
<213> ORGANISM: Artificial Sequence
<220> FEATURE:
<223> OTHER INFORMATION: pBScyclogcpE

<400> SEQUENCE: 49
gtggcacttt tcggggaaat gtgcgcggaa cccctatttg tttatttttc taaatacatt      60
caaatatgta tccgctcatg agacaataac cctgataaat gcttcaataa tattgaaaaa     120
ggaagagtat gagtattcaa catttccgtg tcgcccttat tcccttttt  gcggcatttt     180 gccttcctgt ttttgctcac ccagaaacgc tggtgaaagt aaaagatgct gaagatcagt     240
tgggtgcacg agtgggttac atcgaactgg atctcaacag cggtaagatc cttgagagtt     300
ttcgccccga agaacgtttt ccaatgatga gcacttttaa agttctgcta tgtggcgcgg     360
tattatcccg tattgacgcc gggcaagagc aactcggtcg ccgcatacac tattctcaga     420
atgacttggt tgagtactca ccagtcacag aaaagcatct tacggatggc atgacagtaa     480
gagaattatg cagtgctgcc ataaccatga gtgataacac tgcggccaac ttacttctga     540
caacgatcgg aggaccgaag gagctaaccg ctttttttgca acatgggg   gatcatgtaa     600
```

-continued

```
ctcgccttga tcgttgggaa ccggagctga atgaagccat accaaacgac gagcgtgaca    660
ccacgatgcc tgtagcaatg gcaacaacgt tgcgcaaact attaactggc gaactactta    720
ctctagcttc ccggcaacaa ttaatagact ggatggaggc ggataaagtt gcaggaccac    780
ttctgcgctc ggcccttccg gctggctggt ttattgctga taaatctgga gccggtgagc    840
gtgggtctcg cggtatcatt gcagcactgg ggccagatgg taagccctcc cgtatcgtag    900
ttatctacac gacggggagt caggcaacta tggatgaacg aaatagacag atcgctgaga    960
taggtgcctc actgattaag cattggtaac tgtcagacca agtttactca tatatacttt   1020
agattgattt aaaacttcat ttttaattta aaaggatcta ggtgaagatc ctttttgata   1080
atctcatgac caaatccct taacgtgagt tttcgttcca ctgagcgtca gaccccgtag   1140
aaaagatcaa aggatcttct tgagatcctt ttttctgcg cgtaatctgc tgcttgcaaa    1200
caaaaaaacc accgctacca gcggtggttt gtttgccgga tcaagagcta ccaactcttt   1260
ttccgaaggt aactggcttc agcagagcgc agataccaaa tactgtcctt ctagtgtagc   1320
cgtagttagg ccaccacttc aagaactctg tagcaccgcc tacatacctc gctctgctaa   1380
tcctgttacc agtggctgct gccagtggcg ataagtcgtg tcttaccggg ttggactcaa   1440
gacgatagtt accggataag cgcagcggt cgggctgaac gggggggttcg tgcacacagc   1500 ccagcttgga gcgaacgacc tacaccgaac tgagatacct acagcgtgag ctatgagaaa   1560
gcgccacgct tcccgaaggg agaaaggcgg acaggtatcc ggtaagcggc agggtcggaa   1620
caggagagcg cacgagggag cttccagggg gaaacgcctg gtatctttat agtcctgtcg   1680
ggtttcgcca cctctgactt gagcgtcgat ttttgtgatg ctcgtcaggg gggcggagcc   1740 tatgaaaaa cgccagcaac gcggcctttt tacggttcct ggccttttgc tggccttttg   1800
ctcacatgtt ctttcctgcg ttatcccctg attctgtgga taaccgtatt accgcctttg   1860
agtgagctga taccgctcgc cgcagccgaa cgaccgagcg cagcgagtca gtgagcgagg   1920
aagcggaaga gcgcccaata cgcaaaccgc ctctccccgc gcgttggccg attcattaat   1980
gcagctggca cgacaggttt cccgactgga aagcgggcag tgagcgcaac gcaattaatg   2040
tgagttagct cactcattag gcaccccagg ctttacactt tatgcttccg gctcgtatgt   2100
tgtgtggaat tgtgagcgga taacaatttc acacaggaaa cagctatgac catgattacg   2160
ccaagcgcgc aattaaccct cactaaaggg aacaaaagct ggagctccac cgcgggagga   2220
gaaattaacc atgcataacc aggctccaat tcaacgtaga aaatcaacac gtatttacgt   2280
tgggaatgtg ccgattggcg atggtgctcc catcgccgta cagtccatga ccaatacgcg   2340
tacgacagac gtcgaagcaa cggtcaatca aatcaaggcg ctggaacgcg ttggcgctga   2400
tatcgtccgt gtatccgtac cgacgatgga cgcggcagaa gcgttcaaac tcatcaaaca   2460
gcaggttaac gtgccgctgg tggctgacat ccacttcgac tatcgcattg cgctgaaagt   2520
agcggaatac ggcgtcgatt gtctgcgtat taaccctggc aatatcggta atgaagagcg   2580
tattcgcatg gtggttgact gtgcgcgcga taaaaacatt ccgatccgta ttggcgttaa   2640
cgccggatcg ctggaaaaag atctgcaaga aaagtatggc gaaccgacgc cgcaggcgtt   2700
gctggaatct gccatgcgtc atgttgatca tctcgatcgc ctgaacttcg atcagttcaa   2760
agtcagcgtg aaagcgtctg acgtcttcct cgctgttgag tcttatcgtt tgctggcaaa   2820
acagatcgat cagccgttgc atctggggat caccgaagcc ggtggtgcgc gcagcggggc   2880
agtaaaatcc gccattggtt taggtctgct gctgtctgaa ggcatcggcg acacgctgcg   2940
```

-continued

```
cgtatcgctg gcggccgatc cggtcgaaga gatcaaagtc ggtttcgata ttttgaaatc      3000
gctgcgtatc cgttcgcgag ggatcaactt catcgcctgc ccgacctgtt cgcgtcagga      3060
atttgatgtt atcggtacgg ttaacgcgct ggagcaacgc ctggaagata tcatcactcc      3120
gatggacgtt tcgattatcg gctgcgtggt gaatggccca ggtgaggcgc tggtttctac      3180
actcggcgtc accggcggca acaagaaaag cggcctctat gaagatggcg tgcgcaaaga      3240
ccgtctggac aacaacgata tgatcgacca gctggaagca cgcattcgtg cgaaagccag      3300
tcagctggac gaagcgcgtc gaattgacgt tcagcaggtt gaaaaataag cggccgctct      3360
agaactagtg gatcccccgg gctgcaggaa ttcgaggaga aattaaccat gtatatcggg      3420
atagatcttg gcacctcggg cgtaaaagtt attttgctca acgagcaggg tgaggtggtt      3480
gctgcgcaaa cggaaaagct gaccgtttcg cgcccgcatc cactctggtc ggaacaagac      3540
ccggaacagt ggtggcaggc aactgatcgc gcaatgaaag ctctgggcga tcagcattct      3600
ctgcaggacg ttaaagcatt gggtattgcc ggccagatgc acgagcaac cttgctggat      3660
gctcagcaac gggtgttacg ccctgccatt ttgtggaacg acgggcgctg tgcgcaagag      3720
tgcactttgc tggaagcgcg agttccgcaa tcgcgggtga ttaccggcaa cctgatgatg      3780
cccggattta ctgcgcctaa attgctatgg gttcagcggc atgagccgga gatattccgt      3840
caaatcgaca agtattatt accgaaagat tacttgcgtc tgcgtatgac gggggagttt      3900
gccagcgata tgtctgacgc agctggcacc atgtggctgg atgtcgcaaa gcgtgactgg      3960
agtgacgtca tgctgcaggc ttgcgactta tctcgtgacc agatgcccgc attatacgaa      4020
ggcagcgaaa ttactggtgc tttgttacct gaagttgcga aagcgtgggg tatggcgacg      4080
gtgccagttg tcgcaggcgg tggcgacaat gcagctggtg cagttggtgt gggaatggtt      4140
gatgctaatc aggcaatgtt atcgctgggg acgtcggggg tctattttgc tgtcagcgaa      4200
gggttcttaa gcaagccaga aagcgccgta catagctttt gccatgcgct accgcaacgt      4260
tggcatttaa tgtctgtgat gctgagtgca gcgtcgtgtc tggattgggc cgcgaaatta      4320
accggcctga gcaatgtccc agctttaatc gctgcagctc aacaggctga tgaaagtgcc      4380
gagccagttt ggtttctgcc ttatctttcc ggcgagcgta cgccacacaa taatccccag      4440
gcgaaggggg ttttctttgg tttgactcat caacatggcc ccaatgaact ggcgcgagca      4500
gtgctggaag gcgtgggtta tgcgctggca gatggcatgg atgtcgtgca tgcctgcggt      4560
attaaaccgc aaagtgttac gttgattggg ggcggggcgc gtagtgagta ctggcgtcag      4620
atgctggcgg atatcagcgg tcagcagctc gattaccgta cgggggggga tgtggggcca      4680
gcactgggcg cagcaaggct ggcgcagatc gcggcgaatc cagagaaatc gctcattgaa      4740
ttgttgccgc aactaccgtt agaacagtcg catctaccag atgcgcagcg ttatgccgct      4800
tatcagccac gacgagaaac gttccgtcgc ctctatcagc aacttctgcc attaatggcg      4860
taaaagcttg aggagaaatt aaccatgaag caactcacca ttctgggctc gaccggctcg      4920
attggttgca gcacgctgga cgtggtgcgc cataatcccg aacacttccg cgtagttgcg      4980
ctggtggcag gcaaaaatgt cactcgcatg gtagaacagt gcctggaatt ctctccccgc      5040
tatgccgtaa tggacgatga agcgagtgcg aaacttctta aaacgatgct acagcaacag      5100
ggtagccgca ccgaagtctt aagtgggcaa caagccgctt gcgatatggc agcgcttgag      5160
gatgttgatc aggtgatggc agccattgtt ggcgctgctg ggctgttacc tacgcttgct      5220
gcgatccgcg cgggtaaaac cattttgctg gccaataaag aatcactggt tacctgcgga      5280
cgtctgtttt tggacgccgt aaagcagagc aaagcgcaat tgttaccggt cgatagcgaa      5340
```

```
cataacgcca tttttcagag tttaccgcaa cctatccagc ataatctggg atacgctgac   5400
cttgagcaaa atggcgtggt gtccatttta cttaccgggt ctggtggccc tttccgtgag   5460
acgccattgc gcgatttggc aacaatgacg ccggatcaag cctgccgtca tccgaactgg   5520
tcgatgggc gtaaaatttc tgtcgattcg gctaccatga tgaacaaagg tctggaatac   5580
attgaagcgc gttggctgtt taacgccagc gccagccaga tggaagtgct gattcacccg   5640
cagtcagtga ttcactcaat ggtgcgctat caggacggca gtgttctggc gcagctgggg   5700
gaaccggata tgcgtacgcc aattgcccac accatggcat ggccgaatcg cgtgaactct   5760
ggcgtgaagc cgctcgattt ttgcaaacta agtgcgttga catttgccgc accggattat   5820
gatcgttatc catgcctgaa actggcgatg gaggcgttcg aacaaggcca ggcagcgacg   5880
acagcattga atgccgcaaa cgaaatcacc gttgctgctt ttcttgcgca acaaatccgc   5940
tttacggata tcgctgcgtt gaatttatcc gtactggaaa aaatggatat gcgcgaacca   6000
caatgtgtgg acgatgtgtt atctgttgat gcgaacgcgc gtgaagtcgc cagaaaagag   6060
gtgatgcgtc tcgcaagctg agtcgacgag gagaaattaa ccatggcaac cactcatttg   6120
gatgtttgcg ccgtggttcc ggcggccgga tttggccgtc gaatgcaaac ggaatgtcct   6180
aagcaatatc tctcaatcgg taatcaaacc attcttgaac actcggtgca tgcgctgctg   6240
gcgcatcccc gggtgaaacg tgtcgtcatt gccataagtc ctggcgatag ccgttttgca   6300
caacttcctc tggcgaatca tccgcaaatc accgttgtag atggcggtga tgagcgtgcc   6360
gattccgtgc tggcaggtct gaaagccgct ggcgacgcgc agtgggtatt ggtgcatgac   6420
gccgctcgtc cttgtttgca tcaggatgac ctcgcgcgat tgttggcgtt gagcgaaacc   6480
agccgcacgg gggggatcct cgccgcacca gtgcgcgata ctatgaaacg tgccgaaccg   6540
ggcaaaaatg ccattgctca taccgttgat cgcaacggct tatggcacgc gctgacgccg   6600
caattttttcc ctcgtgagct gttacatgac tgtctgacgc gcgctctaaa tgaaggcgcg   6660
actattaccg acgaagcctc ggcgctggaa tattgcggat ccatcctca gttggtcgaa   6720
ggccgtgcgc ataacattaa agtcacgcgc ccggaagatt tggcactggc cgagttttac   6780
ctcacccgaa ccatccatca ggagaataca taatgcgaat tggacacggt tttgacgtac   6840
atgcctttgg cggtgaaggc ccaattatca ttggtggcgt acgcattcct tacgaaaaag   6900
gattgctggc gcattctgat ggcgacgtgg cgctccatgc gttgaccgat gcattgcttg   6960
gcgcggcggc gctgggggat atcggcaagc tgttcccgga taccgatccg gcatttaaag   7020
gtgccgatag ccgcgagctg ctacgcgaag cctggcgtcg tattcaggcg aagggttata   7080
cccttggcaa cgtcgatgtc actatcatcg ctcaggcacc gaagatgttg ccgcacattc   7140
cacaaatgcg cgtgtttatt gccgaagatc tcggctgcca tatggatgat gttaacgtga   7200
aagccactac tacggaaaaa ctgggattta ccggacgtgg ggaagggatt gcctgtgaag   7260
cggtggcgct actcattaag gcaacaaaat gactcgagga ggagaaatta accatgcgga   7320
cacagtggcc ctctccggca aaacttaatc tgttttttata cattaccggt cagcgtgcgg   7380
atggttacca cacgctgcaa acgctgtttc agtttcttga ttacggcgac accatcagca   7440
ttgagcttcg tgacgatggg gatattcgtc tgttaacgcc cgttgaaggc gtggaacatg   7500
aagataaccct gatcgttcgc gcagcgcgat tgttgatgaa aactgcggca gacagcgggc   7560
gtcttccgac gggaagcggt gcgaaatatca gcattgacaa cgtttgccg atgggcggcg   7620
gtctcggcgg tggttcatcc aatgccgcga cggtcctggt ggcattaaat catctctggc   7680
```

| | |
|---|---|
| aatgcgggct aagcatggat gagctggcgg aaatgggget gacgctgggc gcagatgttc | 7740 |
| ctgtctttgt tcggggcat gccgcgtttg ccgaaggcgt tggtgaaata ctaacgccgg | 7800 |
| tggatccgcc agagaagtgg tatctggtgg cgcaccctgg tgtaagtatt ccgactccgg | 7860 |
| tgatttttaa agatcctgaa ctcccgcgca atacgccaaa aaggtcaata gaaacgttgc | 7920 |
| taaaatgtga attcagcaat gattgcgagg ttatcgcaag aaaacgtttt cgcgaggttg | 7980 |
| atgcggtgct ttcctggctg ttagaatacg ccccgtcgcg cctgactggg acaggggcct | 8040 |
| gtgtctttgc tgaatttgat acagagtctg aagcccgcca ggtgctagag caagcccgg | 8100 |
| aatggctcaa tggctttgtg gcgaaaggcg ctaatctttc cccattgcac agagccatgc | 8160 |
| tttaaggtac ccaattcgcc ctatagtgag tcgtattacg cgcgctcact ggccgtcgtt | 8220 |
| ttacaacgtc gtgactggga aaccctggc gttacccaac ttaatcgcct tgcagcacat | 8280 |
| cccccttcg ccagctggcg taatagcgaa gaggcccgca ccgatcgccc ttcccaacag | 8340 |
| ttgcgcagcc tgaatggcga atggaaattg taagcgttaa tattttgtta aaattcgcgt | 8400 |
| taaattttg ttaaatcagc tcatttttta accataggc cgaaatcggc aaaatccctt | 8460 |
| ataaatcaaa agaatagacc gagataggt tgagtgttgt tccagtttgg aacaagagtc | 8520 |
| cactattaaa gaacgtggac tccaacgtca aagggcgaaa aaccgtctat cagggcgatg | 8580 |
| gcccactacg tgaaccatca ccctaatcaa gttttttggg gtcgaggtgc cgtaaagcac | 8640 |
| taaatcggaa ccctaaaggg agcccccgat ttagagcttg acggggaaag ccggcgaacg | 8700 |
| tggcgagaaa ggaagggaag aaagcgaaag gagcgggcgc tagggcgctg gcaagtgtag | 8760 |
| cggtcacgct gcgcgtaacc accacacccg ccgcgcttaa tgcgccgcta cagggcgcgt | 8820 |
| cag | 8823 |

<210> SEQ ID NO 50
<211> LENGTH: 5793
<212> TYPE: DNA
<213> ORGANISM: Artificial Sequence
<220> FEATURE:
<223> OTHER INFORMATION: pACYClytBgcpE

<400> SEQUENCE: 50

| | |
|---|---|
| gaattccgga tgagcattca tcaggcgggc aagaatgtga ataaaggccg gataaaactt | 60 |
| gtgcttattt ttctttacgg tctttaaaaa ggccgtaata tccagctgaa cggtctggtt | 120 |
| ataggtacat tgagcaactg actgaaatgc ctcaaaatgt tctttacgat gccattggga | 180 |
| tatatcaacg gtggtatatc cagtgatttt tttctccatt ttagcttcct tagctcctga | 240 |
| aaatctcgat aactcaaaaa atacgcccgg tagtgatctt atttcattat ggtgaaagtt | 300 |
| ggaacctctt acgtgccgat caacgtctca ttttcgccaa aagttggccc agggcttccc | 360 |
| ggtatcaaca gggacaccag gatttattta ttctgcgaag tgatcttccg tcacaggtat | 420 |
| ttattcggcg caaagtgcgt cgggtgatgc tgccaactta ctgatttagt gtatgatggt | 480 |
| gtttttgagg tgctccagtg cttctgtttt ctatcagctg tccctcctgt tcagctactg | 540 |
| acggggtggt gcgtaacggc aaaagcaccg ccggacatca gcgctagcgg agtgtatact | 600 |
| ggcttactat gttggcactg atgagggtgt cagtgaagtg cttcatgtgg caggagaaaa | 660 |
| aaggctgcac cggtgcgtca gcagaatatg tgatacagga tatattccgc ttcctcgctc | 720 |
| actgactcgc tacgctcggt cgttcgactg cggcgagcgg aaatggctta cgaacggggc | 780 |
| ggagatttcc tggaagatgc caggaagata cttaacaggg aagtgagagg gccgcggcaa | 840 |
| agccgttttt ccataggctc cgcccccctg acaagcatca cgaaatctga cgctcaaatc | 900 |

-continued

```
agtggtggcg aaacccgaca ggactataaa gataccaggc gtttcccct ggcggctccc      960
tcgtgcgctc tcctgttcct gcctttcggt ttaccggtgt cattccgctg ttatggccgc     1020
gtttgtctca ttccacgcct gacactcagt tccgggtagg cagttcgctc caagctggac     1080
tgtatgcacg aaccccccgt tcagtccgac cgctgcgcct tatccggtaa ctatcgtctt     1140
gagtccaacc cggaaagaca tgcaaaagca ccactggcag cagccactgg taattgattt     1200
agaggagtta gtcttgaagt catgcgccgg ttaaggctaa actgaaagga caagttttgg     1260
tgactgcgct cctccaagcc agttacctcg gttcaaagag ttggtagctc agagaacctt     1320
cgaaaaaccg ccctgcaagg cggttttttc gttttcagag caagagatta cgcgcagacc     1380
aaaacgatct caagaagatc atcttattaa tcagataaaa tatttctaga tttcagtgca     1440
atttatctct tcaaatgtag cacctgaagt cagccccata cgatataagt tgtaattctc     1500
atgtttgaca gcttatcatc gataagcttt aatgcggtag tttatcacag ttaaattgct     1560
aacgcagtca ggcaccgtgt atgaaatcta acaatgcgct catcgtcatc ctcggcaccg     1620
tcaccctgga tgctgtaggc ataggcttgg ttatgccggt actgccgggc ctcttgcggg     1680
atatcgtcca ttccgacagc atcgccagtc actatggcgt gctgctagcg ctatatgcgt     1740
tgatgcaatt tctatgcgca cccgttctcg gagcactgtc cgaccgcttt ggccgccgcc     1800
cagtcctgct cgcttcgcta cttggagcca ctatcgacta cgcgatcatg gcgaccacac     1860
ccgtcctgtg gatccgagga gaaattaacc atgcataacc aggctccaat tcaacgtaga     1920
aaatcaacac gtatttacgt tgggaatgtg ccgattggcg atggtgctcc catcgccgta     1980
cagtccatga ccaatacgcg tacgacagac gtcgaagcaa cggtcaatca aatcaaggcg     2040
ctggaacgcg ttggcgctga tatcgtccgt gtatccgtac cgacgatgga cgcggcagaa     2100
gcgttcaaac tcatcaaaca gcaggttaac gtgccgctgg tggctgacat ccacttcgac     2160
tatcgcattg cgctgaaagt agcggaatac ggcgtcgatt gtctgcgtat taaccctggc     2220
aatatcggta atgaagagcg tattcgcatg gtggttgact gtgcgcgcga taaaaacatt     2280
ccgatccgta ttggcgttaa cgccggatcg ctggaaaaag atctgcaaga aaagtatggc     2340
gaaccgacgc cgcaggcgtt gctggaatct gccatgcgtc atgttgatca tctcgatcgc     2400
ctgaacttcg atcagttcaa agtcagcgtg aaagcgtctg acgtcttcct cgctgttgag     2460
tcttatcgtt tgctggcaaa acagatcgat cagccgttgc atctggggat caccgaagcc     2520
ggtggtgcgc gcagcggggc agtaaaatcc gccattggtt taggtctgct gctgtctgaa     2580
ggcatcggcg acacgctgcg cgtatcgctg gcggccgatc cggtcgaaga gatcaaagtc     2640
ggtttcgata ttttgaaatc gctgcgtatc cgttcgcgag ggatcaactt catcgcctgc     2700
ccgacctgtt cgcgtcagga atttgatgtt atcggtacgg ttaacgcgct ggagcaacgc     2760
ctggaagata tcatcactcc gatggacgtt tcgattatcg gctgcgtggt gaatggccca     2820
ggtgaggcgc tggtttctac actcggcgtc accggcggca acaagaaaag cggcctctat     2880
gaagatggcg tgcgcaaaga ccgtctggac aacaacgata tgatcgacca gctggaagca     2940
cgcattcgtg cgaaagccag tcagctggac gaagcgcgtc gaattgacgt tcagcaggtt     3000
gaaaaataag tcgacgagga gaattaacc atgcagatcc tgttggccaa cccgcgtggt     3060
ttttgtgccg gggtagaccg cgctatcagc attgttgaaa acgcgctggc catttacggc     3120
gcaccgatat atgtccgtca cgaagtggta cataaccgct atgtggtcga tagcttgcgt     3180
gagcgtgggg ctatctttat tgagcagatt agcgaagtac cggacggcgc gatcctgatt     3240
```

```
ttctccgcac acggtgtttc tcaggcggta cgtaacgaag caaaaagtcg cgatttgacg    3300
gtgtttgatg ccacctgtcc gctggtgacc aaagtgcata tggaagtcgc ccgcgccagt    3360
cgccgtggcg aagaatctat tctcatcggt cacgccgggc acccggaagt ggaagggaca    3420
atgggccagt acagtaaccc ggaaggggga atgtatctgg tcgaatcgcc ggacgatgtg    3480
tggaaactga cggtcaaaaa cgaagagaag ctctccttta tgacccagac cacgctgtcg    3540
gtggatgaca cgtctgatgt gatcgacgcg ctgcgtaaac gcttcccgaa aattgtcggt    3600
ccgcgcaaag atgacatctg ctacgccacg actaaccgtc aggaagcggt acgcgccctg    3660
gcagaacagg cggaagttgt gttggtggtc ggttcgaaaa actcctccaa ctccaaccgt    3720
ctggcggagc tggcccagcg tatgggcaaa cgcgcgtttt tgattgacga tgcgaaagac    3780
atccaggaag agtgggtgaa agaggttaaa tgcgtcggcg tgactgcggg cgcatcggct    3840
ccggatattc tggtgcagaa tgtggtggca cgtttgcagc agctgggcgg tggtgaagcc    3900
attccgctgg aaggccgtga agaaaacatt gttttcgaag tgccgaaaga gctgcgtgtc    3960
gatattcgtg aagtcgatta acggccgacg cgctgggcta cgtcttgctg gcgttcgcga    4020
cgcgaggctg gatggccttc cccattatga ttcttctcgc ttccggcggc atcgggatgc    4080
ccgcgttgca ggccatgctg tccaggcagg tagatgacga ccatcaggga cagcttcaag    4140
gatcgctcgc ggctcttacc agcctaactt cgatcactgg accgctgatc gtcacgcgca    4200
tttatgccgc ctcggcgagc acatggaacg ggttggcatg gattgtaggc gccgccctat    4260
accttgtctg cctccccgcg ttgcgtcgcg gtgcatggag ccgggccacc tcgacctgaa    4320
tggaagccgg cggcacctcg ctaacggatt caccactcca agaattggag ccaatcaatt    4380
cttgcggaga actgtgaatg cgcaaaccaa cccttggcag aacatatcca tcgcgtccgc    4440
catctccagc agccgcacgc ggcgcatctc gggcagcgtt gggtcctggc cacgggtgcg    4500
catgatcgtg ctcctgtcgt tgaggacccg gctaggctgg cggggttgcc ttactggtta    4560
gcagaatgaa tcaccgatac gcgagcgaac gtgaagcgac tgctgctgca aaacgtctgc    4620
gacctgagca caacatgaa tggtcttcgg tttccgtgtt tcgtaaagtc tggaaacgcg    4680
gaagtcccct acgtgctgct gaagttgccc gcaacagaga gtggaaccaa ccggtgatac    4740
cacgatacta tgactgagag tcaacgccat gagcggcctc atttcttatt ctgagttaca    4800
acagtccgca ccgctgtccg gtagctcctt ccggtgggcg cggggcatga ctatcgtcgc    4860
cgcacttatg actgtcttct ttatcatgca actcgtagga caggtgccgg cagcgcccaa    4920
cagtcccccg gccacggggc ctgccaccat acccacgccg aaacaagcgc cctgcaccat    4980
tatgttccgg atctgcatcg caggatgctg ctggctaccc tgtggaacac ctacatctgt    5040
attaacgaag cgctaaccgt ttttatcagg ctctgggagg cagaataaat gatcatatcg    5100
tcaattatta cctccacggg gagagcctga gcaaactggc ctcaggcatt tgagaagcac    5160
acggtcacac tgcttccggt agtcaataaa ccggtaaacc agcaatagac ataagcggct    5220
atttaacgac cctgccctga accgacgacc gggtcgaatt tgctttcgaa tttctgccat    5280
tcatccgctt attatcactt attcaggcgt agcaccaggc gtttaagggc accaataact    5340
gccttaaaaa aattacgccc cgccctgcca ctcatcgcag tactgttgta attcattaag    5400
cattctgccg acatggaagc catcacagac ggcatgatga acctgaatcg ccagcggcat    5460
cagcaccttg tcgccttgcg tataatattt gcccatggtg aaaacggggg cgaagaagtt    5520
gtccatattg ccacgttta aatcaaaact ggtgaaactc acccagggat tggctgagac    5580
gaaaaacata ttctcaataa acccttta ggagaataggcc aggttttcac cgtaacacgc    5640
```

-continued

```
cacatcttgc gaatatatgt gtagaaactg ccggaaatcg tcgtggtatt cactccagag      5700
cgatgaaaac gtttcagttt gctcatggaa aacggtgtaa caagggtgaa cactatccca      5760
tatcaccagc tcaccgtctt tcattgccat acg                                   5793
```

```
<210> SEQ ID NO 51
<211> LENGTH: 951
<212> TYPE: DNA
<213> ORGANISM: Escherichia coli
<220> FEATURE:
<221> NAME/KEY: CDS
<222> LOCATION: (1)..(948)

<400> SEQUENCE: 51
```

| | | | | | | | | | | | | | | | | |
|---|---|---|---|---|---|---|---|---|---|---|---|---|---|---|---|---|
| atg | cag | atc | ctg | ttg | gcc | aac | ccg | cgt | ggt | ttt | tgt | gcc | ggg | gta | gac | 48 |
| Met | Gln | Ile | Leu | Leu | Ala | Asn | Pro | Arg | Gly | Phe | Cys | Ala | Gly | Val | Asp | |
| 1 | | | | 5 | | | | | 10 | | | | | 15 | | |
| cgc | gct | atc | agc | att | gtt | gaa | aac | gcg | ctg | gcc | att | tac | ggc | gca | ccg | 96 |
| Arg | Ala | Ile | Ser | Ile | Val | Glu | Asn | Ala | Leu | Ala | Ile | Tyr | Gly | Ala | Pro | |
| | | | 20 | | | | | 25 | | | | | 30 | | | |
| ata | tat | gtc | cgt | cac | gaa | gtg | gta | cat | aac | cgc | tat | gtg | gtc | gat | agc | 144 |
| Ile | Tyr | Val | Arg | His | Glu | Val | Val | His | Asn | Arg | Tyr | Val | Val | Asp | Ser | |
| | | 35 | | | | | 40 | | | | | 45 | | | | |
| ttg | cgt | gag | cgt | ggg | gct | atc | ttt | att | gag | cag | att | agc | gaa | gta | ccg | 192 |
| Leu | Arg | Glu | Arg | Gly | Ala | Ile | Phe | Ile | Glu | Gln | Ile | Ser | Glu | Val | Pro | |
| | 50 | | | | | 55 | | | | | 60 | | | | | |
| gac | ggc | gcg | atc | ctg | att | ttc | tcc | gca | cac | ggt | gtt | tct | cag | gcg | gta | 240 |
| Asp | Gly | Ala | Ile | Leu | Ile | Phe | Ser | Ala | His | Gly | Val | Ser | Gln | Ala | Val | |
| 65 | | | | | 70 | | | | | 75 | | | | | 80 | |
| cgt | aac | gaa | gca | aaa | agt | cgc | gat | ttg | acg | gtg | ttt | gat | gcc | acc | tgt | 288 |
| Arg | Asn | Glu | Ala | Lys | Ser | Arg | Asp | Leu | Thr | Val | Phe | Asp | Ala | Thr | Cys | |
| | | | | 85 | | | | | 90 | | | | | 95 | | |
| ccg | ctg | gtg | acc | aaa | gtg | cat | atg | gaa | gtc | gcc | cgc | gcc | agt | cgc | cgt | 336 |
| Pro | Leu | Val | Thr | Lys | Val | His | Met | Glu | Val | Ala | Arg | Ala | Ser | Arg | Arg | |
| | | | 100 | | | | | 105 | | | | | 110 | | | |
| ggc | gaa | gaa | tct | att | ctc | atc | ggt | cac | gcc | ggg | cac | ccg | gaa | gtg | gaa | 384 |
| Gly | Glu | Glu | Ser | Ile | Leu | Ile | Gly | His | Ala | Gly | His | Pro | Glu | Val | Glu | |
| | | 115 | | | | | 120 | | | | | 125 | | | | |
| ggg | aca | atg | ggc | cag | tac | agt | aac | ccg | gaa | ggg | gga | atg | tat | ctg | gtc | 432 |
| Gly | Thr | Met | Gly | Gln | Tyr | Ser | Asn | Pro | Glu | Gly | Gly | Met | Tyr | Leu | Val | |
| | 130 | | | | | 135 | | | | | 140 | | | | | |
| gaa | tcg | ccg | gac | gat | gtg | tgg | aaa | ctg | acg | gtc | aaa | aac | gaa | gag | aag | 480 |
| Glu | Ser | Pro | Asp | Asp | Val | Trp | Lys | Leu | Thr | Val | Lys | Asn | Glu | Glu | Lys | |
| 145 | | | | | 150 | | | | | 155 | | | | | 160 | |
| ctc | tcc | ttt | atg | acc | cag | acc | acg | ctg | tcg | gtg | gat | gac | acg | tct | gat | 528 |
| Leu | Ser | Phe | Met | Thr | Gln | Thr | Thr | Leu | Ser | Val | Asp | Asp | Thr | Ser | Asp | |
| | | | | 165 | | | | | 170 | | | | | 175 | | |
| gtg | atc | gac | gcg | ctg | cgt | aaa | cgc | ttc | ccg | aaa | att | gtc | ggt | ccg | cgc | 576 |
| Val | Ile | Asp | Ala | Leu | Arg | Lys | Arg | Phe | Pro | Lys | Ile | Val | Gly | Pro | Arg | |
| | | | 180 | | | | | 185 | | | | | 190 | | | |
| aaa | gat | gac | atc | tgc | tac | gcc | acg | act | aac | cgt | cag | gaa | gcg | gta | cgc | 624 |
| Lys | Asp | Asp | Ile | Cys | Tyr | Ala | Thr | Thr | Asn | Arg | Gln | Glu | Ala | Val | Arg | |
| | | 195 | | | | | 200 | | | | | 205 | | | | |
| gcc | ctg | gca | gaa | cag | gcg | gaa | gtt | gtg | ttg | gtg | gtc | ggt | tcg | aaa | aac | 672 |
| Ala | Leu | Ala | Glu | Gln | Ala | Glu | Val | Val | Leu | Val | Val | Gly | Ser | Lys | Asn | |
| | 210 | | | | | 215 | | | | | 220 | | | | | |
| tcc | tcc | aac | tcc | aac | cgt | ctg | gcg | gag | ctg | gcc | cag | cgt | atg | ggc | aaa | 720 |
| Ser | Ser | Asn | Ser | Asn | Arg | Leu | Ala | Glu | Leu | Ala | Gln | Arg | Met | Gly | Lys | |
| 225 | | | | | 230 | | | | | 235 | | | | | 240 | |
| cgc | gcg | ttt | ttg | att | gac | gat | gcg | aaa | gac | atc | cag | gaa | gag | tgg | gtg | 768 |

```
Arg Ala Phe Leu Ile Asp Asp Ala Lys Asp Ile Gln Glu Glu Trp Val
                245                 250                 255 aaa gag gtt aaa tgc gtc ggc gtg act gcg ggc gca tcg gct ccg gat      816
Lys Glu Val Lys Cys Val Gly Val Thr Ala Gly Ala Ser Ala Pro Asp
                260                 265                 270 att ctg gtg cag aat gtg gtg gca cgt ttg cag cag ctg ggc ggt ggt      864
Ile Leu Val Gln Asn Val Val Ala Arg Leu Gln Gln Leu Gly Gly Gly
                275                 280                 285 gaa gcc att ccg ctg gaa ggc cgt gaa gaa aac att gtt ttc gaa gtg      912
Glu Ala Ile Pro Leu Glu Gly Arg Glu Glu Asn Ile Val Phe Glu Val
                290                 295                 300 ccg aaa gag ctg cgt gtc gat att cgt gaa gtc gat taa                  951
Pro Lys Glu Leu Arg Val Asp Ile Arg Glu Val Asp
305                 310                 315

<210> SEQ ID NO 52
<211> LENGTH: 316
<212> TYPE: PRT
<213> ORGANISM: Escherichia coli

<400> SEQUENCE: 52

Met Gln Ile Leu Leu Ala Asn Pro Arg Gly Phe Cys Ala Gly Val Asp
1               5                   10                  15

Arg Ala Ile Ser Ile Val Glu Asn Ala Leu Ala Ile Tyr Gly Ala Pro
                20                  25                  30

Ile Tyr Val Arg His Glu Val His Asn Arg Tyr Val Val Asp Ser
                35                  40                  45

Leu Arg Glu Arg Gly Ala Ile Phe Ile Glu Gln Ile Ser Glu Val Pro
        50                  55                  60

Asp Gly Ala Ile Leu Ile Phe Ser Ala His Gly Val Ser Gln Ala Val
65                  70                  75                  80

Arg Asn Glu Ala Lys Ser Arg Asp Leu Thr Val Phe Asp Ala Thr Cys
                85                  90                  95

Pro Leu Val Thr Lys Val His Met Glu Val Ala Arg Ala Ser Arg Arg
                100                 105                 110

Gly Glu Glu Ser Ile Leu Ile Gly His Ala Gly His Pro Glu Val Glu
            115                 120                 125

Gly Thr Met Gly Gln Tyr Ser Asn Pro Glu Gly Gly Met Tyr Leu Val
        130                 135                 140

Glu Ser Pro Asp Asp Val Trp Lys Leu Thr Val Lys Asn Glu Glu Lys
145                 150                 155                 160

Leu Ser Phe Met Thr Gln Thr Thr Leu Ser Val Asp Asp Thr Ser Asp
                165                 170                 175

Val Ile Asp Ala Leu Arg Lys Arg Phe Pro Lys Ile Val Gly Pro Arg
                180                 185                 190

Lys Asp Asp Ile Cys Tyr Ala Thr Thr Asn Arg Gln Glu Ala Val Arg
            195                 200                 205

Ala Leu Ala Glu Gln Ala Glu Val Val Leu Val Val Gly Ser Lys Asn
        210                 215                 220

Ser Ser Asn Ser Asn Arg Leu Ala Glu Leu Ala Gln Arg Met Gly Lys
225                 230                 235                 240

Arg Ala Phe Leu Ile Asp Asp Ala Lys Asp Ile Gln Glu Glu Trp Val
                245                 250                 255

Lys Glu Val Lys Cys Val Gly Val Thr Ala Gly Ala Ser Ala Pro Asp
                260                 265                 270

Ile Leu Val Gln Asn Val Val Ala Arg Leu Gln Gln Leu Gly Gly Gly
```

```
            275                 280                 285
Glu Ala Ile Pro Leu Glu Gly Arg Glu Glu Asn Ile Val Phe Glu Val
    290                 295                 300

Pro Lys Glu Leu Arg Val Asp Ile Arg Glu Val Asp
305                 310                 315
```

<210> SEQ ID NO 53
<211> LENGTH: 9795
<212> TYPE: DNA
<213> ORGANISM: Artificial Sequence
<220> FEATURE:
<223> OTHER INFORMATION: pBScyclogcpElytB2

<400> SEQUENCE: 53

| | | | | |
|---|---|---|---|---|
| gtggcacttt | tcggggaaat | gtgcgcggaa | cccctatttg | tttatttttc | taaatacatt | 60 |
| caaatatgta | tccgctcatg | agacaataac | cctgataaat | gcttcaataa | tattgaaaaa | 120 |
| ggaagagtat | gagtattcaa | catttccgtg | tcgcccttat | tcccttttt | gcggcatttt | 180 |
| gccttcctgt | ttttgctcac | ccagaaacgc | tggtgaaagt | aaaagatgct | gaagatcagt | 240 |
| tgggtgcacg | agtgggttac | atcgaactgg | atctcaacag | cggtaagatc | cttgagagtt | 300 |
| ttcgccccga | agaacgtttt | ccaatgatga | gcacttttaa | agttctgcta | tgtggcgcgg | 360 |
| tattatcccg | tattgacgcc | gggcaagagc | aactcggtcg | ccgcatacac | tattctcaga | 420 |
| atgacttggt | tgagtactca | ccagtcacag | aaaagcatct | tacggatggc | atgacagtaa | 480 |
| gagaattatg | cagtgctgcc | ataaccatga | gtgataacac | tgcggccaac | ttacttctga | 540 |
| caacgatcgg | aggaccgaag | gagctaaccg | cttttttgca | caacatgggg | gatcatgtaa | 600 |
| ctcgccttga | tcgttgggaa | ccggagctga | atgaagccat | accaaacgac | gagcgtgaca | 660 |
| ccacgatgcc | tgtagcaatg | gcaacaacgt | tgcgcaaact | attaactggc | gaactactta | 720 |
| ctctagcttc | ccggcaacaa | ttaatagact | ggatggaggc | ggataaagtt | gcaggaccac | 780 |
| ttctgcgctc | ggcccttccg | gctggctggt | ttattgctga | taaatctgga | gccggtgagc | 840 |
| gtgggtctcg | cggtatcatt | gcagcactgg | ggccagatgg | taagccctcc | cgtatcgtag | 900 |
| ttatctacac | gacggggagt | caggcaacta | tggatgaacg | aaatagacag | atcgctgaga | 960 |
| taggtgcctc | actgattaag | cattggtaac | tgtcagacca | agtttactca | tatatacttt | 1020 |
| agattgattt | aaaacttcat | ttttaattta | aaaggatcta | ggtgaagatc | ctttttgata | 1080 |
| atctcatgac | caaaatccct | taacgtgagt | tttcgttcca | ctgagcgtca | gaccccgtag | 1140 |
| aaaagatcaa | aggatcttct | tgagatcctt | tttttctgcg | cgtaatctgc | tgcttgcaaa | 1200 |
| caaaaaaacc | accgctacca | gcggtggttt | gtttgccgga | tcaagagcta | ccaactcttt | 1260 |
| ttccgaaggt | aactggcttc | agcagagcgc | agataccaaa | tactgtcctt | ctagtgtagc | 1320 |
| cgtagttagg | ccaccacttc | aagaactctg | tagcaccgcc | tacatacctc | gctctgctaa | 1380 |
| tcctgttacc | agtggctgct | gccagtggcg | ataagtcgtg | tcttaccggg | ttggactcaa | 1440 |
| gacgatagtt | accggataag | gcgcagcggt | cgggctgaac | ggggggttcg | tgcacacagc | 1500 |
| ccagcttgga | gcgaacgacc | tacaccgaac | tgagatacct | acagcgtgag | ctatgagaaa | 1560 |
| gcgccacgct | tcccgaaggg | agaaaggcgg | acaggtatcc | ggtaagcggc | agggtcggaa | 1620 |
| caggagagcg | cacgagggag | cttccagggg | gaaacgcctg | gtatctttat | agtcctgtcg | 1680 |
| ggtttcgcca | cctctgactt | gagcgtcgat | ttttgtgatg | ctcgtcaggg | ggcggagcc | 1740 |
| tatgaaaaaa | cgccagcaac | gcggcctttt | tacggttcct | ggccttttgc | tggccttttg | 1800 |
| ctcacatgtt | ctttcctgcg | ttatcccctg | attctgtgga | taaccgtatt | accgcctttg | 1860 |

-continued

```
agtgagctga taccgctcgc cgcagccgaa cgaccgagcg cagcgagtca gtgagcgagg    1920
aagcggaaga gcgcccaata cgcaaaccgc ctctccccgc gcgttggccg attcattaat    1980
gcagctggca cgacaggttt cccgactgga aagcgggcag tgagcgcaac gcaattaatg    2040
tgagttagct cactcattag gcaccccagg ctttacactt tatgcttccg gctcgtatgt    2100
tgtgtggaat tgtgagcgga taacaatttc acacaggaaa cagctatgac catgattacg    2160
ccaagcgcgc aattaaccct cactaaaggg aacaaaagct ggagctccac cgcgggagga    2220
gaaattaacc atgcataacc aggctccaat tcaacgtaga aaatcaacac gtatttacgt    2280
tgggaatgtg ccgattggcg atggtgctcc catcgccgta cagtccatga ccaatacgcg    2340
tacgacagac gtcgaagcaa cggtcaatca aatcaaggcg ctggaacgcg ttggcgctga    2400
tatcgtccgt gtatccgtac cgacgatgga cgcggcagaa gcgttcaaac tcatcaaaca    2460
gcaggttaac gtgccgctgg tggctgacat ccacttcgac tatcgcattg cgctgaaagt    2520
agcggaatac ggcgtcgatt gtctgcgtat taaccctggc aatatcggta atgaagagcg    2580
tattcgcatg gtggttgact gtgcgcgcga taaaaacatt ccgatccgta ttggcgttaa    2640
cgccggatcg ctggaaaaag atctgcaaga aaagtatggc gaaccgacgc cgcaggcgtt    2700
gctggaatct gccatgcgtc atgttgatca tctcgatcgc ctgaacttcg atcagttcaa    2760
agtcagcgtg aaagcgtctg acgtcttcct cgctgttgag tcttatcgtt tgctggcaaa    2820
acagatcgat cagccgttgc atctggggat caccgaagcc ggtggtgcgc gcagcggggc    2880
agtaaaatcc gccattggtt taggtctgct gctgtctgaa ggcatcggcg acacgctgcg    2940
cgtatcgctg gcggccgatc cggtcgaaga gatcaaagtc ggtttcgata ttttgaaatc    3000
gctgcgtatc cgttcgcgag ggatcaactt catcgcctgc cgacctgtt cgcgtcagga    3060 atttgatgtt atcggtacgg ttaacgcgct ggagcaacgc ctggaagata tcatcactcc    3120 gatgacgtt tcgattatcg gctgcgtggt gaatggccca ggtgaggcgc tggtttctac    3180
actcggcgtc accggcggca acaagaaaag cggcctctat gaagatggcg tgcgcaaaga    3240
ccgtctggac aacaacgata tgatcgacca gctggaagca cgcattcgtg cgaaagccag    3300
tcagctggac gaagcgcgtc gaattgacgt tcagcaggtt gaaaaataag tcgacgagga    3360
gaaattaacc atgcagatcc tgttggccaa cccgcgtggt ttttgtgccg ggtagaccg    3420 cgctatcagc attgttgaaa acgcgctggc catttacggc gcaccgatat atgtccgtca    3480
cgaagtggta cataaccgct atgtggtcga tagcttgcgt gagcgtgggg ctatctttat    3540
tgagcagatt agcgaagtac cggacggcgc gatcctgatt ttctccgcac acggtgtttc    3600
tcaggcggta cgtaacgaag caaaaagtcg cgatttgacg gtgtttgatg ccacctgtcc    3660
gctggtgacc aaagtgcata tggaagtcgc ccgcgccagt cgccgtggcg aagaatctat    3720
tctcatcggt cacgccgggc acccggaagt ggaagggaca atgggccagt acagtaaccc    3780 ggaagggga atgtatctgg tcgaatcgcc ggacgatgtg tggaaactga cggtcaaaaa    3840
cgaagagaag ctctccttta tgacccagac cacgctgtcg gtggatgaca cgtctgatgt    3900
gatcgacgcg ctgcgtaaac gcttcccgaa aattgtcggt ccgcgcaaag atgacatctg    3960
ctacgccacg actaaccgtc aggaagcgg acgcgcctg gcagaacagg cggaagttgt    4020
gttggtggtc ggttcgaaaa actcctccaa ctccaaccgt ctggcggagc tggcccagcg    4080
tatgggcaaa cgcgcgtttt tgattgacga tgcgaaagac atccaggaag agtgggtgaa    4140
agaggttaaa tgcgtcggcg tgactgcggg cgcatcggct ccggatattc tggtgcagaa    4200
```

```
tgtggtggca cgtttgcagc agctgggcgg tggtgaagcc attccgctgg aaggccgtga    4260
agaaaacatt gttttcgaag tgccgaaaga gctgcgtgtc gatattcgtg aagtcgatta    4320
agcggccgct ctagaactag tggatccccc gggctgcagg aattcgagga gaaattaacc    4380
atgtatatcg gatagatct tggcacctcg gcgtaaaag ttatttttgct caacgagcag    4440
ggtgaggtgg ttgctgcgca acggaaaag ctgaccgttt cgcgcccgca tccactctgg    4500
tcggaacaag acccggaaca gtggtggcag gcaactgatc gcgcaatgaa agctctgggc    4560
gatcagcatt ctctgcagga cgttaaagca ttgggtattg ccggccagat gcacggagca    4620
accttgctgg atgctcagca acgggtgtta cgccctgcca ttttgtggaa cgacgggcgc    4680
tgtgcgcaag agtgcacttt gctggaagcg cgagttccgc aatcgcgggt gattaccggc    4740
aacctgatga tgcccggatt tactgcgcct aaattgctat gggttcagcg gcatgagccg    4800
gagatattcc gtcaaatcga caaagtatta ttaccgaaag attacttgcg tctgcgtatg    4860
acggggagt ttgccagcga tatgtctgac gcagctggca ccatgtggct ggatgtcgca    4920
aagcgtgact ggagtgacgt catgctgcag gcttgcgact tatctcgtga ccagatgccc    4980
gcattatacg aaggcagcga aattactggt gctttgttac ctgaagttgc gaaagcgtgg    5040
ggtatggcga cggtgccagt tgtcgcaggc ggtggcgaca atgcagctgg tgcagttggt    5100
gtgggaatgg ttgatgctaa tcaggcaatg ttatcgctgg ggacgtcggg ggtctatttt    5160
gctgtcagcg aagggttctt aagcaagcca gaaagcgccg tacatagctt ttgccatgcg    5220
ctaccgcaac gttggcattt aatgtctgtg atgctgagtg cagcgtcgtg tctggattgg    5280
gccgcgaaat taaccggcct gagcaatgtc ccagctttaa tcgctgcagc tcaacaggct    5340
gatgaaagtg ccgagccagt ttggtttctg ccttatcttt ccggcgagcg tacgccacac    5400
aataatcccc aggcgaaggg ggttttcttt ggtttgactc atcaacatgg ccccaatgaa    5460
ctggcgcgag cagtgctgga aggcgtgggt tatgcgctgg cagatggcat ggatgtcgtg    5520
catgcctgcg gtattaaacc gcaaagtgtt acgttgattg ggggcggggc gcgtagtgag    5580
tactggcgtc agatgctggc ggatatcagc ggtcagcagc tcgattaccg tacggggggg    5640
gatgtggggc cagcactggg cgcagcaagg ctggcgcaga tcgcggcgaa tccagagaaa    5700
tcgctcattg aattgttgcc gcaactaccg ttagaacagt cgcatctacc agatgcgcag    5760
cgttatgccg cttatcagcc acgacgagaa acgttccgtc gcctctatca gcaacttctg    5820
ccattaatgg cgtaaaagct tgaggagaaa ttaaccatga agcaactcac cattctgggc    5880
tcgaccggct cgattggttg cagcacgctg gacgtggtgc gccataatcc cgaacacttc    5940
cgcgtagttg cgctggtggc aggcaaaaat gtcactcgca tggtagaaca gtgcctggaa    6000
ttctctcccc gctatgccgt aatggacgat gaagcgagtg cgaaacttct taaaacgatg    6060
ctacagcaac agggtagccg caccgaagtc ttaagtgggc aacaagccgc ttgcgatatg    6120
gcagcgcttg aggatgttga tcaggtgatg cagccattgt tggcgctgc tgggctgtta    6180
cctacgcttg ctgcgatccg cgcgggtaaa accattttgc tggccaataa agaatcactg    6240
gttacctgcg gacgtctgtt tatggacgcc gtaaagcaga gcaaagcgca attgttaccg    6300
gtcgatagcg aacataacgc catttttcag agtttaccgc aacctatcca gcataatctg    6360
ggatacgctg accttgagca aaatggcgtg gtgtccattt tacttaccgg tctggtggc    6420
ccttttccgtg agacgccatt gcgcgatttg caacaatga cgccggatca agcctgccgt    6480
catccgaact ggtcgatggg gcgtaaaatt tctgtcgatt cggctaccat gatgaacaaa    6540
ggtctggaat acattgaagc gcgttggctg tttaacgcca gcgccagcca gatggaagtg    6600
```

-continued

| | |
|---|---|
| ctgattcacc cgcagtcagt gattcactca atggtgcgct atcaggacgg cagtgttctg | 6660 |
| gcgcagctgg gggaaccgga tatgcgtacg ccaattgccc acaccatggc atggccgaat | 6720 |
| cgcgtgaact ctggcgtgaa gccgctcgat ttttgcaaac taagtgcgtt gacatttgcc | 6780 |
| gcaccggatt atgatcgtta tccatgcctg aaactggcga tggaggcgtt cgaacaaggc | 6840 |
| caggcagcga cgacagcatt gaatgccgca acgaaatca ccgttgctgc ttttcttgcg | 6900 |
| caacaaatcc gctttacgga tatcgctgcg ttgaatttat ccgtactgga aaaatggat | 6960 |
| atgcgcgaac cacaatgtgt ggacgatgtg ttatctgttg atgcgaacgc gcgtgaagtc | 7020 |
| gccagaaaag aggtgatgcg tctcgcaagc tgagtcgacg aggagaaatt aaccatggca | 7080 |
| accactcatt tggatgtttg cgccgtggtt ccggcggccg gatttggccg tcgaatgcaa | 7140 |
| acggaatgtc ctaagcaata tctctcaatc ggtaatcaaa ccattcttga acactcggtg | 7200 |
| catgcgctgc tggcgcatcc ccgggtgaaa cgtgtcgtca ttgccataag tcctggcgat | 7260 |
| agccgttttg cacaacttcc tctggcgaat catccgcaaa tcaccgttgt agatggcggt | 7320 |
| gatgagcgtg ccgattccgt gctggcaggt ctgaaagccg ctggcgacgc gcagtgggta | 7380 |
| ttggtgcatg acgccgctcg tccttgtttg catcaggatg acctcgcgcg attgttggcg | 7440 |
| ttgagcgaaa ccagccgcac gggggggatc ctcgccgcac cagtgcgcga tactatgaaa | 7500 |
| cgtgccgaac cgggcaaaaa tgccattgct cataccgttg atcgcaacgg cttatggcac | 7560 |
| gcgctgacgc cgcaattttt ccctcgtgag ctgttacatg actgtctgac gcgcgctcta | 7620 |
| aatgaaggcg cgactattac cgacgaagcc tcggcgctgg aatattgcgg attccatcct | 7680 |
| cagttggtcg aaggccgtgc ggataacatt aaagtcacgc gcccggaaga tttggcactg | 7740 |
| gccgagtttt acctcacccg aaccatccat caggagaata cataatgcga attggacacg | 7800 |
| gttttgacgt acatgccttt ggcggtgaag gcccaattat cattggtggc gtacgcattc | 7860 |
| cttacgaaaa aggattgctg gcgcattctg atggcgacgt ggcgctccat gcgttgaccg | 7920 |
| atgcattgct tggcgcggcg gcgctggggg atatcggcaa gctgttccgg gataccgatc | 7980 |
| cggcatttaa aggtgccgat agccgcgagc tgctacgcga agcctggcgt cgtattcagg | 8040 |
| cgaagggtta taccctggc aacgtcgatg tcactatcat cgctcaggca ccgaagatgt | 8100 |
| tgccgcacat tccacaaatg cgcgtgttta ttgccgaaga tctcggctgc catatggatg | 8160 |
| atgttaacgt gaaagccact actacggaaa aactgggatt taccggacgt ggggaaggga | 8220 |
| ttgcctgtga gcggtggcg ctactcatta aggcaacaaa atgactcgag gaggagaaat | 8280 |
| taaccatgcg gacacagtgg ccctctccgg caaaacttaa tctgttttta tacattaccg | 8340 |
| gtcagcgtgc ggatggttac cacacgctgc aaacgctgtt tcagtttctt gattacggcg | 8400 |
| acaccatcag cattgagctt cgtgacgatg gggatattcg tctgttaacg cccgttgaag | 8460 |
| gcgtggaaca tgaagataac ctgatcgttc gcgcagcgcg attgttgatg aaaactgcgg | 8520 |
| cagacagcgg gcgtcttccg acgggaagcg gtgcgaatat cagcattgac aagcgtttgc | 8580 |
| cgatgggcgg cggtctcggc ggtggttcat ccaatgccgc gacggtcctg gtggcattaa | 8640 |
| atcatctctg gcaatgcggg ctaagcatgg atgagctggc ggaaatgggg ctgacgctgg | 8700 |
| gcgcagatgt tcctgtcttt gttcgggggc atgccgcgtt tgccgaaggc gttggtgaaa | 8760 |
| tactaacgcc ggtggatccg ccagagaagt ggtatctggt ggcgcaccct ggtgtaagta | 8820 |
| ttccgactcc ggtgattttt aaagatcctg aactcccgcg caatacgcca aaaggtcaa | 8880 |
| tagaaacgtt gctaaaatgt gaattcagca atgattgcga ggttatcgca agaaaacgtt | 8940 |

-continued

```
ttcgcgaggt tgatgcggtg ctttcctggc tgttagaata cgccccgtcg cgcctgactg      9000
ggacaggggc ctgtgtcttt gctgaatttg atacagagtc tgaagcccgc caggtgctag      9060
agcaagcccc ggaatggctc aatggctttg tggcgaaagg cgctaatctt tccccattgc      9120
acagagccat gctttaaggt acccaattcg ccctatagtg agtcgtatta cgcgcgctca      9180
ctggccgtcg ttttacaacg tcgtgactgg gaaaaccctg gcgttaccca acttaatcgc      9240
cttgcagcac atccccsttt cgccagctgg cgtaatagcg aagaggcccg caccgatcgc      9300
ccttcccaac agttgcgcag cctgaatggc gaatggaaat tgtaagcgtt aatattttgt      9360
taaaattcgc gttaaatttt tgttaaatca gctcatttt  taaccaatag gccgaaatcg      9420
gcaaaatccc ttataaatca aagaataga  ccgagatagg gttgagtgtt gttccagttt      9480
ggaacaagag tccactatta agaacgtgg  actccaacgt caaagggcga aaaccgtct      9540 atcagggcga tggcccacta cgtgaaccat caccctaatc aagttttttg gggtcgaggt      9600
gccgtaaagc actaaatcgg aaccctaaag ggagccccg  atttagagct tgacggggaa      9660
agccggcgaa cgtggcgaga aggaaggga  agaaagcgaa aggagcgggc gctagggcgc      9720
tggcaagtgt agcggtcacg ctgcgcgtaa ccaccacacc cgccgcgctt aatgcgccgc      9780
tacagggcgc gtcag                                                      9795
```

```
<210> SEQ ID NO 54
<211> LENGTH: 1986
<212> TYPE: DNA
<213> ORGANISM: Arabidopsis thaliana
<220> FEATURE:
<221> NAME/KEY: CDS
<222> LOCATION: (1)..(1983)

<400> SEQUENCE: 54
```

| | | | | | | | | | | | | | | | | |
|---|---|---|---|---|---|---|---|---|---|---|---|---|---|---|---|---|
| aag | acg | gtg | aga | agg | aag | act | cgt | act | gtt | atg | gtt | gga | aat | gtc | gcc | 48 |
| Lys | Thr | Val | Arg | Arg | Lys | Thr | Arg | Thr | Val | Met | Val | Gly | Asn | Val | Ala | |
| 1 | | | | 5 | | | | | 10 | | | | | 15 | | |

| ctt | gga | agc | gaa | cat | ccg | ata | agg | att | caa | acg | atg | act | act | tcg | gat | 96 |
|---|---|---|---|---|---|---|---|---|---|---|---|---|---|---|---|---|
| Leu | Gly | Ser | Glu | His | Pro | Ile | Arg | Ile | Gln | Thr | Met | Thr | Thr | Ser | Asp | |
| | | | 20 | | | | | 25 | | | | | 30 | | | |

| aca | aaa | gat | att | act | gga | act | gtt | gat | gag | gtt | atg | aga | ata | gcg | gat | 144 |
|---|---|---|---|---|---|---|---|---|---|---|---|---|---|---|---|---|
| Thr | Lys | Asp | Ile | Thr | Gly | Thr | Val | Asp | Glu | Val | Met | Arg | Ile | Ala | Asp | |
| | | 35 | | | | | 40 | | | | | 45 | | | | |

| aaa | gga | gct | gat | att | gta | agg | ata | act | gtt | caa | ggg | aag | aaa | gag | gcg | 192 |
|---|---|---|---|---|---|---|---|---|---|---|---|---|---|---|---|---|
| Lys | Gly | Ala | Asp | Ile | Val | Arg | Ile | Thr | Val | Gln | Gly | Lys | Lys | Glu | Ala | |
| | 50 | | | | | 55 | | | | | 60 | | | | | |

| gat | gcg | tgc | ttt | gaa | ata | aaa | gat | aaa | ctc | gtt | cag | ctt | aat | tac | aat | 240 |
|---|---|---|---|---|---|---|---|---|---|---|---|---|---|---|---|---|
| Asp | Ala | Cys | Phe | Glu | Ile | Lys | Asp | Lys | Leu | Val | Gln | Leu | Asn | Tyr | Asn | |
| 65 | | | | | 70 | | | | | 75 | | | | | 80 | |

| aca | ccg | ctg | gtt | gca | ggt | att | cat | ttt | gcc | cct | act | gta | gcc | tta | cga | 288 |
|---|---|---|---|---|---|---|---|---|---|---|---|---|---|---|---|---|
| Thr | Pro | Leu | Val | Ala | Gly | Ile | His | Phe | Ala | Pro | Thr | Val | Ala | Leu | Arg | |
| | | | | 85 | | | | | 90 | | | | | 95 | | |

| gtc | gct | gaa | tgc | ttt | gac | aag | atc | cgt | gtc | aac | ccc | gga | aat | ttt | gcg | 336 |
|---|---|---|---|---|---|---|---|---|---|---|---|---|---|---|---|---|
| Val | Ala | Glu | Cys | Phe | Asp | Lys | Ile | Arg | Val | Asn | Pro | Gly | Asn | Phe | Ala | |
| | | | 100 | | | | | 105 | | | | | 110 | | | |

| gac | agg | cgg | gcc | cag | ttt | gag | acg | ata | gat | tat | aca | gaa | gat | gaa | tat | 384 |
|---|---|---|---|---|---|---|---|---|---|---|---|---|---|---|---|---|
| Asp | Arg | Arg | Ala | Gln | Phe | Glu | Thr | Ile | Asp | Tyr | Thr | Glu | Asp | Glu | Tyr | |
| | | 115 | | | | | 120 | | | | | 125 | | | | |

| cag | aaa | gaa | ctc | cag | cat | atc | gag | cag | gtc | ttc | act | cct | ttg | gtt | gag | 432 |
|---|---|---|---|---|---|---|---|---|---|---|---|---|---|---|---|---|
| Gln | Lys | Glu | Leu | Gln | His | Ile | Glu | Gln | Val | Phe | Thr | Pro | Leu | Val | Glu | |
| | 130 | | | | | 135 | | | | | 140 | | | | | |

| aaa | tgc | aaa | aag | tac | ggg | aga | gca | atg | cgt | att | ggg | aca | aat | cat | gga | 480 |
|---|---|---|---|---|---|---|---|---|---|---|---|---|---|---|---|---|
| Lys | Cys | Lys | Lys | Tyr | Gly | Arg | Ala | Met | Arg | Ile | Gly | Thr | Asn | His | Gly | |

-continued

```
            145                 150                 155                 160
agt ctt tct gac cgt atc atg agc tat tac ggg gat tct ccc cga gga        528
Ser Leu Ser Asp Arg Ile Met Ser Tyr Tyr Gly Asp Ser Pro Arg Gly
                165                 170                 175 atg gtt gaa tct gcg ttt gag ttt gca aga ata tgt cgg aaa tta gac        576
Met Val Glu Ser Ala Phe Glu Phe Ala Arg Ile Cys Arg Lys Leu Asp
            180                 185                 190 tat cac aac ttt gtt ttc tca atg aaa gcg agc aac cca gtg atc atg        624
Tyr His Asn Phe Val Phe Ser Met Lys Ala Ser Asn Pro Val Ile Met
        195                 200                 205 gtc cag gcg tac cgt tta ctt gtg gct gag atg tat gtt cat gga tgg        672
Val Gln Ala Tyr Arg Leu Leu Val Ala Glu Met Tyr Val His Gly Trp
    210                 215                 220 gat tat cct ttg cat ttg gga gtt act gag gca gga gaa ggc gaa gat        720
Asp Tyr Pro Leu His Leu Gly Val Thr Glu Ala Gly Glu Gly Glu Asp
225                 230                 235                 240 gga cgg atg aaa tct gcg att gga att ggg acg ctt ctt cag gac ggg        768
Gly Arg Met Lys Ser Ala Ile Gly Ile Gly Thr Leu Leu Gln Asp Gly
                245                 250                 255 ctc ggt gac aca aca aga gtt tca ctg acg gag cca cca gaa gag gag        816
Leu Gly Asp Thr Thr Arg Val Ser Leu Thr Glu Pro Pro Glu Glu Glu
            260                 265                 270 ata gat ccc tgc agg cga ttg gct aac ctc ggg aca aaa gct gcc aaa        864
Ile Asp Pro Cys Arg Arg Leu Ala Asn Leu Gly Thr Lys Ala Ala Lys
        275                 280                 285 ctt caa caa ggc gct gca ccg ttt gaa gaa aag cat agg cat tac ttt        912
Leu Gln Gln Gly Ala Ala Pro Phe Glu Glu Lys His Arg His Tyr Phe
    290                 295                 300 gat ttt cag cgt cgg acg ggt gat cta cct gta caa aaa gag gga gaa        960
Asp Phe Gln Arg Arg Thr Gly Asp Leu Pro Val Gln Lys Glu Gly Glu
305                 310                 315                 320 gag gtt gat tac aga aat gtc ctt cac cgt gat ggt tct gtt ctg atg       1008
Glu Val Asp Tyr Arg Asn Val Leu His Arg Asp Gly Ser Val Leu Met
                325                 330                 335 tcg att tct ctg gat caa cta aag gca cct gaa ctc ctc tac aga tca       1056
Ser Ile Ser Leu Asp Gln Leu Lys Ala Pro Glu Leu Leu Tyr Arg Ser
            340                 345                 350 ctc gcc aca aag ctt gtc gtg ggt atg cca ttc aag gat ctg gca act       1104
Leu Ala Thr Lys Leu Val Val Gly Met Pro Phe Lys Asp Leu Ala Thr
        355                 360                 365 gtt gat tca atc tta tta aga gag cta ccg cct gta gat gat caa gtg       1152
Val Asp Ser Ile Leu Leu Arg Glu Leu Pro Pro Val Asp Asp Gln Val
    370                 375                 380 gct cgt ttg gct ctc aaa cgg ttg att gat gtc agt atg gga gtt ata       1200
Ala Arg Leu Ala Leu Lys Arg Leu Ile Asp Val Ser Met Gly Val Ile
385                 390                 395                 400 gca cct tta tca gag caa cta aca aag cca ttg ccc aat gcc atg gtt       1248
Ala Pro Leu Ser Glu Gln Leu Thr Lys Pro Leu Pro Asn Ala Met Val
                405                 410                 415 ctt gtc aac ctc aag gaa cta tct ggt ggc gct tac aag ctt ctc cct       1296
Leu Val Asn Leu Lys Glu Leu Ser Gly Gly Ala Tyr Lys Leu Leu Pro
            420                 425                 430 gaa ggt aca cgc ttg gtt gtc tct cta cga ggc gat gag cct tac gag       1344
Glu Gly Thr Arg Leu Val Val Ser Leu Arg Gly Asp Glu Pro Tyr Glu
        435                 440                 445 gag ctt gaa ata ctc aaa aac att gat gct act atg att ctc cat gat       1392
Glu Leu Glu Ile Leu Lys Asn Ile Asp Ala Thr Met Ile Leu His Asp
    450                 455                 460 gta cct ttc act gaa gac aaa gtt agc aga gta cat gca gct cgg agg       1440
```

```
Val Pro Phe Thr Glu Asp Lys Val Ser Arg Val His Ala Ala Arg Arg
465                 470                 475                 480 cta ttc gag ttc tta tcc gag aat tca gtt aac ttt cct gtt att cat      1488
Leu Phe Glu Phe Leu Ser Glu Asn Ser Val Asn Phe Pro Val Ile His
                485                 490                 495 cgc ata aac ttc cca acc gga atc cac aga gac gaa ttg gtg att cat      1536
Arg Ile Asn Phe Pro Thr Gly Ile His Arg Asp Glu Leu Val Ile His
                500                 505                 510 gca ggg aca tat gct gga ggc ctt ctt gtg gat gga cta ggt gat ggc      1584
Ala Gly Thr Tyr Ala Gly Gly Leu Leu Val Asp Gly Leu Gly Asp Gly
            515                 520                 525 gta atg ctc gaa gca cct gac caa gat ttt gat ttt ctt agg aat act      1632
Val Met Leu Glu Ala Pro Asp Gln Asp Phe Asp Phe Leu Arg Asn Thr
        530                 535                 540 tcc ttc aac tta tta caa gga tgc aga atg cgt aac act aag acg gaa      1680
Ser Phe Asn Leu Leu Gln Gly Cys Arg Met Arg Asn Thr Lys Thr Glu
545                 550                 555                 560 tat gta tcg tgc ccg tct tgt gga aga acg ctt ttc gac ttg caa gaa      1728
Tyr Val Ser Cys Pro Ser Cys Gly Arg Thr Leu Phe Asp Leu Gln Glu
                565                 570                 575 atc agc gcc gag atc cga gaa aag act tcc cat tta cct ggc gtt tcg      1776
Ile Ser Ala Glu Ile Arg Glu Lys Thr Ser His Leu Pro Gly Val Ser
                580                 585                 590 atc gca atc atg gga tgc att gtg aat gga cca gga gaa atg gca gat      1824
Ile Ala Ile Met Gly Cys Ile Val Asn Gly Pro Gly Glu Met Ala Asp
            595                 600                 605 gct gat ttc gga tat gta ggt ggt tct ccc gga aaa atc gac ctt tat      1872
Ala Asp Phe Gly Tyr Val Gly Gly Ser Pro Gly Lys Ile Asp Leu Tyr
610                 615                 620 gtc gga aag acg gtg gtg aag cgt ggg ata gct atg acg gag gca aca      1920
Val Gly Lys Thr Val Val Lys Arg Gly Ile Ala Met Thr Glu Ala Thr
625                 630                 635                 640 gat gct ctg atc ggt ctg atc aaa gaa cat ggt cgt tgg gtc gac ccg      1968
Asp Ala Leu Ile Gly Leu Ile Lys Glu His Gly Arg Trp Val Asp Pro
                645                 650                 655 ccc gtg gct gat gag tag                                              1986
Pro Val Ala Asp Glu
                660

<210> SEQ ID NO 55
<211> LENGTH: 661
<212> TYPE: PRT
<213> ORGANISM: Arabidopsis thaliana

<400> SEQUENCE: 55

Lys Thr Val Arg Arg Lys Thr Arg Thr Val Met Val Gly Asn Val Ala
1               5                   10                  15

Leu Gly Ser Glu His Pro Ile Arg Ile Gln Thr Met Thr Thr Ser Asp
                20                  25                  30

Thr Lys Asp Ile Thr Gly Thr Val Asp Glu Val Met Arg Ile Ala Asp
            35                  40                  45

Lys Gly Ala Asp Ile Val Arg Ile Thr Val Gln Gly Lys Lys Glu Ala
        50                  55                  60

Asp Ala Cys Phe Glu Ile Lys Asp Lys Leu Val Gln Leu Asn Tyr Asn
65                  70                  75                  80

Thr Pro Leu Val Ala Gly Ile His Phe Ala Pro Thr Val Ala Leu Arg
                85                  90                  95

Val Ala Glu Cys Phe Asp Lys Ile Arg Val Asn Pro Gly Asn Phe Ala
            100                 105                 110
```

```
Asp Arg Arg Ala Gln Phe Glu Thr Ile Asp Tyr Thr Glu Asp Glu Tyr
        115                 120                 125

Gln Lys Glu Leu Gln His Ile Glu Gln Val Phe Thr Pro Leu Val Glu
        130                 135                 140

Lys Cys Lys Lys Tyr Gly Arg Ala Met Arg Ile Gly Thr Asn His Gly
145                 150                 155                 160

Ser Leu Ser Asp Arg Ile Met Ser Tyr Tyr Gly Asp Ser Pro Arg Gly
                165                 170                 175

Met Val Glu Ser Ala Phe Glu Phe Ala Arg Ile Cys Arg Lys Leu Asp
            180                 185                 190

Tyr His Asn Phe Val Phe Ser Met Lys Ala Ser Asn Pro Val Ile Met
        195                 200                 205

Val Gln Ala Tyr Arg Leu Leu Val Ala Glu Met Tyr Val His Gly Trp
        210                 215                 220

Asp Tyr Pro Leu His Leu Gly Val Thr Glu Ala Gly Glu Gly Glu Asp
225                 230                 235                 240

Gly Arg Met Lys Ser Ala Ile Gly Ile Gly Thr Leu Leu Gln Asp Gly
                245                 250                 255

Leu Gly Asp Thr Thr Arg Val Ser Leu Thr Glu Pro Pro Glu Glu Glu
            260                 265                 270

Ile Asp Pro Cys Arg Arg Leu Ala Asn Leu Gly Thr Lys Ala Ala Lys
        275                 280                 285

Leu Gln Gln Gly Ala Ala Pro Phe Glu Glu Lys His Arg His Tyr Phe
        290                 295                 300

Asp Phe Gln Arg Arg Thr Gly Asp Leu Pro Val Gln Lys Glu Gly Glu
305                 310                 315                 320

Glu Val Asp Tyr Arg Asn Val Leu His Arg Asp Gly Ser Val Leu Met
                325                 330                 335

Ser Ile Ser Leu Asp Gln Leu Lys Ala Pro Glu Leu Leu Tyr Arg Ser
            340                 345                 350

Leu Ala Thr Lys Leu Val Val Gly Met Pro Phe Lys Asp Leu Ala Thr
        355                 360                 365

Val Asp Ser Ile Leu Leu Arg Glu Leu Pro Pro Val Asp Asp Gln Val
        370                 375                 380

Ala Arg Leu Ala Leu Lys Arg Leu Ile Asp Val Ser Met Gly Val Ile
385                 390                 395                 400

Ala Pro Leu Ser Glu Gln Leu Thr Lys Pro Leu Pro Asn Ala Met Val
                405                 410                 415

Leu Val Asn Leu Lys Glu Leu Ser Gly Gly Ala Tyr Lys Leu Leu Pro
            420                 425                 430

Glu Gly Thr Arg Leu Val Val Ser Leu Arg Gly Asp Glu Pro Tyr Glu
        435                 440                 445

Glu Leu Glu Ile Leu Lys Asn Ile Asp Ala Thr Met Ile Leu His Asp
        450                 455                 460

Val Pro Phe Thr Glu Asp Lys Val Ser Arg Val His Ala Ala Arg Arg
465                 470                 475                 480

Leu Phe Glu Phe Leu Ser Glu Asn Ser Val Asn Phe Pro Val Ile His
                485                 490                 495

Arg Ile Asn Phe Pro Thr Gly Ile His Arg Asp Glu Leu Val Ile His
            500                 505                 510

Ala Gly Thr Tyr Ala Gly Gly Leu Leu Val Asp Gly Leu Gly Asp Gly
        515                 520                 525
```

```
Val Met Leu Glu Ala Pro Asp Gln Asp Phe Asp Phe Leu Arg Asn Thr
    530                 535                 540

Ser Phe Asn Leu Leu Gln Gly Cys Arg Met Arg Asn Thr Lys Thr Glu
545                 550                 555                 560

Tyr Val Ser Cys Pro Ser Cys Gly Arg Thr Leu Phe Asp Leu Gln Glu
                565                 570                 575

Ile Ser Ala Glu Ile Arg Glu Lys Thr Ser His Leu Pro Gly Val Ser
            580                 585                 590

Ile Ala Ile Met Gly Cys Ile Val Asn Gly Pro Gly Glu Met Ala Asp
        595                 600                 605

Ala Asp Phe Gly Tyr Val Gly Gly Ser Pro Gly Lys Ile Asp Leu Tyr
    610                 615                 620

Val Gly Lys Thr Val Val Lys Arg Gly Ile Ala Met Thr Glu Ala Thr
625                 630                 635                 640

Asp Ala Leu Ile Gly Leu Ile Lys Glu His Gly Arg Trp Val Asp Pro
                645                 650                 655

Pro Val Ala Asp Glu
            660

<210> SEQ ID NO 56
<211> LENGTH: 2226
<212> TYPE: DNA
<213> ORGANISM: Arabidopsis thaliana
<220> FEATURE:
<221> NAME/KEY: CDS
<222> LOCATION: (1)..(2223)

<400> SEQUENCE: 56 atg gcg act gga gta ttg cca gct ccg gtt tct ggg atc aag ata ccg    48
Met Ala Thr Gly Val Leu Pro Ala Pro Val Ser Gly Ile Lys Ile Pro
1               5                   10                  15 gat tcg aaa gtc ggg ttt ggt aaa agc atg aat ctt gtg aga att tgt    96
Asp Ser Lys Val Gly Phe Gly Lys Ser Met Asn Leu Val Arg Ile Cys
            20                  25                  30 gat gtt agg agt cta aga tct gct agg aga aga gtt tcg gtt atc cgg   144
Asp Val Arg Ser Leu Arg Ser Ala Arg Arg Arg Val Ser Val Ile Arg
        35                  40                  45 aat tca aac caa ggc tct gat tta gct gag ctt caa cct gca tcc gaa   192
Asn Ser Asn Gln Gly Ser Asp Leu Ala Glu Leu Gln Pro Ala Ser Glu
    50                  55                  60 gga agc cct ctc tta gtg cca aga cag aaa tat tgt gaa tca ttg cat   240
Gly Ser Pro Leu Leu Val Pro Arg Gln Lys Tyr Cys Glu Ser Leu His
65                  70                  75                  80 aag acg gtg aga agg aag act cgt act gtt atg gtt gga aat gtc gcc   288
Lys Thr Val Arg Arg Lys Thr Arg Thr Val Met Val Gly Asn Val Ala
                85                  90                  95 ctt gga agc gaa cat ccg ata agg att caa acg atg act act tcg gat   336
Leu Gly Ser Glu His Pro Ile Arg Ile Gln Thr Met Thr Thr Ser Asp
            100                 105                 110 aca aaa gat att act gga act gtt gat gag gtt atg aga ata gcg gat   384
Thr Lys Asp Ile Thr Gly Thr Val Asp Glu Val Met Arg Ile Ala Asp
        115                 120                 125 aaa gga gct gat att gta agg ata act gtt caa ggg aag aaa gag gcg   432
Lys Gly Ala Asp Ile Val Arg Ile Thr Val Gln Gly Lys Lys Glu Ala
    130                 135                 140 gat gcg tgc ttt gaa ata aaa gat aaa ctc gtt cag ctt aat tac aat   480
Asp Ala Cys Phe Glu Ile Lys Asp Lys Leu Val Gln Leu Asn Tyr Asn
145                 150                 155                 160 aca ccg ctg gtt gca ggt att cat ttt gcc cct act gta gcc tta cga   528
```

```
                    Thr Pro Leu Val Ala Gly Ile His Phe Ala Pro Thr Val Ala Leu Arg
                                    165                 170                 175 gtc gct gaa tgc ttt gac aag atc cgt gtc aac ccc gga aat ttt gcg          576
Val Ala Glu Cys Phe Asp Lys Ile Arg Val Asn Pro Gly Asn Phe Ala
                180                 185                 190 gac agg cgg gcc cag ttt gag acg ata gat tat aca gaa gat gaa tat          624
Asp Arg Arg Ala Gln Phe Glu Thr Ile Asp Tyr Thr Glu Asp Glu Tyr
            195                 200                 205 cag aaa gaa ctc cag cat atc gag cag gtc ttc act cct ttg gtt gag          672
Gln Lys Glu Leu Gln His Ile Glu Gln Val Phe Thr Pro Leu Val Glu
        210                 215                 220 aaa tgc aaa aag tac ggg aga gca atg cgt att ggg aca aat cat gga          720
Lys Cys Lys Lys Tyr Gly Arg Ala Met Arg Ile Gly Thr Asn His Gly
225                 230                 235                 240 agt ctt tct gac cgt atc atg agc tat tac ggg gat tct ccc cga gga          768
Ser Leu Ser Asp Arg Ile Met Ser Tyr Tyr Gly Asp Ser Pro Arg Gly
                245                 250                 255 atg gtt gaa tct gcg ttt gag ttt gca aga ata tgt cgg aaa tta gac          816
Met Val Glu Ser Ala Phe Glu Phe Ala Arg Ile Cys Arg Lys Leu Asp
            260                 265                 270 tat cac aac ttt gtt ttc tca atg aaa gcg agc aac cca gtg atc atg          864
Tyr His Asn Phe Val Phe Ser Met Lys Ala Ser Asn Pro Val Ile Met
        275                 280                 285 gtc cag gcg tac cgt tta ctt gtg gct gag atg tat gtt cat gga tgg          912
Val Gln Ala Tyr Arg Leu Leu Val Ala Glu Met Tyr Val His Gly Trp
    290                 295                 300 gat tat cct ttg cat ttg gga gtt act gag gca gga gaa ggc gaa gat          960
Asp Tyr Pro Leu His Leu Gly Val Thr Glu Ala Gly Glu Gly Glu Asp
305                 310                 315                 320 gga cgg atg aaa tct gcg att gga att ggg acg ctt ctt cag gac ggg         1008
Gly Arg Met Lys Ser Ala Ile Gly Ile Gly Thr Leu Leu Gln Asp Gly
                325                 330                 335 ctc ggt gac aca aca aga gtt tca ctg acg gag cca cca gaa gag gag         1056
Leu Gly Asp Thr Thr Arg Val Ser Leu Thr Glu Pro Pro Glu Glu Glu
            340                 345                 350 ata gat ccc tgc agg cga ttg gct aac ctc ggg aca aaa gct gcc aaa         1104
Ile Asp Pro Cys Arg Arg Leu Ala Asn Leu Gly Thr Lys Ala Ala Lys
        355                 360                 365 ctt caa caa ggc gct gca ccg ttt gaa gaa aag cat agg cat tac ttt         1152
Leu Gln Gln Gly Ala Ala Pro Phe Glu Glu Lys His Arg His Tyr Phe
    370                 375                 380 gat ttt cag cgt cgg acg ggt gat cta cct gta caa aaa gag gga gaa         1200
Asp Phe Gln Arg Arg Thr Gly Asp Leu Pro Val Gln Lys Glu Gly Glu
385                 390                 395                 400 gag gtt gat tac aga aat gtc ctt cac cgt gat ggt tct gtt ctg atg         1248
Glu Val Asp Tyr Arg Asn Val Leu His Arg Asp Gly Ser Val Leu Met
                405                 410                 415 tcg att tct ctg gat caa cta aag gca cct gaa ctc ctc tac aga tca         1296
Ser Ile Ser Leu Asp Gln Leu Lys Ala Pro Glu Leu Leu Tyr Arg Ser
            420                 425                 430 ctc gcc aca aag ctt gtc gtg ggt atg cca ttc aag gat ctg gca act         1344
Leu Ala Thr Lys Leu Val Val Gly Met Pro Phe Lys Asp Leu Ala Thr
        435                 440                 445 gtt gat tca atc tta tta aga gag cta ccg cct gta gat gat caa gtg         1392
Val Asp Ser Ile Leu Leu Arg Glu Leu Pro Pro Val Asp Asp Gln Val
    450                 455                 460 gct cgt ttg gct ctc aaa cgg ttg att gat gtc agt atg gga gtt ata         1440
Ala Arg Leu Ala Leu Lys Arg Leu Ile Asp Val Ser Met Gly Val Ile
465                 470                 475                 480
```

```
gca cct tta tca gag caa cta aca aag cca ttg ccc aat gcc atg gtt      1488
Ala Pro Leu Ser Glu Gln Leu Thr Lys Pro Leu Pro Asn Ala Met Val
            485                 490                 495 ctt gtc aac ctc aag gaa cta tct ggt ggc gct tac aag ctt ctc cct      1536
Leu Val Asn Leu Lys Glu Leu Ser Gly Gly Ala Tyr Lys Leu Leu Pro
        500                 505                 510 gaa ggt aca cgc ttg gtt gtc tct cta cga ggc gat gag cct tac gag      1584
Glu Gly Thr Arg Leu Val Val Ser Leu Arg Gly Asp Glu Pro Tyr Glu
    515                 520                 525 gag ctt gaa ata ctc aaa aac att gat gct act atg att ctc cat gat      1632
Glu Leu Glu Ile Leu Lys Asn Ile Asp Ala Thr Met Ile Leu His Asp
530                 535                 540 gta cct ttc act gaa gac aaa gtt agc aga gta cat gca gct cgg agg      1680
Val Pro Phe Thr Glu Asp Lys Val Ser Arg Val His Ala Ala Arg Arg
545                 550                 555                 560 cta ttc gag ttc tta tcc gag aat tca gtt aac ttt cct gtt att cat      1728
Leu Phe Glu Phe Leu Ser Glu Asn Ser Val Asn Phe Pro Val Ile His
                565                 570                 575 cgc ata aac ttc cca acc gga atc cac aga gac gaa ttg gtg att cat      1776
Arg Ile Asn Phe Pro Thr Gly Ile His Arg Asp Glu Leu Val Ile His
            580                 585                 590 gca ggg aca tat gct gga ggc ctt ctt gtg gat gga cta ggt gat ggc      1824
Ala Gly Thr Tyr Ala Gly Gly Leu Leu Val Asp Gly Leu Gly Asp Gly
        595                 600                 605 gta atg ctc gaa gca cct gac caa gat ttt gat ttt ctt agg aat act      1872
Val Met Leu Glu Ala Pro Asp Gln Asp Phe Asp Phe Leu Arg Asn Thr
    610                 615                 620 tcc ttc aac tta tta caa gga tgc aga atg cgt aac act aag acg gaa      1920
Ser Phe Asn Leu Leu Gln Gly Cys Arg Met Arg Asn Thr Lys Thr Glu
625                 630                 635                 640 tat gta tcg tgc ccg tct tgt gga aga acg ctt ttc gac ttg caa gaa      1968
Tyr Val Ser Cys Pro Ser Cys Gly Arg Thr Leu Phe Asp Leu Gln Glu
                645                 650                 655 atc agc gcc gag atc cga gaa aag act tcc cat tta cct ggc gtt tcg      2016
Ile Ser Ala Glu Ile Arg Glu Lys Thr Ser His Leu Pro Gly Val Ser
            660                 665                 670 atc gca atc atg gga tgc att gtg aat gga cca gga gaa atg gca gat      2064
Ile Ala Ile Met Gly Cys Ile Val Asn Gly Pro Gly Glu Met Ala Asp
        675                 680                 685 gct gat ttc gga tat gta ggt ggt tct ccc gga aaa atc gac ctt tat      2112
Ala Asp Phe Gly Tyr Val Gly Gly Ser Pro Gly Lys Ile Asp Leu Tyr
    690                 695                 700 gtc gga aag acg gtg gtg aag cgt ggg ata gct atg acg gag gca aca      2160
Val Gly Lys Thr Val Val Lys Arg Gly Ile Ala Met Thr Glu Ala Thr
705                 710                 715                 720 gat gct ctg atc ggt ctg atc aaa gaa cat ggt cgt tgg gtc gac ccg      2208
Asp Ala Leu Ile Gly Leu Ile Lys Glu His Gly Arg Trp Val Asp Pro
                725                 730                 735 ccc gtg gct gat gag tag                                              2226
Pro Val Ala Asp Glu
            740

<210> SEQ ID NO 57
<211> LENGTH: 741
<212> TYPE: PRT
<213> ORGANISM: Arabidopsis thaliana

<400> SEQUENCE: 57

Met Ala Thr Gly Val Leu Pro Ala Pro Val Ser Gly Ile Lys Ile Pro
1               5                   10                  15
```

```
Asp Ser Lys Val Gly Phe Gly Lys Ser Met Asn Leu Val Arg Ile Cys
             20                  25                  30

Asp Val Arg Ser Leu Arg Ser Ala Arg Arg Arg Val Ser Val Ile Arg
             35                  40                  45

Asn Ser Asn Gln Gly Ser Asp Leu Ala Glu Leu Gln Pro Ala Ser Glu
 50                  55                  60

Gly Ser Pro Leu Leu Val Pro Arg Gln Lys Tyr Cys Glu Ser Leu His
 65                  70                  75                  80

Lys Thr Val Arg Arg Lys Thr Arg Thr Val Met Val Gly Asn Val Ala
                 85                  90                  95

Leu Gly Ser Glu His Pro Ile Arg Ile Gln Thr Met Thr Thr Ser Asp
                100                 105                 110

Thr Lys Asp Ile Thr Gly Thr Val Asp Glu Val Met Arg Ile Ala Asp
             115                 120                 125

Lys Gly Ala Asp Ile Val Arg Ile Thr Val Gln Gly Lys Lys Glu Ala
 130                 135                 140

Asp Ala Cys Phe Glu Ile Lys Asp Lys Leu Val Gln Leu Asn Tyr Asn
145                 150                 155                 160

Thr Pro Leu Val Ala Gly Ile His Phe Ala Pro Thr Val Ala Leu Arg
                165                 170                 175

Val Ala Glu Cys Phe Asp Lys Ile Arg Val Asn Pro Gly Asn Phe Ala
                180                 185                 190

Asp Arg Arg Ala Gln Phe Glu Thr Ile Asp Tyr Thr Glu Asp Glu Tyr
             195                 200                 205

Gln Lys Glu Leu Gln His Ile Glu Gln Val Phe Thr Pro Leu Val Glu
 210                 215                 220

Lys Cys Lys Lys Tyr Gly Arg Ala Met Arg Ile Gly Thr Asn His Gly
225                 230                 235                 240

Ser Leu Ser Asp Arg Ile Met Ser Tyr Tyr Gly Asp Ser Pro Arg Gly
                245                 250                 255

Met Val Glu Ser Ala Phe Glu Phe Ala Arg Ile Cys Arg Lys Leu Asp
                260                 265                 270

Tyr His Asn Phe Val Phe Ser Met Lys Ala Ser Asn Pro Val Ile Met
             275                 280                 285

Val Gln Ala Tyr Arg Leu Leu Val Ala Glu Met Tyr Val His Gly Trp
 290                 295                 300

Asp Tyr Pro Leu His Leu Gly Val Thr Glu Ala Gly Glu Gly Glu Asp
305                 310                 315                 320

Gly Arg Met Lys Ser Ala Ile Gly Ile Gly Thr Leu Leu Gln Asp Gly
                325                 330                 335

Leu Gly Asp Thr Thr Arg Val Ser Leu Thr Glu Pro Glu Glu Glu
                340                 345                 350

Ile Asp Pro Cys Arg Arg Leu Ala Asn Leu Gly Thr Lys Ala Ala Lys
             355                 360                 365

Leu Gln Gln Gly Ala Ala Pro Phe Glu Glu Lys His Arg His Tyr Phe
 370                 375                 380

Asp Phe Gln Arg Arg Thr Gly Asp Leu Pro Val Gln Lys Glu Gly Glu
385                 390                 395                 400

Glu Val Asp Tyr Arg Asn Val Leu His Arg Asp Gly Ser Val Leu Met
                405                 410                 415

Ser Ile Ser Leu Asp Gln Leu Lys Ala Pro Glu Leu Leu Tyr Arg Ser
             420                 425                 430

Leu Ala Thr Lys Leu Val Val Gly Met Pro Phe Lys Asp Leu Ala Thr
```

```
                435           440             445
Val Asp Ser Ile Leu Leu Arg Glu Leu Pro Val Asp Asp Gln Val
    450                 455             460
Ala Arg Leu Ala Leu Lys Arg Leu Ile Asp Val Ser Met Gly Val Ile
465                 470                 475                 480
Ala Pro Leu Ser Glu Gln Leu Thr Lys Pro Leu Pro Asn Ala Met Val
                485                 490                 495
Leu Val Asn Leu Lys Glu Leu Ser Gly Gly Ala Tyr Lys Leu Leu Pro
            500                 505                 510
Glu Gly Thr Arg Leu Val Val Ser Leu Arg Gly Asp Glu Pro Tyr Glu
        515                 520                 525
Glu Leu Glu Ile Leu Lys Asn Ile Asp Ala Thr Met Ile Leu His Asp
    530                 535                 540
Val Pro Phe Thr Glu Asp Lys Val Ser Arg Val His Ala Ala Arg Arg
545                 550                 555                 560
Leu Phe Glu Phe Leu Ser Glu Asn Ser Val Asn Phe Pro Val Ile His
                565                 570                 575
Arg Ile Asn Phe Pro Thr Gly Ile His Arg Asp Glu Leu Val Ile His
            580                 585                 590
Ala Gly Thr Tyr Ala Gly Gly Leu Leu Val Asp Gly Leu Gly Asp Gly
        595                 600                 605
Val Met Leu Glu Ala Pro Asp Gln Asp Phe Asp Phe Leu Arg Asn Thr
    610                 615                 620
Ser Phe Asn Leu Leu Gln Gly Cys Arg Met Arg Asn Thr Lys Thr Glu
625                 630                 635                 640
Tyr Val Ser Cys Pro Ser Cys Gly Arg Thr Leu Phe Asp Leu Gln Glu
                645                 650                 655
Ile Ser Ala Glu Ile Arg Glu Lys Thr Ser His Leu Pro Gly Val Ser
            660                 665                 670
Ile Ala Ile Met Gly Cys Ile Val Asn Gly Pro Gly Glu Met Ala Asp
        675                 680                 685
Ala Asp Phe Gly Tyr Val Gly Gly Ser Pro Gly Lys Ile Asp Leu Tyr
    690                 695                 700
Val Gly Lys Thr Val Val Lys Arg Gly Ile Ala Met Thr Glu Ala Thr
705                 710                 715                 720
Asp Ala Leu Ile Gly Leu Ile Lys Glu His Gly Arg Trp Val Asp Pro
                725                 730                 735
Pro Val Ala Asp Glu
            740

<210> SEQ ID NO 58
<211> LENGTH: 1401
<212> TYPE: DNA
<213> ORGANISM: Arabidopsis thaliana

<400> SEQUENCE: 58
atggctgttg cgctccaatt cagccgatta tgcgttcgac cggatacttt cgtgcgggag      60
aatcatctct ctggatccgg atctctccgc cgccggaaag ctttatcagt ccggtgctcg     120
tctggcgatg agaacgctcc ttcgccatcg gtggtgatgg actccgattt cgacgccaag     180
gtgttccgta agaacttgac gagaagcgat aattacaatc gtaaagggtt cggtcataag     240
gaggagacac tcaagctcat gaatcgagag taccaccagt gatatattgga gacactgaaa     300 acaaatgggt atacttattc ttggggagat gttactgtga aactcgctaa agcatatggt     360
```

-continued

```
ttttgctggg gtgttgagcg tgctgttcag attgcatatg aagcacgaaa gcagtttcca    420
gaggagaggc tttggattac taacgaaatc attcataacc cgaccgtcaa taagaggttg    480
gaagatatgg atgttaaaat tattccggtt gaggattcaa agaaacagtt tgatgtagta    540
gagaaagatg atgtggttat ccttcctgcg tttggagctg gtgttgacga gatgtatgtt    600
cttaatgata aaaaggtgca aattgttgac acgacttgtc cttgggtgac aaaggtctgg    660
aacacggttg agaagcacaa gaaggggggaa tacacatcag taatccatgg taaatataat    720
catgaagaga cgattgcaac tgcgtctttt gcaggaaagt acatcattgt aaagaacatg    780
aaagaggcaa attacgtttg tgattacatt ctcggtggcc aatacgatgg atctagctcc    840
acaaaagagg agttcatgga gaaattcaaa tacgcaattt cgaagggttt cgatcccgac    900
aatgaccttg tcaaagttgg tattgcaaac caaacaacga tgctaaaggg agaaacagag    960
gagataggaa gattactcga gacaacaatg atgcgcaagt atggagtgga aaatgtaagc    1020
ggacatttca tcagcttcaa cacaatatgc gacgctactc aagagcgaca agacgcaatc    1080
tatgagctag tggaagagaa gattgacctc atgctagtgg ttggcggatg gaattcaagt    1140
aacacctctc accttcagga aatctcagag gcacggggaa tcccatctta ctggatcgat    1200
agtgagaaac ggataggacc tgggaataaa atagcctata agctccacta tggagaactg    1260
gtcgagaagg aaaactttct cccaaaggga ccaataacaa tcggtgtgac atcaggtgca    1320
tcaaccccgg ataaggtcgt ggaagatgct ttggtgaagg tgttcgacat taaacgtgaa    1380
gagttattgc agctggcttg a                                             1401
```

INTERMEDIATES AND ENZYMES OF THE NON-MEVALONATE ISOPRENOID PATHWAY

CROSS-REFERENCE TO RELATED APPLICATIONS

The present application is a 35 U.S.C. § 371 National Phase Application of International Application Serial No. PCT/EP02/04005, filed Apr. 10, 2002 and published in English as PCT Publication No. WO 02/083720 on Oct. 24, 2002, which claims priority to German Patent Application Serial Nos. 101 18 166.3, filed Apr. 11, 2001, 101 30 236.3, filed on Jun. 22, 2001, 101 55 084.7, filed on Nov. 9, 2001 and 102 01 458.2, filed on Jan. 16, 2002, the disclosures of each of which are incorporated herein by reference in their entireties.

FIELD OF THE INVENTION

The present invention relates to cells, cell cultures or organisms or parts thereof for the efficient formation of a biosynthetic product or intermediate or enzyme of a 1-deoxy-D-xylulose 5-phosphate-dependent biosynthetic pathway. Further, the invention relates to vectors for producing them. Further, the invention relates to their use for the formation or production of intermediates or products or enzymes of said biosynthetic pathway as well as to enzymes and intermediates. Further, the invention relates to the screening for inhibitors or enzymes for said biosynthetic pathway.

BACKGROUND OF THE INVENTION

The system of biosynthetic pathways in any organism is highly streamlined, whereby a few central trunk pathways branch into a great number of peripheral pathways. The central trunk pathways involve starting materials which are highly integrated. Therefore, central or trunk pathways are highly regulated. At the same time they are crucial for any attempts to interfere with the metabolism of any organism either by an inhibitor or by metabolic engineering. The isoprenoid pathways are a prime example for this metabolic organisation. They are very long and highly branched, leading to some 30,000 isoprenoid or terpenoid compounds. They all seem to derive from isopentenyl diphosphate (IPP) and dimethylallyl diphosphate (DMAPP). They are produced by two alternative trunk pathways (reviewed in Eisenreich et al., 2001).

By the classical research of Bloch, Cornforth, Lynen and co-workers, isopentenyl pyrophosphate (IPP) and dimethylallyl pyrophosphate (DMAPP) have become established as key intermediates in the biosynthesis of isoprenoids via mevalonate. However, many bacteria, plastids of all plants, and the protozoon *Plasmodium falciparum* synthesize IPP and DMAPP by an alternative pathway via 1-deoxy-D-xylulose 5-phosphate. The discovery of the pathway was mainly based on the incorporation of isotope-labelled 1-deoxy-D-xylulose into the isoprenoid side chain of menaquinones from *Escherichia coli* (Arigoni and Schwarz, 1999).

This mevalonate-independent pathway has so far only been partially explored (FIG. 1). For a better understanding of these aspects of the invention, the pathway shall be briefly explained. It can be divided into three segments:

In a first pathway segment shown in FIG. 1, pyruvate (1) is condensed with glyceraldehyde 3-phosphate (2) to 1-deoxy-D-xylulose 5-phosphate (DXP) (3). Subsequently, DXP is converted into 2C-methyl-D-erythritol 4-phosphate (MEP) (4) by a two-step reaction comprising a rearrangement and a reduction. This establishes the 5-carbon isoprenoid skeleton.

In the subsequent segment of the mevalonate-independent pathway (FIG. 1), MEP (4) is first condensed with CTP to 4-diphosphocytidyl-2C-methyl-D-erythritol (CDP-ME) (5) by 4-diphosphocytidyl-2C-methyl-D-erythritol synthase (PCT/EP00/07548). CDP-ME (5) is subsequently ATP-dependent phosphorylated by 4-diphosphocytidyl-2C-methyl-D-erythritol kinase yielding 4-diphosphocytidyl-2C-methyl-D-erythritol 2-phosphate (CDP-MEP) (6). The intermediate is subsequently converted into 2C-methyl-D-erythritol 2,4-cyclodiphosphate (cMEPP) (7) by 2C-methyl-D-erythritol 2,4-cyclodiphosphate synthase (PCT/EP00/07548). These three enzymatic steps form a biosynthetic unit which activates the isoprenoid $C_5$-skeleton for the third pathway segment (Rohdich et al., 1999; Lüttgen et al., 2000; Herz et al., 2000).

Bioinformatic studies (German Patent Application 10027821.3), as well as studies with mutants of *Synechocystis* sp. (Cunningham et al., 2000) and *Escherichia coli* (Campos et al., 2001; Altincicek et al., 2001) demonstrate the involvement of lytB and gcpE genes in the isoprenoid pathway. However, the function and the reaction catalyzed by the corresponding gene products are still unknown.

Recently, a kinase (XylB) has been described that catalyzes the conversion of 1-deoxy-D-xylulose into 1-deoxy-D-xylulose 5-phosphate at high rates (Wungsintaweekul et al., 2000). Genes and enzymes participating in further downstream reactions have been described. However, the gene functions, the intermediates, and the mechanisms leading to the products are still unknown.

For numerous pathogenic eubacteria as well as for the malaria parasite *P. falciparum*, the enzymes involved in the non-mevalonate pathway are essential. The intermediates of the mevalonate-independent pathway cannot be assimilated from the environment by pathogenic eubacteria and *P. falciparum*. The enzymes of the alternative isoprenoid pathway do not occur in mammalia which synthesize their isoprenoids and terpenoids exclusively via the mevalonate pathway. Moreover, the idiosyncratic nature of the reactions in this pathway reduces the risk of cross-inhibitions with other, notably mammalian enzymes.

Therefore, enzymes of the alternative isoprenoid pathway seem to be specially suited as targets for novel agents against pathogenic microorganisms and herbicides. The elucidation of unknown steps and the identification of these targets, e.g. genes and cognate enzymes of these pathways is obligatory for this purpose.

A further source of interest in the non-mevalonate pathway derives from the fact certain pathogens like *Mycobacteria, Plasmodia, Escherichia* etc. use this pathway to activate γδ T cells (Fournié and Bonneville, 1996). Therefore, γδ T cells likely act as a first line of defense against infections by such pathogens. Intermediates of the non-mevalonate pathway have been suggested to be responsible for γδ T cell activation (Jomaa et al., 1999). Recently, it was show that *E. coli* strains lost the ability to stimulate γδ T cells when the dxr or the gcpE gene was knocked out (Altincicek et al., 2001).

Moreover, there is a great biotechnological interest in these pathways, since they lead to valuable vitamins and isoprenoid or terpenoid products.

Previous attempts to approach these goals have been hampered by the low rate of biosynthesis along these pathways in wild-type cells studied so far.

SUMMARY OF THE INVENTION

It is an object of the invention to provide enzymes and nucleic acids coding for said enzymes as well as intermediates for the conversion of 2C-methyl-D-erythritol 2,4-cyclodiphosphate to isopentenyl diphosphate and/or dimethylallyl diphosphate.

It has surprisingly been found that the intermediate in the conversion of 2C-methyl-D-erythritol 2,4-cyclodiphosphate to isopentenyl diphosphate and/or dimethylallyl diphosphate is 1-hydroxy-2-methyl-2-butenyl 4-diphosphate. This intermediate is formed by an enzyme encoded by gcpE as designated in the *E. coli* genome. It has further been found that this enzyme prefers as reductant NADH or NADPH. Further, it has been found that it is promoted by $Co^{2+}$.

The above intermediate is converted to isopentenyl diphosphate and/or dimethylallyl diphosphate by an enzyme encoded by lytB as designated in the *E. coli* genome. The latter enzyme prefers as reductant NADH or NADPH and FAD as mediator. Further it can be promoted by ions of a metal selected from manganese, iron, cobalt, nickel.

With these findings, the third segment of the trunk non-mevalonate pathway is now established. The key to these findings is the intermediate 1-hydroxy-2-methyl-2-butenyl 4-diphosphate, notably in its E-form. This establishes the unifying principle of the invention for reactions to and from this intermediate.

Further, it is an object of the invention to provide cells, cell cultures, organisms or parts thereof for the efficient biosynthesis of isoprenoid products or intermediates of the non-mevalonate biosynthetic pathway dependent on 1-deoxy-D-xylulose 5-phosphate production from 1-deoxy-D-xylulose and/or glucose.

The present invention produces a novel in vivo system which can be used for the structure elucidation of unknown intermediates and the assignment of biological functions of putative genes or cognate enzymes in the alternative isoprenoid biosynthetic pathway. As an example, the functional assignment of the gcpE gene (now designated as ispG) and of the lytB gene (now designated ispH) in the mevalonate-independent pathway of isoprenoid biosynthesis is achieved.

More specifically, said in vivo system consists of recombinant *E. coli* strains harbouring vector construct(s) carrying and expressing genes for D-xylulokinase (xylB), and genes of further downstream steps of terpenoid biosynthesis, such as dxs, dxr, and/or ispD, and/or ispE, and/or ispF, and/or gcpE, and/or lytB from *E. coli*, and/or a carotenoid gene cluster from *Erwinia uredovora*.

In one aspect of the invention, the genetically modified strains can be fed with 1-deoxy-D-xylulose, notably with isotope-labelled 1-deoxy-D-xylulose, which is converted at high rates into the common intermediate of the mevalonate-independent terpenoid pathway, 1-deoxy-D-xylulose 5-phosphate, and into further intermediates of said pathway, like 2C-methyl-D-erythritol 4-phosphate, 4-diphosphocytidyl-2C-methyl-D-erythritol, 4-diphosphocytidyl-2C-methyl-D-erythritol 2-phosphate, 2C-methyl-D-erythritol 2,4-cyclodiphosphate, 1-hydroxy-2-methyl-2-butenyl 4-diphosphate, isopentenyl diphosphate, and dimethylallyl diphosphate. Further, feeding with glucose or an intermediate of glycolysis for conversion into said further intermediates of said pathway may be performed.

Said systems are useful for the structure elucidation of hitherto elusive intermediates in the biosynthetic pathways, for in vivo screening of novel antibiotics, antimalarials, and herbicides, and as a platform for the bioconversion of exogenous 1-deoxy-D-xylulose and/or glucose into intermediates and products of the non-mevalonate pathway of terpenoid biosynthesis.

Said systems can also be used for screening chemical libraries for potential herbicides, and/or antimalarials, and/or antimicrobial substances by detecting and measuring the amount of certain intermediates formed in vivo in the presence or absence of potential inhibitors of the gene products of mevalonate-independent isoprenoid pathway genes, namely dxs, dxr, ispD, ispE, ispF, gcpE, and lytB.

Said system can further be used for the production of higher isoprenoids (e.g. isoprenoids having 10, 15, 20, 30 or 40 carbon atoms) such as carotene, α-tocopherole or vitamins by boosting the biosynthesis of isopentenyl diphosphate and/or dimethylallyl diphosphate via the non-mevalonate pathway, e.g. by using glucose as feeding material. Further feeding materials which may be used are intermediates or products of glycolysis like glyceraldehyde 3-phosphate or pyruvate.

Further, this invention provides novel compounds of formula I (see below), notably 1-hydroxy-2-methyl-2-butenyl 4-diphosphate as well as enzymatic and chemical methods for preparing said compounds. As demonstrated herein, (E)-1-hydroxy-2-methyl-2-butenyl 4-diphosphate is produced from 2C-methyl-D-erythritol 2,4-cyclodiphosphate by the gcpE gene product.

It is further demonstrated herein that (E)-1-hydroxy-2-methyl-2-butenyl 4-diphosphate is converted to dimethylallyl diphosphate and isopentenyl diphosphate by the lytB gene product.

BRIEF DESCRIPTION OF THE DRAWINGS

FIG. 8: DNA sequence of the vector construct pBSxylB-dxr (SEQ ID NO:41).

FIG. 9: DNA sequence of the vector construct pBSxylB-dxrispD (SEQ ID NO:42).

FIG. 10: DNA sequence of the vector construct pBScyclo (SEQ ID NO:43).

FIG. 11: DNA sequence of the vector construct pACY-CgcpE (SEQ ID NO:44).

FIG. 12: DNA sequence of the vector construct pBScaro14 (SEQ ID NO:45).

FIG. 13: DNA sequence of the vector construct pACY-Ccaro14 (SEQ ID NO:46).

FIG. 14: DNA sequence (SEQ ID NO:47) and corresponding amino acid sequence (SEQ ID NO:48) of the ispG (formerly gcpE) gene from *Escherichia coli*.

FIG. 15: DNA sequence of the vector construct pBScyclogcpE (SEQ ID NO:49).

FIG. 16: DNA sequence of the vector construct pACY-ClytBgcpE (SEQ ID NO:50).

FIG. 17: DNA (SEQ ID NO:51) and corresponding amino acid sequence (SEQ ID NO:52) of the ispH (formerly lytB) gene from *Escherichia coli*.

FIG. 18: DNA sequence of the vector construct pBScyclogcpElytB2 (SEQ ID NO:53).

FIG. 19: DNA (SEQ ID NO:54) and corresponding amino acid sequence (SEQ ID NO:55) of the ispG gene (fragment) from *Arabidopsis thaliana*.

FIG. 20: DNA (SEQ ID NO:56) and corresponding amino acid sequence (SEQ ID NO:57) of the ispG (formly gcpE) gene of *Arabidopsis thaliana*.

FIG. 21: cDNA sequence of 1-hydroxy-2-methyl-2-(E)-butenyl 4-diphosphate reductase (lspH) from *Arabidopsis thaliana* (SEQ ID NO:58)

DETAILED DESCRIPTION OF THE INVENTION

Figure 1:
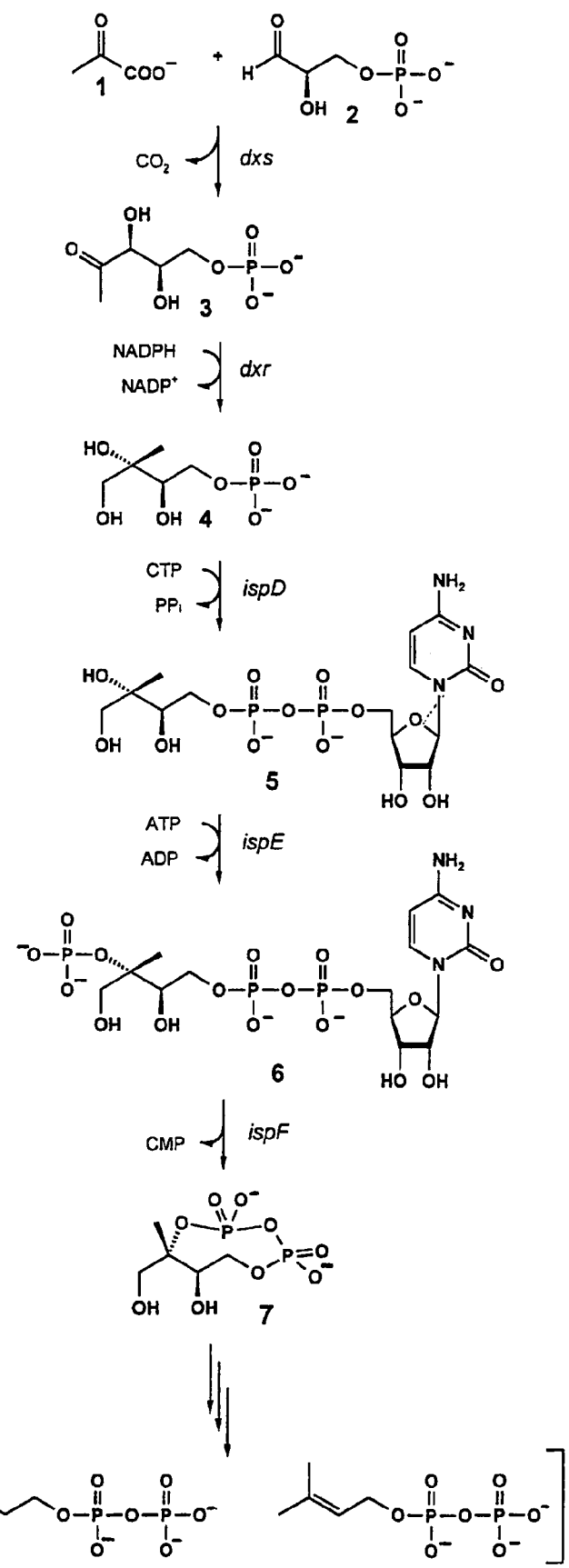
FIG. 1: Biosynthesis of both isoprenoid precursors, isopentenyl pyrophosphate and dimethylallyl pyrophosphate via the mevalonate-independent pathway.
Figure 2:
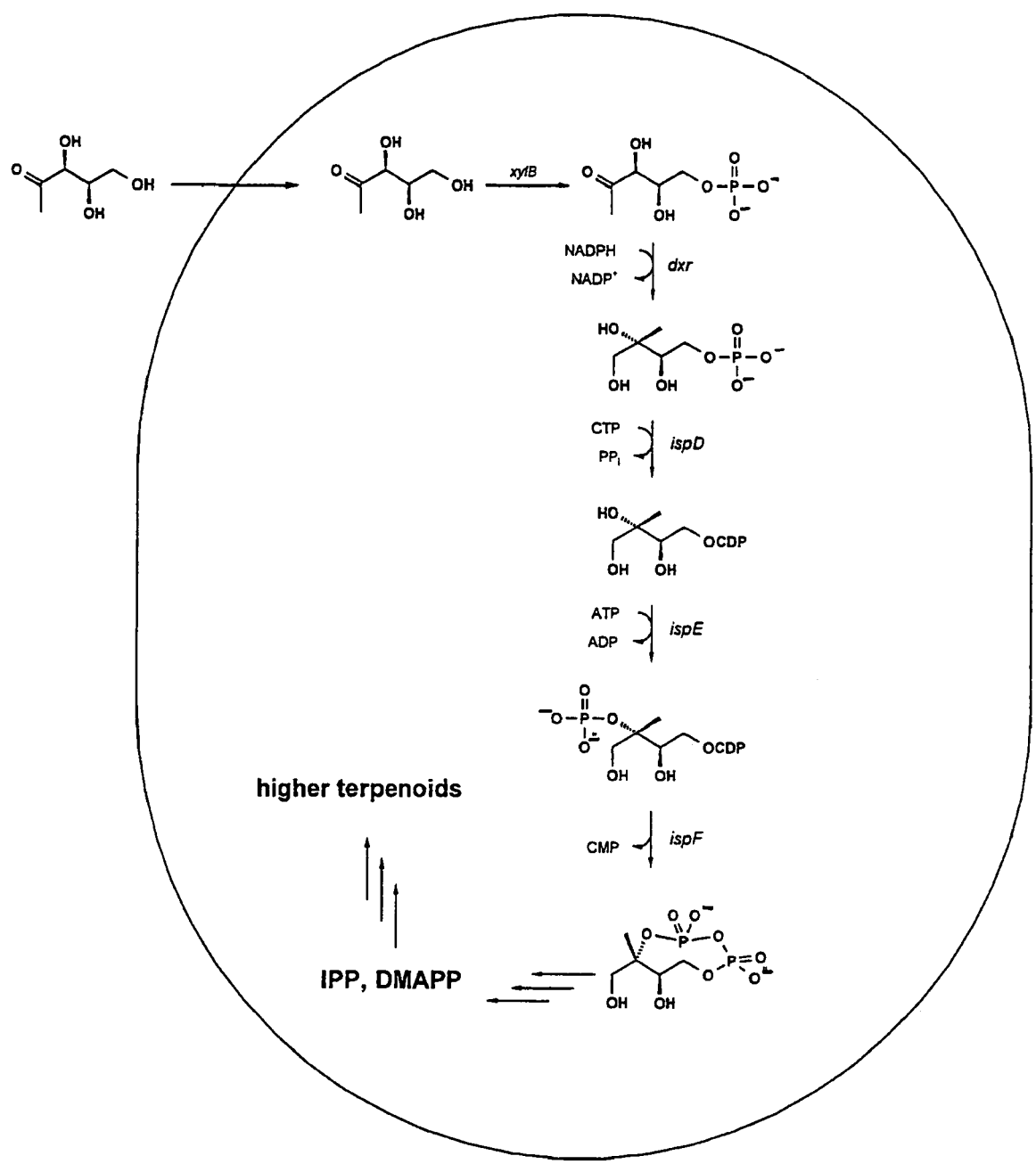
FIG. 2: Scheme of an *Escherichia coli* in vivo system for generating optionally isotopically labelled intermediates of biosynthetic pathways such as the mevalonate-independent isoprenoid biosynthesis, and for the production of higher terpenoids such as carotenoids.

1-Deoxy-D-xylulose 5-phosphate is a common intermediate in the alternative terpenoid pathway via 2C-methyl-D-erythritol 4-phosphate. This latter pathway is operative in bacteria, certain protozoa and most significantly also in the plastids of plants, where it is in charge of the biosynthesis of a great many valuable terpenoid products, like natural rubber, carotenoids, menthol, menthone, camphor or paclitaxel. The alternative terpenoid pathway is now intensely studied. But so far only the initial steps from glyceraldehyde 3-phosphate and pyruvate via 1-deoxy-D-xylulose 5-phosphate and 2C-methyl-D-erythritol 4-phosphate, 4-diphosphocytidyl-2C-methyl-D-erythritol, 4-diphosphocytidyl-2C-methyl-D-erythritol 2-phosphate and 2C-methyl-D-erythritol 2,4-cyclodiphosphate (FIG. 1) have been elucidated.

The intermediate 1-deoxy-D-xylulose 5-phosphate is of most crucial significance for a number of commercial purposes:

(1) It may be used as a key intermediate for commercial screening procedures regarding potential inhibitors of downstream enzymes in the biosynthesis of the alternative terpenoid pathway.

(2) It may be used as a key intermediate for the in vitro production of terpenoids or of intermediates thereof.

(3) It occurs in vivo in the biosynthesis of terpenoids as an enzymatic condensation product of glyceraldehyde 3-phosphate and pyruvate. The latter are central intermediates of the metabolism and obligatory starting materials for numerous biosynthetic pathways. Therefore, it is desirable to generate a high level of 1-deoxy-D-xylulose 5-phosphate in vivo from an exogenous source and thus independent from the pools of glyceraldehyde 3-phosphate and pyruvate for boosting the biosynthesis of terpenoids or of intermediates thereof in microorganisms or cell cultures that are either naturally or recombinantly endowed with the pathway of interest without influencing the basic intermediary metabolism of the cells.

(4) 1-Deoxy-D-xylulose 5-phosphate can be generated from 1-deoxy-D-xylulose by the catalytic action of the xylB gene product. Using recombinant strains comprising the xylB gene the reaction occurs in vivo and exogenous 1-deoxy-D-xylulose is converted into intracellular 1-deoxy-D-xylulose 5-phosphate at high rates.

(5) 1-DXP can be generated fro glucose by the catalytic action of glycolytic enzymes and DXP-synthase. Using recombinant strains comprising the dxs gene, the reaction occurs in vivo and exogeneous glucose is converted to intracellular 1-DXP at high rates.

It is an aspect of the invention to use 1-deoxy-D-xylulose as a precursor in order to boost the rates of biosynthesis of 1-deoxy-D-xylulose 5-phosphate-dependent pathways. 1-Deoxy-D-xylulose can be prepared by various published procedures (Blagg and Poulter, 1999; Kennedy et al., 1995; Piel and Boland, 1997; Shono et al., 1983; Giner, 1998).

It is an aspect of the present invention to use 1-deoxy-D-xylulose in various isotopically labelled forms. It may be labelled by radioactive isotopes or non-radioactive isotopes of C ($^{13}$C or $^{14}$C), H (D or T) or O ($^{17}$O or $^{18}$O) in any combination.

Isotope-labelled 1-deoxy-D-xylulose may be prepared enzymatically using 1-deoxy-D-xylulose 5-phosphate synthase of *Bacillus subtilis* and commercially available glycolytic enzymes and phosphatase from isotope-labelled glucose and/or pyruvate (PCT/EP00/07548).

1-Deoxy-D-xylulose may be used as a free acid or as a salt, preferably as an alkaline (e.g., lithium, sodium, potassium) salt or as an ammonium or amine salt.

It is an aspect of the present invention to use recombinant cells, cell cultures, or organisms or parts thereof for the formation of biosynthetic products or intermediates or enzymes or for the screening for antimicrobials, antimalarials or herbicides.

For carrying out the present invention various techniques in molecular biology, microbiology and recombinant DNA technology are used which are comprehensively described in Sambrock et al., Molecular Cloning, second edition, Cold Spring Harbor Laboratory Press, Cold Sprind Harbor, N.Y.; in DNA Cloning: A Practical Approach, Vol. 1 and 2, 1985 (D. N. Glover, ed.); in Oligonucleotide Synthesis, 1984 (M. L. Gait, ed.); and in Transcription and Translation (Hames and Higgins, eds.).

Nucleic Acids

The present invention comprises nucleic acids which include prokaryotic, protozoal and plant sequences and derived sequences. A derived sequence relates to a nucleic acid sequence corresponding to a region of the sequence or orthologs thereof or complementary to "sequence-conservative" or "function-conservative" variants thereof.

Sequences may be isolated by well known techniques or are commercially available (Clontech, Palto Alto, Calif.; Stratagene, LaJolla, Calif.). Alternatively, PCR-based methods can be used for amplifying related sequence from cDNA or genomic DNA.

The nucleic acids of the present invention comprise purine and pyrimidine containing polymers in various amounts, either polyribonucleotides or polydeoxyribonucleotides or mixed polyribo-polydeoxyribonucleotides. The nucleic acids may be isolated directly from cells. Alternatively, PCR may be used for the preparation of the nucleic acids by use of chemical synthesized strands or by genomic material as template. The primers used in PCR may be synthesized by using the sequence information provided by the present invention or from the database and additionally may be constructed with optionally new restriction sites in order to ease the cloning in a vector for recombinant expression.

The nucleic acids or the present invention may be flanked by natural regulation sequences or may be associated with heterologous sequences, including promoter, enhancer, response elements, signal sequences, polyadenylation sequences, introns, 5'- and 3' noncoding regions or similar. The nucleic acids may be modified on basis of well known methods. Non-limiting examples for these modifications are methylations, "Caps", substitution of one or more natural nucleotides with an analogue, and internucleotide modification, i.e. those with uncharged bond (i.e. methylphosphonates, phosphotriester, phosphoramidates, carbamates, etc.) and with charged bond (i.e. phosphorothiactes, etc.). Nucleic acids may carry additional kovalent bound units such as proteins (i.e. nucleases, toxins, antibodies, signal peptides, poly-L-lysine, etc.), intercalators (i.e. acridine, psoralene, etc.), chelators (i.e. metals, radioactive metals, iron, oxidative metals, etc.) and alkylators. The nucleic acids may be derived by formation of a methyl- or ethylphosphotriester bond or of a alkylphosphoramidate bond. Further, the nucleic acids of the present invention may be modified my labeling, which give an either directly or indirectly detectable signal. Examples for these labeling include radioisotopes, fluorescent molecules, biotin and so on.

Vectors

The invention provides nucleic acid vectors, which comprise the sequences provided by the present invention or derivatives thereof. Various vectors, including plasmids or vectors for fungi have been described for the replication and/or expression in various eucaryotic and procaryotic hosts. High copy replication vectors are preferred for the purposes of the invention. Non-limiting examples include pKK plasmids (Clontech), pUC plasmids (Invitrogen, San Diego, Calif.), pET plasmids (Novagen, Inc., Madison, Wis.) or pRSET or pREP (Invitrogen) and various suitable host cells on basis of well known techniques. Recombinant cloning vectors comprise often more than one replication system for the cloning and expression, one or more marker for the selection in the host; i.e. antibiotic resistance and one or more expression cartridge. Suitable hosts may be transformed/transfected/infected by a method as suitable including electroporation, $CaCl_2$-mediated DNA incorporation, tungae infection, microinjection, microbombardment or other established methods.

Suitable hosts include bacteria, archaebacteriae, fungi, notable yeast, plants, notably *Arabidopsis thaliana, Mentha piperita* or *Taxus* sp. and animal cells, notably mammalian cells. Most important are *E. coli, Bacillus subtilis, Saccharomyces cerevisiae, Saccharomyces carlsbergensis, Schizosaccharomyces pombe*, SF9 cells, C129 cells, 293 cells, *Neurospora*, and CHO cells, COS cells, HeLa cells and immortalized myeloid and lymphoid mammalian cells. Preferred replication systems include M13, ColE1, SV40, baculovirus, lambda, adenovirus and so on. A great number of transcription, initiation (including ribosomal binding sites) and termination regulation regions have been isolated and there efficiency for the transcription and translation of heterologous proteins has been demonstrated in various hosts. Examples for these regions, methods for the isolation, the way for using are well known. Under suitable conditions for expression host cells may be used as source for the recombinant synthesized proteins.

Expression Systems

Preferable vectors may include a transcription element (that is a promoter), functionally connected with the enzyme domain. Optionally, the promoter may include parts of operator region and/or ribosomal binding sites. Non-limiting examples for bacterial promoters, which are compatible with *E. coli*, include: trc promoter, b-lactamase (penicillinase) promoter; lactose promoter, tryptophan (trp) promoter, arabinose BAD operon-promoter, lambda-derived P1 promoter and N gene ribosomal binding site and the hybrid Tac promoter, derived from sequences of trp and lac UV5 promoters. Non-limiting examples for yeast promoters include 3-phosphoglycerate kinase promoter, glyceraldehyde 3-phosphate dehydrogenase (GAPDH) promoter, galactokinase (GALI) promoter, galactoepimerase promoter and alcoholdehydrogenase (ADH) promoter. Suitable promoters for mammalian cells include without limiting viral promoters such as i.e. simian virus 40 (SV40), rous sarcoma virus (RSV), adenovirus (ADV) and bovine papilloma virus (BPV). Mammalian cells may also need terminator sequences and poly-A sequences and enhancer sequences, which may increase the expression. Sequences, which amplify the genes, may also be preferred. Further on, sequences may be included, which ease the secretion of the recombinant protein from the cell, which may be but non-limiting a bacterial, yeast or animal cell, such as i.e. a secretion signal sequence and/or prehormon sequence.

It is an important aspect of the invention that the combined recombinant endowment with xylB and other gene(s) of the alternative C5-isoprenoid pathway and optionally gene(s) for higher isoprenoids or terpenoids boost(s) these pathways. Preferably, xylB is combined with complete sets of genes to convert 1-deoxy-D-xylulose 5-phosphate into the desired intermediate or end products. For intermediates in the C5-isoprenoid pathway, cells are preferably endowed with one of the combinations of genes given in claim 76.

For the genes cited herein, the common *E. coli* designation were used. Other genes from *E. coli* or from other organisms (orthologous genes) may also be used if they have the same functions (function-conservative genes), notably if their gene products catalyze the same reaction. Further, deletion or insertion variants or fusions of these genes with other genes or nucleic acids may be used, as long as these variants are function-conservative. The above genes may be derived from bacteria, protozoa, or from higher or lower plants, It is another important aspect of the invention that the function of gcpE as following immediately downstream from ispF has been determined. Our findings show that the gcpE gene product is involved in the formation of the novel compound 1-hydroxy-2-methyl-2-butenyl 4-diphosphate from 2C-methyl-D-erythritol 2,4-cyclodiphosphate. Therefore, we rename gcpE in ispG.

In a further aspect of the invention it was shown that the gene product of gcpE is involved in the formation of the E-isomer of 1-hydroxy-2-methyl-2-butenyl 4-diphosphate from 2C-methyl-D-erythritol 2,4-cyclodiphosphate by comparison with chemically synthesized (E)- and (Z)-isomers of 1-hydroxy-2-methyl-2-butenyl 4-diphosphate. Therefore, this invention further pertains to the (E) and (Z) isomers of 1-hydroxy-2-methyl-2-butenyl 4-diphosphate salts or protonated forms thereof.

It is another important aspect of the invention that the function of lytB has been determined as following immediately downstream from ispG. Therefore, it is renamed ispH. It is our finding that ispH is involved in the conversion of (E)-1-hydroxy-2-methyl-2-butenyl 4-diphosphate into isopentenyl 4-diphosphate and/or dimethylallyl 4-diphosphate.

It should be understood that "1-hydroxy-2-methyl-2-butenyl 4-phosphate" and "1-hydroxy-2-methyl-2-butenyl 4-diphosphate" comprise the free phosphoric and diphosphoric acids, respectively, and the singly or multiply deprotonated forms thereof, i.e. salts which may be salts of any cation (including Na, K, $NH_4^+$, Li, Mg, Ca, Zn, Mn, and Co cations). The protonation state of (di)phosphates and phosphate derivatives or their conjugated acids in aqueous solution depends on the pH value of the solution, as is known to persons skilled in the art. The same applies to other phoshates or phosphate derivatives.

In another aspect of the invention, (E)-1-hydroxy-2-methyl-2-butenyl 4-diphosphate has been successfully incorporated into the lipid soluble fraction of *Capsicum annuum* chromoplasts. A $^{14}C$ label of this compound was incorporated into the geranylgeraniol, b-carotene, phytoene and phytofluene fractions of *C. annuum* chromoplasts establishing (E)-1-hydroxy-2-methyl-2-butenyl 4-diphosphate as intermediate of the non-mevalonate pathway downstream from 2C-methyl-D-erythritol 2,4-cyclodiphosphate and upstream from isopentenyl diphosphate.

It is another aspect of the invention that xylB can be combined with gcpE and optionally other genes of the alternative C5 isoprenoid pathway and/or of the higher isoprenoid pathways in vector(s) for recombinant engineering.

As a consequence of our findings regarding gcpE (now ispG) it follows that the gene lytB operates downstream of gcpE and thus in service of the conversion of 1-hydroxy-2-methyl-2-butenyl 4-diphosphate to IPP and/or DMAPP. Therefore, it is another aspect of the invention to combine the gene lytB with xylB and optionally other genes of the common C5-isoprenoid pathway or of a higher isoprenoid pathway.

Our finding allows the efficient formation or production of intermediates or products of the isoprenoid pathway with any desired labelling, notably the following intermediates: 2C-methyl-D-erythritol 4-phosphate; 4-diphosphocytidyl-2C-methyl-D-erythritol; 4-diphosphocytidyl-2C-methyl-D-erythritol 2-phosphate; 2C-methyl-D-erythritol 2,4-cyclodiphosphate; 1-hydroxy-2-methyl-2-butenyl 4-diphosphate, isopentenyl diphosphate; dimethylallyl diphosphate.

The formation of end products of the terpenoid pathway (e.g., b-carotene, zeaxanthine, paclitaxel, menthol, menthone, cannabinoids), may be boosted following the process of the invention.

The strains harbouring the recombinant plasmids can be cultivated in conventional culture media, preferably in terrific broth medium, at 15 to 40° C. The preferred temperature is 37° C. The *E. coli* strains are induced with 0.5 to 2 mM isopropyl-b-D-thiogalactoside (IPTG) at an optical density at 600 nm from 0.5 to 5. The cells are incubated after addition of 1-deoxy-D-xylulose at a concentration of 0.001 mM to 1 M preferably at a concentration of 0.01 to 30 mM for 30 min to 15 h, preferably 1 to 5 h.

It has been found that the process of producing isoprenoid intermediates or products by the genetically engineered organisms of the invention can be boosted by supplying a source for CTP, for example cytidine and/or uridine and/or cytosine and/or uracil and/or ribose and/or ribose 5-phosphate and/or any biosynthetic precursors of CTP at a concentration of 0.01 to 10 mM, preferably at a concentration of 0.3 to 1 mM, and/or by supplying a source for phosphorylation activity, for example glycerol 3-phosphate and/or phosphoenolpyruvate and/or ribose 5-phosphate at a concentration of 0.1 to 100 mM, preferably at a concentration of 0.5 to 10 mM and/or inorganic phosphate and/or inorganic pyrophosphate at a concentration of 1 to 500 mM, preferably at a concentration of 10 to 100 mM and/or any organic phosphate and/or pyrophosphate, and/or by supplying a source for reduction equivalents, for example 0.1 to 1000 mM, preferably 10 to 1000 mM, lactate and/or succinate and/or glycerol and/or glucose and/or lipids at a concentration of 0.1 to 100 mM, preferably at a concentration of 0.5 to 10 mM. A particularly efficient production process is specified in claims 72 and 80 to 84.

This process can also be used with great advantages for screening for inhibitors of the enzymes involved or of downstream enzymes, dependent on the choice of the isoprenoid intermediate or product for detection. The enzymes dxs, dxr, ispD, ispE, ispF, ispG (formerly gcpE) and ispH (formerly lytB) do not occur in animals. Therefore inhibitors against dxs, dxr, ispD, ispE, ispF, ispG (formerly gcpE) and ispH (formerly lytB) have great value as (a) herbicides against weed plants or algae; (b) antibiotic agents against pathogenic bacteria; (c) agents against protozoa, like *Plasmodium falciparum*, the causative pathogen of malaria.

The activity of the said enzymes can be detected (in the presence or absence of a potential inhibitor) by measuring either the formation of a product or the consumption of an intermediate, preferably by TLC, HPLC or NMR.

With the finding that 1-hydroxy-2-methyl-2-butenyl 4-diphosphate is an intermediate of the non-mevalonate terpenoid pathway we have acquired essential determinants of the structure of inhibitors. Namely, the structures of a subset of inhibitors should be similar to at least a portion of the starting compound or the product or the transition state between the starting compound e.g. 2C-methyl-D-erythritol 2,4-cyclodiphosphate and the product e.g. 1-hydroxy-2-methyl-2-butenyl 4-diphosphate.

This invention discloses novel compounds, or salts thereof, of the following formula I:

whereby $R^1$ and $R^2$ are different from each other and one of $R^1$ and $R^2$ is hydrogen and the other is selected from the group consisting of —$CH_2$—O—PO(OH)—O—$PO(OH)_2$, —$CH_2$—O—$PO(OH)_2$, and —$CH_2OH$, and whereby A stands for —$CH_2OH$ or —CHO. These compounds may be isotope-labelled.

In formula I, A preferably stands for —$CH_2OH$.

Among $R^1$ and $R^2$, $R^1$ is preferably hydrogen and $R^2$ is preferably selected from the group consisting of —$CH_2$—O—PO(OH)—O—$PO(OH)_2$ and —$CH_2$—O—$PO(OH)_2$.

In the group consisting of —$CH_2$—O—PO(OH)—O—$PO(OH)_2$ and —$CH_2$—O—$PO(OH)_2$, —$CH_2$—O—PO(OH)—O—$PO(OH)_2$ is preferred.

If a compound of formula I is a salt, it may e.g. be a lithium, sodium, potassium, magnesium, ammonium, manganese salt. These salts may derive from a single or from multiple deprotonations from the (di)phosphoric acid moiety.

The novel compounds disclosed herein are useful for various applications e.g. for screening for genes, enzymes or inhibitors of the biosynthesis of isoprenoids or terpenoids, either in vitro in the presence of an electron donor or in vivo.

This invention further provides a process for the chemical preparation of a compound of formula I or a salt thereof:

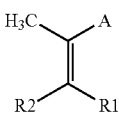

(I)

wherein A represents —CH$_2$OH and R$^1$ and R$^2$ are different from each other and one of R$^1$ and R$^2$ is hydrogen and the other is —CH$_2$—O—PO(OH)—O—PO(OH)$_2$, —CH$_2$—O—PO(OH)$_2$, or —CH$_2$—OH by the following steps:

(a) converting a compound of the following formula (II):

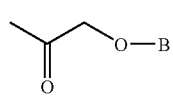

(II)

wherein B is a protective group into a compound of the following formula (III) or (IV):

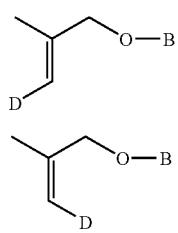

(III)

(IV)

by a Wittig or Horner reagent, wherein the group D is a precursor group convertible reductively to a —CH$_2$—OH group;

(b) reductively converting group D to a —CH$_2$—OH group;

(c) optionally converting group —CH$_2$—OH obtained in step (b) into —CH$_2$—O—PO(OH)—O—PO(OH)$_2$ or —CH$_2$—O—PO(OH)$_2$ or salts thereof in a manner known per se;

(d) optionally conversion to a desired salt;

(e) removing the protective group B.

In the above process, said protective group B may be any group that allows to regenerate an hydroxy group at the position it is attached to. Said protective group B is preferably stable under the conditions of step (a) to step (d). Said protective group B is removed in step (e) of said process in order to generate a hydroxy group. Protective groups for hydroxy groups are known to the skilled person. Group B may for example form an acetal group together with the remaining moiety of the compound of formula (II), (III) or (IV). Acetals can be hydrolysed under acidic conditions. Most preferably, group B is a 2-tetrahydropyranyl group.

In the above process, said group D is a precursor group convertible reductively to a —CH$_2$—OH group. Group D may be a derivative of a carbon acid. Examples of such a group include alkoxycarbonyl and aminocarbonyl groups. Said aminocarbonyl groups may be substituted at the amino group with one or two alkyl groups. It is most preferred to use alkoxycarbonyl groups. The alkyl group of said alkoxycarbonyl groups or said alkyl groups of said aminocarbonyl groups may be a linear or branched alkyl groups which may be singly or multiply substituted. Preferred are C$_1$–C$_6$ alkyl groups like methyl, ethyl, propyl, butyl, pentyl or hexyl groups. Most preferred are methyl or ethyl groups. The most preferred example of said group D is an ethoxycarbonyl group.

Said compound of formula (II) may be prepared by protecting the hydroxy group of hydroxy acetone with said group B. If group B is a tetrahydropyranyl group, the compound of formula (II) may be prepared from hydroxy acetone and 3,4-dihydro-2H-pyran, preferably employing pyridinium toluene-4-sulfonate as a catalyst. A specific method for preparing acetonyl tetrahydropyranyl ether is described in example 24.

In step (a) of said process, the compound of formula (II) is converted to a compound of formula (III) or (IV) by a Wittig or a Horner reagent. Wittig-type reactions and reagents are known to skilled persons (see e.g. Watanabe et al. 1996 and references cited therein). Common Wittig reagents to be used for the above process are methylentriphenylphosphoranes which may be substituted at the methylene group. For the above process of this invention, a methylene-triphenylphosphorane is employed which is substituted with the above-defined group D at the methylene group. Such Wittig reagents are commercially available or can be prepared according to known methods.

The olefin produced in step (a) may be formed as a mixture of the cis/trans isomers of formulas (III) and (IV). If one of said isomers is preferred, it may be enriched or separated from the other isomer by methods known in the art, preferably by chromatography. Alternatively, a separation of said isomers may be carried out after one of the following steps (b) to (e).

In step (b) of the above process, group D of the compound of formula (III) or (IV) or a mixture of said compounds is reductively converted to a —CH$_2$—OH group. Various methods are known in the art to perform such a reduction. Conditions are chosen such that group D is reduced whereas the olefin moiety is not. Examples for reductants to be used in this step are molecular hydrogen or metal hydrides. Examples for useful metal hydrides include boron hydrides like sodium borohydride, aluminium hydrides like lithium aluminium hydride or diisobutyl aluminiumhydride (DIBAH), alkali metal or metal earth hydrides like sodium hydride or calcium hydride. Aluminium hydrides are preferred. A specific example for carrying out step (b) is described in example 24.

If the desired end product of said process is a compound of formula (I), wherein R$^1$ or R$^2$ is —CH$_2$—OH, the compound or mixture of compounds obtained in step (b) may be directly subjected to step (d) or step (e). Preferably, it is subjected to step (e) for removing protective group B. If the desired end product of said process is a compound of formula (I), wherein R$^1$ or R$^2$ is —CH$_2$—O—PO(OH)—O—PO(OH)$_2$ or —CH$_2$—O—PO(OH)$_2$, compound or mixture of compounds obtained in step (b) is subjected to step (c) of said process for converting —CH$_2$—OH group obtained in step (b) into a —CH$_2$—O—PO(OH)—O—PO(OH)$_2$ or a —CH$_2$—O—PO(OH)$_2$ group.

Step (c) may be carried in several ways which are known to the skilled person. Step (c) may comprise substituting the hydroxy group of said —CH$_2$—OH group obtained in step (b) by a leaving group. Step (c) may comprise converting said —CH$_2$—OH group to a —CH$_2$-halide group by a halogenating agent. A sulfuric, sulfonic or phosphoric acid halogenide may be employed as halogenating agent. Tosyl chloride is most preferred. Said halide may be fluoride, chloride, bromide or iodide, preferably chloride. The compound carrying said —$CH_2$-halide group is preferably isolated. Said leaving group may further be created by reacting said —$CH_2$—OH group obtained in step (b) with a sulfonic acid halide, preferably tosyl chloride. Said intermediate having said leaving group may then be reacted with phosphoric or diphosphoric acid or singly or multiply deprotonated forms thereof. Preferably an alkylammonium salt of phosphoric or diphosphoric acid is used, more preferably a tetraalkylammonium salt, and most preferably a tetra-butylammonium salt. A polar aprotic solvent is preferred for this reaction. Preferably, the compound or mixture of compounds obtained is purified according to standard procedures. A specific example for carrying out step (c) is described in example 24.

In step (d), the compound or mixture of compounds obtained in step (c) may be converted to a desired salt. Methods for carrying out step (d) are well known. Such methods may comprise adjusting the pH of an aqueous solution with an appropriate acid or salt to a desired pH value.

In step (e), the protective group B of a compound obtained in one of steps (b) to (d) is removed in order to obtain a compound of formula (I) wherein A is —$CH_2$—OH. The method for removing a protective group depends on the type of the protective group. Such methods are well known. If the protective groups forms an acetal, removing said protecting group may be achieved by acid hydrolysis (see example 24).

This invention provides protein in a form that is functional for the enzymatic conversion of 2C-methyl-D-erythritol 2,4-cyclodiphosphate to 1-hydroxy-2-methyl-2-butenyl 4-diphosphate notably in its (E)-form, preferably in the presence of NADH and/or NADPH and/or in the presence of $Co^{2+}$. Said enzyme preferably has a sequence encoded by the ispG (formerly gcpE) gene of *E. coli* or a function-conservative homologue of said sequence, i.e. said homologue is capable of performing the same function as said protein. For many applications of said protein, it may be expressed and purified as a fusion protein, notably a fusion with maltose binding protein. In this way, enzymatically active protein may be readily obtained.

This invention further provides a protein in a form that is functional for the enzymatic conversion of 1-hydroxy-2-methyl-2-butenyl 4-diphosphate, notably in its (E)-form, to isopentenyl diphosphate and/or dimethylallyl diphosphate. Said protein preferably requires FAD and NAD(P)H for said functionality. Further, said protein may require a metal ion selected from the group of manganese, iron, cobalt, or nickel ion. Said protein preferably has a sequence encoded by the ispH (formerly lytB) gene of *E. coli* or a function-conservative homologue of said sequence. For many applications of said protein, it may be expressed and purified as a fusion protein, notably a fusion with maltose binding protein. In this way, enzymatically active protein may be readily obtained.

The above proteins may be plant proteins, notably from *Arabidopsis thaliana*, bacterial proteins, notably from *E. coli*, or protozoal proteins, notably from *Plasmodium falciparum*.

The invention further provides a purified isolated nucleic acid encoding one or both of the above proteins with or without introns. Further, the invention provides a DNA expression vector containing the sequence of said purified isolated nucleic acid.

The invention further provides cells, cell cultures, organisms or parts thereof recombinantly endowed with the sequence of said purified isolated nucleic acid or with said DNA expression vector, wherein said cell is selected from the group consisting of bacterial, protozoal, fungal, plant, insect and mammalian cells. Said cells, cell cultures, organisms or parts thereof may further be endowed with at least one gene selected from the following group: dxs, dxr, ispD (formerly ygbP); ispE (formerly ychB); ispF (formerly ygbB) of *E. coli* or a function-conservative homologue thereof, or a function-conservative fusion, deletion or insertion variant of any of the above genes.

The invention further provides cells, cell cultures, or organisms or parts thereof transformed or transfected for an increased rate of formation of 1-hydroxy-2-methyl-2-butenyl 4-diphosphate, notably in its (E)-form, compared to cells, cell cultures, or organisms or parts thereof absent said transformation or transfection. The transformation or transfection preferably comprises endowment with the gcpE gene of *E. coli* or with a function-conservative homologue from an other organism, e.g. plant or protozoal organism.

The invention also provides cells, cell cultures, or organisms or parts thereof transformed or transfected for an increased rate of conversion of (E)-1-hydroxy-2-methyl-2-butenyl 4-diphosphate to isopentenyl diphosphate and/or dimethylallyl diphosphate compared to cells, cell cultures, or organisms or parts thereof absent said transformation or transfection. The transformation or transfection preferably comprises endowment with the lytB gene of *E. coli* or with a function-conservative homologue from an other organism, e.g. plant or protozoal organism.

The invention provides also cells, cell cultures, or organisms or parts thereof transformed or transfected for an increased expression level of the protein of one of claims 1 to 4 and/or the protein of one of claims 5 to 8 compared to cells, cell cultures, or organisms or parts thereof absent said transformation or transfection.

Moreover, the invention provides a method of altering the expression level of the gene product(s) of ispG and/or ispH or function-conservative homologues from other organisms or variants thereof in cells comprising
(a) transforming host cells with the ispG and/or ispH gene,
(b) growing the transformed host cells of step (a) under conditions that are suitable for the efficient expression of ispG and/or ispH, resulting in production of altered levels of the ispG and/or ispH gene product(s) in the transformed cells relative to expression levels of untransformed cells.

Furthermore, the invention provides a method of identifying an inhibitor of an enzyme functional for the conversion of 2C-methyl-D-erythritol 2,4-cyclodiphosphate to 1-hydroxy-2-methyl-2-butenyl 4-diphosphate, notably its E-form, of the non-mevalonate isoprenoid pathway by the following steps:
(a) incubating a mixture containing said enzyme with its, optionally isotope-labeled, substrate 2C-methyl-D-erythritol-2,4-cyclodiphosphate under conditions suitable for said conversion in the presence and in the absence of a potential inhibitor,
(b) subsequently determining the concentration of 2C-methyl-D-erythritol 2,4-cyclodiphosphate and/or 1-hydroxy-2-methyl-2-butenyl 4-diphosphate, and
(c) comparing the concentration in the presence and in the absence of said potential inhibitor.

Furthermore, the invention provides a method of identifying an inhibitor of an enzyme functional for the conversion of 1-hydroxy-2-methyl-2-butenyl 4-diphosphate, notably its E-form, to isopentenyl diphosphate or dimethylallyl diphosphate of the non-mevalonate isoprenoid pathway by the following steps:

(a) incubating a mixture containing said enzyme with its, optionally isotope-labeled, substrate 1-hydroxy-2-methyl-2-butenyl 4-diphosphate under conditions suitable for said conversion in the presence and in the absence of a potential inhibitor, whereby said mixture preferably contains FAD, (b) determining the concentration of 1-hydroxy-2-methyl-2-butenyl 4-diphosphate and/or isopentenyl diphosphate or dimethylallyl diphosphate, and (c) comparing the concentration in the presence and in the absence of said potential inhibitor.

The above methods of identifying an inhibitor are preferably carried out by following the consumption of NADPH or NADH making use of its characteristic absorbance spectrum. Alternatively, the fluorescence of NADH or NADPH can be followed when excited around 340 nm. The above methods of identifying an inhibitor may advantageously be performed as high-throughput screening assays for inhibitors, notably in combination with photometric detection of the consumption of NADH or NADPH. Further, one or more flavin analogues (e.g. FAD, FMN) may be added to the incubation mixtures in said methods, preferably in catalytic amounts. Most preferred is the addition of FAD. Said enzymes may be employed in said methods as fusion proteins with maltose binding protein (examples 38 to 41, 44, 45), which allows straightforward expression and purification of said enzymes in enzymatically active form. Further embodiments of said methods of identifying are defined in the subclaims to these methods.

It is known that intermediates of the non-mevalonate pathway are responsible for γδ T cell activation by various pathogenic bacteria. γδ T cell activation is followed by T cell proliferation, secretion of cytokines and chemokines and is very likely crucial for regulating the immune response following pathogen infection (Altincicek et al., 2001 and references cited therein). Recently, it was shown that *E. coli* strains lost the ability to stimulate γδ T cells when the dxr or the gcpE gene was knocked out, strongly indicating that an intermediate downstream of gcpE and upstream of isopentenyl pyrophosphate exhibits the most potent antigenic activity (Altincicek et al., 2001). However, the intermediate produced by the gcpE gene product in the pathway has been unknown. Herein, this intermediate has surprisingly been identified as an hitherto unprecedented compound, which opens up a whole range of novel applications for this compound.

The compounds of formula I can be used as immunomodulatory or immunostimulating agents, e.g. for activating γδ T cells. Immunomodulation via γδ T cell activation by said compounds may prove useful not only to support combat against pathogens but for various conditions for which a stimulation of the immune system is desirable. The novel compounds of the invention may therefore be used for medical treatment of pathogen infections. Such a treatment stimulates the activity of the immune system against the pathogen. Preferably, the compound wherein $R^1$=H and/or A is —CH$_2$OH is used for this application. Alternatively, the oxidation product with A=CHO may prove to be highly active. Among the compounds of formula I, the one with the highest or most suitable γδ T cell stimulating activity may be selected in a test system known in the art (e.g. that described by Altincicek et al., 2001). Importantly, since the compounds of the invention do not act as antibiotics, development of resistances is not a problem for the method of treatment disclosed herein.

In an advantageous embodiment, said compounds may be combined with an antibiotically active compound for treating a pathogen infection. Such a treatment combines the advantages of inhibiting pathogen proliferation by an antibiotic and stimulating the immune system against the pathogen resulting in a much faster and more efficient treatment. Such an antibiotically active compound may be a bacteriostatic antibiotic (e.g. tetracyclines). Therefore, the novel compounds of this invention may be used for the preparation of a medicament. The invention further pertains to a pharmaceutical composition containing a compound of formula I and a pharmaceutically acceptable carrier. Said pharmaceutical composition may further contain an antibiotically active compound as mentioned above.

This invention further comprises antibodies against the compounds of formula I. Said antibodies may be polyclonal or monoclonal and may be raised according to conventional techniques. Raising such antibodies will comprise coupling of a compound of formula I has hapten to a macromolecular carrier like a protein in order to be immunogenic. Such an immunogenic compound of formula I may further be used as a vaccine.

The antibodies of the invention may be used for detecting a compound of formula I. Since said compounds are produced by organisms having the non-mevalonate isoprenoid pathway, such organisms may be detected using said antibodies. Preferably, such organisms may be detected in body fluids in a diagnostic method, thereby indicating an infection by a pathogen having the non-mevalonate pathway. A positive result in such a diagnostic method may at the same time indicate possible treatment by the compounds of the invention.

When an antibody of the invention is used for detecting a compound of formula I, it is preferably labelled to allow photometric detection and/or immobilized to a support. Such methods are well-known in the art.

This invention further provides a process for the chemical preparation of a compound of formula I or a salt thereof (see FIG. 7):

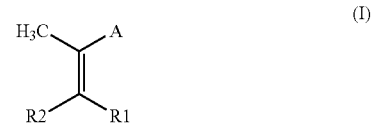

(I)

wherein A represents —CH$_2$OH or —CHO, $R^1$ is hydrogen, and $R^2$ is —CH$_2$—O—PO(OH)—O—PO(OH)$_2$, —CH$_2$—O—PO(OH)$_2$ or —CH$_2$—OH by the following steps:

(a) converting 2-methyl-2-vinyl-oxiran into 4-chloro-2-methyl-2-buten-1-al;

(b) converting 4-chloro-2-methyl-2-buten-1-al to its acetal;

(c) substituting the chlorine atom in the product of step (b) by a hydroxyl group, a phosphate group or a pyrophosphate group;

(d) hydrolysing the acetal obtained in step (c) to produce an aldehyde group;

(e) optionally converting the aldehyde group of the product of step (d) to a —CH$_2$OH group.

Preferred embodiments of this process are defined in the subclaims and are exemplified in example 42.

The invention will now be described in detail with reference to specific examples.

EXAMPLE 1

Construction of a Vector Carrying the xylB Gene of *Escherichia coli* Capable for Transcription and Expression of D-xylulokinase Chromosomal DNA from *Escherichia coli* strain XL1-Blue (Bullock et al. 1987; commercial source: Stratagene, LaJolla, Calif., USA) is isolated according to a method described by Meade et al. 1982.

The *E. coli* ORF xylB (accession no. gb AE000433) from base pair (bp) position 8596 to 10144 is amplified by PCR using chromosomal *E. coli* DNA as template. The reaction mixture contains 10 pmol of the primer 5'-CCGTCGGAAT-TCGAGGAGAAATTAACCATGTATATCGG-GATAGATCTTGG-3' (SEQ ID NO:1), 10 pmol of the primer 5'-GCAGTGAAGCTTTTACGCCATTAATG-GCAGAAGTTGC-3' (SEQ ID NO:2), 20 ng of chromosomal DNA, 2 U of Taq DNA polymerase (Eurogentec, Seraing, Belgium) and 20 nmol of dNTPs in a total volume of 100 μl containing 1.5 mM $MgCl_2$, 50 mM KCl, 10 mM Tris-hydrochloride, pH 8.8 and 0.1% (w/w) Triton X-100.

The mixture is denaturated for 3 min at 94° C. Then 30 PCR cycles for 60 sec at 94° C., 60 sec at 50° C. and 75 sec at 72° C. followed. After further incubation for 10 min at 72° C., the mixture is cooled to 4° C. An aliquot of 2 μl is subjected to agarose gel electrophoresis.

The PCR amplificate is purified with the PCR purification kit from Qiagen (Hilden, Germany).

1.0 μg of the vector pBluescript SKII⁻ (Stratagene) and 0.5 μg of the purified PCR product are digested with EcoRI and HindIII in order to produce DNA fragments with overlapping ends. The restriction mixtures are prepared according to the conditions supplied by the customer (New England Biolabs, Frankfurt am Main, Germany (NEB)) and are incubated for 3 h at 37° C. Digested vector DNA and PCR product are purified using the PCR purification kit from Qiagen.

20 ng of the purified vector DNA and 20 ng of the purified PCR product are ligated together with 1 U of T4-Ligase (Gibco), 2 μl of T4-Ligase buffer (Gibco) in a total volume of 10 μl, yielding the plasmid pBSxylB. The ligation mixture is incubated for 2 h at 25° C. 1 μl of the ligation mixture is transformed into electrocompetent *E. coli* XL1-Blue cells according to a method described by Dower et al., 1988. The plasmid pBSxylB is isolated with the plasmid isolation kit from Qiagen.

The DNA insert of the plasmid pBSxylB is sequenced by the automated dideoxynucleotide method (Sanger et al., 1992) using an ABI Prism 377™ DNA sequencer from Perkin Elmer (Norwalk, USA) with the ABI Prism™ Sequencing Analysis Software from Applied Biosystems Divisions (Foster city, USA). It is identical with the DNA sequence of the database entry (gb AE000433).

EXAMPLE 2

Construction of a Vector Carrying the xylB and dxr Genes of *Escherichia coli* Capable for Transcription and Expression of D-xylulokinase and DXP Reductoisomerase The *E. coli* ORF dxr (accession no. gb AE000126) from base pair (bp) position 9887 to 11083 is amplified by PCR using chromosomal *E. coli* DNA as template. The reaction mixture contains 10 pmol of the primer 5'-CTAGC-CAAGCTTGAGGAGAAATTAACCATGAAG-CAACTCACCATTCTGG-3' (SEQ ID NO:3), 10 pmol of the primer 5'-GGAGATGTCGACTCAGCTTGC-GAGACGC-3' (SEQ ID NO:4), 20 ng of chromosomal DNA, 2 U of Taq DNA polymerase (Eurogentec) and 20 nmol of dNTPs in a total volume of 100 μl containing 1.5 mM $MgCl_2$, 50 mM KCl, 10 mM Tris-hydrochloride, pH 8.8 and 0.1% (w/w) Triton X-100.

The mixture is denaturated for 3 min at 94° C. Then 30 PCR cycles for 60 sec at 94° C., 60 sec at 50° C. and 75 sec at 72° C. followed. After further incubation for 10 min at 72° C., the mixture is cooled to 4° C. An aliquot of 2 μl is subjected to agarose gel electrophoresis.

The PCR amplificate is purified with the PCR purification kit from Qiagen (Hilden).

1.2 μg of the vector pBSxylB (Example 1) and 0.6 μg of the purified PCR product are digested with HindIII and SalI in order to produce DNA fragments with overlapping ends. The restriction mixtures are prepared according to the conditions supplied by the customer (NEB) and are incubated for 3 h at 37° C. Digested vector DNA and PCR product are purified using the PCR purification kit from Qiagen.

20 ng of the purified vector DNA and 18 ng of the purified PCR product are ligated together with 1 U of T4-Ligase (Gibco), 2 μl of T4-Ligase buffer (Gibco) in a total volume of 10 μl, yielding the plasmid pBSxylBdxr. The ligation mixture is incubated for 2 h at 25° C. 1 μl of the ligation mixture is transformed into electrocompetent *E. coli* XL1-Blue cells. The plasmid pBSxylBdxr is isolated with the plasmid isolation kit from Qiagen.

The DNA insert of the plasmid pBSxylBdxr is sequenced by the automated dideoxynucleotide method using an ABI Prism 377™ DNA sequencer from Perkin Elmer with the ABI Prism™ Sequencing Analysis Software from Applied Biosystems Divisions. It is identical with the DNA sequence of the database entry (gb AE000126).

The DNA sequence of the vector construct pBSxylBdxr is shown in FIG. 8.

EXAMPLE 3

Construction of a Vector Carrying the xylB, dxr and ispD Genes of *Escherichia coli* Capable for Transcription and Expression of D-xylulokinase, DXP Reductoisomerase and CDP-ME Synthase The *E. coli* ORF ispD (accession no. gb AE000358) from base pair (bp) position 6754 to 7464 is amplified by PCR using chromosomal *E. coli* DNA as template. The reaction mixture contains 10 pmol of the primer 5'-CCGGGAGTC-GACGAGGAGAAATTAACCATGGCAAC-CACTCATTTGGATG-3' (SEQ ID NO:5), 10 pmol of the primer 5'-GTCCAACTCGAGTTATGTATTCTCCT-TGATGG-3' (SEQ ID NO:6), 20 ng of chromosomal DNA, 2 U of Taq DNA polymerase (Eurogentec) and 20 nmol of dNTPs in a total volume of 100 μl containing 1.5 mM $MgCl_2$, 50 mM KCl, 10 mM Tris-hydrochloride, pH 8.8 and 0.1% (w/w) Triton X-100.

The mixture is denaturated for 3 min at 94° C. Then 30 PCR cycles for 30 sec at 94° C., 30 sec at 50° C. and 45 sec at 72° C. followed. After further incubation for 10 min at 72° C., the mixture is cooled to 4° C. An aliquot of 2 μl is subjected to agarose gel electrophoresis.

The PCR amplificate is purified with the PCR purification kit from Qiagen (Hilden).

1.5 μg of the vector pBSxylBdxr (Example 2) and 0.8 μg of the purified PCR product are digested with SalI and XhoI in order to produce DNA fragments with overlapping ends.

The restriction mixtures are prepared according to the conditions supplied by the customer (NEB) and are incubated for 3 h at 37° C. Digested vector DNA and PCR product are purified using the PCR purification kit from Qiagen.

20 ng of the purified vector DNA and 12 ng of the purified PCR product are ligated together with 1 U of T4-Ligase (Gibco), 2 µl of T4-Ligase buffer (Gibco) in a total volume of 10 µl, yielding the plasmid pBSxylBdxrispD. The ligation mixture is incubated for 2 h at 25° C. 1 µl of the ligation mixture is transformed into electrocompetent *E. coli* XL1-Blue cells. The plasmid pBSxylBdxrispD is isolated with the plasmid isolation kit from Qiagen.

The DNA insert of the plasmid pBSxylBdxrispD is sequenced by the automated dideoxynucleotide method using an ABI Prism 377™ DNA sequencer from Perkin Elmer with the ABI Prism™ Sequencing Analysis Software from Applied Biosystems Divisions. It is identical with the DNA sequence of the database entry (gb AE000126).

The DNA sequence of the vector construct pBSxylBdxrispD is shown in FIG. 9.

EXAMPLE 4

Construction of a Vector Carrying the xylB, dxr, ispD and ispF Genes of *Escherichia coli* Capable for Transcription and Expression of D-xylulokinase, DXP Reductoisomerase, CDP-ME Synthase, and cMEPP Synthase The *E. coli* ORF's ispD and ispF (accession no. gb AE000358) from base pair (bp) position 6275 to 7464 is amplified by PCR using chromosomal *E. coli* DNA as template. The reaction mixture contains 10 pmol of the primer 5'-CCGGGAGTCGACGAGGAGAAATTAAC-CATGGCAACCACTCATTTGGATG-3' (SEQ ID NO:7), 10 pmol of the primer 5'-TATCAACTCGAGTCATTTGT-TGCCTTAATGAG-3' (SEQ ID NO:8), 20 ng of chromosomal DNA, 2 U of Taq DNA polymerase (Eurogentec) and 20 nmol of dNTPs in a total volume of 100 µl containing 1.5 mM MgCl$_2$, 50 mM KCl, 10 mM Tris-hydrochloride, pH 8.8 and 0.1% (w/w) Triton X-100.

The mixture is denaturated for 3 min at 94° C. Then 30 PCR cycles for 60 sec at 94° C., 60 sec at 50° C. and 75 sec at 72° C. followed. After further incubation for 10 min at 72° C., the mixture is cooled to 4° C. An aliquot of 2 µl is subjected to agarose gel electrophoresis.

The PCR amplificate is purified with the PCR purification kit from Qiagen (Hilden).

1.4 µg of the vector pBSxylBdxr (Example 2) and 0.7 µl of the purified PCR product are digested with SalI and XhoI in order to produce DNA fragments with overlapping ends. The restriction mixtures are prepared according to the conditions supplied by the customer (NEB) and are incubated for 3 h at 37° C. Digested vector DNA and PCR product are purified using the PCR purification kit from Qiagen.

20 ng of the purified vector DNA and 18 ng of the purified PCR product are ligated together with 1 U of T4-Ligase (Gibco), 2 µl of T4-Ligase buffer (Gibco) in a total volume of 10 µl yielding the plasmid pBSxylBdxrispDF. The ligation mixture is incubated for 2 h at 25° C. 1 µl of the ligation mixture is transformed into electrocompetent *E. coli* XL1-Blue cells. The plasmid pBSxylBdxrispDF is isolated with the plasmid isolation kit from Qiagen.

The DNA insert of the plasmid pBSxylBdxrispDF is sequenced by the automated dideoxynucleotide method using an ABI Prism 377™ DNA sequencer from Perkin Elmer with the ABI Prism™ Sequencing Analysis Software from Applied Biosystems Divisions. It is identical with the DNA sequence of the database entry (gb AE000126).

EXAMPLE 5

Construction of a Vector Carrying the xylB, dxr, ispD, ispE and ispF Genes of *Escherichia coli* Capable for Transcription and Expression of D-xylulokinase, DXP Reductoisomerase, CDP-ME Synthase, CDP-ME Kinase and cMEPP Synthase The *E. coli* ORF ispE (accession no. gb AE000219) from base pair (bp) position 5720 to 6571 is amplified by PCR using chromosomal *E. coli* DNA as template. The reaction mixture contains 10 pmol of the primer 5'-GCGAACCTC-GAGGAGGAGAAATTAACCATGCGGACA-CAGTGGCCC-3' (SEQ ID NO:9), 10 pmol of the primer 5'-CCTGACGGTACCTTAAAGCATGGCTCTGTGC-3' (SEQ ID NO:10), 20 ng of chromosomal DNA, 2 U of Taq DNA polymerase (Eurogentec) and 20 nmol of dNTPs in a total volume of 100 µl containing 1.5 mM MgCl$_2$, 50 mM KCl, 10 mM Tris-hydrochloride, pH 8.8 and 0.1% (w/w) Triton X-100.

The mixture is denaturated for 3 min at 94° C. Then 30 PCR cycles for 45 sec at 94° C., 45 sec at 50° C. and 60 sec at 72° C. followed. After further incubation for 10 min at 72° C., the mixture is cooled to 4° C. An aliquot of 2 µl is subjected to agarose gel electrophoresis.

The PCR amplificate is purified with the PCR purification kit from Qiagen (Hilden).

1.2 µg of the vector pBSxylBdxrispDF (Example 4) and 0.6 µg of the purified PCR product are digested with XhoI and KpnI in order to produce DNA fragments with overlapping ends. The restriction mixtures are prepared according to the conditions supplied by the customer (NEB) and are incubated for 3 h at 37° C. Digested vector DNA and PCR product are purified using the PCR purification kit from Qiagen.

20 ng of the purified vector DNA and 15 ng of the purified PCR product are ligated together with 1 U of T4-Ligase (Gibco), 2 µl of T4-Ligase buffer (Gibco) in a total volume of 10 µl, yielding the plasmid pBScyclo. The ligation mixture is incubated for 2 h at 25° C. 1 µl of the ligation mixture is transformed into electrocompetent *E. coli* XL1-Blue cells. The plasmid pBScyclo is isolated with the plasmid isolation kit from Qiagen.

The DNA insert of the plasmid pBScyclo is sequenced by the automated dideoxynucleotide method using an ABI Prism 377™ DNA sequencer from Perkin Elmer with the ABI Prism™ Sequencing Analysis Software from Applied Biosystems Divisions. It is identical with the DNA sequence of the database entry (gb AE000219). The DNA sequence of the vector construct pBScyclo is shown in FIG. 10.

EXAMPLE 6

Construction of a Vector Carrying the gcpE Gene of *Escherichia coli* Capable for its Transcription and Expression The *E. coli* ORF gcpE (accession no. gb AE000338) from base pair (bp) position 372 to 1204 is amplified by PCR using chromosomal *E. coli* DNA as template. The reaction mixture contains 10 pmol of the primer 5'-CGTACCG-GATCCGAGGAGAAATTAACCATGCAT-AACCAGGCTCCAATTC-3' (SEQ ID NO:11), 10 pmol of the primer 5'-CCCATCGTCGACTTATTTTTCAACCT- GCTGAACGTC-3' (SEQ ID NO:12), 20 ng of chromosomal DNA, 2 U of Taq DNA polymerase (Eurogentec) and 20 nmol of dNTPs in a total volume of 100 µl containing 1.5 mM $MgCl_2$, 50 mM KCl, 10 mM Tris-hydrochloride, pH 8.8 and 0.1% (w/w) Triton X-100.

The mixture is denaturated for 3 min at 94° C. Then 30 PCR cycles for 60 sec at 94° C., 60 sec at 50° C. and 90 sec at 72° C. followed. After further incubation for 10 min at 72° C., the mixture is cooled to 4° C. An aliquot of 2 µl is subjected to agarose gel electrophoresis.

The PCR amplificate is purified with the PCR purification kit from Qiagen (Hilden).

2.0 µg of the vector pACYC184 (Chang and Cohen 1978, NEB) and 0.7 µg of the purified PCR product are digested with BamHI and SalI in order to produce DNA fragments with overlapping ends. The restriction mixtures are prepared according to the conditions supplied by the customer (NEB) and are incubated for 3 h at 37° C. Digested vector DNA and PCR product are purified using the PCR purification kit from Qiagen.

20 ng of the purified vector DNA and 20 ng of the purified PCR product are ligated together with 1 U of T4-Ligase (Gibco), 2 µl of T4-Ligase buffer (Gibco) in a total volume of 10 µl, yielding the plasmid pACYCgcpE. The ligation mixture is incubated for 2 h at 25° C. 1 µl of the ligation mixture is transformed into electrocompetent E. coli XL1-Blue cells. The plasmid pACYCgcpE is isolated with the plasmid isolation kit from Qiagen.

The DNA insert of the plasmid pACYCgcpE is sequenced by the automated dideoxynucleotide method using an ABI Prism 377™ DNA sequencer from Perkin Elmer with the ABI Prism™ Sequencing Analysis Software from Applied Biosystems Divisions. It is identical with the DNA sequence of the database entry (gb AE000338).

The DNA sequence of the vector construct pACYCgcpE is shown in FIG. 11.

EXAMPLE 7

Construction of Vectors Carrying a Carotenoid Operon from *Erwinia uredovora* Capable for the In Vivo Production of β-carotene The open reading frames crtY, crtI and crtB of a carotenoid operon from *Erwinia uredovora* (accession no. gb D90087) from base pair (bp) position 2372 to 6005 is amplified by PCR using chromosomal *E. uredovora* DNA as template. The reaction mixture contains 10 pmol of the primer 5'-CATTGAGAAGCTTATGTGCACCG-3' (SEQ ID NO:13), 10 pmol of the primer 5'-CTCCGGGGTCGA-CATGGCGC-3' (SEQ ID NO:14), 40 ng of chromosomal DNA of *E. uredovora*, 8 U of Taq DNA polymerase (Eurogentec), 20 nmol of dNTPs, Taq Extender (Stratagene) in a total volume of 100 µl 1×Taq Extender buffer (Stratagene).

The mixture is denaturated for 3 min at 94° C. Then 40 PCR cycles for 60 sec at 94° C., 60 sec at 50° C. and 300 sec at 72° C. followed. After further incubation for 20 min at 72° C., the mixture is cooled to 4° C. An aliquot of 2 µl is subjected to agarose gel electrophoresis.

The PCR amplificate is purified with the PCR purification kit from Qiagen (Hilden, Germany).

1.0 µg of the vector pBluescript SKII⁻ (Stratagene) and 2.0 µg of the purified PCR product are digested with HindIII and SalI in order to produce DNA fragments with overlapping ends. The restriction mixtures are prepared according to the conditions supplied by the customer (NEB) and are incubated for 3 h at 37° C. Digested vector DNA and PCR product are purified using the PCR purification kit from Qiagen.

20 ng of the purified vector DNA and 40 ng of the purified PCR product are ligated together with 1 U of T4-Ligase (Gibco), 2 µl of T4-Ligase buffer (Gibco) in a total volume of 10 µl, yielding the plasmid pBScaro34. The ligation mixture is incubated for 2 h at 25° C. 1 µl of the ligation mixture is transformed into electrocompetent E. coli XL1-Blue cells. The plasmid pBScaro34 is isolated with the plasmid isolation kit from Qiagen.

The DNA insert of the plasmid pBScaro34 is sequenced by the automated dideoxynucleotide method using an ABI Prism 377™ DNA sequencer from Perkin Elmer with the ABI Prism™ Sequencing Analysis Software from Applied Biosystems Divisions. It is identical with the DNA sequence of the database entry (gb D90087).

The *E. uredovora* ORF crtE (accession no. gb D90087) from base pair (bp) position 175 to 1148 is amplified by PCR using chromosomal *E. coli* DNA as template. The reaction mixture contains 10 pmol of the primer 5'-CCG-CATCTTTCCAATTGCCG-3' (SEQ ID NO:15), 10 pmol of the primer 5'-ATGCAGCAAGCTTAACTGACGGC-3' (SEQ ID NO:16), 20 ng of chromosomal DNA, 2 U of Taq DNA polymerase (Eurogentec, Seraing, Belgium) and 20 nmol of dNTPs in a total volume of 100 µl containing 1.5 mM $MgCl_2$, 50 mM KCl, 10 mM Tris-hydrochloride, pH 8.8 and 0.1% (w/w) Triton X-100.

The mixture is denaturated for 3 min at 94° C. Then 30 PCR cycles for 45 sec at 94° C., 45 sec at 50° C. and 60 sec at 72° C. followed. After further incubation for 10 min at 72° C., the mixture is cooled to 4° C. An aliquot of 2 µl is subjected to agarose gel electrophoresis. The PCR amplificate is purified with the PCR purification kit from Qiagen (Hilden, Germany).

1.5 µg of the vector pBScaro34 (see above) is digested with EcoRI and HindIII and 0.6 µg of the purified PCR product are digested with MfeI and HindIII in order to produce DNA fragments with overlapping ends. The restriction mixtures are prepared according to the conditions supplied by the customer (NEB) and are incubated for 3 h at 37° C. Digested vector DNA and PCR product are purified using the PCR purification kit from Qiagen.

20 ng of the purified vector DNA and 16 ng of the purified PCR product are ligated together with 1 U of T4-Ligase (Gibco), 2 µl of T4-Ligase buffer (Gibco) in a total volume of 10 µl, yielding the plasmid pBScaro14. The ligation mixture is incubated for 2 h at 25° C. 1 µl of the ligation mixture is transformed into electrocompetent E. coli XL1-Blue cells. The plasmid pBScaro14 is isolated with the plasmid isolation kit from Qiagen.

The DNA insert of the plasmid pBScaro14 is sequenced by the automated dideoxynucleotide method using an ABI Prism 377™ DNA sequencer from Perkin Elmer with the ABI Prism™ Sequencing Analysis Software from Applied Biosystems Divisions. It is identical with the DNA sequence of the database entry (gb D90087). The DNA sequence of the plasmid pBScaro14 is shown in FIG. 12.

5 µg of the vector pBScaro14 (see above) is digested with BamHI and SalI. The restriction mixture is prepared according to the conditions supplied by the customer (NEB) and are incubated for 3 h at 37° C. The restriction mixture is separated on a agarose gel and the fragments of 2237 and 2341 bp size are purified with the gel extraction kit from Qiagen.

3 µg of the vector pACYC184 (see above) is digested with BamHI and SalI. The restriction mixture is prepared according to the conditions supplied by the customer (NEB) and are incubated for 3 h at 37° C. The restriction mixture is separated on a agarose gel and the fragment of 3968 bp size is purified with the gel extraction kit from Qiagen.

30 ng of the purified vector DNA and each 25 ng of the purified 2237 and 2341 bp fragments are ligated together with 1 U of T4-Ligase (Gibco), 2 µl of T4-Ligase buffer (Gibco) in a total volume of 10 µl, yielding the plasmid pACYCcaro14. The ligation mixture is incubated for 2 h at 25° C. 1 µl of the ligation mixture is transformed into electrocompetent E. coli XL1-Blue cells. The plasmid pACYCcaro14 is isolated with the plasmid isolation kit from Qiagen.

The DNA insert of the plasmid pACYCcaro14 is sequenced by the automated dideoxynucleotide method using an ABI Prism 377™ DNA sequencer from Perkin Elmer with the ABI Prism™ Sequencing Analysis Software from Applied Biosystems Divisions. It is identical with the DNA sequence of the database entry (gb D90087). The DNA sequence of the plasmid pACYCcaro14 is shown in FIG. 13.

EXAMPLE 8

Enzymatic Preparation of [U—$^{13}C_5$]1-deoxy-D-xylulose 5-phosphate

A reaction mixture containing 960 mg of [U—$^{13}C_6$] glucose (5.1 mmol), 6.1 g of ATP (10.2 mmol), 337 mg of thiamine pyrophosphate, 1.14 g of [2,3-$^{13}C_2$]pyruvate (10.2 mmol), 10 mM MgCl$_2$, 5 mM dithiothreitol in 150 mM Tris hydrochloride, pH 8.0 is prepared. 410 Units of triose phosphate isomerase (from rabbit muscle, Type III-S, E. C. 5.3.1.1., Sigma), 100 U hexokinase (from Bakers Yeast, Type VI, E. C. 2.7.1.1, Sigma), 100 U phosphoglucose isomerase (from Bakers Yeast, Type III, E. C. 5.3.1.9, Sigma), 100 U phosphofructokinase (from Bacillus stearothermophilus, Type VII, E. C. 2.7.1.11, Sigma), 50 U aldolase (from rabbit muscle, E. C. 4.1.2.13, Sigma) and 12 U of recombinant DXP synthase from B. subtilis are added to a final volume of 315 ml. The reaction mixture is incubated at 37° C. overnight and during incubation the pH is hold at a constant value of 8.0. The reaction is monitored by $^{13}$C NMR spectroscopy.

EXAMPLE 9

Enzymatic Preparation of [3,4,5-$^{13}C_3$]1-deoxy-D-xylulose 5-phosphate

A solution containing 150 mM Tris hydrochloride, 10 mM MgCl$_2$, 1.0 g of [U—$^{13}C_6$]glucose (5.4 mmol), 0.23 g (1.5 mmol) of dithiothreitol, 0.3 g (0.7 mmol) of thiamine pyrophosphate, 0.1 g (0.2 mmol) of ATP (disodium salt), and 2.2 g (11 mmol) of phosphoenol pyruvate (potassium salt) is adjusted to pH 8.0 by the addition of 8 M sodium hydroxide. 403 U (2.8 mg) of pyruvate kinase (from rabbit muscle, E. C. 2.7.1.40), 410 Units of triose phosphate isomerase (from rabbit muscle, Type III-S, E. C. 5.3.1.1., Sigma), 100 U hexokinase (from Bakers Yeast, Type VI, E. C. 2.7.1.1, Sigma), 100 U phosphoglucose isomerase (from Bakers Yeast, Type III, E. C. 5.3.1.9, Sigma), 100 U phosphofructokinase (from Bacillus stearothermophilus, Type VII, E. C. 2.7.1.11, Sigma), 50 U aldolase (from rabbit muscle, E. C. 4.1.2.13, Sigma) and 12 U recombinant DXP synthase from B. subtilis are added to a final volume of 300 ml. The reaction mixture is incubated at 37° C. for overnight.

EXAMPLE 10

Enzymatic Preparation of 1-deoxy-D-xylulose

The pH value of the reaction mixture obtained in example 8 or 9 is adjusted to 9.5. Magnesium chloride is added to a concentration of 30 mM. 50 mg (950 Units) of alkaline phosphatase from bovine intestinal mucosa (Sigma, E. C. 3.1.3.1) are added and the reaction mixture is incubated for 16 h. The conversion is monitored by $^{13}$C-NMR spectroscopy. The pH is adjusted to a value of 7.0 and the solution is centrifuged at 14,000 upm for 5 minutes. Starting from labelled glucose (examples 8 or 9) the overall yield of 1-deoxy-D-xylulose is approximately 50%.

The supernatant or the lyophilised supernatant is used in incorporation experiments (see examples 11 to 17).

EXAMPLE 11

Incorporation Experiment with Recombinant Escherichia coli XL1-pBSxylB Using [3,4,5-$^{13}C_3$] 1-deoxy-D-xylulose 0.2 liter of Luria Bertani (LB) medium containing 36 mg of ampicillin are inoculated with 10 ml of an overnight culture of E. coli strain XL1-Blue harbouring the plasmid pBSxylB (see example 1). The cells are grown in a shaking culture at 37° C. At an optical density (600 nm) of 0.6 the culture is induced with 2 mM IPTG. Two hours after induction with IPTG, 50 ml (0.9 mmol) of crude [3,4,5-$^{13}C_3$]1-deoxy-D-xylulose (pH 7.0) (see examples 9 and 10), are added. Aliquots of 25 ml are taken at time intervals of 30 minutes and centrifuged for 20 min at 5,000 rpm and 4° C. The cells are washed with water containing 0.9% NaCl and centrifuged as described above. The cells are suspended in 700 µl of 20 mM NaF in D$_2$O, cooled on ice and sonified 3×10 sec with a Branson Sonifier 250 (Branson SONIC Power Company) set to 90% duty cycle output, control value of 4. The suspension is centrifuged at 15,000 rpm for 15 min. $^{13}$C NMR spectra of the supernatant are recorded directly, without further purification, with a Bruker AVANCE DRX 500 spectrometer (Karlsruhe, Germany). The NMR analysis is based on published signal assignments (Wungsintaweekul et al., 2001).

30 min after the addition of [3,4,5-$^{13}C_3$]1-deoxy-D-xylulose, the formation of [3,4,5-$^{13}C_3$]1-deoxy-D-xylulose 5-phosphate can be observed. The maximum yield of [3,4, 5-$^{13}C_3$]1-deoxy-D-xylulose 5-phosphate is observed 3–5 h after addition of [3,4,5-$^{13}C_3$]1-deoxy-D-xylulose to the medium. The $^{13}$C NMR signals reveal a mixture of [3,4,5-$^{13}C_3$]1-deoxy-D-xylulose and [3,4,5-$^{13}C_3$]1-deoxy-D-xylulose-5-phosphate at a molar ratio of approximately 1:9. The intracellular concentration of [3,4,5-$^{13}C_3$]1-deoxy-D-xylulose 5-phosphate is estimated as 20 mM by quantitative NMR spectroscopy.

EXAMPLE 12

Incorporation Experiment with Recombinant Escherichia coli XL1-pBSxylBdxr Using [U-$^{13}C_5$]1-deoxy-D-xylulose 0.12 liter of Luria Bertani (LB) medium containing 22 mg of ampicillin are inoculated with 10 ml of an overnight culture of E. coli strain XL1-Blue harbouring plasmid pBSxylBdxr (see example 2). The cells are grown in a shaking culture at 37° C. At an optical density (600 nm) of 0.6 the culture is induced with 2 mM IPTG. Two hours after induction with IPTG, ca. 1.0 mmol of crude [U—$^{13}C_5$]1-deoxy-D-xylulose (pH 7.0) (see examples 8 and 10) are added. Aliquots of 25 ml are taken in time intervals of 1 h and centrifuged for 20 min at 5,000 rpm and 4° C. The cells are washed with water containing 0.9% NaCl and centrifuged as described above. The cells are suspended in 700 µl of 20 mM NaF in $D_2O$, cooled on ice and sonified 3×10 sec with a Branson Sonifier 250 (Branson SONIC Power Company) set to 90% duty cycle output, control value of 4. The suspension is centrifuged at 15,000 rpm for 15 min. NMR spectra of the supernatant are recorded directly, without further purification, with a Bruker AVANCE DRX 500 spectrometer (Karlsruhe, Germany).

HMQC and HMQC-TOCSY experiments reveal $^1H$—$^{13}C$ and $^1H$—$^1H$ spin systems (Table 1) of [U—$^{13}C_5$]2C-methyl-D-erythritol 4-phosphate, [U—$^{13}C_5$]2C-methyl-D-erythritol and [1,2,2',3,4-$^{13}C_5$]4-diphosphocytidyl-2C-methyl-D-erythritol at a molar ratio of approximately 6.6:7:1, respectively. The intracellular concentration of [U—$^{13}C_5$]2C-methyl-D-erythritol 4-phosphate is estimated as 10 mM by quantitative NMR spectroscopy.

The NMR data summarized in Table 1 are identical with published NMR data of the authentic compounds (Takahashi et al., 1998; Rohdich et al., 1999).

TABLE 1

NMR data of $^{13}C$-labeled products in cell extracts of
E. coli XL1-pBSxylBdxr after feeding of
[U-$^{13}C_5$]1-deoxy-D-xylulose Chemical shifts, ppm

| Position | 1 | 1* | 2 | 2-Methyl | 3 | 4 | 4* |
|---|---|---|---|---|---|---|---|
| [U-$^{13}C_5$]2C-methyl-D-erythritol 4-phosphate | | | | | | | |
| $^{13}C$ | 66.1 | n.d. | 18.1 | | 73.4 | 648 | |
| $^1H$ | 3.25 | 3.36 | | 0.93 | 3.56 | 3.62 | 3.81 |
| [U-$^{13}C_5$]2C-methyl-D-erythritol | | | | | | | |
| $^{13}C$ | 66.6 | n.d. | 18.0 | | 74.6 | 616 | |
| $^1H$ | 3.26 | 3.34 | | 0.9 | 3.44 | 3.36 | 3.61 |
| [1,2,2',3,4-$^{13}C_5$]4-diphosphocytidyl-2C-methyl-D-erythritol | | | | | | | |
| $^{13}C$ | 66.8 | n.d. | 18.0 | | 73.0 | 667 | |
| $^1H$ | 3.4 | 3.55 | | 0.9 | 3.6 | 3.74 | 4 |

EXAMPLE 13

Incorporation Experiment with Recombinant
Escherichia coli XL1-pBSxylBdxrispDF Using
[3,4,5-$^{13}C_3$]1-deoxy-D-xylulose 0.1 liter of Luria Bertani (LB) medium containing 18 mg of ampicillin are inoculated with 10 ml of an overnight culture of E. coli strain XL1-Blue harbouring the plasmid pBSxylBdxrispDF (see example 4). The cells are grown in a shaking culture at 37° C. At an optical density (600 nm) of 0.5, the culture is induced with 2 mM IPTG. Two hours after induction with IPTG, ca. 1.0 mmol of crude [3,4,5-$^{13}C_3$]1-deoxy-D-xylulose (see examples 9 and 10) are added. After three hours, cells were harvested and centrifuged for 20 min at 5,000 rpm and 4° C. The cells are washed with water containing 0.9% NaCl and centrifuged as described above. The cells are suspended in 1.5 ml of 20 mM NaF in $D_2O$, cooled on ice and sonified 3×15 sec. with a Branson Sonifier 250 (Branson SONIC Power Company) set to 90% duty cycle output, control value of 4. The suspension is centrifuged at 15,000 rpm for 15 min. NMR spectra of the supernatant are recorded directly, without further purification, with a Bruker AVANCE DRX 500 spectrometer (Karlsruhe, Germany).

HMQC and HMQC-TOCSY experiments reveal $^1H$—$^{13}C$ and $^1H$—$^1H$ spin systems of [1,3,4-$^{13}C_3$]2C-methyl-D-erythritol 4-phosphate, [1,3,4-$^{13}C_3$]2C-methyl-D-erythritol and [1,3,4-$^{13}C_5$]4-diphosphocytidyl-2C-methyl-D-erythritol (Table 1). The molar ratios of [1,3,4-$^{13}C_3$]2C-methyl-D-erythritol 4-phosphate, [1,3,4-$^{13}C_3$]2C-methyl-D-erythritol and [1,3,4-$^{13}C_5$]4-diphosphocytidyl-2C-methyl-D-erythritol are 1:0.6:0.9, respectively.

This result indicates that the intracellular amount of CTP required for the synthesis of 4-diphosphocytidyl-2C-methyl-D-erythritol is limiting. Therefore, a modified fermentation protocol was developed (see example 14).

EXAMPLE 14

Incorporation Experiment with Recombinant
Escherichia coli XL1-pBSxylBdxrispDF Using
[3,4,5-$^{13}C_3$]1-deoxy-D-xylulose 0.1 liter of Luria Bertani (LB) medium containing 18 mg of ampicillin are inoculated with 10 ml of an overnight culture of E. coli strain XL1-Blue harbouring plasmid pBSxylBispDF (see example 4). The cells are grown in a shaking culture at 37° C. At an optical density (600 nm) of 0.5, the culture is induced with 2 mM IPTG. Two hours after induction with IPTG, 10 mg (0.041 mmol) of cytidine and 5 ml of 1 M $NaKHPO_4$, pH 7.2, and ca. 1 mmol of crude [3,4,5-$^{13}C_3$]1-deoxy-D-xylulose (see examples 9 and 10) are added. After three hours, the cells are harvested and centrifuged for 20 min at 5,000 rpm and 4° C. The cells are washed with water containing 0.9% NaCl and centrifuged as described above. The cells are suspended in 700 µl of 20 mM NaF in $D_2O$, cooled on ice and sonified 3×10 sec with a Branson Sonifier 250 (Branson SONIC Power Company) set to 90% duty cycle output, control value of 4. The suspension is centrifuged at 15,000 rpm for 15 min. NMR spectra of the supernatant are recorded directly, without further purification, with a Bruker AVANCE DRX 500 spectrometer. HMQC and HMQC-TOCSY experiments reveal $^1H$—$^{13}C$ and $^1H$—$^1H$ spin systems (Table 1) of [1,3,4-$^{13}C_3$]2C-methyl-D-erythritol 4-phosphate, [1,3,4-$^{13}C_3$]2C-methyl-D-erythritol and [1,3,4-$^{13}C_3$]4-diphosphocytidyl-2C-methyl-D-erythritol at a molar ratio of approximately 1:3.4:4.2, respectively. The relative amount of [1,3,4-$^{13}C_3$]4-diphosphocytidyl-2C-methyl-D-erythritol is increased by a factor of 2 as compared to the relative amount in example 13. The intracellular concentration of [1,3,4-$^{13}C_3$]4-diphosphocytidyl-2C-methyl-D-erythritol is estimated as 10 mM by quantitative NMR spectroscopy. The relative high amount of 2C-methyl-D-erythritol indicates that unspecific phosphatases convert intermediary formed 2C-methyl-D-erythritol 4-phosphate into 2C-methyl-D-erythritol. Therefore, a modified fermentation protocol was developed to supply the cells with sufficient amounts of organic phosphates and in order to suppress the activity of phosphatases (see examples 15 to 17).

EXAMPLE 15

Incorporation Experiment with Recombinant
Escherichia coli XL1-pBScyclo Using [U—$^{13}C_5$]1-deoxy-D-xylulose 0.2 liter of Luria Bertani (LB) medium containing 36 mg of ampicillin are inoculated with 10 ml of an overnight culture of E. coli strain XL1-Blue harbouring the plasmid pBScyclo (see example 5). The cells are grown in a shaking culture at 37° C. At an optical density (600 nm) of 1.3, the culture is induced with 2 mM IPTG. Two hours after induction with IPTG, 30 mg (0.12 mmol) of cytidine, 300 mg (0.95 mmol) of DL-α-glycerol 3-phosphate and 10 ml of 1 M NaKHPO$_4$, pH 7.2, are added. After 30 min, ca. 1 mmol of [U—$^{13}$C$_5$]1-deoxy-D-xylulose (see example 8 and 10) are added. Aliquots of 25 ml are taken at time intervals of 1 h and centrifuged for 20 min at 5,000 rpm and 4° C. The cells are washed with water containing 0.9% NaCl and centrifuged as described above. The cells are suspended in 700 μl of 20 mM NaF in D$_2$O, cooled on ice and sonified 3×10 sec with a Branson Sonifier 250 (Branson SONIC Power Company) set to 90% duty cycle output, control value of 4. The suspension is centrifuged at 15,000 rpm for 15 min. NMR spectra of the cell free extract are recorded directly, without further purification, with a Bruker AVANCE DRX 500 spectrometer (Karlsruhe, Germany). $^{13}$C NMR spectra, as well as HMQC and HMQC-TOCSY spectra established [U—$^{13}$C$_5$]2C-methyl-D-erythritol 2,4-cyclodiphosphate (Herz et al., 2000) as the only product. Formation of [U—$^{13}$C$_5$]2C-methyl-D-erythritol 2,4-cyclodiphosphate can be observed 30 min after addition of [U—$^{13}$C$_5$]1-deoxy-D-xylulose, whereas the maximum yield is observed 5 h after addition of [U—$^{13}$C$_5$]1-deoxy-D-xylulose. The intracellular concentration of [U—$^{13}$C$_5$]2C-methyl-D-erythritol 2,4-cyclodiphosphate is estimated as 20 mM by quantitative NMR spectroscopy. The formation of any other isotope-labelled products, such as [U—$^{13}$C$_5$]2C-methyl-erythritol is completely suppressed.

EXAMPLE 16

Incorporation Experiment with Recombinant *Escherichia coli* XL1-pBScyclo-pACYCgcpE Using [2-$^{14}$C]- and [U-13C$_5$]1-deoxy-D-xylulose 0.2 liter of Terrific Broth (TB) medium containing 36 mg of ampicillin and 2.5 mg of chloramphenicol are inoculated with the *E. coli* strain XL1-Blue harbouring the plasmids pBScyclo and pACYCgcpE (see example 5 to 6). The cells are grown in a shaking culture at 37° C. overnight. At an optical density (600 nm) of 4.8 to 5.0, 30 mg (0.1 mmol) of cytidine, 300 mg (0.94 mmol) of DL-α-glycerol 3-phosphate and 10 ml of 1 M NaKHPO$_4$, pH 7.2, are added. After 30 minutes, a mixture of 2.6 μmol [2-$^{14}$C]1-deoxy-D-xylulose (15 μCi μmol$^{-1}$) (Wungsintaweekul et al., 2001) and 1 ml of crude [U—$^{13}$C$_5$]1-deoxy-D-xylulose (0.02 mmol) (see examples 8 and 10) are added. After 1.5 h, cells are harvested and centrifuged for 10 min at 5,000 rpm and 4° C. The cells are washed with water containing 0.9% NaCl and centrifuged as described above. The cells are suspended in a mixture of 20 mM NaF (2 ml) and methanol (2 ml), cooled on ice and sonified 3×15 sec with a Branson Sonifier 250 (Branson SONIC Power Company) set to 90% duty cycle output, control value of 4. The suspension is centrifuged at 15,000 rpm for 15 min. The radioactivity of the supernatant is measured by scintillation counting (Beckmann, LS 7800). 10% of the radioactivity initially added as $^{14}$C labelled 1-deoxy-D-xylulose is detected in the supernatant. Aliquots are analysed by TLC and HPLC, as described in example 19, and the products are purified as described in example 20.

On basis of these data, 1-hydroxy-2-methyl-2-butenyl 4-diphosphate and 2-C-methyl-D-erythritol 2,4-cyclodiphosphate were identified as products at a molar ratio of 7:3 (see also examples 17 and 18).

EXAMPLE 17

Incorporation Experiment with Recombinant *Escherichia coli* XL1-pBScyclo-pACYCgcpE Using [U—$^{13}$C$_5$]- or [3,4,5-$^{13}$C$_3$]1-deoxy-D-xylulose 0.2 liter of Terrific Broth (TB) medium containing 36 mg of ampicillin and 2.5 mg of chloramphenicol are inoculated with the *E. coli* strain XL1-Blue harbouring the plasmids pBScyclo and pACYCgcpE. The cells are grown in a shaking culture at 37° C. for overnight. At an optical density (600 nm) of 4.8–5.0, 30 mg (0.1 mmol) of cytidine, 300 mg (0.93 mmol) of DL-α-glycerol 3-phosphate and 10 ml of 1 M NaKHPO$_4$, pH 7.2, are added. After 30 minutes, 3 ml of crude [3,4,5-$^{13}$C$_3$]- or [U—$^{13}$C$_5$]1-deoxy-D-xylulose (0.05 mmol) (see examples 8, 9, and 10) are added. Aliquots of 25 ml are taken at time intervals of 1 h and centrifuged for 20 min at 5,000 rpm and 4° C. The cells are washed with water containing 0.9% NaCl and centrifuged as described above. The cells are suspended in 700 μl of 20 mM NaF in D$_2$O or in 700 μl of a mixture of methanol and D$_2$O (6:4; v/v) containing 10 mM NaF, cooled on ice and sonified 3×10 sec with a Branson Sonifier 250 (Branson SONIC Power Company) set to 90% duty cycle output, control value of 4 output. The suspension is centrifuged at 15,000 rpm for 15 min. NMR spectra of the cell free extracts are recorded directly with a Bruker AVANCE DRX 500 spectrometer (Karlsruhe, Germany). In order to avoid degradation during work-up, the structures of the products are determined by NMR spectroscopy without further purification (see example 18).

EXAMPLE 18

Structure Determination of 1-hydroxy-2-methyl-2-butenyl 4-diphosphate

The $^1$H-decoupled $^{13}$C NMR spectrum using [U—$^{13}$C$_5$] 1-deoxy-D-xylulose as starting material displays 5 $^{13}$C—$^{13}$C coupled signals belonging to 2C-methyl-D-erythritol 2,4-cyclodiphosphate (Herz et al., 2000) and 5 $^{13}$C—$^{13}$C coupled signals at 14.7, 64.5, 68.6, 122.7 and 139.5 ppm (Table 2) belonging to an unknown metabolite. The chemical shifts of the unknown metabolite suggest a double bond motif (signals at 122.7 and 139.5 ppm), a methyl group (signal at 14.7 ppm), and two carbon atoms (signals at 64.5 and 68.6 ppm) connected to OR (R=unknown). The three signals accounting for carbon atoms with sp$^3$ hybridisation (14.7, 64.5 and 68.5 ppm) show $^{13}$C—$^{13}$C coupling to one adjacent $^{13}$C atom with coupling constants of 40–50 Hz (Table 2). The signal at 122.7 ppm shows $^{13}$C couplings to two adjacent $^{13}$C neighbours (coupling constants, 74 and 50 Hz), whereas the signal at 141.5 ppm shows $^{13}$C couplings to three neighboured $^{13}$C atoms (coupling constants, 74, 43 and 43 Hz). In conjunction with the chemical shift topology, this coupling signature is indicative for a 2-methyl-2-butenyl skeleton.

HMQC and HMQC-TOCSY experiments reveal the $^1$H NMR chemical shifts (Table 2), as well as $^{13}$C—$^1$H and $^1$H—$^1$H spin systems (Table 3). More specifically, the $^{13}$C NMR signal at 122.7 ppm correlates to a $^1$H NMR signal at 5.6 ppm which is in the typical chemical shift range for H-atoms attached to CC double bonds, whereas the signal at 139.5 ppm gives no $^{13}$C—$^1$H correlations. The signals at 64.5 and 68.6 ppm give $^{13}$C—$^1$H correlations to $^1$H-signals at 4.5 and 3.9 ppm, respectively. The methyl signal at 14.7 ppm correlates to a proton signal at 1.5 ppm. In connection with $^{13}$C—$^{13}$C coupling patterns (Table 2), as well as with $^1$H—$^{13}$C long range correlations (HMBC experiment, Table 3), these data establish a 1,4-dihydroxy-2-methyl-2-butenyl system.

Starting from [3,4,5-$^{13}$C$_3$]1-deoxy-D-xylulose as feeding material three signals at 64.5, 68.6 and 122.7 ppm accounting for atoms 4, 1 and 3, respectively, of the new product are observed. It can be concluded that the carbon atoms at 1, 3 and 4 of the new product are biogenetically equivalent to the carbon atoms 3, 4 and 5 of [3,4,5-$^{13}$C$_3$]1-deoxy-D-xylulose 5-phosphate. This coupling topology is similar to the coupling pattern of 2C-methyl-D-erythritol 4-phosphate (see example 13) confirming that the new compound is derived via 2C-methyl-D-erythritol 4-phosphate.

The C-4 and C-3 $^{13}$C NMR signals at 64.5 and 122.7 ppm show $^{13}$C—$^{31}$P coupling of 5.5 and 8.0 Hz, respectively. These couplings indicate the presence of a phosphate or pyrophosphate group at position 4 of the 2-methyl-2-butenyl skeleton.

In line with this observation, the $^1$H-decoupled $^{31}$P NMR spectrum of the product displays a doublet at −9.2 ($^{31}$P—$^{31}$P coupling constant, 20.9 Hz) and a double-double-doublet at −10.6 ppm ($^{31}$P—$^{13}$C coupling constants, 5.8 and 7.4 Hz, $^{31}$P—$^{31}$P coupling constant, 20.9 Hz). Without $^1$H-decoupling, the $^{31}$P NMR signal at −10.6 ppm is broadened whereas the signal at −9.2 ppm is not affected by $^1$H coupling. The chemical shifts as well as the observed coupling pattern confirm the presence of a free diphosphate moiety at position 4.

In summary, all these data establish the structure as 1-hydroxy-2-methyl-2-butenyl 4-diphosphate.

TABLE 2

NMR data of 1-hydroxy-2-methyl-2-butenyl 4-diphosphate

| Position | Chemical shifts, ppm | | | Coupling constants, Hz | | |
|---|---|---|---|---|---|---|
| | 1H[a] | $^{13}$C[b] | $^{31}$P[c] | $J_{PC}$ | $J_{PP}$ | $J_{CC}$ |
| 1 | 3.91 | 68.6[d,e] | | | | 43.0[e], 5.5[d], 3.5[d] |
| 2 | | 139.5[d,e] | | | | 74.3[e], 43.3[e], 43.3[e] |
| 2-Methyl | 1.51 | 14.7[e] | | | | 42.2[e], 4.0[e], 4.0[e] |
| 3 | 5.57 | 122.7[e] | | 8.0[d] | | 73.9[e], 49.8[d], 4.0[d] |
| 4 | 4.46 | 64.5[d,e] | | 5.5[d] | | 49.3[d], 5.5[d] |
| P$_b$ | | | −9.2 | | 20.9 | |
| P$_a$ | | | −10.6 | 5.8[d], 7.4[d] | 20.9 | |

[a]referenced to external trimethylsilylpropane sulfonate.
[b]referenced to external trimethylsilylpropane sulfonate.
[c]referenced to external 85% orthophosphoric acid.
[d]observed with [1,3,4-$^{13}$C$_3$]1-hydroxy-2-methyl-2-butenyl 4-diphosphate
[e]observed with [U-$^{13}$C$_5$]1-hydroxy-2-methyl-2-butenyl 4-diphosphate

TABLE 3

Correlation pattern of [1,3,4-$^{13}$C$_3$]1-hydroxy-2-methyl-2-butenyl 4-diphosphate and of [U-$^{13}$C$_5$]1-hydroxy-2-methyl-2-butenyl 4-diphosphate
NMR Correlation pattern

| Position | HMQC | HMQC-TOCSY | HMBC |
|---|---|---|---|
| 1 | 1[a,b] | 1[a,b] | 2-methyl[a], 2[a] |
| 2 | | | |
| 2-methyl | 2-methyl[b] | 2-methyl[b] | |
| 3 | 3[a,b] | 3[a,b], 4[a,b] | 2-methyl[a], 1[a] |
| 4 | 4[a,b] | 4[a,b], 3[a,b] | |

[a]observed with [1,3,4-$^{13}$C$_3$]1-hydroxy-2-methyl-2-butenyl 4-diphosphate
[b]observed with [U-$^{13}$C$_5$]1-hydroxy-2-methyl-2-butenyl 4-diphosphate

EXAMPLE 19

Detection of Phosphorylated Metabolites of the Mevalonate-Independent Pathway

Method A) By a TLC Method

Aliquots (10 μl) of the cell-free extracts from recombinant cells prepared as described above (see example 16) are spotted on a Polygram® SIL NH—R thin layer plate (Macherey-Nagel, Düren, Germany). The TLC plate is then developed in a solvent system of n-propanol: ethyl acetate: water; 6:1:3 (v/v/v). The running time is about 4 h. The radio chromatogram is monitored and evaluated by a Phosphor Imager (Storm 860, Molecular Dynamics, USA). The R$_f$-values of the compounds under study are shown in Table 4.

TABLE 4

R$_f$-values of precursors and intermediates of the mevalonate-independent terpenoid pathway

| Chemical compound | R$_f$-value |
|---|---|
| 1-deoxy-D-xylulose | 0.80 |
| 1-deoxy-D-xylulose 5-phosphate | 0.5 |
| 2C-methyl-D-erythritol 4-phosphate | 0.42 |
| 4-diphosphocytidyl-2C-methyl-D-erythritol | 0.33 |
| 4-diphosphocytidyl-2C-methyl-D-erythritol 2-phosphate | 0.27 |
| 2C-methyl-D-erythritol 2,4-cyclodiphosphate | 0.47 |
| 1-hydroxy-2-methyl-2-butenyl 4-diphosphate | 0.17 |

Method B) By a HPLC Method

Aliquots (100 μl) of the cell-free extracts from recombinant cells prepared as described above (see example 16), are analyzed by HPLC using a column of Multospher 120 RP 18-AQ-5 (4.6×250 mm, particle size 5 μm, CS-Chromatographic Service GmbH, Langerwehe, Germany) that has been equilibrated for 15 min with 10 mM tetrabutylammonium hydrogensulfate (TBAS), pH 6.0, at a flow rate of 0.75 ml min$^{-1}$. After injection of the sample, the column is developed for 20 min with 10 mM TBAS, then for 60 min with a linear gradient of 0–42% (v/v) methanol in 10 mM TBAS. The effluent is monitored by a continuous-flow radio detector (Beta-RAM, Biostep GmbH, Jahnsdorf, Germany). The retention volumes of the compounds under study are shown in Table 5.

TABLE 5

Retention volumes of precursors and intermediates of the mevalonate-independent terpenoid pathway

| Chemical compound | Retention volume [ml] |
|---|---|
| 1-deoxy-D-xylulose | 6.0 |
| 1-deoxy-D-xylulose 5-phosphate | 15 |
| 2C-methyl-D-erythritol 4-phosphate | 13.5 |
| 4-diphosphocytidyl-2C-methyl-D-erythritol | 30.8 |
| 4-diphosphocytidyl-2C-methyl-D-erythritol 2-phosphate | 41.3 |
| 2C-methyl-D-erythritol 2,4-cyclodiphosphate | 31.5 |
| 1-hydroxy-2-methyl-2-butenyl 4-diphosphate | 42.8 |

EXAMPLE 20

Purification of 1-hydroxy-2-methyl-2-butenyl 4-diphosphate

The crude cell free extract obtained from the feeding experiment with recombinant *Escherichia coli* XL1-pBScyclo-pACYCgcpE using [2-$^{14}$C]- and [U—$^{13}$C$_5$]1-deoxy-D-xylulose (see example 16) is lyophilized. The residue is dissolved in 600 µl of water and centrifuged for 10 min at 14,000 ppm. Aliquots of 90 µl are applied on a column of Nucleosil 10 SB (4.6×250 mm, Macherey & Nagel, Düren, Germany) which is developed with a linear gradient of 0.1–0.25 M ammonium formate in 70 ml at a flow rate of 2 ml min$^{-1}$. The retention volumes for 2C-methyl-D-erythritol-2,4-cyclodiphosphate and 1-hydroxy-2-methyl-2-butenyl 4-diphosphate are 25 and 44 ml, respectively. Fractions are collected and lyophilized. NMR data of 1-hydroxy-2-methyl-2-butenyl 4-diphosphate are identical with the data shown in example 18, Table 2.

EXAMPLE 21

Construction of a Vector Carrying the xylB, dxr, ispD, ispE, ispF and ispG Genes of *Escherichia coli* Capable for Transcription and Expression of D-xylulokinase, DXP Reductoisomerase, CDP-ME Synthase, CDP-ME Kinase cMEPP Synthase and 1-hydroxy-2-methyl-2-butenyl 4-diphosphate Synthase The *E. coli* ORF ispG (accession no. gb AE000338) from base pair (bp) position 372 to 1204 is amplified by PCR using chromosomal *E. coli* DNA as template. The reaction mixture contains 10 pmol of the primer 5'-GCGGGAGAC-CGCGGGAGGAGAAATTAACCATGCAT-AACCAGGCTCCAATTCG-3' (SEQ ID NO:17), 10 pmol of the primer 5'-CGCTTCCCAGCGGCCGCT-TATTTTTCAACCTGCTGAACG-3' (SEQ ID NO:18), 20 ng of chromosomal DNA, 2 U of Taq DNA polymerase (Eurogentec) and 20 nmol of dNTPs in a total volume of 100 µl containing 1.5 mM MgCl$_2$, 50 mM KCl, 10 mM Tris-hydrochloride, pH 8.8 and 0.1% (w/w) Triton X-100.

The mixture is denaturated for 3 min at 94° C. Then 30 PCR cycles for 60 sec at 94° C., 60 sec at 50° C. and 90 sec at 72° C. followed. After further incubation for 10 min at 72° C., the mixture is cooled to 4° C. An aliquot of 2 µl is subjected to agarose gel electrophoresis. The PCR amplificate is purified with the PCR purification kit from Qiagen (Hilden).

1.4 µg of the vector pBScyclo (Example 5) and 0.8 µg of the purified PCR product are digested with SacII and NotI in order to produce DNA fragments with overlapping ends. The restriction mixtures are prepared according to the conditions supplied by the customer (NEB) and are incubated for 3 h at 37° C. Digested vector DNA and PCR product are purified using the PCR purification kit from Qiagen.

20 ng of the purified vector DNA and 18 ng of the purified PCR product are ligated together with 1 U of T4-Ligase (Gibco), 2 µl of T4-Ligase buffer (Gibco) in a total volume of 10 µl, yielding the plasmid pBScyclogcpE. The ligation mixture is incubated for 2 h at 25° C. 1 µl of the ligation mixture is transformed into electrocompetent *E. coli* XL1-Blue cells. The plasmid pBScyclogcpE is isolated with the plasmid isolation kit from Qiagen.

The DNA insert of the plasmid pBScyclogcpE is sequenced by the automated dideoxynucleotide method using an ABI Prism 377™ DNA sequencer from Perkin Elmer with the ABI Prism™ Sequencing Analysis Software from Applied Biosystems Divisions. It is identical with the DNA sequence of the database entry (gb AE000338). The DNA sequence of the vector construct pBScyclogcpE is shown in FIG. 15.

EXAMPLE 22

Construction of a Vector Carrying the xylB, dxr, ispD, ispE, ispF, ispG and lytB Genes of *Escherichia coli* Capable for Transcription and Expression of D-xylulokinase, DXP Reductoisomerase, CDP-ME Synthase, CDP-ME Kinase, cMEPP Synthase, 1-hydroxy-2-methyl-2-butenyl 4-diphosphate Synthase and LytB The *E. coli* ORF lytB (accession no. gb AE005179) from base pair (bp) position 7504 to 8454 is amplified by PCR using chromosomal *E. coli* DNA as template. The reaction mixture contains 10 pmol of the primer 5'-AAATCG-GAGCTCGAGGAGAAATTAACCATGCA-GATCCTGTTGGCC-3' (SEQ ID NO:19), 10 pmol of the primer 5'-GCTGCTCCGCGGTTAATCGACTTCAC-GAATATCG-3' (SEQ ID NO:20), 20 ng of chromosomal DNA, 2 U of Taq DNA polymerase (Eurogentec) and 20 nmol of dNTPs in a total volume of 100 µl containing 1.5 mM MgCl$_2$, 50 mM KCl, 10 mM Tris-hydrochloride, pH 8.8 and 0.1% (w/w) Triton X-100.

The mixture is denaturated for 3 min at 94° C. Then 30 PCR cycles for 45 sec at 94° C., 45 sec at 50° C. and 60 sec at 72° C. followed. After further incubation for 10 min at 72° C., the mixture is cooled to 4° C. An aliquot of 2 µl is subjected to agarose gel electrophoresis.

The PCR amplificate is purified with the PCR purification kit from Qiagen (Hilden).

1.3 µg of the vector pBScyclogcpE (Example 21) and 0.7 µg of the purified PCR product are digested with SacI and SacII in order to produce DNA fragments with overlapping ends. The restriction mixtures are prepared according to the conditions supplied by the customer (NEB) and are incubated for 3 h at 37° C. Digested vector DNA and PCR product are purified using the PCR purification kit from Qiagen.

20 ng of the purified vector DNA and 16 ng of the purified PCR product are ligated together with 1 U of T4-Ligase (Gibco), 2 µl of T4-Ligase buffer (Gibco) in a total volume of 10 µl, yielding the plasmid pBScyclogcpElytB. The ligation mixture is incubated for 2 h at 25° C. 1 µl of the ligation mixture is transformed into electrocompetent *E. coli* XL1-Blue cells. The plasmid pBScyclogcpElytB is isolated with the plasmid isolation kit from Qiagen.

The DNA insert of the plasmid pBScyclogcpElytB is sequenced by the automated dideoxynucleotide method using an ABI Prism 377™ DNA sequencer from Perkin Elmer with the ABI Prism™ Sequencing Analysis Software from Applied Biosystems Divisions. It is identical with the DNA sequence of the database entry (gb AE005179).

EXAMPLE 23

Incorporation Experiment with Recombinant *Escherichia coli* XL1-pBScyclogcpE Using [U—$^{13}$C$_5$]1-deoxy-D-xylulose 0.1 liter of Terrific Broth (TB) medium containing 18 mg of ampicillin are inoculated with *E. coli* strain Xl1-Blue harbouring the plasmid pBScyclogcpE. The cells are grown in a shaking culture at 37° C. overnight. At an optical density (600 nm) of 4.8–5.0, 30 mg (0.1 mmol) of cytidine are added. A solution containing 1.2 g of lithium lactate (12.5 mmol), 6 ml of crude [U—$^{13}$C$_5$]1-deoxy-D-xylulose (0.05 mmol) (see examples 8, 9 and 10) in 0.1 M Tris hydrochloride (pH=7.5) at a final volume of 30 ml are added continuously within 2 hours. Aliquots of 25 ml are taken at time intervals of 1 h and centrifuged for 20 min at 5,000 rpm and 4° C. The cells are washed with water containing 0.9% NaCl and centrifuged as described above. The cells are suspended in 700 μl of 20 mM NaF in $D_2O$ or in 700 μl of a mixture of methanol and $D_2O$ (6:4, v/v) containing 10 mM NaF, cooled on ice and sonified 3×10 sec with a Branson Sonifier 250 (Branson SONIC Power Company) set to 90% duty cycle output, control value of 4 output. The suspension is centrifuged at 15,000 rpm for 15 min. NMR spectra of the cell free extracts are recorded directly with a Bruker AVANCE DRX 500 spectrometer (Karlsruhe, Germany). In order to avoid degradation during work-up, the structures of the products are determined by NMR spectroscopy without further purification. The relative amount of 1-hydroxy-2-methyl-2-butenyl 4-diphosphate to 2C-methyl-D-erythritol 2,4-cyclodiphosphate could be raised by a factor of approximately 2–3 by the addition of lithium lactate to the medium.

EXAMPLE 24

Preparation of (E)-1-hydroxy-2-methyl-2-butenyl Diphosphate Triammonium Salt (8)

General. Chemicals are obtained from Acros Organics (Fisher Scientific GmbH, Schwerte, Germany), SIGMA-ALDRICH (Deisenhofen, Germany), MERCK (Darmstadt, Germany) and used without further purification. Solvents are used distilled and/or dried. Chromatography is performed on silica gel 60 (230–400 mesh, Fluka Riedel-de Haen, Taufkirchen, Germany), DOWEX 50 WX8 (200–400 mesh, SERVA, Heidelberg, Germany), and Cellulose (Avicel, Cellulose mikrokristallin, Merck, Darmstadt, Germany). TLC is performed on silica gel 60 $F_{254}$ plastic sheets (MERCK) or cellulose F plastic sheets (MERCK), detection by anisaldeyde solution (anisaldehyde:$H_2SO_4$:HAc 0.5:1:50 v/v/v). NMR-spectra are recorded on BRUKER AMX 400, DRX 500, and AC 250 spectrometer at room temperature.

Acetonyl Tetrahydropyranyl Ether (12) (Hagiwara et al., 1984)

A mixture of 339 mg (1.35 mmol) of pyridinium-toluene-4-sulfonate, 9.35 ml (10.0 g, 0.135 mol) of hydroxyacetone, and 24.7 ml (22.7 g, 0.270 mol) of 3,4-dihydro-2H-pyran is stirred at room temperature for 2.5 h. Residual 3,4-dihydro-2H-pyran is removed under reduced pressure. The crude mixture is purified by FC on silicagel (hexanes/acetone 4:1, 6.5×20 cm) to yield 18.7 g (0.118 mol, 88%) of a colorless liquid.
$^1$H NMR (CDCl$_3$, 500 MHz) δ 4.62 (t, J=3.6 Hz, 1H), 4.22 (d, J=17.3 Hz, 1H), 4.09 (d, J=17.3 Hz, 1H), 3.83–3.79 (m, 1H), 3.51–3.47 (m, 1H), 2.15 (s, 3H), 1.87–1.49 (m, 6H); $^{13}$C NMR (CDCl$_3$, 126 MHz) δ 206.7, 98.7, 72.3, 62.3, 30.2, 26.5, 25.2, 19.2; MS (Cl, isobutane) m/z 159 [M+1]$^+$.

(E,Z)-Ethyl-2-methyl-1-tetrahydropyranyloxy-but-2-enoate (13) (Watanabe et al., 1996)

33.0 g (94.8 mmol) of (ethoxycarbonylmethylen)-triphenylphosphorane are dissolved in 500 ml of dry toluene under nitrogen atmosphere at room temperature. Then, 10.0 g (63.2 mmol) of acetonyl tetrahydropyranyl ether 12 are added and the mixture is heated to reflux. After 39 h at this temperature the solvent is evaporated under reduced pressure to yield an orange oil. Major amounts of triphenylphosphinoxide are precipitated by the addition of 100 ml hexanes/acetone 9:1. After filtration the filtrate is concentrated and another 100 ml of hexanes/acetone 9:1 are added. The solid is filtered off and the solvent removed to yield 18 g of an orange oil that is purified by FC on silicagel (hexanes/acetone 9:1, 6.5×28 cm) to yield 12.9 g (56.5 mmol, 89%) of a mixture of (E)-13/(Z)-13=5:1.

(E)-(13). $^1$H NMR (CDCl$_3$, 500 MHz) δ 5.96 (q, J=1.4 Hz, 1H), 4.62 (t, J=3.5 Hz, 1H), 4.20 (dd, J=15.5 Hz, 1.3 Hz, 1H), 4.14 (q, J=7.1 Hz, 2H), 3.93 (dd, J=15.6, 1.3 Hz, 1H), 3.84–3.79 (m, 1H), 3.52–3.48 (m, 1H), 2.08 (d, J=1.4 Hz, 3H), 1.88–1.50 (m, 6H), 1.26 (t, J=7.1 Hz, 3H); $^{13}$C NMR (CDCl$_3$, 126 MHz) δ 166.8, 154.7, 114.5, 98.0, 70.6, 62.0, 59.7, 30.3, 25.3, 19.1, 15.9, 14.3; MS (Cl, isobutane) m/z 229 [M+1]$^+$.

(Z)-(13). $^1$H NMR (CDCl$_3$, 500 MHz) δ 5.71 (q, J=1.4 Hz, 1H), 4.60 (t, J=3.6 Hz, 1H), 4.20 (dd, J=15.5 Hz, 1.3 Hz, 1H), 4.11 (q, J=7.1 Hz, 2H), 3.93 (dd, J=15.6, 1.3 Hz, 1H), 3.84–3.79 (m, 1H), 3.52–3.48 (m, 1H), 1.97 (d, J=1.4 Hz, 3H), 1.88–1.50 (m, 6H), 1.24 (t, J=7.1 Hz, 3H); $^{13}$C NMR (CDCl$_3$, 126 MHz) δ 165.9, 156.8, 116.9, 98.7, 66.5, 62.3, 59.8, 30.6, 25.3, 21.9, 19.5, 14.3; MS (Cl, isobutane) m/z 229 [M+1]$^+$.

(E,Z)-2-Methyl 1-tetrahydropyranyloxy-but-2-ene-4-ol (14) (Watanabe et al., 1996)

A solution of ester 13 (8.73 g, 38.2 mmol) in 100 ml of dry CH$_2$Cl$_2$ is cooled to −78° C. Then, 91.8 ml (91.8 mmol) of 1.0 M DIBAH in hexanes are added slowly under an atmosphere of nitrogen. The resulting solution is stirred for 3 h at −78° C. before the reaction is quenched by the addition of 1.5 ml of 1 M NaOH. After warming to room temperature the solvent is removed under reduced pressure. The resulting gummy residue is widely dissolved by adding twice 100 ml of MeOH. The resulting mixture is passed through a column of SiO$_2$, evaporated from the solvent and then loaded on a column of SiO$_2$/Na$_2$SO$_4$ that is purged with 1400 ml of MeOH. Evaporation of the solvent gives 9.5 g of a colorless liquid that is purified by FC on silica gel (hexanes/acetone 1:3, 6.5×16 cm) to yield 6.98 g (37.4 mmol, 98%) of a colorless liquid (E)-14/(Z)-14=6:1.

(E)-(14). $^1$H NMR (CDCl$_3$, 500 MHz) δ 5.68 (tq, J=6.6, 1.3 Hz, 1H), 4.60 (t, J=3.6 Hz, 1H), 4.20 (d, J=6.8 Hz, 2H), 4.12 (d, J=12.0 Hz, 1H), 3.87–3.82 (m, 1H), 3.85 (d, J=12.5 Hz, 1H), 3.52–3.48 (m, 1H), 1.86–1.48 (m, 6H), 1.69 (s, 3H); $^{13}$C NMR (CDCl$_3$, 126 MHz) δ 135.7, 125.4, 97.8, 71.9, 62.1, 59.1, 30.5, 25.4, 19.4, 14.1; MS (Cl, isobutane) m/z 169 [M−H$_2$O+1]$^+$.

(Z)-(14). $^1$H NMR (CDCl$_3$, 500 MHz) δ 5.64 (tq, J=6.6, 1.3 Hz, 1H), 4.63 (t, J=3.3 Hz, 1H), 4.20 (d, J=6.8 Hz, 2H), 4.15 (d, J=11.8 Hz, 1H), 3.87–3.82 (m, 1H), 3.83 (d, J=11.3 Hz, 1H), 3.52–3.48 (m, 1H), 1.86–1.48 (m, 6H), 1.79 (s, 3H); $^{13}$C NMR (CDCl$_3$, 126 MHz) 6136.2, 128.6, 96.6, 65.1, 61.8, 58.1, 30.3, 25.3, 21.9, 19.0; MS (Cl, isobutane) m/z 169 [M−H$_2$O+1]$^+$.

(E,Z)-4-Chloro-2-methyl 1-tetrahydropyranyloxy-but-2-en (15) (Hwang et al., 1984)

To a solution of alcohol 14 (1.00 g, 5.37 mmol) in 10 ml of dry CH$_2$Cl$_2$ are added 918 mg (7.52 mmol) of DMAP in 10 ml of dry CH$_2$Cl$_2$ and 1.23 g (6.44 mmol) of p-TsCl in 10 ml of dry CH$_2$Cl$_2$. The resulting solution is stirred at room temperature for 1 h. After evaporation of the solvent under reduced pressure the residue is purified by FC on silica gel (CH$_2$Cl$_2$, 5×20 cm) to obtain 693 mg (3.39 mmol, 63%) of a colorless liquid (E)-15/(Z)-15=6:1.

(E)-(15). $^1$H NMR (CDCl$_3$, 500 MHz) δ 5.77 (tq, J=8.0, 1.5 Hz, 1H), 4.64 (t, J=3.6 Hz, 1H), 4.18 (d, J=12.8 Hz, 1H), 4.15 (d, J=8.0 Hz, 2H), 3.92 (d, J=12.8 Hz, 1H), 3.90–3.86 (m, 1H), 3.59–3.52 (m, 1H), 1.92–1.52 (m, 6H), 1.77 (s, 3H); $^{13}$C NMR (CDCl$_3$, 126 MHz) δ 138.6, 121.7, 97.8, 71.3, 62.1, 40.2, 30.5, 25.4, 19.3, 13.9; MS (Cl, isobutane) m/z 205 [M+1]$^+$.

(Z)-(15). $^1$H NMR (CDCl$_3$, 500 MHz) δ 5.65 (t, J=8.1 Hz, 1H), 4.61 (t, J=3.6 Hz, 1H), 4.18 (d, J=12.8 Hz, 1H), 4.15 (d, J=8.0 Hz, 2H), 3.92 (d, J=12.8 Hz, 1H), 3.90–3.86 (m, 1H), 3.59–3.52 (m, 1H), 1.92–1.52 (m, 6H), 1.86 (s, 3H); $^{13}$C NMR (CDCl$_3$, 126 MHz) δ 138.3, 124.6, 97.5, 64.7, 62.2, 40.1, 30.5, 25.4, 21.8, 19.4; MS (Cl, isobutane) m/z 205 [M+1]$^+$.

(E,Z)-2-Methyl 1-tetrahydropyranyloxy-but-2-enyl diphosphate triammonium salt (16) (Davisson et al., 1986)

To a solution of chloride 15 (260 mg, 1.27 mmol) in 1.3 ml of MeCN a solution of 1.38 g (1.52 mmol) tris(tetra-n-butylammonium) hydrogen pyrophosphate in 3.0 ml of MeCN is added slowly at room temperature, obtaining an orange-red solution. The reaction is followed by $^1$H-NMR, taking advantage of the up field shift of the multiplet of H-3. After 2 h the reaction is finished and the solvent removed under reduced pressure. The orange oil is dissolved in 2.5 ml of H$_2$O and passed through a column of DOWEX 50 WX8 (2.5×3 cm) cation-exchange resin (NH$_4^+$ form) that has been equilibrated with two column volumes (40 ml) of 25 mM NH$_4$HCO$_3$. The column is eluted with 60 ml of 25 mM NH$_4$HCO$_3$. The resulting solution is lyophilized, dissolved in 5 ml of isopropanol/100 mM NH$_4$HCO$_3$ 1:1 and loaded on a cellulose column (2×18 cm) that is eluted by isopropanol/100 mM NH$_4$HCO$_3$ 1:1. The effluent is lyophilized obtaining 495 mg (1.25 mmol, 98%) of (E)-16/(Z)-16=6:1 as a white solid.

(E)-(16). $^1$H NMR (D$_2$O, 500 MHz) δ 5.52 (tq, J=6.8 Hz, 1H), 4.65 (s, 1H), 4.34 (t, J=7.0 Hz, 2H), 3.98 (d, J=12.3 Hz, 1H), 3.84 (d, J=12.1 Hz, 1H), 3.74–3.70 (m, 1H), 3.42–3.38 (m, 1H), 1.61–1.57 (m, 2H), 1.54 (s, 3H), 1.40–1.32 (m, 4H); $^{13}$C NMR (D$_2$O, 126 MHz) δ 136.4, 123.9 (dd, J=8.0, 2.3 Hz), 98.5, 72.5, 63.2, 62.2 (d, J=5.3 Hz), 29.9, 24.5, 19.0, 13.4; $^{31}$P NMR (D$_2$O, 101 MHz) δ–5.62 (d, J=20.9 Hz), –7.57 (d, J=20.8 Hz).

(Z)-(16). $^1$H NMR (D$_2$O, 500 MHz) δ 5.52 (t, J=6.8, 1H), 4.65 (s, 1H), 4.31 (t, J=7.1 Hz, 2H), 3.98 (d, J=12.3 Hz, 1H), 3.84 (d, J=12.1 Hz, 1H), 3.74–3.70 (m, 1H), 3.42–3.38 (m, 1H), 1.64 (s, 3H), 1.61–1.57 (m, 2H), 1.40–1.32 (m, 4H); $^{13}$C NMR (D$_2$O, 126 MHz) δ 136.3, 125.8 (d, J=8.6 Hz), 98.6, 72.5, 63.2, 61.8 (d, J=5.1 Hz), 29.9, 24.5, 20.8, 19.0; $^{31}$P NMR (D$_2$O, 101 MHz) δ–5.69 (d, J=20.8 Hz), –7.68 (d, J=20.8 Hz).

(E,Z)-1-Hydroxy-2-methyl-but-2-enyl diphosphate triammonium salt (8) (Davisson et al., 1986)

268 mg (0.675 mmol) of protected pyrophosphate 16 are dissolved in 2.0 ml of D$_2$O and the pH is adjusted to 1 by addition of 40 µl of 37% DCl in D$_2$O. After 1 min at this pH the solution is neutralized by addition of 40 µl of 40% NaOD in D$_2$O and an $^1$H NMR is measured that demonstrated 50% deprotection. The procedure is repeated until deprotection is finished and just small amounts of decomposition product are formed to get in total 7 min at pH 1. Purification is performed by loading the neutral solution that is diluted by addition of 2 ml of isopropanol/100 mM NH$_4$HCO$_3$ 1:1 on a cellulose column (isopropanol/100 mM NH$_4$HCO$_3$ 1:1, 2×10.5 cm) to yield 193 mg (0.616 mmol, 91%) of a white solid of (E)-8/(Z)-8=7:1.

(E)-(8). $^1$H NMR (D$_2$O, 500 MHz) δ 5.51 (tq, J=6.8, 1.2 Hz, 1H), 4.41 (t, J=7.2 Hz, 2H), 3.90 (s, 2H), 1.59 (s, 3H); $^{13}$C NMR (D$_2$O, 126 MHz) δ 139.8, 120.6 (d, J=7.7 Hz), 66.5, 62.4 (d, J=5.3 Hz), 13.2; $^{31}$P NMR (D$_2$O, 101 MHz) δ–4.48 (d, J=20.8 Hz), –7.06 (d, J=20.8 Hz).

(Z)-(8). $^1$H NMR (D$_2$O, 500 MHz) δ 5.49 (tm, J=6.8 Hz, 1H), 4.41 (t, J=7.3 Hz, 2H), 4.03 (s, 2H), 1.70 (s, 3H); $^{13}$C NMR (D$_2$O, 126 MHz) δ 139.8, 123.5 (d, J=7.7 Hz), 61.7 (d, J=5.1 Hz), 59.9, 20.6; $^{31}$P NMR (D$_2$O, 101 MHz) δ–4.48 (d, J=20.8 Hz), –7.06 (d, J=20.8 Hz).

Figure 4:
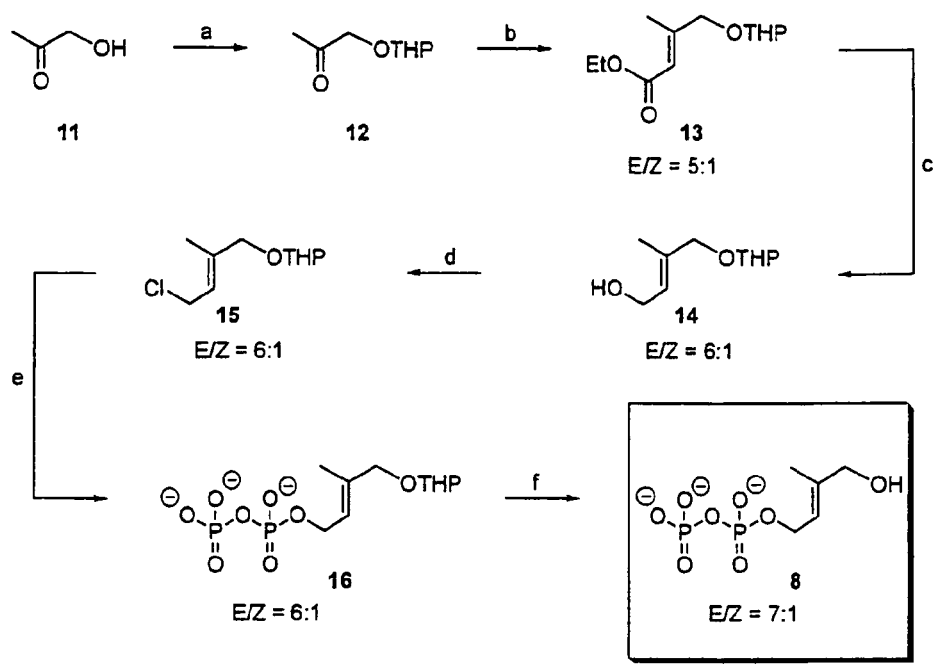
FIG. 4: Preparation of 1-hydroxy-2-methyl-2-butenyl 4-diphosphate according to Example 24. Reagents and conditions were as follows: (a) DHP, PPTS, 25° C. (2.5 h); (b) $Ph_3PCHCO_2Et$, toluene, reflux (39 h); (c) (1) DIBAH, $CH_2Cl_2$, −78° C. (3 h), (2) 1 M $NaOH/H_2O$; (d) p-TsCl, DMAP, $CH_2Cl_2$, 25° C. (1 h); (e) $((CH_3CH_2CH_2CH_2)_4N)_3$ $HP_2O_7$, MeCN, 25° C. (2 h); (f), $HCl/H_2O$ pH 1, 25° C. (7 min).
Figure 5:
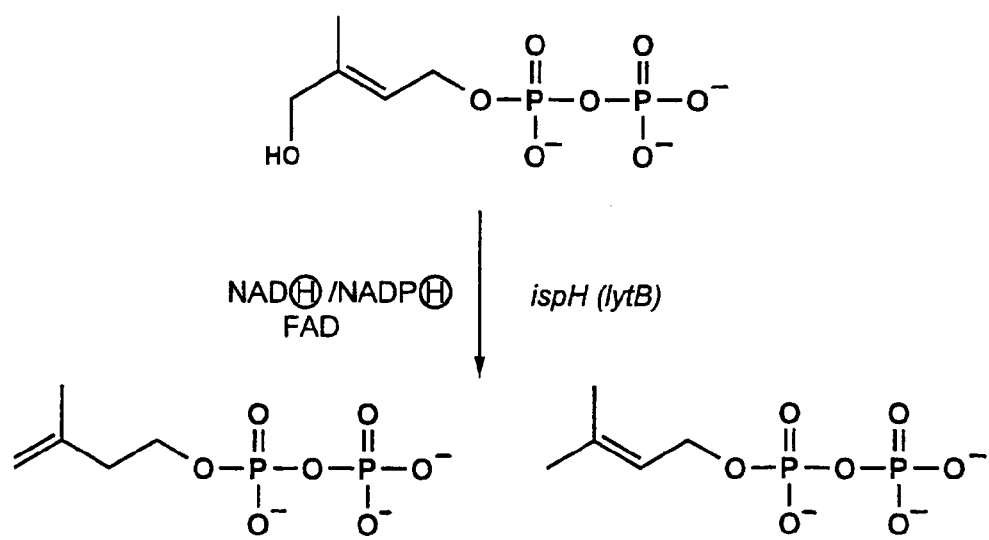
FIG. 5: The reaction catalyzed by the ispH (formerly lytB) gene product.
Figure 6:
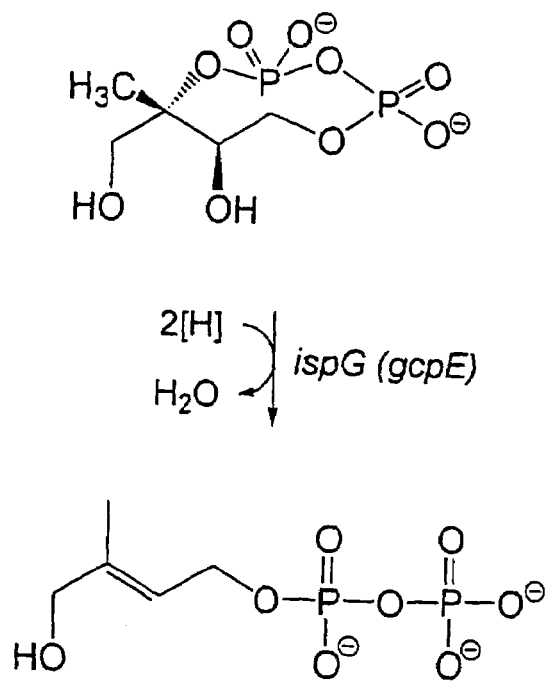
FIG. 6: The reaction catalyzed by the ispG (formerly gcpE) gene product.

Reagents and conditions (steps (a) to (f) in FIG. 4: 1): (a) DHP, PPTS, 25° C. (2.5 h); (b) Ph$_3$PCHCO$_2$Et, toluene, reflux (39 h); (c) (1) DIBAH, CH$_2$Cl$_2$, –78° C. (3 h), (2) 1 M NaOH/H$_2$O; (d) p-TsCl, DMAP, CH$_2$Cl$_2$, 25° C. (1 h); (e) ((CH$_3$CH$_2$CH$_2$CH$_2$)$_4$N)$_3$HP$_2$O$_7$, MeCN, 25° C. (2 h); (f), HCl/H$_2$O pH 1, 25° C. (7 min).

EXAMPLE 25

Identification of (E)-1-hydroxy-2-methyl-2-butenyl 4-diphosphate

The structure of the GcpE product is further analyzed by comparison with the chemical shifts of a synthetic sample of 1-hydroxy-2-methyl-2-(E)-butenyl 4-diphosphate.

For this purpose, [2-$^{14}$C]1-hydroxy-2-methyl-2-(E)-butenyl 4-diphosphate (0.36 µCi) is added to a cell extract obtained from bioengineered *Escherichia coli* cells endowed with artificial gene constructs expressing xylB, ispC, ispD, ispE, ispF and gcpE gene which are supplied with [U—$^{13}$C$_5$]-1-deoxy-D-xylulose (see example 16). The supernatant of the cell extract is purified by HPLC (Nucleosil 5 SB, 7.5×250 mm, developed with a gradient of 100 mM to 250 mM NH$_4$HCOO, flow rate 2 ml/min, 35 min). The product is eluted at 23 min and collected. After lyophilization the residue is dissolved in D$_2$O (pH 6) and subjected to $^1$H NMR analysis (FIG. 3-A).

Figure 3:
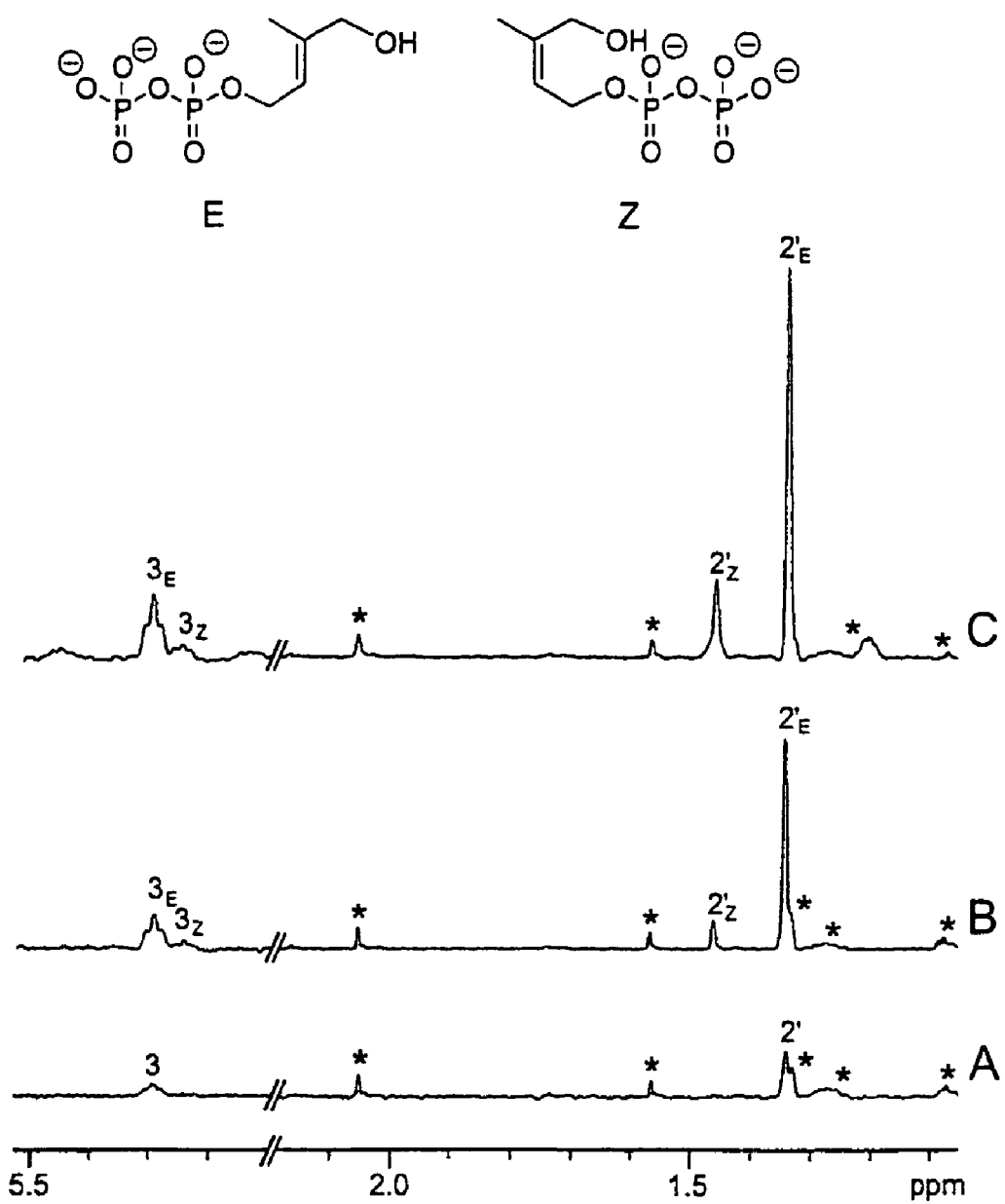
FIG. 3: $^1H$ NMR spectra in $D_2O$ (pH 6) obtained according to Example 25. * indicates impurities.

Then, 40 µl of a solution of synthetically prepared (E,Z)-1-hydroxy-2-methyl-2-butenyl 4-diphosphate (E/Z=7:1) (D$_2$O, pH 7) are added to the NMR sample and again analyzed by $^1$H NMR spectroscopy (FIG. 3-B). On the one hand, as shown in FIG. 3-B, signals accounting for (E)-1-hydroxy-2-methyl-2-butenyl are selectively increased, providing evidence that the biologically produced structure is identical with the synthetically produced one, i.e. the (E)-isomer. On the other hand, the minor (Z)-isomer raises without any correlation to signals of the biologically afforded product. FIG. 3-C shows the same effects after addition of another 40 µl of solution of the synthetically prepared (E,Z)-1-hydroxy-2-methyl-2-butenyl 4-diphosphate.

EXAMPLE 26

Incorporation of (E)-1-hydroxy-2-methyl-2-butenyl 4-diphosphate into the Lipid Soluble Fraction of *Capsicum annuum* Chromoplasts Chromoplasts are isolated by a slight modification of a method described by Camara (Camara, 1985; Camara, 1993). Pericarp of red pepper (650 g) is homogenized at 4° C. in 600 ml of 50 mM Hepes, pH 8.0, containing 1 mM DTE, 1 mM EDTA and 0.4 M sucrose (buffer A). The suspension is filtered through four layers of nylon cloth (50 μm) and centrifuged (10 min, 4,500 rpm, GSA rotor) to obtain a pellet of crude chromoplasts which is homogenized in 200 ml of buffer A. The suspension is centrifuged (10 min, 4,500 rpm, GSA rotor). The pellet is homogenized and resuspended in 3 ml of 50 mM Hepes, pH 7.6, containing 1 mM DTE. The suspension is filtered through one layer of nylon cloth (50 μm). Reaction mixtures contain 100 mM Hepes, pH 7.6, 2 mM $MnCl_2$, 10 mM $MgCl_2$, 5 mM NaF, 2 mM $NADP^+$, 1 mM NADPH, 6 mM ATP, 20 μM FAD and 2 mg of chromoplasts. 8.8 nmol of [$2-^{14}C$]2C-methyl-D-erythritol 2,4-cyclodiphosphate, [$2-^{14}C$]1-hydroxy-2-methyl-2-(E)-butenyl diphosphate or [$2-^{14}C$]isopentenyl diphosphate (specific concentrations 15.8 μCi/μmol) are added and the mixtures are incubated at 30° C. overnight. The reaction is terminated by methylene chloride extraction. The organic phase is concentrated under a stream of nitrogen. Aliquots are spotted on silica gel plates (Polygram SIL-G, UV254, Macherey-Nagel, Düren, Germany). The plates are developed with hexane: ether=6:1 (system I) and/or hexane: toluene=9:1 (system II), respectively. The chromatograms are monitored with a phosphor imager (Storm 860, Molecular dynamics, Sunnyvale, Calif., USA). The $R_f$-values of geranylgeraniol and the carotene fraction in system I are 0.35 and 0.9, respectively. The $R_f$-values of β-carotene, phytoene and phytofluene in system II are 0.65, 0,60 and 0.55, respectively.

The evaluation of the chromatogramms show that radioactivity can be efficiently diverted from 1-hydroxy-2-methyl-2-(E)-butenyl diphosphate into the geranylgeraniol, β-carotene, phytoene and phytofluene fractions of *C. annuum* chromoplasts establishing 1-hydroxy-2-methyl-2-(E)-butenyl diphosphate as a real intermediate of the non-mevalonate pathway downstream from 2C-methyl-D-erythritol 2,4-cyclodiphosphate and upstream from isopentenyl diphosphate.

EXAMPLE 27

Construction of a Vector Carrying the ispG (gcpE) and ispH (lytB) Genes of *Escherichia coli* Capable for Transcription and Expression Thereof The *E. coli* ORF ispH (lytB) (accession no. gb AE000113) from base pair (bp) position 5618 to 6568 is amplified by PCR using chromosomal *E. coli* DNA as template. The reaction mixture contains 10 pmol of the primer 5'-GCT-TGCGTCGACGAGGAGAAATTAACCATG-CAGATCCTGTTGGCCACC-3' (SEQ ID NO:21), 10 pmol of the primer 5'-GCTGCTCGGCCGTTAATCGACTTCAC-GAATATCG-3' (SEQ ID NO:22), 20 ng of chromosomal DNA, 2 U of Taq DNA polymerase (Eurogentec) and 20 nmol of dNTPs in a total volume of 100 μl containing 1.5 mM $MgCl_2$, 50 mM KCl, 10 mM Tris-hydrochloride, pH 8.8 and 0.1% (w/w) Triton X-100.

The mixture is denatured for 3 min at 94° C. Then 30 PCR cycles for 45 sec at 94° C., 45 sec at 50° C. and 60 sec at 72° C. followed. After further incubation for 10 min at 72° C., the mixture is cooled to 4° C. An aliquot of 2 μl is subjected to agarose gel electrophoresis.

The PCR amplificate is purified with the PCR purification kit from Qiagen (Hilden).

2.4 μg of the vector pACYC184 (Chang and Cohen 1978, NEB) and 0.7 μg of the purified PCR product are digested with SalI and EagI in order to produce DNA fragments with overlapping ends. The restriction mixtures are prepared according to the conditions supplied by the customer (NEB) and are incubated for 3 h at 37° C. Digested vector DNA and PCR product are purified using the PCR purification kit from Qiagen.

20 ng of the purified vector DNA and 18 ng of the purified PCR product are ligated together with 1 U of T4-Ligase (Gibco), 2 μl of T4-Ligase buffer (Gibco) in a total volume of 10 μl, yielding the plasmid pACYClytB. The ligation mixture is incubated for 2 h at 25° C. 1 μl of the ligation mixture is transformed into electrocompetent *E. coli* XL1-Blue cells. The plasmid pACYClytB is isolated with the plasmid isolation kit from Qiagen.

The DNA insert of the plasmid pACYClytB is sequenced by the automated dideoxynucleotide method using an ABI Prism 377™ DNA sequencer from Perkin Elmer with the ABI Prism™ Sequencing Analysis Software from Applied Biosystems Divisions. It is identical with the DNA sequence of the database entry (gb AE000113).

The *E. coli* ORF ispG (gcpE) (accession no. gb AE000338) from base pair (bp) position 372 to 1204 is amplified by PCR using chromosomal *E. coli* DNA as template. The reaction mixture contains 10 pmol of the primer 5'-CGTACCGGATCCGAGGAGAAATTAAC-CATGCATAACCAGGCTCCAATTC-3' (SEQ ID NO:23), 10 pmol of the primer 5'-CCCATCGTCGACT-TATTTTTCAACCTGCTGAACGTC-3' (SEQ ID NO:24), 20 ng of chromosomal DNA, 2 U of Taq DNA polymerase (Eurogentec) and 20 nmol of dNTPs in a total volume of 100 μl containing 1.5 mM $MgCl_2$, 50 mM KCl, 10 mM Tris-hydrochloride, pH 8.8 and 0.1% (w/w) Triton X-100.

The mixture is denatured for 3 min at 94° C. Then 30 PCR cycles for 60 sec at 94° C., 60 sec at 50° C. and 90 sec at 72° C. followed. After further incubation for 10 min at 72° C., the mixture is cooled to 4° C. An aliquot of 2 μl is subjected to agarose gel electrophoresis.

The PCR amplificate is purified with the PCR purification kit from Qiagen (Hilden).

2.0 μg of the vector pACYClytB and 0.9 μg of the purified PCR product are digested with BamHI and SalI in order to produce DNA fragments with overlapping ends. The restriction mixtures are prepared according to the conditions supplied by the customer (NEB) and are incubated for 3 h at 37° C. Digested vector DNA and PCR product are purified using the PCR purification kit from Qiagen.

20 ng of the purified vector DNA and 23 ng of the purified PCR product are ligated together with 1 U of T4-Ligase (Gibco), 2 μl of T4-Ligase buffer (Gibco) in a total volume of 10 μl, yielding the plasmid pACYClytBgcpE. The ligation mixture is incubated for 2 h at 25° C. 1 μl of the ligation mixture is transformed into electrocompetent *E. coli* XL1-Blue cells. The plasmid pACYClytBgcpE is isolated with the plasmid isolation kit from Qiagen.

The DNA insert of the plasmid pACYClytBgcpE is sequenced by the automated dideoxynucleotide method using an ABI Prism 377™ DNA sequencer from Perkin Elmer with the ABI Prism™ Sequencing Analysis Software from Applied Biosystems Divisions. It is identical with the DNA sequence of the database entry (gb AE000338).

The DNA sequence of the vector construct pACYClytBgcpE is shown in FIG. 16.

The DNA and corresponding amino acid sequence of ispH (lytB) from *Escherichia coli* is shown in FIG. 17.

EXAMPLE 28

Construction of a Vector Carrying the xylB, dxr, ispD, ispE, ispF, ispG and ispH Genes of Escherichia coli Capable for Transcription and Expression of D-xylulokinase, DXP Reductoisomerase, CDP-ME Synthase, CDP-ME Kinase cMEPP Synthase, 1-hydroxy-2-methyl-2-butenyl 4-diphosphate Synthase and IPP/DMAPP Synthase The *E. coli* ORFs ispG (formerly gcpE) and ispH (formerly lytB) are amplified by PCR using the plasmid pACY-ClytBgcpE (see example 27) as template. The reaction mixture contains 10 pmol of the primer 5'-GCGGGAGAC-CGCGGGAGGAGAAATTAACCATGCAT-AACCAGGCTCCAATTCAACG-3' (SEQ ID NO:25), 10 pmol of the primer 5'-AGGCTGGCGGCCGCTTAATC-GACTTCACGAATATCG-3' (SEQ ID NO:26), 2 ng of pACYCgcpElytB DNA, 2 U of Taq DNA polymerase (Eurogentec) and 20 nmol of dNTPs in a total volume of 100 µl containing 1.5 mM $MgCl_2$, 50 mM KCl, 10 mM Tris-hydrochloride, pH 8.8 and 0.1% (w/w) Triton X-100.

The mixture is denaturated for 3 min at 94° C. Then 30 PCR cycles for 60 sec at 94° C., 60 sec at 50° C. and 150 sec at 72° C. followed. After further incubation for 20 min at 72° C., the mixture is cooled to 4° C. An aliquot of 2 µl is subjected to agarose gel electrophoresis.

The PCR amplificate is purified with the PCR purification kit from Qiagen (Hilden).

1.7 µg of the vector pBScyclo (Example 5) and 1.3 µg of the purified PCR product are digested with SacII and NotI in order to produce DNA fragments with overlapping ends. The restriction mixtures are prepared according to the conditions supplied by the customer (NEB) and are incubated for 3 h at 37° C. Digested vector DNA and PCR product are purified using the PCR purification kit from Qiagen.

22 ng of the purified vector DNA and 19 ng of the purified PCR product are ligated together with 1 U of T4-Ligase (Gibco), 2 µl of T4-Ligase buffer (Gibco) in a total volume of 10 µl, yielding the plasmid pBScyclogcpElytB2. The ligation mixture is incubated for 2 h at 25° C. 1 µl of the ligation mixture is transformed into electrocompetent *E. coli* XL1-Blue cells. The plasmid pBScyclogcpElytB2 is isolated with the plasmid isolation kit from Qiagen.

The DNA insert of the plasmid pBScyclogcpElytB2 is sequenced by the automated dideoxynucleotide method using an ABI Prism 377™ DNA sequencer from Perkin Elmer with the ABI Prism™ Sequencing Analysis Software from Applied Biosystems Divisions. The DNA sequence of the vector construct pBScyclogcpElytB2 is shown in FIG. 18.

EXAMPLE 29

Incorporation Experiment with Recombinant *Escherichia coli* XL1-pBScyclogcpElytB2 Using [U—$^{13}C_5$]1-deoxy-D-xylulose 0.1 liter of Terrific Broth (TB) medium containing 18 mg of ampicillin are inoculated with *E. coli* strain XI1-Blue harbouring the plasmid pBScyclogcpElytB2. The cells are grown in a shaking culture at 37° C. for overnight. At an optical density (600 nm) of 1.3–1.7 a solution containing 2.4 g of lithium lactate (25 mmol), 10 ml of crude [U—$^{13}C_5$] 1-deoxy-D-xylulose (0.05 mmol) (see example 8) at a final volume of 30 ml (pH=7.4) are added continuously within 2 hours. Aliquots of 40 ml are taken at time intervals of 30 minutes and centrifuged for 20 min at 5,000 rpm and 4° C. The cells are washed with water containing 0.9% NaCl and centrifuged as described above. The cells are suspended in 700 ml of a mixture of methanol and $D_2O$ (6:4, v/v) containing 10 mM NaF, cooled on ice and sonified 3×10 sec with a Branson Sonifier 250 (Branson SONIC Power Company) set to 90% duty cycle output, control value of 4 output. The suspension is centrifuged at 15,000 rpm for 15 min. NMR spectra of the cell free extracts are recorded directly with a Bruker AVANCE DRX 500 spectrometer (Karlsruhe, Germany). In order to avoid degradation during work-up, the structures of the products are determined by NMR spectroscopy without further purification.

EXAMPLE 30

Structure Determination of Isopentenyl Diphosphate (IPP) and Dimethylallyl Diphosphate (DMAPP)

The $^1$H-decoupled $^{13}$C NMR spectrum using [U—$^{13}C_5$] 1-deoxy-D-xylulose as starting material (see examples 8 and 30) displays five intense $^1$C—$^{13}$C coupled signals belonging to 2C-methyl-D-erythritol 2,4-cyclodiphosphate (Herz et al., 2000) and five $^{13}$C—$^{13}$C coupled signals with low intensities belonging to 1-hydroxy-2-methyl-2-butenyl 4-diphosphate (see example 18) (100:3 ratio for the 2-methyl $^{13}$C NMR signal intensities of 2C-methyl-D-erythritol 2,4-cyclodiphosphate and 1-hydroxy-2-methyl-2-butenyl 4-diphosphate, respectively).

In addition a set of, five $^{13}$C—$^{13}$C coupled signals at 21.6 (doublet), 37.8 (triplet), 64.1 (doublet), 111.6 (doublet), and 143.3 ppm (doublet of triplets) (unknown metabolite A) accompanied by signals at 21.1 (doublet), 39.6 (triplet), 59.3 (doublet), 111.8 (doublet), and 143.2 ppm (doublet of triplets) (unknown metabolite B) is detected. The ratio of the 2-methyl signal of 2C-methyl-D-erythritol 2,4-cyclodiphosphate and the putative methyl signals of the unknown compounds at 21.6 ppm (metabolite A) and 21.1 ppm (metabolite B) is 100:24:4, respectively.

Moreover, $^{13}$C coupled signals with low intensities belonging to another unknown compound (metabolite C) at 17.1 (doublet), 24.9 (doublet), 62.7 (doublet), 119.6 (double-doublet) and 139.4 ppm (multiplet) are detected. The ratio of the intensities of the putative methyl signals at 21.6 (metabolite A), 17.1 and 24.9 (metabolite C) is 100:13:13, respectively.

The $^{31}$P NMR spectrum of the reaction mixture is characterized by intense signals for 2C-methyl-D-erythritol 2,4-cyclodiphosphate (Herz et al., 2000). Furthermore, $^{31}P^{31}P$ coupled broadened signals are observed at a chemical shift range typical for organic diphosphates (−6 to −13 ppm, $^{31}P^{31}P$ coupling constants, 20 Hz).

Metabolite A:

The signals of metabolite A at 111.6 and 143.3 ppm are conducive of a double bond motif, and the signals at 64.1, 37.8 and 21.6 ppm reflect three aliphatic carbon atoms one of which (signal at 64.1 ppm) appears to be connected to OH or OR (R=unknown).

Additional information about the structure of the unknown metabolite A can be gleaned from the $^{13}$C coupling pattern. Three of the $^{13}$C NMR signals (21.6, 64.1 and 111.6 ppm) are split into doublets indicating three $^{13}$C atoms each connected to only one $^{13}$C-labelled neighbour, one signal (37.8 ppm) displays a pseudo-triplet signature indicating a $^{13}$C atom with two adjacent $^{13}$C atoms, and one signal (143.3 ppm) is split into a doublet of triplets indicating a $^{13}C$ atom with three $^{13}C$ connections. In conjunction with the chemical shifts, this connectivity pattern establish metabolite A as an isopentenyl derivative.

The complex signature for the signal at 143.3 ppm deserves a more detailed analysis. The large coupling (71 Hz) is typical for $^{13}C^{13}C$ couplings between carbon atoms involved in carbon—carbon double bonds. A 71 Hz coupling is also found for the doublet signal at 111.6 ppm representing the second carbon of the double bond. Due to the coupling pattern and the chemical shifts the presence of an exo-methylene function is obvious. The two additional $^{13}C$ couplings found in the triplet substructure of the signal at 143.3 ppm are both 41 Hz, and establish the respective carbon as the branching point of the structure.

HMQC experiments reveal the $^1H$ NMR chemical shifts, as well as $^{13}C$—$^1H$ and $^1$-$^1H$ spin systems. More specifically, the $^{13}C$ NMR signal at 111.6 ppm correlates to a $^1H$ NMR signal at 4.73 ppm, whereas the signal at 143.3 ppm gives no $^{13}C$—$^1H$ correlation. The signals at 64.1, 37.8, and 21.6 ppm give $^{13}C$—$^1H$ correlations to $^1H$-signals at 4.00, 2.31, and 1.68 ppm, respectively. As shown by HMQC-TOCSY experiments, the proton signals at 2.31 and 4.00 are coupled, whereas the signals at 4.73 and 1.68 ppm are found as singlets in the HMQC-TOCSY experiment. The observed $^1H$ NMR chemical shifts in combination with the coupling patterns demonstrate that metabolite A is an isopentenyl derivative with a single bonded heteroatom (most plausibly 0) at position 1.

The $^{31}C$ and $^1H$ chemical shifts of an authentic sample of isopentenyl diphosphate (IPP, measured in the same solvent mixture) are identical to the chemical shifts assigned to metabolite A. Thus, metabolite A is identified as [U—$^{13}C_5$] IPP.

Metabolite B:

As noted above, the coupling and correlation pattern of metabolite B observed in the $^{13}C$ NMR signals, as well as in the HMQC and HMQC-TOCSY spectra, is virtually the same as for metabolite A (IPP) suggesting that the carbon connectivities of metabolite B and IPP are identical. As the most significant difference between the NMR data of metabolite B and IPP the $^{13}C$ NMR chemical shift of one doublet signal for metabolite B (59.3 ppm) corresponding to the C-1 signal of IPP (64.1 ppm) is upfield shifted by 4.9 ppm. This suggests that a phosphate moiety is missing at C-1 in metabolite B. Therefore, metabolite B is assigned as [U—$^{13}C_5$]isopentene-1-ol. Presumably, isopentene-1-ol is formed from IPP by the catalytic action of pyrophosphatases and phosphatases present in the experimental system.

Metabolite C:

As described above for metabolite A (IPP), the structure of metabolite C is assigned by NMR analysis. The $^{13}C$ coupling pattern of the signals attributed to metabolite C (three doublets, one double-doublet, one multiplet) suggests that the compound is another isopentane derivative. The chemical shifts observed for the double-doublet (119.6 ppm) and the multiplet (139.4 ppm) show that a carbon—carbon double bond connects C-2 (coupled to two $^{13}C$ neighbours) and C-3 (coupled to three $^{13}C$ neighbours) of the molecule.

The $^1H$ NMR chemical shifts of metabolite C are revealed by HMQC and HMQC-TOCSY experiments showing two singlets at 1.75 and 1.71 ppm, and a spin system comprising signals at 5.43 and 4.45 ppm. In conjunction with the chemical shifts, this correlation pattern shows that metabolite C is a dimethylallyl derivative.

The $^{13}C$ and $^1H$ NMR chemical shifts of an authentic sample of dimethylallyl diphosphate (DMAPP) are identical to the chemical shifts of the signals attributed to metabolite C. This leaves no doubt that metabolite C is [U—$^{13}C_5$] dimethylallyl diphosphate (DMAPP).

NMR data of metabolite A (IPP) and metabolite C (DMAPP) are summarized in Tables 6 and 7.

TABLE 6

NMR data of isopentenyl diphosphate (IPP)

| | Chemical shifts, ppm | | | Coupling constants, Hz | | | | |
|---|---|---|---|---|---|---|---|---|
| Position | $^1H^a$ | $^{13}C^b$ | $^{31}P^c$ | $J_{PC}$ | $J_{HH}$ | $J_{PP}$ | $J_{PH}$ | $J_{CC}{}^d$ |
| 1 | 4.00 | 64.1 | | 4.9 | 6.6 | | 6.6 | 34 |
| 2 | 2.31 | 37.8 | | 8.0 | 6.7 | | | 40, 40 |
| 3 | | 143.3 | | | | | | 71, 41, 41 |
| 4 | 4.73 | 111.6 | | | | | | 71 |
| 5 | 1.68 | 21.6 | | | | | | 41 |
| P | | | −7.8 | | | nd | | |
| P | | | −11.9 | | | 19, 5 | | |

$^a$referenced to external trimethylsilylpropane sulfonate.
$^b$referenced to external trimethylsilylpropane sulfonate.
$^c$referenced to external 85% orthophosphoric acid.
$^d$observed with [U-$^{13}C_5$]IPP

TABLE 7

NMR data of dimethylallyl diphosphate (DMAPP)

| | Chemical shifts, ppm | | | Coupling constants, Hz | | | | |
|---|---|---|---|---|---|---|---|---|
| Position | $^1H^a$ | $^{13}C^b$ | $^{31}P^c$ | $J_{PC}$ | $J_{HH}$ | $J_{PP}$ | $J_{PH}$ | $J_{CC}{}^d$ |
| 1 | 4.45 | 62.7 | | 3.6 | 6.6 | | 6.6 | 47 |
| 2 | 5.43 | 119.6 | | 9.0 | 7.2 | | | 75, 48 |
| 3 | | 139.4 | | | | | | nd |
| 4 | 1.75 | 24.9 | | | | | | 42 |
| 5 | 1.71 | 17.1 | | | | | | 41 |
| P | | | −9.1 | | | 21.7 | | |
| P | | | −6.4 | | | 21.5 | | |

$^a$referenced to external trimethylsilylpropane sulfonate.
$^b$referenced to external trimethylsilylpropane sulfonate.
$^c$referenced to external 85% orthophosphoric acid.
$^d$observed with [U-$^{13}C_5$]DMAPP

EXAMPLE 31

Cloning of the ispG Gene (Fragment) from *Arabidopsis thaliana*

RNA is isolated from 1 g of 2 weeks old *Arabidopsis thaliana* var. Columbia plants (stems and leafs) by published procedures (Logemann et al. 1987).

A mixture containing 2.75 µg RNA, 50 nmol dNTP's, 1 µg random hexameric primer, 1 µg T$_{15}$-primer and 20% first strand 5× buffer (Promega) in a total volume of 50 µl is incubated for 5 min. at 95° C., cooled on ice and 500 U M-MLV reverse transcriptase (Promega) are added. The mixture is incubated for 1 h at 42° C. After incubation at 92° C. for 5 min, RNase A (20 U) and RNase H (2 U) are added and the mixture is incubated for 30 min. at 37° C.

The resulting cDNA (1 µl of this mixture) is used for the amplification of ispG by PCR.

The *A. thaliana* ORF ispG (accession no. dbj AB005246) without the coding region for the putative leader sequence from basepair (bp) position 2889 to 6476 is amplified by PCR using cDNA from *A. thaliana* as template. The reaction mixture contains 25 pmol of primer CCTGCATCCGAAG- GAAGCCC (SEQ ID NO:27), 25 pmol of primer CAGTTTTCAAAGAATGGCCC (SEQ ID NO:28), 1 µl of cDNA, 2 U of Taq DNA polymerase (Eurogentec, Seraing, Belgium) and 20 nmol of dNTPs in a total volume of 100 µl in 1.5 mM $MgCl_2$, 50 mM KCl, 10 mM Tris-hydrochloride, pH 8.8 and 0.1% (w/w) Triton X-100.

The mixture is denatured for 3 min at 95° C. Then 40 PCR cycles for 60 sec at 94° C., 60 sec at 50° C. and 90 sec at 72° C. followed. After further incubation for 20 min at 72° C., the mixture is cooled to 4° C. An aliquot of 2 µl is subjected to agarose gel electrophoresis. The PCR amplificate is purified with the PCR purification kit from Qiagen. 1.7 µg of purified PCR product are obtained.

The PCR amplificate is used as template for a second PCR reaction. The reaction mixture contains 25 pmol of primer TGAATCAGGATCCAAGACGGTGAGAAGG (SEQ ID NO:29), 25 pmol of primer TCCGTTTGGTACCCTACT-CATCAGCCACGG (SEQ ID NO:30), 2 µl of the first PCR amplification, 2 U of Taq DNA polymerase (Eurogentec, Seraing, Belgium) and 20 nmol of dNTPs in a total volume of 100 µl containing 1.5 mM $MgCl_2$, 50 mM KCl, 10 mM Tris-hydrochloride, pH 8.8 and 0.1% (w/w) Triton X-100.

The mixture is denatured for 3 min at 95° C. Then 40 PCR cycles for 60 sec at 94° C., 60 sec at 50° C. and 90 sec at 72° C. follow. After further incubation for 20 min at 72° C., the mixture is cooled to 4° C. An aliquot of 2 µl is subjected to agarose gel electrophoresis. An aliquot of 2 µl is subjected to agarose gel electrophoresis.

The PCR amplificate is purified with PCR purification kit from Qiagen. 1.4 µg of purified PCR product are obtained. 2.0 µg of the vector pQE30 and 1.4 µg of the purified PCR product are digested with BamHI and KpnI in order to produce cohesive ends. The restriction mixtures are prepared according to the conditions supplied by the customer (NEB) and are incubated for 3 h at 37° C. Digested vector DNA and PCR product are purified using the PCR purification kit from Qiagen.

20 ng of vector DNA and 12 ng of PCR product are ligated together with 1 U of T4-Ligase (Gibco), 2 µl of T4-Ligase buffer (Gibco) in a total volume of 10 µl, yielding the plasmid pQEgcpEara. The ligation mixture is incubated over night at 4° C. 2 µl of the ligation mixture is transformed into electrocompetent E. coli XL1-Blue and M15[pREP4] (Zamenhof et al., 1972) cells. The plasmid pQEgcpEara is isolated as described above. 7 µg of plasmid DNA are obtained.

The DNA insert of the plasmid pQEgcpEara is sequenced as described above. The DNA sequence is found not to be identical with the sequence in the database (accession no. dbj AB005246, see FIG. 19).

EXAMPLE 32

Screening of IspG (GcpE) Enzyme Activity 0.2 g cells of XL1-pACYClytBgcpE are suspended in 1 ml 50 mM Tris hydrochloride, pH 7.4 and 2 mM DTT, cooled on ice and sonified 3×7 sec with a Branson Sonifier 250 (Branson SONIC Power Company) set to 80% duty cycle output, control value of 4 output. The suspension is centrifuged at 14000 rpm for 15 minutes. The supernatant is used as crude cell extract in assays described as follows.

The assay mixture contains 100 mM Tris hydrochloride, pH 7.4, 1.2 mM dithiothreitol, 10 mM NaF, 1 mM $CoCl_2$, 2 mM NADH, 20 mM (18 µCi $mol^{-1}$) [2-$^{14}C$□2C-methyl-erythritol 2,4-cyclodiphophate, 0.5 mM pamidronate and 100 µl crude cell extract of XL1-pACYClytBgcpE in a total volume of 150 µl. The mixture is incubated for 10 to 45 min at 37° C. and cooled on ice. 10 µl of 30% (g/v) trichloroacetic acid are added and the mixture is neutralized with 20 µl of 1 M NaOH. The mixture is centrifuged at 14.000 rpm for 10 minutes. Aliquotes of 130 µl of the supernatant are analyzed by reversed-phase ion-pair HPLC using a column of Multospher 120 RP 18-AQ-5 (4.6×250 mm, CS-Chromatographie Service GmbH, Langerwehe, Germany). The column is developed with a linear gradient of 7–21% (v/v) methanol in 20 ml of 10 mM tetra-n-butylammonium hydrogen phosphate, pH 6.0 at a flow rate of 1 ml $min^{-1}$ and further with a linear gradient of 21–49% (v/v) methanol in 15 ml of 10 mM tetra-n-butylammonium hydrogen phosphate, pH 6.0. After washing the column with 49% (v/v) methanol in 5 ml of 10 mM tetra-n-butylammonium hydrogen phosphate, pH 6.0, the column is equilibrated with 7% (v/v) methanol in 20 ml of 10 mM tetra-n-butylammonium hydrogen phosphate, pH 6.0. The effluent is monitored by a continuous-flow radio detector (Beta-RAM, Biostep GmbH, Jahnsdorf, Germany). The retention volumes of 2C-methyl-erythritol 2,4-cyclodiphophate, 1-hydroxy-2-methyl-2-(E)-butenyl-4-diphosphate, DMAPP/IPP are 18, 24 and 39 ml respectively.

After 10 minutes of incubation, about 13% of 2C-methyl-erythritol 2,4-cyclodiphophate have been converted into 1-hydroxy-2-methyl-2-(E)-butenyl-4-diphosphate (5%) and into DMAPP/IPP (8%), respectively.

After 45 min, no 1-hydroxy-2-methyl-2-(E)-butenyl-4-diphosphate, but about 21% of DMAPP/IPP was found in the assay mixture.

EXAMPLE 33

Screening of IspH (LytB) Activity

Assay mixtures contain 100 mM Tris hydrochloride, pH 7.4, 1.2 mM DTT, 10 mM NaF, 0.5 mM NADH, 60 µM FAD, 0.004 µM (18 µCi $pmol^{-1}$) [2-$^{14}C$]1-hydroxy-2-methyl-2-(E)-butenyl-4-diphosphate, 0.5 mM pamidronate (Dunford et al., 2001) and 20 µl of crude cell extract of M15-pMALlytB cells (prepared as described in example 2) in a total volume of 150 µl. The mixture is incubated for 30 min at 37° C. The reaction is terminated by cooling on ice, addition of 10 µl of 30% (g/v) trichloroacetic acid and immediate neutralization with 20 µl 1 M sodium hydroxide. The mixtures are centrifuged and aliquots (130 µl) of the supernatant are analyzed by reversed-phase ion-pair HPLC using a column of Multospher 120 RP 18-AQ-5 (4.6×250 mm, CS-Chromatographie Service GmbH, Langerwehe, Germany) analyzed by reversed-phase ion-pair HPLC using a column of Multospher 120 RP 18-AQ-5 (4.6×250 mm, CS-Chromatographie Service GmbH, Langerwehe, Germany). The column is developed with a linear gradient of 7–21% (v/v) methanol in 20 ml of 10 mM tetra-n-butylammonium hydrogen phosphate, pH 6.0 at a flow rate of 1 ml $min^{-1}$ and further with a linear gradient of 21–49% (v/v) methanol in 15 ml of 10 mM tetra-n-butylammonium hydrogen phosphate, pH 6.0. After washing the column with 49% (v/v) methanol in 5 ml of 10 mM tetra-n-butylammonium hydrogen phosphate, pH 6.0, the column is equilibrated with 7% (v/v) methanol in 20 ml of 10 mM tetra-n-butylammonium hydrogen phosphate, pH 6.0. The effluent is monitored by a continuous-flow radio detector (Beta-RAM, Biostep GmbH, Jahnsdorf, Germany).

Under standard assay conditions, the HPLC peak corresponding to the substrate 1-hydroxy-2-methyl-2-(E)-butenyl 4-diphosphate is completely diminished, whereas two new peaks corresponding to DMAPP and IPP appear, when crude cell extract of *E. coli* M15-pMALlytB cells is used as protein source. No conversion of 1-hydroxy-2-methyl-2-(E)-butenyl 4-diphosphate into DMAPP and IPP can be observed, when crude cell extract of *E. coli* wild-type is used as protein source. This findings clearly show that the FAD and NADH- or NADPH-dependent conversion of 1-hydroxy-2-methyl-2-(E)-butenyl 4-diphosphate into DMAPP and IPP is catalyzed by the recombinant LytB protein. The addition of pamidronate in the assay mixtures prevents a further metabolization of IPP and DMAPP by highly active prenyl transferases present in crude *E. coli* extracts and affects therefore the complete conversion of 1-hydroxy-2-methyl-2-(E)-butenyl 4-diphosphate into DMAPP and IPP.

EXAMPLE 34

Construction of a Vector Carrying the dxs, xylB and ispC Genes Capable for the Transcription and Expression Thereof The *B. subitis* ORF dxs (accession no. dbj D84432) from base pair (bp) position 193991 to 195892 is amplified by PCR using pBSDXSBACSU plasmid DNA as template (see patent application PCT/EP00/07548). The reaction mixture contains 10 pmol of the primer 5'-GGCGACTCGC-GAGAGGAGAAATTAACCATGGATCTTT-TATCAATACAGGACC-3' (SEQ ID NO:31), 10 pmol of the primer 5'-GGCACCCGGCCGTCATGATCCAATTC-CTTTGTGTG-3' (SEQ ID NO:32), 20 ng DNA of pBSDX-SBACSU plasmid, 2 U of Taq DNA polymerase (Eurogentec) and 20 nmol of dNTPs in a total volume of 100 µl containing 1.5 mM $MgCl_2$, 50 mM KCl, 10 mM Tris-hydrochloride, pH 8.8 and 0.1% (w/w) Triton X-100.

The mixture is denaturated for 3 min at 94° C. Then 30 PCR cycles for 60 sec at 94° C., 60 sec at 50° C. and 120 sec at 72° C. followed. After further incubation for 10 min at 72° C., the mixture is cooled to 4° C. An aliquot of 2 µl is subjected to agarose gel electrophoresis. The PCR amplificate is purified with the PCR purification kit from Qiagen (Hilden).

2.4 µg of the vector pACYC184 (Chang and Cohen 1978, NEB) and 1.8 µg of the purified PCR product are digested with NruI and EagI in order to produce DNA fragments with overlapping ends. The restriction mixtures are prepared according to the conditions supplied by the customer (NEB) and are incubated for 3 h at 37° C. Digested vector DNA and PCR product are purified using the PCR purification kit from Qiagen.

20 ng of the purified vector DNA and 19 ng of the purified PCR product are ligated together with 1 U of T4-Ligase (Gibco), 2 µl of T4-Ligase buffer (Gibco) in a total volume of 10 µl, yielding the plasmid pACYCdxs. The ligation mixture is incubated for 2 h at 25° C. 1 µl of the ligation mixture is transformed into electrocompetent *E. coli* XL1-Blue cells. The plasmid pACYCdxs is isolated with the plasmid isolation kit from Qiagen.

The DNA insert of the plasmid pACYCdxs is sequenced by the automated dideoxynucleotide method using an ABI Prism 377™ DNA sequencer from Perkin Elmer with the ABI Prism™ Sequencing Analysis Software from Applied Biosystems Divisions. It is identical with the DNA sequence of the database entry (dbj D84432).

2.0 µg of the vector pACYCdxs and 8 µg of the vector pBScyclo (see example XXx) are digested with EagI and SalI in order to produce DNA fragments with overlapping ends. The restriction mixtures are prepared according to the conditions supplied by the customer (NEB) and are incubated for 3 h at 37° C. Digested vector DNA and PCR product are purified using the PCR purification kit from Qiagen.

20 ng of the digested and purified pACYCdxs vector DNA and 30 ng of a by DNA electrophoresis separated and purified 2.7 kb EagI/SalI fragment (containing the ORFs xylB and ispC from *E. coli*) are ligated together with 1 U of T4-Ligase (Gibco), 2 µl of T4-Ligase buffer (Gibco) in a total volume of 10 µl, yielding the plasmid pACYCdxsxylBispC. The ligation mixture is incubated for 2 h at 25° C. 1 µl of the ligation mixture is transformed into electrocompetent *E. coli* XL1-Blue cells. The plasmid pACYCdxsxylBispC is isolated with the plasmid isolation kit from Qiagen.

The DNA insert of the plasmid pACYCdxsxylBispC is sequenced by the automated dideoxynucleotide method using an ABI Prism 377™ DNA sequencer from Perkin Elmer with the ABI Prism™ Sequencing Analysis Software from Applied Biosystems Divisions.

EXAMPLE 35

Construction of a Vectors Carrying the dxs, xylB, ispC, and ispG and Optionally ispH Genes Capable for the Transcription and Expression Thereof The *E. coli* ORF ispH (lytB) (accession no. gb AE000113) from base pair (bp) position 5618 to 6568 is amplified by PCR using chromosomal *E. coli* DNA as template. The reaction mixture contains 10 pmol of the primer 5'-GCT-TGCGTCGACGAGGAGAAATTAACCATG-CAGATCCTGTTGGCCACC-3' (SEQ ID NO:33), 10 pmol of the primer 5'-GCTGCTCTCGAGTTAATCGACTTCAC-GAATATCG-3' (SEQ ID NO:34), 20 ng of chromosomal DNA, 2 U of Taq DNA polymerase (Eurogentec) and 20 nmol of dNTPs in a total volume of 100 µl containing 1.5 mM $MgCl_2$, 50 mM KCl, 10 mM Tris-hydrochloride, pH 8.8 and 0.1% (w/w) Triton X-100.

The mixture is denaturated for 3 min at 94° C. Then 30 PCR cycles for 45 sec at 94° C., 45 sec at 50° C. and 60 sec at 72° C. followed. After further incubation for 10 min at 72° C., the mixture is cooled to 4° C. An aliquot of 2 µl is subjected to agarose gel electrophoresis. The PCR amplificate is purified with the PCR purification kit from Qiagen (Hilden).

2.5 µg of the vector pACYCdxsxylBispC (see example 34) are linearized with SalI and 0.9 µg of the purified PCR product are digested with SalI and XhoI in order to produce DNA fragments with overlapping ends. The restriction mixtures are prepared according to the conditions supplied by the customer (NEB) and are incubated for 3 h at 37° C. Digested vector DNA and PCR product are purified using the PCR purification kit from Qiagen.

15 ng of the purified vector DNA and 18 ng of the purified PCR product are ligated together with 1 U of T4-Ligase (Gibco), 2 µl of T4-Ligase buffer (Gibco) in a total volume of 10 µl, yielding the plasmid pACYCdxsxylBispClytB. The ligation mixture is incubated for 2 h at 25° C. 1 µl of the ligation mixture is transformed into electrocompetent *E. coli* XL1-Blue cells. The plasmid pACYCdxsxylBispClytB is isolated with the plasmid isolation kit from Qiagen.

The DNA insert of the plasmid pACYCdxsxylBispClytB is sequenced by the automated dideoxynucleotide method using an ABI Prism 377™ DNA sequencer from Perkin Elmer with the ABI Prism™ Sequencing Analysis Software from Applied Biosystems Divisions. It is identical with the DNA sequence of the database entry (gb AE000113).

The *E. coli* ORF ispG (gcpE) (accession no. gb AE000338) from base pair (bp) position 372 to 1204 is amplified by PCR using chromosomal *E. coli* DNA as template. The reaction mixture contains 10 pmol of the primer 5'-GGTCGAGTCGACGAGGAGAAATTAAC-CATGCATAACCAGGCTCCAATTC-3' (SEQ ID NO:35), 10 pmol of the primer 5'-CCCATCCTCGAGT-TATTTTTCAACCTGCTGAACGTC-3' (SEQ ID NO:36), 20 ng of chromosomal DNA, 2 U of Taq DNA polymerase (Eurogentec) and 20 nmol of dNTPs in a total volume of 100 µl containing 1.5 mM $MgCl_2$, 50 mM KCl, 10 mM Tris-hydrochloride, pH 8.8 and 0.1% (w/w) Triton X-100.

The mixture is denatured for 3 min at 94° C. Then 30 PCR cycles for 60 sec at 94° C., 60 sec at 50° C. and 90 sec at 72° C. followed. After further incubation for 10 min at 72° C., the mixture is cooled to 4° C. An aliquot of 2 µl is subjected to agarose gel electrophoresis.

The PCR amplificate is purified with the PCR purification kit from Qiagen (Hilden).

Each 2.0 µg of the vectors pACYCdxsxylBispC (see example 34) and pACYCdxsxylBispClytB (see above) are linearized with SalI and 1.1 µg of the purified PCR product are digested with SalI and XhoI in order to produce DNA fragments with overlapping ends. The restriction mixtures are prepared according to the conditions supplied by the customer (NEB) and are incubated for 3 h at 37° C. Digested vector DNA and PCR product are purified using the PCR purification kit from Qiagen.

18 ng of the purified vector DNAs and 23 ng of the purified PCR product are ligated together with 1 U of T4-Ligase (Gibco), 2 µl of T4-Ligase buffer (Gibco) in a total volume of 10 µl, yielding the plasmids pACYCdxsxy-lBispCgcpE and pACYCdxsxylBispClytBgcpE. The ligation mixtures are incubated for 2 h at 25° C. 1 µl of the ligation mixture is transformed into electrocompetent *E. coli* XL1-Blue cells. The plasmids pACYCdxsxylBispCgcpE and pACYCdxsxylBispClytBgcpE are isolated with the plasmid isolation kit from Qiagen.

The DNA inserts of the plasmids pACYCdxsxyl-BispCgcpE and pACYCdxsxylBispClytBgcpE are sequenced by the automated dideoxynucleotide method using an ABI Prism 377™ DNA sequencer from Perkin Elmer with the ABI Prism™ Sequencing Analysis Software from Applied Biosystems Divisions. They are identical with the DNA sequence of the database entry (gb AE000338).

EXAMPLE 36

Incorporation Experiment with Recombinant *Escherichia coli* XL1-pACYCdxsxylBispCgcpE Using [U—$^{13}C_6$]glucose 0.2 liter of Terrific Broth (TB) medium containing 5 mg of chloramphenicol are inoculated with *E. coli* strain XL1-Blue harbouring the plasmid pACYCdxsxylBispCgcpE. The cells are grown in a shaking culture at 37° C. overnight. At an optical density (600 nm) of 1.7–2.4 a solution containing 1 g of lithium lactate (10 mmol), 200 mg [U—$^{13}C_6$]glucose (1.1 mmol) at a final volume of 24 ml (pH=7.4) are added continuously within 2 hours. Then, after 1 hour an aliquot of 40 ml was taken and centrifuged for 20 min at 5,000 rpm and 4° C. The cells are washed with water containing 0.9% NaCl and centrifuged as described above. The cells are suspended in 700 µl of a mixture of methanol-$d_4$ and $D_2O$ (6:4, v/v) containing 10 mM NaF, cooled on ice and sonified 3×10 sec with a Branson Sonifier 250 (Branson SONIC Power Company) set to 90% duty cycle output, control value of 4 output. The suspension is centrifuged at 15,000 rpm for 15 min. NMR spectra of the cell free extracts are recorded directly with a Bruker AVANCE DRX 500 spectrometer (Karlsruhe, Germany). In order to avoid degradation during work-up, the structures of the products are determined by NMR spectroscopy without further purification.

The $^{13}$C-NMR spectra showed signals accounting for 1-hydroxy-2-methyl-2-(E)-butenyl 4-diphosphate (cf. Tables 2 and 4, example 18) as major product. A formation of 2C-methyl-D-erythritol 2,4-cylodiphosphate could not be detected.

EXAMPLE 37

Incorporation Experiment with Recombinant *Escherichia coli* XL1-pACYCdxsxylBispClytBgcpE Using Glucose Example 36 can be carried out with recombinant *Escherichia coli* XL1-pACYCdxsxylBispClytBgcpE using glucose for converting glucose to isopentenyl diphosphate and/or dimethylallyl diphosphate.

EXAMPLE 38

Cloning of the ispG Gene of *Escherichia coli* and Expression as Maltose Binding Fusion Protein (MBP-lspG)

The *E. coli* ORF ispG (gcpE) (accession no. gb AE000338) from base pair (bp) position 372 to 1204 is amplified by PCR using chromosomal *E. coli* DNA as template. The reaction mixture contains 10 pmol of the primer 5'-GAACCGGAATTCATGCATAACCAGGCTC-CAATTC-3' (SEQ ID NO:37), 10 pmol of the primer 5'-CGAGGCGGATCCCATCACG-3' (SEQ ID NO:38), 20 ng of chromosomal DNA, 2 U of Taq DNA polymerase (Eurogentec) and 20 nmol of dNTPs in a total volume of 100 µl containing 1.5 mM $MgCl_2$, 50 mM KCl, 10 mM Tris-hydrochloride, pH 8.8 and 0.1% (w/w) Triton X-100.

The mixture is denatured for 3 min at 94° C. Then 30 PCR cycles for 60 sec at 94° C., 60 sec at 50° C. and 90 sec at 72° C. followed. After further incubation for 10 min at 72° C., the mixture is cooled to 4° C. An aliquot of 2 µl is subjected to agarose gel electrophoresis.

The PCR amplificate is purified with the PCR purification kit from Qiagen (Hilden).

2.2 µg of the vector pMAL-C2 (NEB) and 0.8 µg of the purified PCR product are digested with EcoRI and BamHI in order to produce DNA fragments with overlapping ends. The restriction mixtures are prepared according to the conditions supplied by the customer (NEB) and are incubated for 3 h at 37° C. Digested vector DNA and PCR product are purified using the PCR purification kit from Qiagen.

20 ng of the purified vector DNA and 15 ng of the purified PCR product are ligated together with 1 U of T4-Ligase (Gibco), 2 µl of T4-Ligase buffer (Gibco) in a total volume of 10 µl, yielding the plasmid pMALgcpE. The ligation mixture is incubated for 2 h at 25° C. 1 µl of the ligation mixture is transformed into electrocompetent *E. coli* XL1-Blue cells. The plasmid pMALgcpE is isolated with the plasmid isolation kit from Qiagen.

The DNA insert of the plasmid pMALgcpE is sequenced by the automated dideoxynucleotide method using an ABI Prism 377™ DNA sequencer from Perkin Elmer with the ABI Prism™ Sequencing Analysis Software from Applied Biosystems Divisions. It is identical with the DNA sequence of the database entry (gb AE000338).

EXAMPLE 39

Cloning of the ispH Gene of Escherichia coli and Expression as Maltose Binding Fusion Protein (MBP-lspH)

The E. coli ORF ispH (lytB) (accession no. gb AE000113) from base pair (bp) position 5618 to 6568 is amplified by PCR using chromosomal E. coli DNA as template. The reaction mixture contains 10 pmol of the primer 5'-TGGAGGGGATCCATGCAGATCCTGTTGGCCACC-3' (SEQ ID NO:39), 10 pmol of the primer 5'-GCATTTCTGCAGAACTTAGGC-3' (SEQ ID NO:40), 20 ng of chromosomal DNA, 2 U of Taq DNA polymerase (Eurogentec) and 20 nmol of dNTPs in a total volume of 100 µl containing 1.5 mM $MgCl_2$, 50 mM KCl, 10 mM Tris-hydrochloride, pH 8.8 and 0.1% (w/w) Triton X-100.

The mixture is denatured for 3 min at 94° C. Then 30 PCR cycles for 45 sec at 94° C., 45 sec at 50° C. and 60 sec at 72° C. followed. After further incubation for 10 min at 72° C., the mixture is cooled to 4° C. An aliquot of 2 µl is subjected to agarose gel electrophoresis.

The PCR amplificate is purified with the PCR purification kit from Qiagen (Hilden).

2.2 µg of the vector pMAL-C2 (NEB) and 0.7 µg of the purified PCR product are digested with BamHI and PstI in order to produce DNA fragments with overlapping ends. The restriction mixtures are prepared according to the conditions supplied by the customer (NEB) and are incubated for 3 h at 37° C. Digested vector DNA and PCR product are purified using the PCR purification kit from Qiagen.

20 ng of the purified vector DNA and 14 ng of the purified PCR product are ligated together with 1 U of T4-Ligase (Gibco), 2 µl of T4-Ligase buffer (Gibco) in a total volume of 10 µl, yielding the plasmid pMALlytB. The ligation mixture is incubated for 2 h at 25° C. 1 µl of the ligation mixture is transformed into electrocompetent E. coli XL1-Blue cells. The plasmid pMallytB is isolated with the plasmid isolation kit from Qiagen.

The DNA insert of the plasmid pMALlytB is sequenced by the automated dideoxynucleotide method using an ABI Prism 377™ DNA sequencer from Perkin Elmer with the ABI Prism™ Sequencing Analysis Software from Applied Biosystems Divisions. It is identical with the DNA sequence of the database entry (gb AE000113).

EXAMPLE 40

Preparation and Purification of Recombinant lspG Maltose Binding Fusion Protein (MRP-lspG)

0.5 liter of Luria Bertani (LB) medium containing 90 mg of ampicillin are inoculated with 10 ml of an overnight culture of E. coli strain XL1-Blue harboring plasmid pMAL-gcpE. The culture is grown in a shaking culture at 37° C. At an optical density (600 nm) of 0.7, the culture is induced with 2 mM IPTG. The culture is grown for further 5 h. The cells are harvested by centrifugation for 20 min at 5,000 rpm and 4° C. The cells are washed with 20 mM Tris hydrochloride pH 7.4, centrifuged as above and frozen at –20° C. for storage.

2 g of the cells are thawed in 20 ml of 20 mM Tris hydrochloride pH 7.4, 0.2 M sodium chloride and 0.02% (g/v) sodium acide (buffer A) in the presence of 1 mg $ml^{-1}$ lysozyme and 100 µg $ml^{-1}$ DNaseI. The mixture is incubated at 37° C. for 30 min, cooled on ice and sonified 6×10 sec with a Branson Sonifier 250 (Branson SONIC Power Company) set to 70% duty cycle output, control value of 4 output. The suspension is centrifuged at 15,000 rpm at 4° C. for 30 min. The cell free extract is applied on a column of amylose resin FF (column volume 25 ml, NEB) previously equilibrated with buffer A at a flowrate of 2 ml $min^{-1}$. The column is washed with 130 ml of buffer A. MRP-lspG is eluted with a linear gradient of 0–10 mM maltose in buffer A. MRP-lspG containing fractions are combined according to SDS-PAGE and dialyzed overnight against 100 mM Tris hydrochloride pH 7.4. The homogeneity of MRP-lspG is judged by SDS-PAGE. One band at 84 kDa is visible, which is in line with the calculated molecular mass. The yield of pure MRP-lspG is 9 mg.

EXAMPLE 41

Preparation and Purification of Recombinant lspH Maltose Binding Fusion Protein (MRP-lspH)

0.5 liter of Luria Bertani (LB) medium containing 90 mg of ampicillin are inoculated with 10 ml of an overnight culture of E. coli strain XL1-Blue harboring plasmid pMAL-lytB. The culture is grown in a shaking culture at 37° C. At an optical density (600 nm) of 0.7, the culture is induced with 2 mM IPTG. The culture is grown for further 5 h. The cells are harvested by centrifugation for 20 min at 5,000 rpm and 4° C. The cells are washed with 20 mM Tris hydrochloride pH 7.4, centrifuged as above and frozen at –20° C. for storage.

2 g of the cells are thawed in 20 ml of 20 mM Tris hydrochloride pH 7.4, 0.2 M sodium chloride and 0.02% (g/v) sodium acide (buffer A) in the presence of 1 mg $ml^{-1}$ lysozyme and 100 µg $ml^{-1}$ DNaseI. The mixture is incubated at 37° C. for 30 min, cooled on ice and sonified 6×10 sec with a Branson Sonifier 250 (Branson SONIC Power Company) set to 70% duty cycle output, control value of 4 output. The suspension is centrifuged at 15,000 rpm at 4° C. for 30 min. The cell free extract is applied on a column of amylose resin FF (column volume 25 ml, NEB) previously equilibrated with buffer A at a flowrate of 2 ml $min^{-1}$. The column is washed with 130 ml of buffer A. MRP-lspH is eluted with a linear gradient of 0–10 mM maltose in buffer A. MRP-lspH containing fractions are combined according to SDS-PAGE and dialyzed overnight against 100 mM Tris hydrochloride pH 7.4. The homogeneity of MRP-lspH is judged by SDS-PAGE. One band at 78 kDa is visible, which is in line with the calculated molecular mass. The yield of pure MRP-lspH is 14 mg.

EXAMPLE 42

Figure 7:
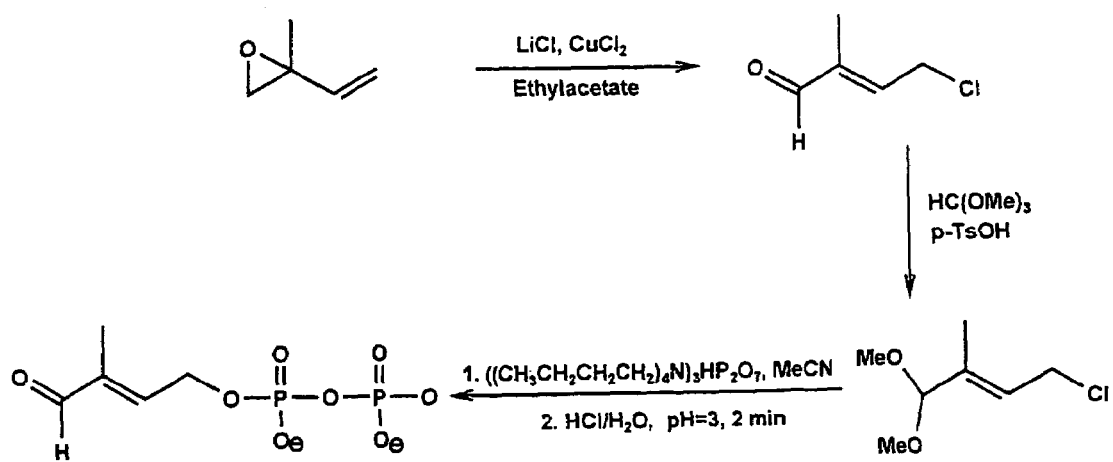
FIG. 7: Chemical preparation of 3-formyl-but-2-enyl 1-diphosphate (see example 42).

Synthesis of 1-hydroxy-2-methyl-but-2-enyl-4-diphosphate (see FIG. 7)

4-Chloro-2-methyl-2-buten-1-al (Choi et al. (1999) J. Org. Chem. 64, 8051–8053)

A solution containing 1.17 ml of 2-methyl-2-vinyl-oxirane (12 mmol), 1.6 g of $CuCl_2$ (12 mmol) and 510 mg of LiCl (12 mmol) in 10 ml of ethylactetate was heated to 80° C. for 30 min. The reaction was stopped by adding 50 g of ice. The mixture was filtered through a sintered glass funnel under reduced pressure. 100 ml of $CH_2Cl_2$ was added and the organic phase was separated. The aqueous layer was extracted two times with 100 ml of $CH_2Cl_2$. The combined organic phase was dried over anhydrous $MgSO_4$, filtered, and concentrated. The crude product was purified by chromatography over silica gel ($CH_2Cl_2$, 3×37 cm) to yield 0.755 g of a yellow liquid (6.4 mmol, 53%).

$^1$H NMR ($CDCl_3$, 500 MHz) δ 9.43 (s, 1H), 6.50 (t, J=7.5 Hz, 1H), 4.24 (d, J=7.5 Hz, 2H), 1.77 (s, 3H)

$^{13}$C NMR ($CDCl_3$, 125 MHz) δ 194.3, 145.7, 141.1, 38.6, 9.1

4-Chloro-2-methyl-2-buten-1-al-dimethyl-acetal

A solution of 184 mg 4-chloro-2-methyl-2-buten-1-al (1.55 mmol), 600 μl of HC(OMe)$_3$ (5.6 mmol) and a catalytic amount of p-TsOH was incubated for 3 h at room temperature. The crude mixture was purified by chromatography over silica gel (n-hexane/ethylacetate 7:3) to yield 177 mg of a colourless liquid (1.08 mmol, 72%).

$^1$H NMR ($CDCl_3$, 500 MHz) δ 5.78 (t, 1H, J=7.9), 4.47 (s, 1H), 4.15 (d, J=7.9 Hz, 2H), 3.33 (s, 6H), 1.73 (s, 3H)

$^{13}$C NMR ($CDCl_3$ 125 MHz) δ 137.6, 124.4, 106.0, 53.5, 39.6, 11.4

(E)-3-Formyl-2-buten-1-diphosphate triammonium salt (Davisson et al. (1986) *J. Org. Chem.*, 51, 4768) To a solution of 4-chloro-2-methyl-2-buten-1-al-dimethyl-acetal chloride (25 mg, 0.15 mmol) in 250 μl of MeCN a solution of 0.162 g (0.18 mmol) of tris(tetra-n-butylammonium) hydrogen pyrophosphate in 400 μL of MeCN was added slowly at room temperature, leading to an orange-red solution. After 2 h the reaction was finished and the solvent was removed under reduced pressure. The orange oil was dissolved in 3 mL of $H_2O$ and passed through a column of DOWEX 50 WX8 (1□4 cm) cation-exchange resin ($NH_4^+$ form) that has been equilibrated with 20 mL of 25 mM $NH_4HCO_3$. The column was eluted with 20 mL of 25 mM $NH_4HCO_3$. The resulting solution was lyophilized. The obtained solid was dissolved in 2 ml water and acidified with aqueouus HCl to pH=3. After 2 minutes the solution was neutralized and lyophylisized.

$^1$H NMR ($D_2O$, 360 MHz) δ 9.37 (s, 1H), 6.86 (t, 1H, 5.6 Hz), 4.85 (dd, J=7.9, J=5.8 Hz, 2H), 1.72 (s, 3H)

$^{13}$C NMR ($D_2O$, 90 MHz) δ 199.2, 153.1 (d, J=7.5 Hz), 138.5, 63.2 (d, J=4.9), 8.5

[1-$^3$H]1-hydroxy-2-methyl-but-2-enyl-4-diphosphate

A solution containing 50 mCi (15 μmol) NaBH$_3$T, 15 μmol 3-formyl-2-buten-1-diphosphate triammonium salt and 100 mM Tris/HCl pH=8 was incubated for 30 minutes at room temperature. The solution was acidified by adding 1 M HCl to pH=2. After 2 minutes the solution was neutralizied by adding 1 M NaOH.

The product was characterizied by ion-exchange chromatography (see examples 20 and 25).

EXAMPLE 43

γδ T Cell Stimulation Assays

PBMCs from healthy donors (donor A and donor B) are isolated from heparinized peripheral blood by density centrifugation over Ficoll-Hypaque (Amersham Pharmacia Biotech, Freiburg, Germany). 5×10$^5$ PBMCs/well are cultivated in 1 mL RPMI 1640 medium supplemented with 10% human AB serum (Klinik rechts der Isar, München, Germany), 2 mM L-glutamine, 10 μM mercaptoethanol. Amounts of recombinant human IL-2 (kindly provided by Eurocetus, Amsterdam, The Netherlands) and substrates are varied from 1 to 10 U and 10 to 0.1 μM, respectively. 20 μM IPP (Echelon, Research Laboratories Inc., Salt Lake City, USA) serves as a positive control whereas medium alone serves as negative control. Incubation is done for seven days at 37° C. in the presence of 7% $CO_2$. The harvested cells are double-stained with fluorescein isothiocyanate (FITC)-conjugated mouse anti-human monoclonal antibody Vδ2 TCR and phycoerythrin (PE)-conjugated monoclonal CD3 antibody. The cells are analyzed using a FACScan supported with Cellquest (Becton Dickinson, Heidelberg, Germany).

The substrates (E)-1-hydroxy-3-methyl-but-2-enyl 4-diphosphate (HMBPP) and 3-formyl-but-2-enyl 1-diphosphate (Aldehyde) were prepared synthetically as described above.

It is found that both synthetically prepared substrates (HMBPP and Aldehyde) show at least double stimulation compared to IPP when used at a concentration that is 200-fold lower than the concentration of the IPP sample (Table 8).

TABLE 8

Activation of γδT-cells by phosphororganic compounds

| Substrate | Concentration [μM] | IL-2 [U] | % γδT-cells Donor A | % γδT-cells Donor B |
|---|---|---|---|---|
| Medium | — | 1 | 1.51 | 2.75 |
| Medium | — | 5 | 1.45 | 2.23 |
| Medium | — | 10 | 1.32 | 1.68 |
| IPP | 20 | 1 | 8.19 | 6.24 |
| IPP | 20 | 5 | 14.42 | 9.32 |
| IPP | 20 | 10 | 16.6 | 11.86 |
| IPP | 1 | 1 | 1.56 | 2.22 |
| IPP | 1 | 5 | 1.59 | 2.67 |
| IPP | 1 | 10 | 1.71 | 2.19 |
| IPP | 0.1 | 1 | 1.3 | 2.15 |
| IPP | 0.1 | 5 | 1.3 | 2.26 |
| IPP | 0.1 | 10 | 1.01 | 2.54 |
| HMBPP | 10 | 1 | 3.3 | 31.42 |
| HMBPP | 10 | 5 | 17.38 | 63.48 |
| HMBPP | 10 | 10 | 24.94 | 63.34 |
| HMBPP | 1 | 1 | 5.57 | 35.34 |
| HMBPP | 1 | 5 | 14.4 | 54.12 |
| HMBPP | 1 | 10 | 19.85 | 55.90 |
| HMBPP | 0.1 | 1 | 11.78 | 32.21 |
| HMBPP | 0.1 | 5 | 22.92 | 44.69 |
| HMBPP | 0.1 | 10 | 34.69 | 36.33 |
| HMBPP/IPP | 0.5/0.5 | 1 | 7 | 30.35 |
| HMBPP/IPP | 0.5/0.5 | 5 | 15.38 | 53.76 |
| HMBPP/IPP | 0.5/0.5 | 10 | 24.19 | 46.58 |
| Aldehyd | 10 | 1 | 12.19 | 30.69 |
| Aldehyd | 10 | 5 | 34.69 | 30.33 |
| Aldehyd | 10 | 10 | 38.99 | 38.85 |
| Aldehyd | 1 | 1 | 15.91 | 21.18 |
| Aldehyd | 1 | 5 | 40.13 | 30.76 |
| Aldehyd | 1 | 10 | 48.28 | 36.69 |
| Aldehyd | 0.1 | 1 | 10 | 13.54 |
| Aldehyd | 0.1 | 5 | 19.77 | 18.45 |
| Aldehyd | 0.1 | 10 | 21.93 | 25.82 |
| Aldehyd/IPP | 0.5/0.5 | 1 | 13.98 | 22.11 |
| Aldehyd/IPP | 0.5/0.5 | 5 | 33.94 | 32.06 |
| Aldehyd/IPP | 0.5/0.5 | 10 | 42.84 | 36.25 |

IPP: isopentenyl diphosphate
HMBPP: (E)-1-hydroxy-3-methyl-but-2-enyl 4-diphosphate
Aldehyd: (E)-3-formyl-but-2-enyl 1-diphosphate (prepared according to example 42)

EXAMPLE 44

High Through-Put Screening Assay of 1-hydroxy-2-methyl-2-(E)-butenyl 4-diphosphate Synthase (lspG) Activity Assay mixtures contain 20 mM potassium phosphate, pH 7.0, 0.4 mM NADH, 0.5 mM $CoCl_2$, 0.2 mM 2C-methyl-D-erythritol 2,4-cyclodiphosphate, and 50 µl protein in a total volume of 1 ml. The mixtures are incubated at 37° C. The oxidation of NADH is monitored photometrically at 340 nm. Alternatively, the concentration of NADH is determined by measuring the relative fluorescence of NADH at 340 nm excitation/460 nm emission.

EXAMPLE 45

High Through-Put Screening Assay of 1-hydroxy-2-methyl-2-(E)-butenyl 4-diphosphate Reductase (lspH) Activity Assay mixtures contain 20 mM potassium phosphate, pH 7.0, pH 8.0, 0.4 mM NADH, 20 µM FAD, 0.5 mM $CoCl_2$, 0.2 mM 1-hydroxy-2-methyl-2-(E)-butenyl 4-diphosphate, and 50 µl protein in a total volume of 1 ml. The mixtures are incubated at 37° C. The oxidation of NADH is monitored photometrically at 340 nm. Alternatively, the concentration of NADH is determined by measuring the relative fluorescence of NADH at 340 nm excitation/460 nm emission.

REFERENCES

Altincicek, B., Kollas, A. K., Sanderbrand, S., Wiesner, J., Hintz, M., Beck, E. & Jomaa, H. (2001). GcpE Is Involved in the 2-C-Methyl-D-Erythritol 4-Phosphate Pathway of Isoprenoid Biosynthesis in *Escherichia coli*. *J. Bacteriol.* 183, 2411–2416.

Altincicek, B. et al. and Jomaa, H. (2001) *J. Immunology*, 166, 3655–3658.

Arigoni D. & Schwarz M. K. (1999) Ginkgolide biosynthesis. In *Comprehensive natural product chemistry* (Barton D. and Nakanishi K., eds.), Vol. 2, pp. 367–399, Pergamon.

Begley, T. P., Downs, D. M., Ealick, S. E., McLafferty, F. W., VanLoon, A. P. G. M., Taylor, S., Campobasso, N., Chiu, H.-J., Kinsland, C., Reddick, J. J. & Xi, J. (1999) Thiamin biosynthesis in prokaryotes. *Arch. Microbiol.* 171, 293–300.

Blagg, B. S. J. & Poulter, C. D. (1999) Synthesis of 1-deoxy-D-xylulose and 1-deoxy-D-xylulose 5-phosphate. J. Org. Chem. 64, 1508–1511.

Bullock, W. O., Fernandez, J. M., & Short, J. M. (1987). XL1-Blue: a high efficiency plasmid transforming recA *Escherichia coli* with β-galactosidase selection. BioTechniques 5, 376–379.

Camara, B. *Methods in Enzymology* 1985, eds. Law, J. H. & Rilling, H. C. (Academic Press, London) Vol. 110, pp. 267–273.

Camara, B. *Methods in Enzymology* 1993, ed. Packer, L. (Academic Press, London) Vol. 214, pp. 352–365.

Campos, N., Rodriguez-Concepcion, M., Seemann, M., Rohmer, M. and Boronat, A. (2001) Identification of gcpE as a novel gene of the 2-C-methyl-D-erythritol 4-phosphate pathway for isoprenoid biosynthesis in *Escherichia coli*. *FEBS Lett.* 488, 170–173.

Chang, A. C. Y. & Cohen, S. N. (1978) Construction and characterization of amplifiable multicopy DNA cloning vehicles derived from the P15A cryptic miniplasmid. *J. Bacteriol.* 134, 1141–1145.

Cunningham, F. X. Jr., Lafond, T. P. & Gantt E. (2000). Evidence of a role for LytB in the nonmevalonate pathway of isoprenoid biosynthesis. *J. Bacteriol.* 182, 5841–5848.

Davisson, V. J.; Woodside, A. B.; Neal, T. R.; Stremler, K. E.; Muehlbacher, M.; Poulter, C. D. *J. Org. Chem.* 1986, 51, 4768.

Dower, W. J., Miller, J. F., & Ragsdale, C. (1988). High efficiency transformation of *E. coli* by high voltage electroporation. *Nucleic Acids Res.* 16, 6127–6145.

Eisenreich, W., Rohdich, F. & Bacher, A. (2001) Deoxyxylulose phosphate pathway to terpenoids. *Trends in Plant Science* 6, 78–84.

Fournié, J. J. and Bonneville, M. (1996) Res. Immunol. 147, 338–347.

Giner, J.-L. (1998) New and efficient synthetic routes to 1-deoxy-D-xylulose. *Tetrahedron Lett.* 39, 2479–2482.

Hagiwara, H.; Uda, H. *J. Chem. Soc. Trans. I* 1984, 91.

Hwang, C. K.; Li, W. S.; Nicolaou, K. C. *Tetrahedron Lett.* 1984, 25, 2295.

Herz, S., Wungsintaweekul, J., Schuhr, C. A., Hecht, S., Lüttgen, H., Sagner, S., Fellermeier, M., Eisenreich, W., Zenk, M. H., Bacher, A. & Rohdich, F. (2000). Biosynthesis of terpenoids: YgbB protein converts 4-diphosphocytidyl-2C-methyl-D-erythritol 2-phosphate to 2C-methyl-D-erythritol 2,4-cyclodiphosphate. *Proc. Natl. Acad. Sci. USA* 97, 2486–2490.

Jomaa, H., Feurle, J., Lühs, K., Kunzmann, V., Tony, H. P., Herderich, M. and Wilhelm, M. (1999) *FEMS Immunology and Medical Microbiology* 25, 371–378.

Kennedy, I. A., Hemscheidt, T., Britten, J. F., Spenser, I. D. (1995) 1-Deoxy-D-xylulose *Can. J. Chem.* 73, 1329–1333.

Lüttgen, H., Rohdich, F., Herz, S., Wungsintaweekul, J., Hecht, S., Schuhr, C. A., Fellermeier, M., Sagner, S., Zenk, M. H., Bacher, A. & Eisenreich, W. (2000). Biosynthesis of terpenoids: YchB protein of *Escherichia Coli* phosphorylates the 2-hydroxy group of 4-diphosphocytidyl-2C-methyl-D-erythritol. *Proc. Natl. Acad. Sci. USA* 97, 1062–1067.

Meade, H. M., Long, S. R., Ruvkun, C. B., Brown, S. E., & Auswald, F. M. (1982). Physical and genetic characterization of symbiotic and auxotrophic mutants of *Rhizobium meliloti* induced by transposon Tn5 mutagenis. *J. Bacteriol.* 149, 114–122.

Piel, J. & Boland, W. (1997) Highly efficient and versatile synthesis of isotopically labeled 1-deoxy-D-xylulose *Tetrahedron Lett.* 38, 6387–6390.

Rohdich, F., Wungsintaweekul, J., Fellermeier, M., Sagner, S., Herz, S., Kis, K., Eisenreich, W., Bacher, A & Zenk, M. H. (1999). Cytidine 5′-triphosphate biosynthesis of isoprenoids: YgbP protein of *Escherichia coli* catalyzes the formation of 4-diphosphocytidyl-2C-methylerythritol. *Proc. Nat. Acad. Sci. USA* 96, 11758–11763.

Sanger, F., Nicklen, S., & Coulson, A. R. (1992). DNA sequencing with chain-terminating inhibitors. *Biotechnology* 24, 104–8.

Shono, T., Matsumura, Y., Hamaguchi, H. & Naitoh, S. (1983) Synthesis of 2-methyl-3-hydroxy-4H-pyrane-4-one and 4-hydroxy-5-methyl-2H-furane-3-one from carbohydrates. *J. Org. Chem.* 48, 5126–5128.

Takahashi, S., Kuzuyama, T., Watanabe H. & Seto, H. (1998) A 1-deoxy-D-xylulose 5-phosphate reductoisomerase catalysing the formation of 2-C-methyl-D- erythritol 4-phosphate in an alternative nonmevalonate pathway for terpenoid biosynthesis. *Proc. Natl. Acad. Sci. USA* 95, 9879–9884.

Watanabe, H.; Hatakeyama, S.; Tazumi, K.; Takano, S.; Masuda, S.; Okano, T.; Kobayashi, T.; Kubodera, N. *Chem. Pharm. Bull.* 1996, 44, 2280. Wungsintaweekul, J., Herz, S., Hecht, S., Eisenreich, W., Feicht, R., Rohdich, F., Bacher, A. & Zenk, M. H. (2001). Phosphorylation of 1-deoxy-D-xylulose by D-xylulokinase of *Escherichia coli*. *Eur. J. Biochem.* 268, 310–316.

---

The invention claimed is:

1. A method of identifying an inhibitor of an enzyme functional for the conversion of 2C-methyl-D-erythritol 2,4-cyclodiphosphate to 1-hydroxy-2-methyl-2-butenyl 4-diphosphate, in its E-form, of the non-mevalonate isoprenoid pathway comprising:
    (a) incubating a mixture containing said enzyme with its, optionally isotope labeled, substrate 2C-methyl-D-erythritol 2,4-cyclodiphosphate and NADH or NADPH under conditions suitable for said conversion in the presence and in the absence of a potential inhibitor,
    (b) subsequently determining the concentration of 2C-methyl-D-erythritol 2,4-cyclodiphosphate and/or 1-hydroxy-2-methyl-2-butenyl 4-diphosphate by measuring the consumption of NADH or NADPH, and
    (c) comparing the concentration of 2C-methyl-D-erythritol 2,4-cyclodiphosphate and/or 1-hydroxy-2-methyl-2-butenyl 4-diphosphate in the presence and in the absence of said potential inhibitor.

2. The method according to claim 1, wherein said enzyme is a plant enzyme.

3. The method according to according to claims 1, wherein said enzyme is an enzyme of *Plasmodium falciparum*.

4. The method according to according to claim 1, wherein said enzyme is a bacterial enzyme.

5. The method according to according to claim 1, wherein the incubation of step (a) is carried out in the presence of a sulfhydryl reductant.

6. The method according to according to claim 1, wherein the incubation in step (a) is carried out in the presence of a phosphatase inhibitor.

7. The method according to claim 6, wherein the phosphatase inhibitor is an alkali fluoride.

8. The method according to claim 1, wherein the incubation in step (a) is carried out in the presence of pamidronate.

9. The method according to claim 1, wherein the incubation of step (a) is carried out in the presence of a salt selected from the group of $Co^{2+}$, $Mn^{2+}$, $Fe^{2+}$, $Ni^{2+}$ salts.

10. The method according to claim 1, wherein step (b) is carried out by measuring the consumption of NADH or NADPH by absorbance and/or fluorescence spectrophotometry.

11. The method according to claim 1 further comprising simultaneously or consecutively performing steps (a) through (c) with at least one other potential inhibitor.

12. The method according to claim 5, wherein the sulfhydryl reductant is dithiothreitol.

* * * * *

UNITED STATES PATENT AND TRADEMARK OFFICE
CERTIFICATE OF CORRECTION

| | | |
|---|---|---|
| PATENT NO. | : 7,297,509 B2 | Page 1 of 1 |
| APPLICATION NO. | : 10/474536 | |
| DATED | : November 20, 2007 | |
| INVENTOR(S) | : Bacher et al. | |

It is certified that error appears in the above-identified patent and that said Letters Patent is hereby corrected as shown below:

On Title Page:

Item (30) Foreign Application Priority Data: Should read

--Apr. 11, 2001 (DE)   101 18 166.3
  Jun. 22, 2001 (DE)   101 30 236.3
  Nov. 9, 2001 (DE)    101 55 084.7
  Jan. 16, 2002 (DE)   102 01 458.2--

Signed and Sealed this

Twenty-fifth Day of March, 2008

JON W. DUDAS
*Director of the United States Patent and Trademark Office*